(12) United States Patent
Eber

(10) Patent No.: US 9,433,577 B2
(45) Date of Patent: Sep. 6, 2016

(54) PHARMACEUTICAL COMPOSITION COMPRISING OLIGOPEPTIDES

(75) Inventor: Marcus Eber, Floersheim (DE)

(73) Assignee: Merck Patent GmbH, Darmstadt (DE)

( * ) Notice: Subject to any disclaimer, the term of this patent is extended or adjusted under 35 U.S.C. 154(b) by 154 days.

(21) Appl. No.: 13/515,244

(22) PCT Filed: Dec. 6, 2010

(86) PCT No.: PCT/EP2010/007396
§ 371 (c)(1),
(2), (4) Date: Jun. 11, 2012

(87) PCT Pub. No.: WO2011/069629
PCT Pub. Date: Jun. 16, 2011

(65) Prior Publication Data
US 2012/0288539 A1    Nov. 15, 2012

Related U.S. Application Data

(60) Provisional application No. 61/416,628, filed on Nov. 23, 2010, provisional application No. 61/285,313, filed on Dec. 10, 2009.

(51) Int. Cl.
| | |
|---|---|
| A61K 38/12 | (2006.01) |
| A61K 38/02 | (2006.01) |
| A61K 9/14 | (2006.01) |
| A61K 9/10 | (2006.01) |
| A61K 9/00 | (2006.01) |
| A61K 9/16 | (2006.01) |

(52) U.S. Cl.
CPC ............. *A61K 9/10* (2013.01); *A61K 9/0019* (2013.01); *A61K 9/1617* (2013.01); *A61K 38/12* (2013.01); *A61K 9/0095* (2013.01)

(58) Field of Classification Search
None
See application file for complete search history.

(56) References Cited

U.S. PATENT DOCUMENTS

| | | | |
|---|---|---|---|
| 5,633,226 A | 5/1997 | Owen et al. | |
| 6,001,961 A | 12/1999 | Jonczyk et al. | |
| 6,228,399 B1 | 5/2001 | Parikh | |
| 8,586,545 B2 * | 11/2013 | Joncyk et al. | 514/19.3 |
| 2003/0108626 A1 | 6/2003 | Benita et al. | |
| 2005/0239692 A1 | 10/2005 | Lindenblatt et al. | |
| 2007/0196284 A1 * | 8/2007 | Tournier et al. | 424/9.321 |

FOREIGN PATENT DOCUMENTS

| | | |
|---|---|---|
| WO | WO 92/18147 | 10/1992 |
| WO | WO 93/02665 | 2/1993 |
| WO | WO 03/032949 | 4/2003 |
| WO | WO 2009/040071 | 4/2009 |
| WO | WO 2009/124754 | * 10/2009 |
| WO | WO 2010/133367 | 11/2010 |
| WO | WO-2010-133367 | * 11/2010 |

OTHER PUBLICATIONS

U.S. Appl. No. 14/028,222, Jonczyk et al.

* cited by examiner

*Primary Examiner* — Frederick Krass
*Assistant Examiner* — Celeste A Roney
(74) *Attorney, Agent, or Firm* — Ronald J. Kamis; Debora Plehn-Dujowich; Prismatic Law Group, PLLC

(57) ABSTRACT

The present invention relates to a pharmaceutical composition of oligopeptides, preferably cyclic oligopeptides, said composition further comprising one or more lipophilic and/or amphiphilic compounds, in the presence or absence of water as the main ingredients, the use of the lipophilic and/or amphiphilic compounds for making pharmaceutical compositions of said oligopeptides, and methods of making said pharmaceutical composition.

29 Claims, 27 Drawing Sheets

Single crystal structure of form A1

FTIR spectrum of form A1

Single crystal structure of form S3

FTIR spectrum of form S3

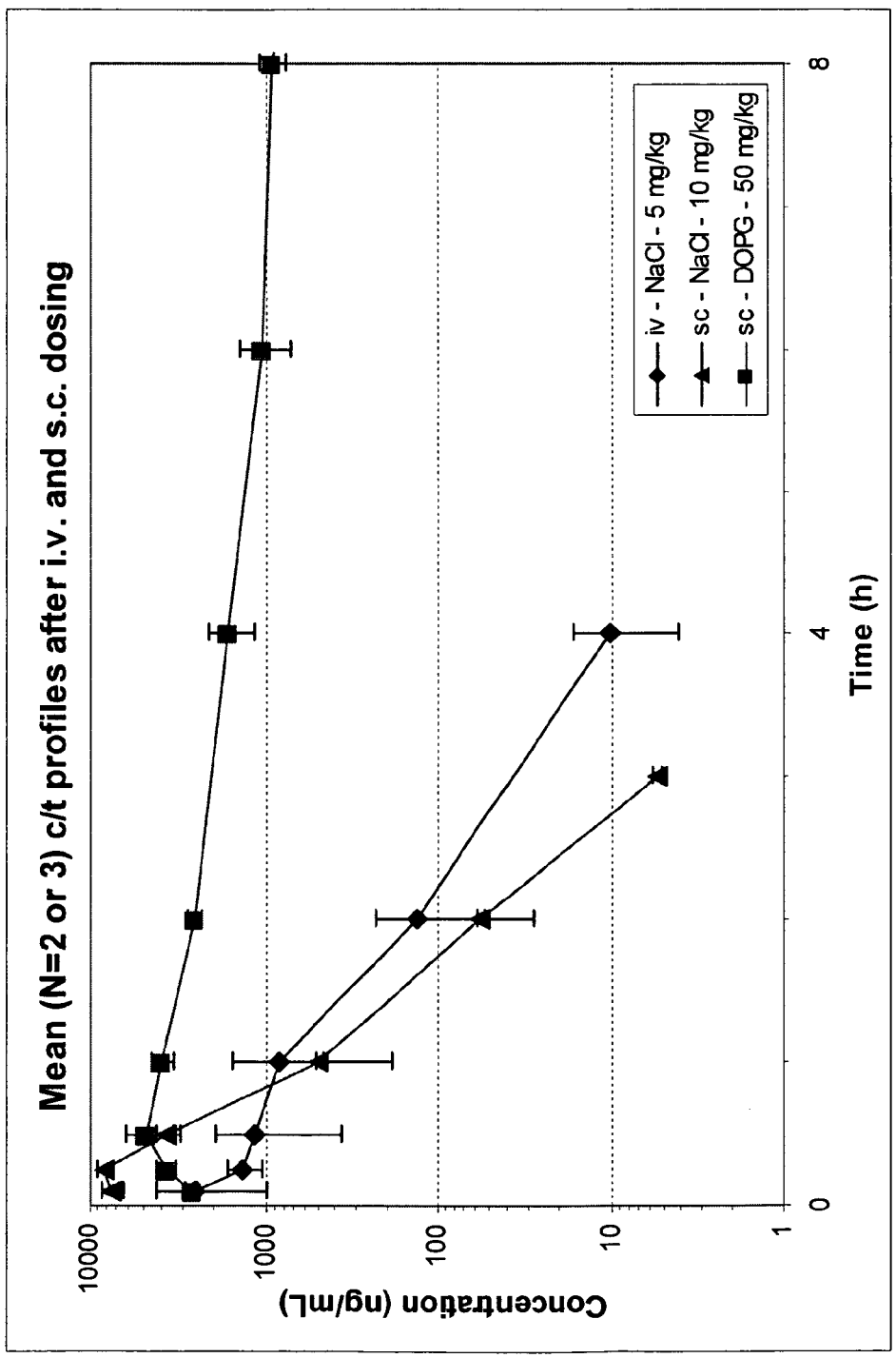

PHARMACEUTICAL COMPOSITION COMPRISING OLIGOPEPTIDES

This application is a 371 of PCT/EP2010/0077396 filed Dec. 6, 2010, which claims priority to U.S. Provisional Application Nos., 61/285,313 filed Dec. 10, 2009 and 61/416,628, filed Nov. 23, 2010. The entire contents of the above-identified applications are hereby incorporated by reference.

The present invention relates to a pharmaceutical composition of oligopeptides, preferably cyclic oligopeptides, said composition further comprising one or more lipophilic and/or amphiphilic compounds, in the presence or absence of water as the main ingredients, the use of the lipophilic and/or amphiphilic compounds for making pharmaceutical compositions of said oligopeptides, and methods of making said pharmaceutical composition.

Solubility of active pharmaceutical ingredients (API) represents one main issue for formulators as inadequate aqueous solubility may hinder development of parenterals for IV, IM or SC administration. Many new therapeutic compounds are of poor solubility; such compounds with insufficient solubility bring along a higher risk of failure during discovery and development since insufficient solubility may compromise both pharmacokinetic and pharmacodynamic properties of the compound. Commonly used excipients have a substantial potential for drug-excipient interactions, e.g. by altering protein binding and blood cell/plasma distribution. In consequence, the formulation vehicle can be an important determinant for the disposition of drug doses. Therefore, solubility may affect the overall commercial developability of the compound.

Solubility of peptides may range from low micrograms per ml to several hundreds of milligrams per ml, and is often very specific for the respective class of peptides. Even rather small structural differences can lead to significant changes in the characteristics of the respective class of peptides, including rather dramatic changes in the solubility. The required dose and route of administration may demand a higher concentration than possible in simple formulations, challenging the development of a clinically or commercially viable product. One important challenge is that peptides and proteins are typically administered via injections due to poor bioavailability by other delivery which restricts the types and concentration of excipients. On top, only small volumes of administration are appropriate for subcutaneous and intramuscular delivery routes in order to comply with patient compliance and ease of delivery, in contrast to volume and concentration constraints as known for intravenous administration settings. For subcutaneously delivery approximately 1.5 mL may be considered acceptable, preferably presented as clear solutions of low viscosity. This requires formulations which contain up to hundreds of mg/mL peptide or protein. Moreover, toxicological studies may assess approximately 10-fold higher doses than those planned for clinical studies in order to establish a safety window. This necessitates even higher concentrations for non-clinical formulations than for clinical formulations.

During formulation development, excipients are added to enhance the API's solubility (solubilizers) and/or stability (buffers, antioxidants, and chelating agents), as well as to assure safety (antimicrobial preservatives), to minimize pain and irritation upon injection (tonicity agents), and control or prolong drug delivery (polymers). On the down-side, incorporation of excipients, such as surfactants, can enhance solubility but may have negative impact on regulatory approval, toxicity and/or overall stability of the drug product.

Active pharmaceutical ingredients that belong to the class of peptidic compounds generally additionally face stability problems in many types of formulations. In formulations having about neutral pH-values, the peptides tend to show satisfying stability, but a rather low or even very low solubility in the presence of many solvents and/or excipients, even solvents and/or excipients having a rather high polarity, e.g. water. In formulations showing lower or higher than neutral pH-values, however, the solubility of said peptidic compounds often dramatically increases, but in most cases also the degradation of the peptidic structure increases dramatically.

As an alternative, liquid pharmaceutical preparations that contain at least a part of the active ingredient(s) or API as solid particles, generally referred to as suspensions, have been successfully developed and commercialized, for example suspensions with controlled-/sustained release of the active ingredients or API. Prominent examples of such pharmaceutical preparations in the form of suspensions are liquid insulin or hormone preparations. Generally, such suspensions allow subcutaneous, intramuscular, intraarticular, intravitreal, etc. injection. Typically, these pharmaceutical suspensions are oil or water based (fluid) systems.

For physico-chemical stability of suspensions it is essential that there is any or hardly any particle growth over shelf-time—known in literature as Ostwalt ripening, defined as the growth of large particles at the expense of smaller ones as a result of a difference in the solubility of the particles of varying sizes. As a direct consequence, it is common knowledge that only poorly-soluble drugs can be formulated as physically stable suspensions, i.e. with drug solubilities well below 1 mg/mL in the respective water or oil based (fluid) systems.

Pharmaceutically active oligopeptides are generally not suitable for oral administration, mostly due to poor resorption, short half life and/or lack of stability against metabolic degradation. Since such oligopeptides generally have a solubility in water well above 1 mg/mL, mostly well above 10 mg/mL, but usually well below 100 mg/mL, they are generally formulated and administered to the patient as aqueous solutions, for example solutions for (topical) ophthalmic use and intravenous (i.v.) infusion solutions for systemic administration. However, if high drug loads or high dosages regarding said oligopeptides for systemic administration are required or desired in the treatment of the patients, the only possible way of administration for said oligopeptides is the i.v. infusion of rather high volumes of said aqueous solutions.

Measures to improve the solubility or generally raise the concentration of pharmaceutically active oligopeptides in the respective formulation are little known and/or have serious disadvantages. For example, adjusting the pH value of the formulation to higher or lower pH than at physiological conditions generally improves the solubility of the pharmaceutically active oligopeptide, but leads to serious disadvantages, such as a accelerated chemical degradation and poor tonicity.

If a formulation of a pharmaceutically active oligopeptide is intended to be administrable several times per week or even several times per day, additional functional requirements have to be fulfilled, such as high tolerability, high chemical stability, high physical stability, ease of use and/or high reliability. Additionally, a convenient method of manufacturing such a formulation of a pharmaceutical active oligopeptide is highly desirous.

Subject of the instant invention is therefore to provide an advantageous formulation concept for peptidic compounds, preferably oligopeptides, more preferably cyclic oligopeptides, and especially cyclic oligopeptides as described herein, and compounds for use as formulation partners with advantageous effects on the desired formulation of said peptides.

Preferably, said formulation concept and/or said formulation partners should provide for more stable formulations of said peptides, higher concentration of said peptides in said formulations, improved routes or forms of administration of said formulation, an improved pharmacological profile of said formulation, an improved efficacy and/or an optimised efficacy at a comparable dose or even at a lower dose when applied to the respective patient.

In this context, a suitable formulation for oligopeptides from the class of RGD containing oligopeptides and especially from the class of RGD containing cyclic oligopeptides, such as cyclo-(Arg-Gly-Asp-DPhe-NMeVal), should be developed, especially for use as a pharmaceutical composition or preparation. This formulation or pharmaceutical preparation should satisfy a variety of requirements. For example, it should allow a more convenient administration than i.v. infusion, e.g. subcutaneous administration, intramuscular administration or the like. Thus, as a target product profile for this formulation, it should fulfill one or more of the following criteria, preferably among others:

enable convenient administration, such as intramuscular, subcutaneous, etc.
enable self-administration,
enable chronic or semi-chronic administration
enable daily administration, preferably in multiple daily doses (preferably up to 3 or more),
enable high drug concentration, preferably exceeding 50 mg/mL and more preferably exceeding, 100 mg/mL
enable controlled release and preferably sustained release of the drug, and
enable suitable shelf-life of pharmaceutical preparation.

Moreover, the applied raw materials, excipients, and drug delivery technologies should preferably be compliant with the respective toxicological and clinical requirements predetermined by the intended chronic and/or multiple daily administration.

For the oligopeptide Cilengitide (EMD121974), various salts and/or polymorphic forms have been isolated which are soluble in aqueous preparations, ranging from about 8 mg/mL to about 20 mg/mL. Many of such salts and/or polymorphic forms and methods for obtaining them are described in EP 0 770 622 A1, U.S. Pat. No. 6,001,961 B1, WO 2000/053627 A1, EP 09006790.1, filed by the same applicant on May 20, 2009, and/or PCT/EP2010/003100, the disclosure of which is included herein by reference in their entirety. In general, such above described aqueous solubilities do not allow development of physically stable pharmaceutical suspensions due to expected growth of particles (see above).

During formulation experiments, solubility screening studies with the polymorphic form A1-anhydrate of EMD 121974 in oils or oily systems (such as soybean oil, sesame oil or Miglyol® 812) have been performed. These oils or oily systems, hereinafter also referred to as lipophilic compounds, surprisingly show that the typical coarse A1-anhydrate crystals as obtained by synthesis and purification (typical particle size distribution of d(10)=13 µm, d(50)=61 µm, and d(90)=241 µm) are subject to further size reduction and micronisation just when contacted to said oily systems. For example, modest stirring on a magnetic stirrer at room temperature of such coarse, non milled or non-micronized A1-anhydrate crystals makes the large drug particles disappear over time, while in return a fully homogenous, milky white suspension of very fine particles results. Depending on the size or size distribution of the employed particles and the stirring speed, this process is generally completed within 24 to 36 h, and the above described milky white suspension of very fine particles is obtained. Typically, the thus obtained homogenous, milky white suspensions do not contain any of the initially added course drug particles, but these course drug particles are "ground" and/or "micronized" in the liquid phase without introducing any relevant mechanical energy as know from ball mills or jet milling. Depending on the respective oily system, typically the drug particle size is reduced spontaneously (i.e. without grinding and/or milling processes) to d(10)=1-5 µm, d(50)=5-10 µm, and d(90)=20-30 µm) over time. Even after storage over several weeks at room temperature, this particle size distribution is maintained without any noticeable particle re-growth, thus indicating the formation of a physically stable suspension. Although the underlying mechanism of this spontaneous micronisation of the macroscopic drug particles in the presence of the liquid phase is not fully understood, it is believed that the drug particle size will converge to discrete preferred particle size distribution.

Based on the above described formation of stable suspensions of oligopeptides due to "spontaneous" drug particle size reduction in oily systems, water-based systems with lipid-like excipients were tested. As a result, such lipid-like excipients, hereinafter also referred to as amphiphilic compounds, surprisingly show a "spontaneous" drug particle size reduction in water-based systems and thus also enable stable suspensions of oligopeptides in water or water-based systems in the presence of said lipid-like excipients. It is thus believed that such amphiphilic compounds interact with the oligopeptides in a similar manner as said lipophilic compounds due to having or being composed of groups, moieties or structural units being similar or having similar properties and characteristics as the groups, moieties or structural units found in such lipophilic compounds or oils. More specifically, phospholipids have been selected as especially preferred lipid-like excipients or amphiphilic compounds, as they contain various fatty acids which are also found in the said lipophilic compounds or oils. Even more specifically, glycerophospholipids and their derivates, such as DOPG, DMPC, DMPG, DPPG, DSPG, DSPE and soy lecithin, were tested as they are ubiquitous in the human body and are major components of biological membranes. Aqueous systems containing glycerophospholipids also show that the typical coarse A1-anhydrate crystals as obtained by synthesis and purification (typical particle size distribution of d(10)=13 µm, d(50)=61 µm, and d(90)=241 µm) are subject to further size reduction and micronisation just when contacted to said aqueous systems containing said glycerophospholipid(s). Also here, modest stirring on a magnetic stirrer at room temperature makes the course, non-micronized drug particles disappear over time (generally completed within 24 to 36 h), while in return a fully homogenous, milky white suspension of very fine particles results. Typically, the obtained homogenous, milky white suspension does not contain any of the initially added course drug particles, but these course drug particles have been ground and micronized in the liquid phase without introduction of any relevant mechanical energy as known from ball mills or jet milling. Potentially depending on the aqueous system and the phospholipid applied, the drug particle size is reduced "spontaneously" (i.e. without grinding and/or milling processes) to d(10)=1-5 µm, d(50)=5-10 µm, and d(90)=20-30 µm) or to d(10)=1-10 µm, d(50)=10-25 µm and d(90)=25-60 µm over time (more than 24 hours). Even after storage over several weeks at room temperature, this particle size distribution is maintained without any noticeable particle re-growth, thus indicating the formation of a physically stable suspension of the oligopeptide also in the water based system in the presence of one or more amphiphilic compounds. Although the underlying mechanism of this spontaneous micronisation of the macroscopic drug particles in the presence of the liquid phase is not yet fully understood, it is believed that the drug particle size will converge to discrete preferred particle size distribution, not only in the previous described oily systems, but also in aqueous systems if suitable excipients, i.e. the lipid-like excipients or amphiphilic compounds, are added as described herein. Additionally, the formation of the above discussed stable suspensions can preferably be facilitated and/or accelerated by grinding or preferably micronizing the particles of the respective oligopeptide before they are contacted with the liquid phase consisting of or containing the lipophilic compounds and/or the amphiphilic compounds.

The accordingly obtained suspensions show advantageous properties which make them very suitable pharmaceutical compositions or at least a very suitable basis for pharmaceutical compositions. This is discussed in more detail below.

Thus, an advantageous formulation or composition of peptides can be achieved by contacting one or more peptides and especially one or more oligopeptides with one or more lipophilic and/or amphiphilic compounds. Advantageously, novel compositions can be formed which can preferably be characterised as suspensions. Generally, these compositions comprise a continuous liquid phase, containing a major amount of said one or more lipophilic and/or amphiphilic compounds, and a discontinuous phase, containing the major amount of said one or more peptides. These advantageous formulations can be water-based or essentially free of water, depending inter-alia on the amount of the lipophilic and/or amphiphilic compounds employed in said formulation

BRIEF DESCRIPTION OF THE DRAWINGS

FIG. 23 shows the mean (N=2 or 3) c/t profiles after i.v. and s.c. dosing in mice. See Example 16 below.

Figure 1:
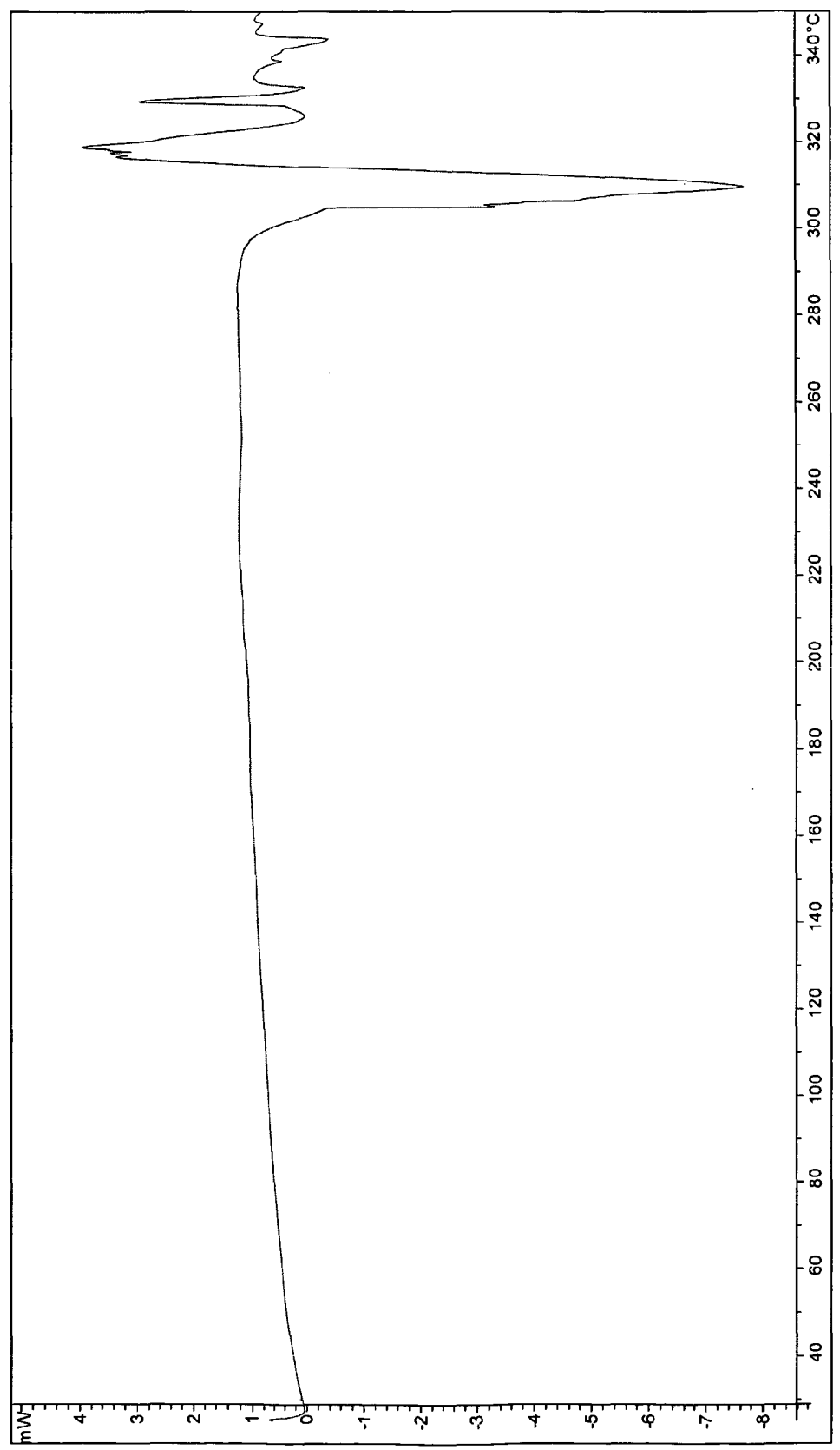
FIG. 1 shows a DSC scan of form A1 (Mettler-Toledo DSC 821, 5 K/min, nitrogen purge gas 50 ml/min).

Subject of the instant invention is thus a new formulation, composition or pharmaceutical composition as described below. The new formulation, composition or pharmaceutical composition as described below preferably shows one or more of the advantageous properties described herein.

Thus, subjects of the instant invention are:

[1] A composition, preferably a pharmaceutical composition, comprising a) 12 to 90% of at least one oligopeptide, preferably at least one cyclic oligopeptide, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, even more preferably between 6 mg/ml and 10 mg/ml, and especially between 5 mg/ml and 9 mg/ml, b) 0.01 to 90%, preferably 0.01 to 80 percent, more preferably, 0.01 to 70 percent and especially 0.1 to 60%, of one or more lipophilic and/or amphiphilic compounds having a molar weight in the range of 200 g/mol to 2000 g/mol, preferably 300 g/mol to 1500 g/mol, more preferably 500 g/mol to 1000 g/mol, and especially 700 g/mol to 900 g/mol, and optionally c) 0 to 89% of water, with the proviso that the sum of a), b) and c) makes up to 40 or more %, preferably 50 or more percent, more preferably 70 or more percent, even more preferably 90 percent or more and especially 95 percent or more, of the total composition.

The solubility of said cyclic oligopeptide(s) is preferably determined as described herein.

Amphiphilic compounds according to the invention in the broadest sense preferably are molecules which comprise both a polar (hydrophilic) moiety or group and an apolar (hydrophobic or lipophilic) moiety or group; preferably, the amphiphilic compounds according to the invention show interfacial activity and/or surface activity. For example, they preferably are surface active agents and/or surfactants, or preferably are able to act as surface active agents and/or surfactants.

Lipophilic compounds according to the invention in the broadest sense preferably are molecules which either i) exclusively consist of one or more apolar (hydrophobic or lipophilic) moieties or groups, but contain no polar (hydrophobic or lipophilic) moiety or group; or ii) are predominantly comprised of one or more apolar (hydrophobic or lipophilic) moieties or groups and contain an only to a minor extent polar (hydrophobic or lipophilic) moiety or group, so that it is not or hardly soluble in water, but very soluble in oils; preferably, the lipophilic compounds according to the invention show no interfacial activity and/or no surface activity.

[2] Composition as described herein and especially as described in paragraph numbered [1] and preferably also as described in the paragraphs relating thereto, wherein at least one of the lipophilic and/or amphiphilic compounds according to b) comprises:

α) a glycerol moiety,

β) one or more fatty acid moieties, and/or

γ) one or more fatty alcohol moieties; and more preferably

α) a glycerol moiety, and/or

β) one or more fatty acid moieties.

More preferably, the amphiphilic compounds according to b) comprise:

α) a glycerol moiety, and at least one moiety selected from

β) one or more fatty acid moieties and γ) one or more fatty alcohol moieties.

Even more preferably, the amphiphilic compounds according to b) comprise:

α) a glycerol moiety, and

β) one or more fatty acid moieties.

A glycerol moiety according to the invention preferably is a moiety that is derived from glycerol or can be derived from glycerol. More specifically, the glycerol moiety is preferably selected from the following structures in the squares:

i)

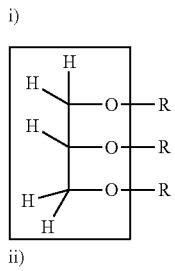

ii)

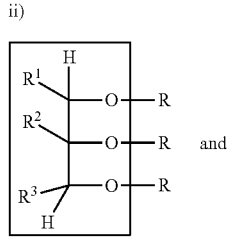

iii)

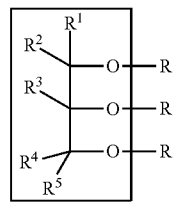

wherein $R^1$, $R^2$, $R^3$, $R^4$ and $R^5$ are independently from each other are selected from H, methyl, ethyl and hydrophilic moieties, more preferably from H and hydrophilic moieties; preferably with the proviso that only one or two of $R^1$, $R^2$, $R^3$, $R^4$ and $R^5$ are hydrophilic moieties, and more preferably that only one of $R^1$, $R^2$, $R^3$, $R^4$ and $R^5$ is a hydrophilic moiety;

and all salts and/or stereoisomers thereof.

The glycerol moiety is preferably selected from the following structures in the squares:

i)

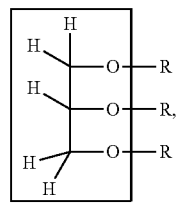

ii)

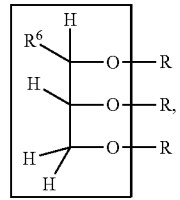

iii)

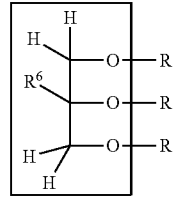 and iv)

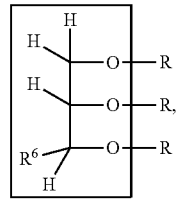

wherein $R^6$ is selected from methyl, ethyl and hydrophilic moieties, more preferably from methyl and hydrophilic moieties; and all salts and/or stereoisomers thereof.

Hydrophilic moieties in this regard are preferably selected from the group consisting of:
α) —OH, —ONa, —OK, —O⁻, —NH$_2$, —NH$_3^+$, —N(CH$_3$)$_3^+$, —PO$_3$H, —PO$_3$Na, —PO$_3$K, —PO$_3^-$, —O—PO$_3$H, —O—PO$_3$Na, —O—PO$_3$K, —O—PO$_3^-$;
β) —(CH$_2$)$_n$—OH, —(CH$_2$)$_n$—ONa, —(CH$_2$)$_n$—OK, —(CH$_2$)$_n$—O⁻, —(CH$_2$)$_n$—NH$_2$,
β) —(CH$_2$)$_n$—NH$_3^+$, —(CH$_2$)$_n$—N(CH$_3$)$_3^+$, —(CH$_2$)$_n$—PO$_3$H, —(CH$_2$)$_n$—PO$_3$Na, —(CH$_2$)$_n$—PO$_3$K, —(CH$_2$)$_n$—PO$_3^-$, —(CH$_2$)$_n$—O—PO$_3$H, —(CH$_2$)$_n$—O—PO$_3$Na, —(CH$_2$)$_n$—O—PO$_3$K, —(CH$_2$)$_n$—O—PO$_3^-$,
wherein n is 1, 2, 3 or 4, preferably 1, 2 or 3 and especially 1 or 2; and/or
γ) an ethanolamine moiety, a choline moiety, a phosphatidyl moiety, a phosphatidylcholine moiety, a sulfatidyl and a sulfatidylcholine moiety; and a salt or other salt thereof.

The glycerol moieties in lipophilic compounds preferably do not comprise hydrophilic residues (which are bound to the carbon backbone of the glycerol moiety) as described above.

A fatty acid moiety in the context of the instant invention preferably is a moiety that is derived from a fatty acid or can be derived from a fatty acid. More preferably, a fatty acid moiety is the part of fatty acid, preferably a fatty acid as defined below, that is chemically bound to another moiety, e.g. esterified to another moiety, that is part of said lipophilic and/or amphiphilic compound.

The meaning of the term fatty acid is well known in the art and is preferably to be understood here in its broadest context. More preferably, a fatty acid in the context of the instant invention is an aliphatic saturated or (ethylenically) unsaturated, branched or unbranched carboxylic acid having 4 to 35 carbon atoms, more preferably 6 to 30 carbon atoms and especially 8 to 25 carbon atoms. Even more preferably, a fatty acid in the context of the instant invention is an aliphatic saturated or once, twice, three times or four times (ethylenically) unsaturated, branched or unbranched, preferably unbranched, carboxylic acid having 4 to 35 carbon atoms, more preferably 6 to 30 carbon atoms and especially 8 to 25 carbon atoms. Even more preferably, a fatty acid in the context of the instant invention is an aliphatic saturated or once or twice (ethylenically) unsaturated, branched or unbranched, preferably unbranched, carboxylic acid having 4 to 35 carbon atoms, more preferably 6 to 30 carbon atoms and especially 8 to 25 carbon atoms.

Thus, the fatty acid moiety according to the invention preferably is one of the structures given in the squares below, whereas the structures in the circles constitute the fatty acid as the whole:

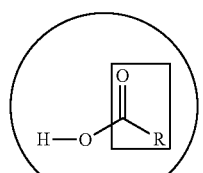

and/or

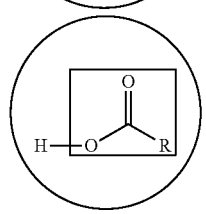, preferably 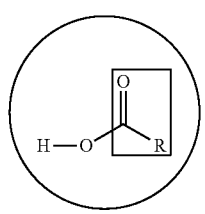

Thus, especially preferably, a fatty acid moiety according to the invention is the acyl moiety or acyl residue of the corresponding fatty acid.

Even more preferred fatty acid moieties are selected from the following formulae:

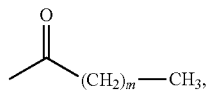

wherein m is 2 to 33, more preferably 4 to 28 and even more preferably 6 to 23;

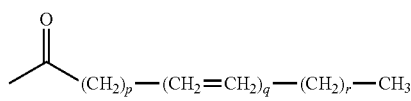

wherein
p is 1 to 20, more preferably 3 to 18, even more preferably 4 to 15 and especially 6 to 13,
q is 0 to 6, more preferably 1 to 5, more preferably 1, 2, 3, or 4 and especially 1, 2 or 3,
r is 1 to 20, more preferably 3 to 15, even more preferably 6 to 12 and especially 6, 7 or 8,
preferably with the proviso that the sum of p and r is 4 to 30, more preferably 5 to 25, even more preferably 8 to 22 and especially 10 to 20 and/or with the proviso that the sum of p, q and r is 5 to 30, more preferably 6 to 25, even more preferably 9 to 23 and especially 11 to 21;

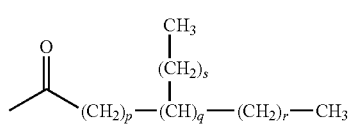

wherein
p is 1 to 20, more preferably 3 to 18, even more preferably 4 to 15 and especially 6 to 13,
q is 0 to 6, more preferably 1 to 5, more preferably 1, 2, 3, or 4 and especially 1, 2 or 3,
r is 1 to 20, more preferably 3 to 15, even more preferably 6 to 12 and especially 6, 7 or 8, and
s is 1 to 20, more preferably 1 to 15, even more preferably 1 to 10 and especially 1 to 5,
preferably with the proviso that the sum of p, r and s is 4 to 30, more preferably 5 to 25, even more preferably 8 to 22 and especially 10 to 20 and/or with the proviso that the sum of p, q, r and s is 5 to 30, more preferably 6 to 25, even more preferably 9 to 23 and especially 11 to 21;
and/or

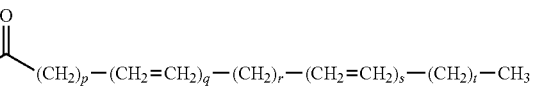

wherein
p is 1 to 20, more preferably 3 to 15, even more preferably 6 to 12 and especially 6, 7 or 8,
q is 0 to 6, more preferably 1 to 5, more preferably 1, 2, 3, or 4 and especially 1, 2 or 3, r is 1 to 20, more preferably 3 to 18, even more preferably 4 to 15 and especially 6 to 12, and s is 0 to 6, more preferably 1 to 5, more preferably 1, 2, 3, or 4 and especially 1, 2 or 3, t is 1 to 20, more preferably 1 to 15, even more preferably 1 to 10, even more preferably 3 to 8 and especially 4, 5, 6, 7 or 8, preferably with the proviso that the sum of p, r and t is 4 to 30, more preferably 6 to 25, even more preferably 8 to 22 and especially 10 to 20 and/or with the proviso that the sum of p, q, r, s and t is 5 to 30, more preferably 7 to 25, even more preferably 9 to 23 and especially 11 to 21.

Even more preferably, the fatty acid moieties are selected from the group of:

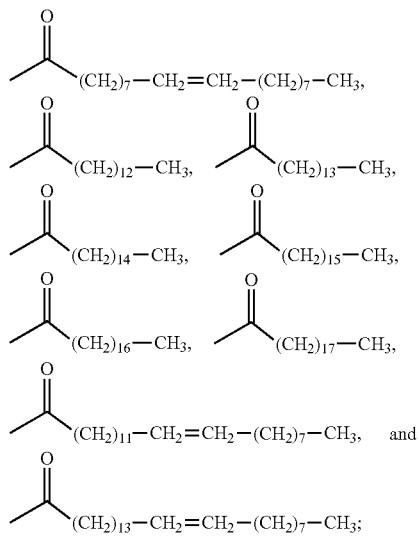

and, in case of the unsaturated fatty acid moieties, all stereoisomers thereof.

Even more preferably, the fatty acid moieties are selected from the group consisting of myristoyl (corresponds to myristic acid), oleoyl (corresponds to oleic acid), palmitoyl (corresponds to palmitic acid), stearoyl (corresponds to stearic acid), margaroyl (corresponds to margaric acid), arachidoyl (corresponds to arachic or arachidic acid), behenoyl (corresponds to behenic acid), erucoyl (corresponds to erucic acid), linoleoyl (corresponds to linoleic acid) and linolenoyl (corresponds to linolenic acid).

Even more preferably, the fatty acid moieties are selected from the group consisting of myristoyl, oleoyl, palmitoyl and stearoyl.

Even more preferably, the fatty acid moieties are selected from the group consisting of myristoyl, palmitoyl and stearoyl.

Especially preferably, the fatty acid moiety is myristoyl.

A fatty alcohol moiety in the context of the instant invention preferably is a moiety that is derived from a fatty alcohol or can be derived from a fatty alcohol. More preferably, a fatty alcohol moiety is a fatty alcohol, preferably a fatty alcohol as defined below, that is chemically bound to another moiety, e.g. esterified to another moiety, that is part of said lipophilic and/or amphiphilic compound.

The meaning of the term fatty alcohol is well known in the art and is preferably to be understood here in its broadest context. More preferably, a fatty alcohol in the context of the instant invention is an aliphatic saturated or (ethylenically) unsaturated, branched or unbranched carboxylic acid having 4 to 35 carbon atoms, more preferably 6 to 30 carbon atoms and especially 8 to 25 carbon atoms. Even more preferably, a fatty alcohol in the context of the instant invention is an aliphatic saturated or once, twice, three times or four times (ethylenically) unsaturated, branched or unbranched, preferably unbranched, carboxylic acid having 4 to 35 carbon atoms, more preferably 6 to 30 carbon atoms and especially 8 to 25 carbon atoms. Even more preferably, a fatty alcohol in the context of the instant invention is an aliphatic saturated or once or twice (ethylenically) unsaturated, branched or unbranched, preferably unbranched, alcohol having 4 to 35 carbon atoms, more preferably 6 to 30 carbon atoms and especially 8 to 25 carbon atoms. Typically, such fatty alcohols are derived, can be derived or are obtainable from the corresponding alcohol, e.g. by a reduction of the corresponding fatty acid.

Thus, the fatty alcohol moiety according to the invention preferably are the structures given in the squares below, whereas the structures in the circles constitute the fatty alcohol as the whole:

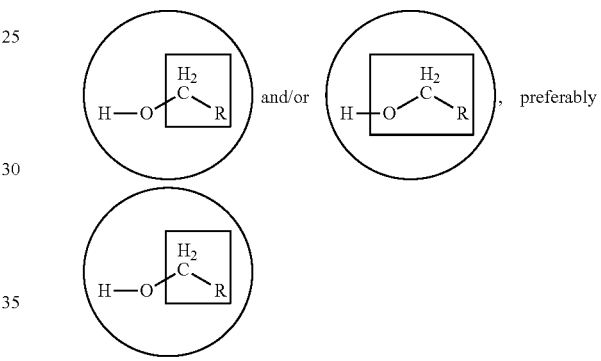

Thus, especially preferably, a fatty alcohol moiety according to the invention is the alkyl moiety or alkyl residue of the corresponding fatty alcohol.

Even more preferred fatty alcohol moieties are selected from the following formulae:

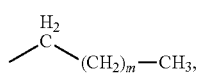

wherein m is 2 to 33, more preferably 4 to 28 and even more preferably 6 to 23;

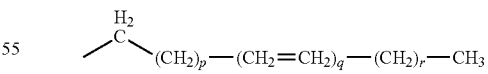

wherein p is 1 to 20, more preferably 3 to 18, even more preferably 4 to 15 and especially 6 to 13, q is 0 to 6, more preferably 1 to 5, more preferably 1, 2, 3, or 4 and especially 1, 2 or 3, r is 1 to 20, more preferably 3 to 15, even more preferably 6 to 12 and especially 6, 7 or 8, preferably with the proviso that the sum of p and r is 4 to 30, more preferably 5 to 25, even more preferably 8 to 22 and especially 10 to 20 and/or with the proviso that the sum of p, q and r is 5 to 30, more preferably 6 to 25, even more preferably 9 to 23 and especially 11 to 21;

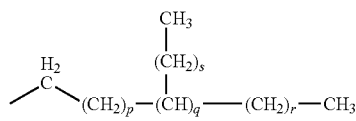

wherein
p is 1 to 20, more preferably 3 to 18, even more preferably 4 to 15 and especially 6 to 13,
q is 0 to 6, more preferably 1 to 5, more preferably 1, 2, 3, or 4 and especially 1, 2 or 3,
r is 1 to 20, more preferably 3 to 15, even more preferably 6 to 12 and especially 6, 7 or 8, and
s is 1 to 20, more preferably 1 to 15, even more preferably 1 to 10 and especially 1 to 5,
preferably with the proviso that the sum of p, r and s is 4 to 30, more preferably 5 to 25, even more preferably 8 to 22 and especially 10 to 20 and/or with the proviso that the sum of p, q, r and s is 5 to 30, more preferably 6 to 25, even more preferably 9 to 23 and especially 11 to 21;
and/or

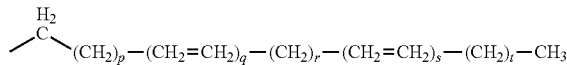

wherein
p is 1 to 20, more preferably 3 to 15, even more preferably 6 to 12 and especially 6, 7 or 8,
q is 0 to 6, more preferably 1 to 5, more preferably 1, 2, 3, or 4 and especially 1, 2 or 3,
r is 1 to 20, more preferably 3 to 18, even more preferably 4 to 15 and especially 6 to 12, and
s is 0 to 6, more preferably 1 to 5, more preferably 1, 2, 3, or 4 and especially 1, 2 or 3,
t is 1 to 20, more preferably 1 to 15, even more preferably 1 to 10, even more preferably 3 to 8 and especially 4, 5, 6, 7 or 8, preferably with the proviso that the sum of p, r and t is 4 to 30, more preferably 6 to 25, even more preferably 8 to 22 and especially 10 to 20 and/or with the proviso that the sum of p, q, r, s and t is 5 to 30, more preferably 7 to 25, even more preferably 9 to 23 and especially 11 to 21.

Even more preferably, the fatty alcohol moieties are selected from the group of:

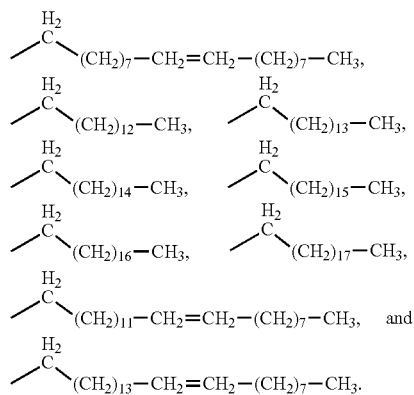

Even more preferably, the fatty alcohol moieties are independently selected from the alkyl residues of the fatty alcohols of the group consisting of oleic alcohol, myristic alcohol, palmitic alcohol, stearic alcohol, margaric alcohol, arachic alcohol, behenic alcohol, erucic alcohol, linolic alcohol and linolenic alcohol.

[3] Preferred are compositions as described herein and especially as described in one or more of the paragraphs numbered [1], [2] and/or the paragraphs relating thereto, wherein
at least one of the lipophilic and/or amphiphilic compounds according to b) comprises a hydrophilic moiety, and especially wherein
at least one of the amphiphilic compounds according to b) comprises a hydrophilic moiety. Suitable hydrophilic moieties are known to the skilled artisan.

[4] Preferred are compositions as described herein and especially as described in the paragraph numbered [3], wherein the hydrophilic moiety comprises an ethanolamine moiety, a choline moiety, a phosphatidyl moiety and/or a sulfatidyl moiety, and/or a salt thereof, or more preferably is an ethanolamine moiety, a choline moiety, a phosphatidyl moiety and/or a sulfatidyl moiety, and/or a salt thereof.

[5] Preferred are compositions as described herein and especially as described in the paragraph numbered [3] and/or [4], wherein the hydrophilic moiety comprises, a phosphoethanolamine moiety, a phosphatidylcholine moiety, a phosphatidylglycerol moiety and/or a sulfatidylglycerol moiety, and/or a salt thereof, or more preferably is phosphoethanolamine moiety, a phosphatidylcholine moiety, a phosphatidylglycerol moiety and/or a sulfatidylglycerol moiety and especially a phosphatidylglycerol moiety, and/or a salt thereof.

As regards the salts thereof, a basic hydrophilic moiety can be present as a salt, such as an acid addition salt, or can be converted into a salt with an acid, such as into the associated acid addition salt, for example by reacting equivalent quantities of the compound comprising the basic hydrophilic moiety and the acid in an inert solvent such as ethanol and then concentrating by evaporation. Suitable acids for such salts are, in particular, those which give rise to physiologically harmless salts. Thus, use can be made of inorganic acids, for example sulphuric acid, nitric acid, hydrohalic acids such as hydrochloric acid or hydrobromic acid, phosphoric acids such as orthophosphoric acid, and sulphamic acid, and, in addition, organic acids, in particular aliphatic, alicyclic, araliphatic, aromatic or heterocyclic monobasic or polybasic carboxylic, sulphonic or sulphuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methanesulphonic acid, ethanesulphonic acid, ethanedisulphonic acid, 2-hydroxyethanesulphonic acid, benzenesulphonic acid, p-toluenesulphonic acid, naphthalenemonosulphonic acid, naphthalenedisulphonic acid and lauryl sulphuric acid. Alternatively, an acidic hydrophilic moiety can be present as a salt, such as a base addition salt, or can be converted into a salt with a base, e.g. into the associated base addition salt. In this regard, the sodium, potassium, magnesium, calcium and ammonium salts of the acidic hydrophilic moieties are particularly preferred. Also preferred are substituted ammonium salts, for example the dimethyl-, diethyl- or diisopropylammonium salts, monoethanol-, diethanol- or diisopropylammonium salts, cyclohexyl- and dicyclohexylammonium salts, and dibenzylethylenediammonium salts, and also, for example, salts with arginine or lysine.

Especially preferred in this regard are the sodium salts, the potassium salts, ammonium salts and the hydrochloric acid salts. Especially preferred in this regard are the sodium salts.

[6] Preferred are compositions as described herein and especially as described in one or more of the paragraphs numbered [1], [2], [3], [4] and/or the paragraphs relating thereto, wherein the at least one lipophilic compounds according to b) comprise one or more compounds selected from natural oils and synthetic oils, and mixtures thereof, and especially preferred are compositions as described herein and especially as described in one or more of the paragraphs numbered [1], [2], [3], [4] and/or the paragraphs relating thereto, wherein the at least one amphiphilic compounds according to b) comprise one or more compounds selected from amphiphilic lipids, preferably having phosphatidyl-polyol or sulfatidyl-polyol groups as the hydrophilic part, and derivatives, salts and/or alcoholates thereof and more preferably the salts thereof.

Lipophilic compounds and especially natural and/or synthetic oils are known to the skilled artisan. Preferred are natural and/or synthetic oils having a molar weight in the range of 200 g/mol to 2000 g/mol, preferably 300 g/mol to 1500 g/mol, more preferably 500 g/mol to 1000 g/mol, and especially 700 g/mol to 900 g/mol. Preferably, the natural and/or synthetic oils are liquid at about room temperature (about 25° C.) and especially are liquid at physiological conditions and/or physiological temperatures (about 37° C.). Thus, the melting point of said natural and/or synthetic oils, and preferably also of the mixtures thereof, is +20° C. or lower, preferably +10° C. or lower and even more preferably 0° C. or lower. However, typically a melting point below the above given values, but above −50° C., above −40° C., above −30° C., above −20° C. or even above −10° C. is sufficient.

Preferred lipophilic compounds that are natural and/or synthetic oils include, but are not limited to
i) fatty acid mono-, di-, tri- or polyesters of mono-, di-, tri- and polyoles,
ii) fatty acid diester of di-, tri- or polyoles,
iii) fatty acid triester of tri- or polyoles, and/or
iv) fatty alcohol mono-, di-, tri- or polyesters of mono-, di-, tri- and polyoles,
v) fatty alcohol diether of di-, tri- or polyoles,
vi) fatty alcohol triether of tri- or polyoles,
and preferably also mixtures thereof.

Especially preferred in this regard are fatty acid diester of dioles and/or fatty acid triester of trioles, wherein the fatty acids or fatty acid moieties preferably are as defined herein and/or wherein the dioles and trioles preferably are as defined herein.

Even more preferred are natural and/or synthetic oils that are fatty acid triester of trioles, wherein the fatty acid moiety is as described herein and/or the triol moiety is a glycerol moiety as described herein.

Preferably, said natural and/or synthetic oils and especially the fatty acid triester of trioles do not comprise a hydrophilic moiety as described herein.

Preferred examples of natural oils are selected from vegetable oils, and more preferably selected from sesame oil, rapeseed oil, soybean oil, sunflower oil and olive oil, and mixtures thereof.

Preferred examples of synthetic oils are selected from pharmaceutically acceptable oils, e.g. the pharmaceutically acceptable oils described in the Pharmacopeia, and more preferably selected from pharmaceutically acceptable triglycerides, preferably middle sized chain triglycerides, such as Miglyols®, preferably Miglyol® 810, Miglyol® 812, Miglyol® 818, Miglyol® 829 and Miglyol® 840, and especially Miglyol® 812, and mixtures thereof.

Said Miglyols are preferably selected from the group consisting of caprylic/capric triglycerides (Miglyol® 810, Miglyol® 812), caprylic/capric/linoleic triglycerides (Miglyol® 818), caprylic/capric/succinic triglycerides (Miglyol® 829) and propylene glycol dicaprylate/dicaprate (Miglyol® 840 and more preferably selected from caprylic/capric triglycerides (Miglyol® 810, Miglyol® 812), caprylic/capric/linoleic triglycerides (Miglyol® 818), caprylic/capric/succinic triglycerides (Miglyol® 829).

However, all triacylglycerides or fatty acid triester of trioles that are pharmaceutically acceptable and have a melting point in the herein given ranges are deemed suitable lipophilic compounds according the invention.

[7] Composition as described herein and especially as described in one or more of the paragraphs numbered [1] to [6] and preferably also as described in the paragraphs relating thereto, comprising a) 12 to 90%, preferably 20 to 80%, more preferably 20 to 60% and especially 20 to 40% of at least one oligopeptide, preferably at least one cyclic oligopeptide, more preferably at least one oligopeptide or cyclic oligopeptide as described herein, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml, b) 10 to 90%, preferably 20 to 80% more preferably 40 to 80% and especially 60 to 80% of at least one lipophilic compound selected from natural oils and synthetic oils and mixtures thereof, preferably pharmaceutically acceptable natural oils and/or synthetic oils and mixtures thereof, and especially fatty acid triester of trioles, wherein the fatty acid moiety is as described herein and the triol moiety is a glycerol moiety as described herein, and optionally c) 0 to 30%, preferably 0 to 20%, more preferably 0 to 10% and especially 0.01 to 5% of water, with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

Preferred in this regard are oligopeptides or cyclic oligopeptides which comprise the Arg-Gly-Asp-subsequence.

A Composition as described herein and especially as described in one or more of the paragraphs numbered [1] to [6] or [1] to [7] and preferably also as described in the paragraphs relating thereto, comprising a) 12 to 90%, preferably 20 to 80%, more preferably 20 to 60% and especially 20 to 40% of a cyclic oligopeptide selected from cyclo-(Arg-Gly-Asp-DPhe-NMeVal), cyclo-(Arg-Gly-Asp-DPhe-Val) and the pharmaceutically acceptable derivatives, solvates and/or salts thereof, and preferably selected from cyclo-(Arg-Gly-Asp-DPhe-NMeVal) and the pharmaceutically acceptable solvates and/or salts, preferably having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml, b) 10 to 90%, preferably 20 to 80% more preferably 40 to 80% and especially 60 to 80% of at least one lipophilic compound selected from natural oils and synthetic oils and mixtures thereof, preferably pharmaceutically acceptable natural oils and/or synthetic oils and mixtures thereof, and especially fatty acid triester of trioles, wherein the fatty acid moiety is as described herein and the triol moiety is a glycerol moiety as described herein, and optionally c) 0 to 30%, preferably 0 to 20%, more preferably 0 to 10% and especially 0.01 to 5% of water, with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

A Composition as described herein and especially as described in one or more of the paragraphs numbered [1] to [6] or [1] to [7] and preferably also as described in the paragraphs relating thereto, comprising a) 12 to 90%, preferably 20 to 80%, more preferably 20 to 60% and especially 20 to 40% of cyclo-(Arg-Gly-Asp-DPhe-NMeVal), more preferably of an anhydrate of the inner salt of cyclo-(Arg-Gly-Asp-DPhe-NMeVal) and especially of the crystalline form A1 of the inner salt of cyclo-(Arg-Gly-Asp-DPhe-NMeVal), b) 10 to 90%, preferably 20 to 80% more preferably 40 to 80% and especially 60 to 80% of at least one lipophilic compound selected from natural oils and synthetic oils and mixtures thereof, preferably pharmaceutically acceptable natural oils and/or synthetic oils and mixtures thereof, and especially fatty acid triester of trioles, wherein the fatty acid moiety is as described herein and the triol moiety is a glycerol moiety as described herein, and optionally c) 0 to 30%, preferably 0 to 20%, more preferably 0 to 10% and especially 0.01 to 5% of water, with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

A Composition as described herein and especially as described in one or more of the paragraphs numbered [1] to [6] or [1] to [7] and preferably also as described in the paragraphs relating thereto, comprising a) 12 to 90%, preferably 20 to 80%, more preferably 20 to 60% and especially 20 to 40% of cyclo-(Arg-Gly-Asp-DPhe-NMeVal), more preferably of an anhydrate of the inner salt of cyclo-(Arg-Gly-Asp-DPhe-NMeVal) and especially of the crystalline form A1 of the inner salt of cyclo-(Arg-Gly-Asp-DPhe-NMeVal), preferably having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml, b) 10 to 90%, preferably 20 to 80% more preferably 40 to 80% and especially 60 to 80% of at least one lipophilic compound selected from natural oils and synthetic oils and mixtures thereof, preferably pharmaceutically acceptable natural oils and/or synthetic oils and mixtures thereof, and especially fatty acid triester of trioles, wherein the fatty acid moiety is as described herein and the triol moiety is a glycerol moiety as described herein, and optionally c) 0 to 30%, preferably 0 to 20%, more preferably 0 to 10% and especially 0.01 to 5% of water, with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

A Composition as described herein and especially as described in one or more of the paragraphs numbered [1] to [6] or [1] to [7] and preferably also as described in the paragraphs relating thereto, comprising a) 12 to 90%, preferably 15 to 80%, preferably 15 to 60%, more preferably 15 to 50% and especially 20 to 40% of at least one oligopeptide, preferably at least one cyclic oligopeptide, more preferably at least one oligopeptide or cyclic oligopeptide as described herein, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml b) 0.01 to 60%, preferably 0.01 to 30%, more preferably 0.01 to 15%, even more preferably 0.05 to 10%, even more preferably 0.05 to 5% and especially 0.1 to 5%, of one or more amphiphilic compounds, c) 10 to 89.99%, preferably 20 to 89.99%, more preferably 30 to 84.99%, even more preferably 40 to 84.99%, even more preferably 50 to 84.95% and especially 60 to 79.95% of water, with the proviso that the sum of a), b) and c) makes up to 70 or more %, preferably 80 or more %, more preferably 90 or more %, even more preferably 95 or more % and especially 95 to 99.9% of the total composition.

Amphiphilic compounds and especially amphiphilic lipids are known to the skilled artisan. Amphiphilic compounds in the context of the instant invention preferably comprise one or more lipophilic parts and one or more hydrophilic parts. Preferred are amphiphilic compounds and especially amphiphilic lipids having a molar weight in the range of 200 g/mol to 2000 g/mol, preferably 300 g/mol to 1500 g/mol, more preferably 500 g/mol to 1000 g/mol, and especially 700 g/mol to 900 g/mol. Preferably, amphiphilic lipids in the context of the instant invention comprise at least one fatty acid moiety or at least one fatty alcohol moiety, preferably as a part of the lipophilic part, and/or a mono-, di-, tri- or polyole, preferably a diole or triole, preferably as a part of the hydrophilic part. Preferably, said mono-, di-, tri- or polyole, preferably a diole or triole, additionally comprises a hydrophilic moiety as described herein. More preferably, amphiphilic lipids in the context of the instant invention comprise at least one or two fatty acid moieties, preferably as a part of the lipophilic part, and/or a triole, preferably glycerol, preferably as a part of the hydrophilic part. Thus, preferred are amphiphilic lipids having phosphatidyl-polyol or sulfatidyl-polyol moieties as the hydrophilic part, and derivatives, salts and/or alcoholates thereof and more preferably the salts thereof. Even more preferred are amphiphilic lipids having phosphatidyl-glycerol or sulfatidyl-glycerol moieties as the hydrophilic part, and derivatives, salts and/or alcoholates thereof and more preferably the salts thereof.

Thus, even more preferred are amphiphilic lipids having
α) phosphatidyl-glycerol or sulfatidyl-glycerol moieties, preferably as the hydrophilic part, and
β) one or two, preferably two fatty acid moieties, preferably as the lipophilic part,
and derivatives, salts and/or alcoholates thereof and more preferably the salts thereof.

Preferably, the amphiphilic compounds according to b) can be selected from the group consisting of:
fatty acid monoesters of phosphatidylpolyoles, and derivatives, salts and alcoholates thereof;
fatty acid diesters of phosphatidylpolyoles, and derivatives, salts and alcoholates thereof;
and the salts and alcoholates thereof;
fatty acid triesters of phosphatidylpolyoles, and derivatives, salts and alcoholates thereof;
fatty acid polyesters of phosphatidylpolyoles, and derivatives, salts and alcoholates thereof;
fatty acid monoesters of sulfatidylpolyoles, and derivatives, salts and alcoholates thereof;
fatty acid diesters of sulfatidylpolyoles, and derivatives, salts and alcoholates thereof;
and the salts and alcoholates thereof;
fatty acid triesters of sulfatidylpolyoles, and derivatives, salts and alcoholates thereof;
fatty acid polyesters of sulfatidylpolyoles, and derivatives, salts and alcoholates thereof.

Alternatively preferably, the amphiphilic compounds according to b) can be selected from the group consisting of:
fatty alcohol monoethers of phosphatidylpolyoles, and derivatives, salts and alcoholates thereof;
fatty alcohol diethers of phosphatidylpolyoles, and derivatives, salts and alcoholates thereof;
and the salts and alcoholates thereof;
fatty alcohol triethers of phosphatidylpolyoles, and derivatives, salts and alcoholates thereof;
fatty alcohol polyethers of phosphatidylpolyoles, and derivatives, salts and alcoholates thereof;
fatty alcohol monoethers of sulfatidylpolyoles, and derivatives, salts and alcoholates thereof;
fatty alcohol diethers of sulfatidylpolyoles, and derivatives, salts and alcoholates thereof; and the salts and alcoholates thereof;
fatty alcohol triethers of sulfatidylpolyoles, and derivatives, salts and alcoholates thereof;
fatty alcohol polyethers of sulfatidylpolyoles, and derivatives, salts and alcoholates thereof.

Phosphatidylpolyoles according to the invention preferably comprise mono- and pyrophosphatidylpolyoles, including, but not limited to, monophosphatidylpolyoles, diphosphatidylpolyoles, triphosphatidylpolyoles, tetraphosphatidylpolyoles and higher polyphosphatidylpolyoles. Preferably, the phosphatidylpolyoles according to the invention are selected from monophosphatidylpolyoles, diphosphatidylpolyoles and triphosphatidylpolyoles, and/or the salts thereof.

Sulfatidylpolyoles according to the invention preferably comprise mono- and pyrosulfatidylpolyoles, including, but not limited to, monosulfatidylpolyoles, disulfatidylpolyoles, trisulfatidylpolyoles, tetrasulfatidylpolyoles and higher polypsulfatidylpolyoles. Preferably, the sulfatidylpolyoles according to the invention are selected from monosulfatidylpolyoles, disulfatidylpolyoles and trisulfatidylpolyoles, and/or the salts thereof.

Preferred for use according to the invention are phosphatidylpolyoles and/or sulfatidylpolyoles, wherein the polyol-substructure therein is preferably derived or selected from dioles, trioles, tetroles, pentoles and hexyles, including, but not limited to glycol, propanedioles, including, but not limited to propane-1,3-diol and propane-1,2-diol, diethylene glycol, glycerol, butanedioles, including, but not limited to butane-1,2-diol, butane-1,3-diol, butane-1,4-diol, butane-2,2-diol, butane-2,3-diol, butanetrioles, including, but not limited to 2-Hydroxymethyl-propane-1,3-diol, 2-Methyl-propane-1,2,3-triol, butane-1,2,3-triol and butane-1,2,4-triol, and 1,2,3,4-butane-1,2,3,4-tetrol, including, but not limited to erythritol and threitol.

More preferred for use according to the invention are phosphatidylpolyoles and/or sulfatidylpolyoles, wherein the polyol-substructure therein is preferably derived or selected from dioles, trioles and tetroles, and especially selected from trioles, preferably trioles as described above.

Generally, the fatty acid esters of polyoles are preferred over the fatty alcohol ethers of polyoles.

[10] Preferably, the phosphatidyl- or sulfatidyl-polyoles are selected from
a) polyphosphatidylglycerol, triphosphatidylglycerol, diphosphatidylglycerol and monophosphatidylglycerol, and/or
b) polysulfatidylglycerol, trisulfatidylglycerol, disulfatidylglycerol and monosulfatidylglycerol,
and/or the salts thereof.

More preferably, the phosphatidyl- or sulfatidyl-polyoles are selected from
a) triphosphatidylglycerol, diphosphatidylglycerol, monophosphatidylglycerol, especially monophosphatidylglycerol, and/or
b) polysulfatidylglycerol, trisulfatidylglycerol, disulfatidylglycerol, and monosulfatidylglycerol, especially monosulfatidylglycerol, and/or the salts thereof.

If not explicitly referred to otherwise, monophosphatidylglycerol and monosulfatidylglycerol are preferably also referred to as phosphatidylglycerol and sulfatidylglycerol, respectively.

Especially preferably, the fatty acids are in each case independently selected from the group consisting of myristic acid, oleic acid, palmitic acid, stearic acid, margaric acid, arachic or arachidic acid, behenic acid, erucic acid, linoleic acid and linolenic acid. Even more preferably, the fatty acids are in each case independently selected from the group consisting of myristic acid, oleic acid, palmitic acid and stearic acid.

Thus, in the fatty acid esters comprising more than one fatty acid, the fatty acids can be all the same or different. For example, in a fatty acid diester, both fatty acid moieties can be the same, e.g. both oleoyl or both palmitoyl, or different, e.g. one oleoyl and one palmitoyl. Alternatively, fatty acid diesters or triesters can comprise two or more different fatty acid moieties in a mixture, e.g. a statistical mixture.

Thus, preferred amphiphilic compounds according to the invention are preferably selected from one or more of the following formulae:

i)

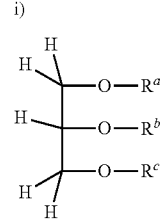

-continued ii)

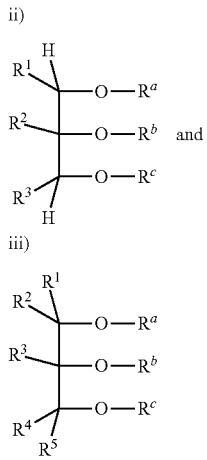

iii)

wherein
α) $R^1$, $R^2$, $R^3$, $R^4$ and $R^5$ are independently from each other are selected from H, methyl, ethyl and hydrophilic moieties, more preferably from H, methyl and ethyl; preferably with the proviso that only one or two of $R^1$, $R^2$, $R^3$, $R^4$ and $R^5$ are other than H, and more preferably that only one of $R^1$, $R^2$, $R^3$, $R^4$ and $R^5$ is other than H;
β) $R^a$, $R^b$ and $R^c$ are independently from each other are selected from H and $R^6$,
wherein each $R^6$ is independently selected from the group consisting of
i) fatty acid moieties and fatty alcohol moieties, preferably fatty acid moieties and fatty alcohol moieties as described herein and especially fatty acid moieties as described herein, and
ii) hydrophilic moieties, preferably hydrophilic moieties as described herein;
with the proviso that one or more of $R^a$, $R^b$ and $R^c$, preferably two or more of $R^a$, $R^b$ and $R^c$ and especially all of $R^a$, $R^b$ and $R^c$ are $R^6$,
and with the further proviso that only one or two, preferably only one of $R^6$ is a hydrophilic moiety;
and the salts and/or stereoisomers thereof, and preferably the salts thereof.

Thus, more preferred amphiphilic compounds according to the invention are preferably selected from the following formula:

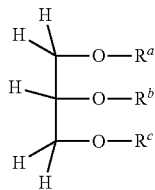

wherein
$R^a$, $R^b$ and $R^c$ are independently from each other are selected from H and $R^6$,
wherein each $R^6$ is independently selected from the group consisting of
i) fatty acid moieties and fatty alcohol moieties, preferably fatty acid moieties and fatty alcohol moieties as described herein and especially fatty acid moieties as described herein, and ii) hydrophilic moieties, preferably hydrophilic moieties as described herein;
with the proviso that one or more of $R^a$, $R^b$ and $R^c$, preferably two or more of $R^a$, $R^b$ and $R^c$ and especially all of $R^a$, $R^b$ and $R^c$ are $R^6$,
and with the further proviso that only one or two, preferably only one of $R^6$ is a hydrophilic moiety,
and the salts and/or stereoisomers thereof, and preferably the salts thereof.

Thus, even more preferred amphiphilic compounds according to the invention are preferably selected from the following formula:

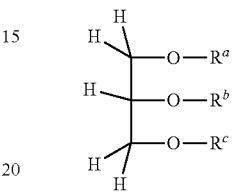

wherein
a) both $R^a$ and $R^b$ independently of each other are selected from acid moieties and fatty alcohol moieties, preferably fatty acid moieties and fatty alcohol moieties as described herein and especially fatty acid moieties as described herein, and $R^c$ is a hydrophilic moiety, preferably a hydrophilic moiety as described herein,
b) both $R^a$ and $R^c$ independently of each other are selected from acid moieties and fatty alcohol moieties, preferably fatty acid moieties and fatty alcohol moieties as described herein and especially fatty acid moieties as described herein, and $R^b$ is a hydrophilic moiety, preferably a hydrophilic moiety as described herein, or
c) both $R^b$ and $R^c$ independently of each other are selected from acid moieties and fatty alcohol moieties, preferably fatty acid moieties and fatty alcohol moieties as described herein and especially fatty acid moieties as described herein, and $R^a$ is a hydrophilic moiety, preferably a hydrophilic moiety as described herein
and the salts and/or stereoisomers thereof, and preferably the salts thereof.

With regard to $R^a$, $R^b$ and/or $R^c$ the hydrophilic moieties are preferably selected from the group consisting of:
i) $-PO_3H$, $-PO_3Na$, $-PO_3K$, $-PO_3^-$;
ii) $-(PO_2-O)_v-PO_3H$, $-(PO_2-O)_v-PO_3Na$, $-(PO_2-O)_v-PO_3K$, $-(PO_2-O)_v-PO_3^-$
iii) $-SO_3H$, $-SO_3Na$, $-SO_3K$, $-SO_3^-$;
iv) $-(SO_2-O)_w-SO_3H$, $-(SO_2-O)_w-SO_3Na$, $-(SO_2-O)$, $-SO_3K$, $-(SO_2-O)_w-SO_3^-$
v) $-(CH_2)_n-OH$, $-(CH_2)_n-ONa$, $-(CH_2)_n-OK$, $-(CH_2)_n-O^-$, $-(CH_2)_n-NH_2$, $-(CH_2)_n-NH_3^+$, $-(CH_2)_n-N(CH_3)_3^+$, $-(CH_2)_n-PO_3H$, $-(CH_2)_n-PO_3Na$, $-(CH_2)_n-PO_3K$, $-(CH_2)_n-PO_3^-$, $-(CH_2)_n-O-PO_3H$, $-(CH_2)_nO-PO_3Na$, $-(CH_2)_n-O-PO_3K$, $-(CH_2)_n-O-PO_3^-$
vi) $-(CH_2)_n-(PO_2-O)_x-PO_3H$, $-(CH_2)_n-(PO_2-O)_x-PO_3Na$, $-(CH_2)_n-(PO_2-O)_x-PO_3K$, $-(CH_2)_n-(PO_2-O)_x-PO_3^-$,
vii) $-(CH_2)_n-(SO_2-O)_y-SO_3H$, $-(CH_2)_n-(SO_2-O)_y-SO_3Na$, $-(CH_2)_n-(SO_2-O)_y-SO_3K$, $-(CH_2)_n-(SO_2-O)_y-SO_3^-$,
wherein
n is 1, 2, 3 or 4, preferably 1, 2 or 3 and especially 1 or 2,
v is 1, 2, 3 or 4, preferably 1, 2 or 3 and especially 1 or 2, w is 1, 2, 3 or 4, preferably 1, 2 or 3 and especially 1 or 2, x is 1, 2, 3 or 4, preferably 1, 2 or 3 and especially 1 or 2, and y is 1, 2, 3 or 4, preferably 1, 2 or 3 and especially 1 or 2;

and/or

γ) an ethanolamine moiety, a choline moiety, a phosphatidyl moiety, a phosphatidylcholine moiety, a sulfatidyl and a sulfatidylcholine moiety;

and a salt or other salt thereof.

With regard to $R^a$, $R^b$ and/or $R^c$ the hydrophilic moieties are even more preferably selected from the group consisting of:

i) —$PO_3H$, —$PO_3Na$, —$PO_3K$, —$PO_3^-$;

ii) —$(PO_2-O)_v$—$PO_3H$, —$(PO_2-O)_v$—$PO_3Na$, —$(PO_2-O)_v$—$PO_3K$, —$(PO_2-O)_v$—$PO_3^-$ iii) —$(CH_2)_n$—OH, —$(CH_2)_n$—ONa, —$(CH_2)_n$—OK, —$(CH_2)_n$—$O^-$, —$(CH_2)_n$—$NH_2$, —$(CH_2)_n$—$NH_3^+$, —$(CH_2)_n$—$N(CH_3)_3^+$, —$(CH_2)_n$—$PO_3H$, —$(CH_2)_n$—$PO_3Na$, —$(CH_2)_n$—$PO_3K$, —$(CH_2)_n$—$PO_3^-$, —$(CH_2)_n$—O—$PO_3H$, —$(CH_2)_n$—O—$PO_3Na$, —$(CH_2)_n$—O—$PO_3K$, —$(CH_2)_n$—O—$PO_3^-$, wherein n is 1, 2, 3 or 4, preferably 1, 2 or 3 and especially 1 or 2, and v is 1, 2, 3 or 4, preferably 1, 2 or 3 and especially 1 or 2, and/or iv) an ethanolamine moiety, a choline moiety, a phosphatidyl moiety, a phosphatidylcholine moiety, a sulfatidyl and a sulfatidylcholine moiety;

and a salt or other salt thereof.

With regard to $R^a$, $R^b$ and/or $R^c$, the fatty acid moieties are preferably selected from the group of:

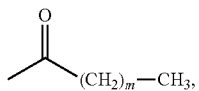

wherein m is 2 to 33, more preferably 4 to 28 and even more preferably 6 to 23;

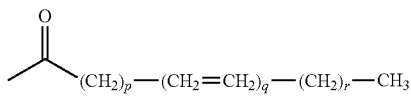

wherein p is 1 to 20, more preferably 3 to 18, even more preferably 4 to 15 and especially 6 to 13, q is 0 to 6, more preferably 1 to 5, more preferably 1, 2, 3, or 4 and especially 1, 2 or 3, r is 1 to 20, more preferably 3 to 15, even more preferably 6 to 12 and especially 6, 7 or 8, preferably with the proviso that the sum of p and r is 4 to 30, more preferably 5 to 25, even more preferably 8 to 22 and especially 10 to 20 and/or with the proviso that the sum of p, q and r is 5 to 30, more preferably 6 to 25, even more preferably 9 to 23 and especially 11 to 21;

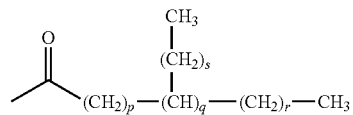

wherein p is 1 to 20, more preferably 3 to 18, even more preferably 4 to 15 and especially 6 to 13, q is 0 to 6, more preferably 1 to 5, more preferably 1, 2, 3, or 4 and especially 1, 2 or 3, r is 1 to 20, more preferably 3 to 15, even more preferably 6 to 12 and especially 6, 7 or 8, and s is 1 to 20, more preferably 1 to 15, even more preferably 1 to 10 and especially 1 to 5, preferably with the proviso that the sum of p, r and s is 4 to 30, more preferably 5 to 25, even more preferably 8 to 22 and especially 10 to 20 and/or with the proviso that the sum of p, q, r and s is 5 to 30, more preferably 6 to 25, even more preferably 9 to 23 and especially 11 to 21;

and/or

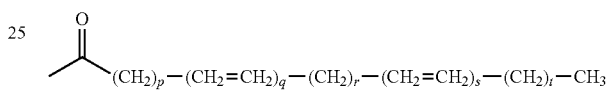

wherein p is 1 to 20, more preferably 3 to 15, even more preferably 6 to 12 and especially 6, 7 or 8, q is 0 to 6, more preferably 1 to 5, more preferably 1, 2, 3, or 4 and especially 1, 2 or 3, r is 1 to 20, more preferably 3 to 18, even more preferably 4 to 15 and especially 6 to 12, and s is 0 to 6, more preferably 1 to 5, more preferably 1, 2, 3, or 4 and especially 1, 2 or 3, t is 1 to 20, more preferably 1 to 15, even more preferably 1 to 10, even more preferably 3 to 8 and especially 4, 5, 6, 7 or 8, preferably with the proviso that the sum of p, r and t is 4 to 30, more preferably 6 to 25, even more preferably 8 to 22 and especially 10 to 20 and/or with the proviso that the sum of p, q, r, s and t is 5 to 30, more preferably 7 to 25, even more preferably 9 to 23 and especially 11 to 21.

With regard to $R^a$, $R^b$ and/or $R^c$, the fatty acid moieties are even more preferably selected from the group of:

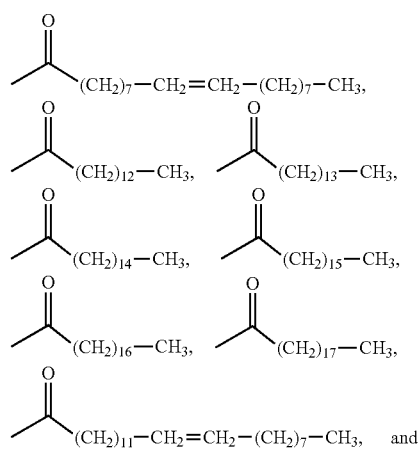

-continued

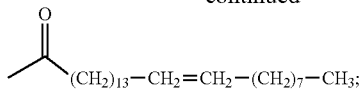

and, in case of the unsaturated fatty acid moieties, all stereoisomers thereof.

With regard to $R^a$, $R^b$ and/or Rc, the fatty acid moieties are even more preferably selected from the group of:
the fatty acid moieties are selected from the group consisting of myristoyl, oleoyl, palmitoyl (corresponds to palmitic acid), stearoyl, margaroyl, arachidoyl, behenoyl, erucoyl, linoleoyl and linolenoyl.

With regard to $R^a$, $R^b$ and/or Rc, the fatty acid moieties are selected from the group consisting of myristoyl, oleoyl, palmitoyl and stearoyl.

Especially preferred amphiphilic compounds according to the invention are preferably selected from dioleoylphosphatidylglycerol (DOPG), dimyristoylphosphatidylcholine (DMPC), distearoylphosphatidylglycerol (DSPG), dioleoylglycerophosphocholine (DOPC), dipalmitoylglycerophosphoglycerol (DPPG), distearoylglycerophosphoethanolamine (DSPE), egg phosphatidylcholine (EPC) and soy phosphatidylcholine (SPC), more preferably dioleoylphosphatidylglycerol (DOPG), dimyristoylphosphatidylglycerol (DMPG), distearoylphosphatidylglycerol (DSPG), dioleoylglycerophosphocholine (DOPC), dipalmitoylglycerophosphoglycerol (DPPG), even more preferably dioleoylphosphatidylglycerol (DOPG), dimyristoylphosphatidylglycerol (DMPG), distearoylphosphatidylglycerol (DSPG), dipalmitoylglycerophosphoglycerol (DPPG), even more preferably dioleoylphosphatidylglycerol (DOPG) and dimyristoylphosphatidylglycerol (DMPG), and especially dimyristoylphosphatidylglycerol (DMPG);
and/or the salts thereof, preferably the salts described herein, and especially the alkaline and/or ammonium salts thereof. Also preferred are mixtures of said amphiphilic compounds and/or the salts thereof, preferably including mixtures of different salts of the same compound and mixtures of different salts of different compounds.

Alternatively preferred amphiphilic compounds according to the invention are amphiphilic compounds which comprise two different fatty acids, fatty acids as described herein. More preferably, these amphiphilic compounds are selected from
myristoylstearoylphosphatidylcholine (MSPC),
myristoylpalmitoylphosphatidylcholine (MPPC),
myristoyloleoylphosphatidylcholine (MOPC),
palmitoylstearoylphosphatidylcholine (PSPC),
palmitoyloleoylphosphatidylcholine (POPC),
stearoyloleoylphosphatidylcholine (SOPC),
myristoylstearoylphosphatidylglycerol (MSPG),
myristoyloleoylphosphatidylglycerol (MOPG),
myristoylpalmitoylphosphatidylglycerol (MPPG),
palmitoylstearoylphosphatidylglycerol (PSPG),
palmitoyloleoylphosphatidylglycerol (POPG),
stearoyloleoylphosphatidylglycerol (SOPG),
myristoylstearoylglycerophosphocholine (MSPC),
myristoyloleoylglycerophosphocholine (MOPC),
myristoylpalmitoylglycerophosphocholine (MPPC),
paimitoylstearoyiglycerophosphocholine (PSPC),
palmitoyloleoylglycerophosphocholine (POPC),
stearoyloleoylglycerophosphocholine (SOPC),
myristoylstearoylglycerophosphoethanolamine (MSPE),
myristoyloleoylglycerophosphoethanolamine (MOPE),
myristoylpalmitoylglycerophosphoethanolamine (MPPE),
palmitoylstearoylglycerophosphoethanolamine (PSPE),
palmitoyloleoylglycerophosphoethanolamine (POPE), and
stearoyloleoylglycerophosphoethanolamine (SOPE);
and/or the salts thereof, preferably the salts described herein, and especially the alkaline and/or ammonium salts thereof. Also preferred are mixtures of said amphiphilic compounds and/or the salts thereof, preferably including mixtures of different salts of the same compound and mixtures of different salts of different compounds.

Especially preferred amphiphilic compounds and/or the salts thereof according to the invention can preferably also defined by their Chemical Abstracts Numbers (CAS-Numbers):
DOPG (sodium salt): 67254-28-8
DMPC: 18194-24-6
DMPG (sodium salt): 67232-80-8
DSPG (sodium salt): 108347-80-4
DOPC: 4235-95-4
DPPG (sodium salt): 42367232-81-9
DSPE: 1069-79-0
SPC: 97281-47-5.

Especially preferred amphiphilic compounds and/or the salts thereof according to the invention can preferably also defined by their Chemical Abstracts Numbers (CAS-Numbers):
DOPG (sodium salt): 67254-28-8, and/or
DMPG (sodium salt): 67232-80-8

From a toxicological point of view, negatively charged or uncharged amphiphilic compounds may be preferred over positively charged amphiphilic compounds (Recent advances in tumor vasculature targeting using liposomal drug delivery systems Amr S Abu Lila, Tatsuhiro Ishida, Hiroshi Kiwada, Expert Opinion on Drug Delivery, DOI 10.1517/17425240903289928.

Examples of negatively charged amphiphilic compounds include, but are not limited to:
dioleoylphosphatidylglycerol (DOPG)
dimyristoylphosphatidylglycerol (DMPG)
distearoylphosphatidylglycerol (DSPG)
dipalmitoylglycerophosphoglycerol (DPPG).

Examples of neutral amphiphilic compounds include, but are not limited to:
distearoylglycerophosphoethanolamine (DSPE).

Examples of positively charged amphiphilic compounds include, but are not limited to:
dimyristoylphosphatidylcholine (DMPC)
dioleoylglycerophosphocholine (DOPC)
soy phosphatidylcholine (SPC).

A preferred amphiphilic compound according to the invention and/or for use according to the invention is dioleoylphosphatidylglycerol (DOPG) and/or the sodium salt thereof, preferably as defined by the CAS-Number 67254-28-8.

An especially preferred amphiphilic compound according to the invention and/or for use according to the invention is dimyristoylphosphatidylglycerol (DMPG) and/or the sodium salt thereof, preferably as defined by the CAS Number 67232-80-8.

[8] Composition as described herein and especially as described in one or more of the paragraphs numbered [1] to [6] or [1] to [7] and preferably also as described in the paragraphs relating thereto, comprising a) 12 to 90%, preferably 12 to 60%, more preferably 15 to 40% and especially 20 to 40% of at least one oligopeptide, preferably at least one cyclic oligopeptide, more preferably at least one oligopeptide or cyclic oligopeptide as described herein, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml, b) 0.01 to 60%, preferably 0.01 to 40%, more preferably 0.01 to 20%, even more preferably 0.01 to 10%, even more preferably 0.05 to 10%, even more preferably 0.05 to 5% and especially 0.1 to 10% or 0.1 to 5%, of one or more amphiphilic compounds, preferably one or more amphiphilic compounds as described herein, and c) 10 to 94.99%, preferably 30 to 89.99%, more preferably 40 to 84.99%, even more preferably 60 to 79.99% and especially 60 to 79.9 of water, with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

A Composition as described herein and especially as described in one or more of the paragraphs numbered [1] to [6] or [1] to [8] and preferably also as described in the paragraphs relating thereto, comprising a) 12 to 90%, preferably 15 to 80%, preferably 15 to 60%, more preferably 15 to 50% and especially 20 to 40% of at least one oligopeptide, preferably at least one cyclic oligopeptide, more preferably at least one oligopeptide or cyclic oligopeptide as described herein, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml b) 0.01 to 60%, preferably 0.01 to 30%, more preferably 0.01 to 15%, even more preferably 0.05 to 10%, even more preferably 0.05 to 5% and especially 0.1 to 5%, of one or more amphiphilic compounds, c) 10 to 89.99%, preferably 20 to 89.99%, more preferably 30 to 84.99%, even more preferably 40 to 84.99%, even more preferably 50 to 84.95% and especially 60 to 79.95% of water, with the proviso that the sum of a), b) and c) makes up to 70 or more %, preferably 80 or more %, more preferably 90 or more %, even more preferably 95 or more % and especially 95 to 99.9% of the total composition.

Preferred in this regard are oligopeptides or cyclic oligopeptides which comprise the Arg-Gly-Asp-subsequence.

A Composition as described herein and especially as described in one or more of the paragraphs numbered [1] to [6] or [1] to [8] and preferably also as described in the paragraphs relating thereto, comprising a) 12 to 90%, preferably 12 to 60%, more preferably 15 to 40% and especially 20 to 40% of a cyclic oligopeptide selected from cyclo-(Arg-Gly-Asp-DPhe-NMeVal), cyclo-(Arg-Gly-Asp-DPhe-Val) and the pharmaceutically acceptable derivatives, solvates and/or salts thereof, and preferably selected from cyclo-(Arg-Gly-Asp-DPhe-NMeVal) and the pharmaceutically acceptable solvates and/or salts, preferably having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml, b) 0.01 to 60%, preferably 0.01 to 40%, more preferably 0.01 to 20%, even more preferably 0.01 to 10%, even more preferably 0.05 to 10%, even more preferably 0.05 to 5% and especially 0.1 to 10% or 0.1 to 5%, of one or more amphiphilic compounds, preferably one or more amphiphilic compounds as described herein, and c) 10 to 94.99%, preferably 30 to 89.99%, more preferably 40 to 84.99%, even more preferably 60 to 79.99% and especially 60 to 79.9 of water, with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

A Composition as described herein and especially as described in one or more of the paragraphs numbered [1] to [6] or [1] to [8] and preferably also as described in the paragraphs relating thereto, comprising a) 12 to 90%, preferably 12 to 60%, more preferably 15 to 40% and especially 20 to 40% of cyclo-(Arg-Gly-Asp-DPhe-NMeVal), more preferably of an anhydrate of the inner salt of cyclo-(Arg-Gly-Asp-DPhe-NMeVal) and especially of the crystalline form A1 of the inner salt of cyclo-(Arg-Gly-Asp-DPhe-NMeVal), preferably having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml, b) 0.01 to 60%, preferably 0.01 to 40%, more preferably 0.01 to 20%, even more preferably 0.01 to 10%, even more preferably 0.05 to 10%, even more preferably 0.05 to 5% and especially 0.1 to 10% or 0.1 to 5%, of one or more amphiphilic compounds, preferably one or more amphiphilic compounds as described herein, and c) 10 to 94.99%, preferably 30 to 89.99%, more preferably 40 to 84.99%, even more preferably 60 to 79.99% and especially 60 to 79.9 of water, with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

[9] Alternatively preferred is a composition comprising
a) 12 to 90%, preferably 12 to 60%, more preferably 15 to 40% and especially 20 to 40% of at least one oligopeptide, preferably at least one cyclic oligopeptide, more preferably at least one oligopeptide or cyclic oligopeptide as described herein, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml, b) 0.01 to 60%, preferably 0.01 to 40%, more preferably 0.01 to 20%, even more preferably 0.01 to 10%, even more preferably 0.05 to 10%, even more preferably 0.05 to 5% and especially 0.1 to 10% or 0.1 to 5%, one or more amphiphilic compounds, selected from
b1) fatty acid mono-, di- or polyesters of phosphatidyl- or sulfatidyl-polyoles, and derivatives, salts and/or alcoholates thereof, and
b2) fatty alcohol mono-, di- or polyethers of phosphatidyl- or sulfatidyl-polyoles, and derivatives, salts and/or alcoholates thereof,
c) 10 to 94.99%, preferably 30 to 89.99%, more preferably 40 to 84.99%, even more preferably 60 to 79.99% and especially 60 to 79.9 of water,
preferably with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

Preferably, said oligopeptide or cyclic oligopeptide as described herein is selected from cyclo-(Arg-Gly-Asp-DPhe-NMeVal), an anhydrate of the inner salt of cyclo-(Arg-Gly-Asp-DPhe-NMeVal) and the crystalline form A1 of the inner salt of cyclo-(Arg-Gly-Asp-DPhe-NMeVal), said oligopeptide or cyclic oligopeptide preferably having a solubility in water at 20° C. between 1 mg/ml and 25 mg/ml, preferably between 2 mg/ml and 20 mg/ml, more preferably between 2 mg/ml and 15 mg/ml, even more preferably between 3 mg/ml and 10 mg/ml, and especially between 5 mg/ml and 9 mg/ml.

Even more preferably, said oligopeptide or cyclic oligopeptide as described herein is selected from cyclo-(Arg-Gly-Asp-DPhe-NMeVal), an anhydrate of the inner salt of cyclo-(Arg-Gly-Asp-DPhe-NMeVal) and the crystalline form A1 of the inner salt of cyclo-(Arg-Gly-Asp-DPhe-NMeVal), said oligopeptide or cyclic oligopeptide preferably having a solubility in water at 20° C. between 5 mg/ml and 20 mg/ml, more preferably between 5 mg/ml and 15 mg/ml, even more preferably between 6 mg/ml and 10 mg/ml, and especially between 5 mg/ml and 9 mg/ml.

[10] Composition as described herein and especially as described in the paragraphs numbered [6] and/or [9] and preferably also as described in the paragraphs relating thereto, wherein the phosphatidyl- or sulfatidyl-polyoles are selected from
a) polyphosphatidylglycerol, triphosphatidylglycerol, diphosphatidylglycerol, monophosphatidylglycerol, and/or
b) polysulfatidylglycerol, trisulfatidylglycerol, disulfatidylglycerol, and monosulfatidylglycerol,
and/or the salts thereof.

[11] Composition as described herein and especially as described in one or more of the paragraphs numbered [1] to [10] and preferably also as described in the paragraphs relating thereto, wherein
a) the fatty acids are independently selected from the group consisting of oleic acid, myristic acid, palmitic acid, stearic acid, margaric acid, arachic acid, behenic acid, erucic acid, linolic acid and linolenic acid, and
b) the fatty alcohols are independently selected from the group consisting of oleic alcohol, myristic alcohol, palmitic alcohol, stearic alcohol, margaric alcohol, arachic alcohol, behenic alcohol, erucic alcohol, linolic alcohol and linolenic alcohol,
c) the fatty acid moietys are independently selected from the acyl residues of the fatty acids according to a), and/or
d) the fatty alcohol moietys are independently selected from the alkyl residues of the fatty alkohols according to b).

[12] Composition as described herein and especially as described in one or more of the paragraphs numbered [1] to [11] and preferably also as described in the paragraphs relating thereto, wherein amphiphilic compounds and/or the fatty acid di- or polyesters of polyphosphatidyl-polyoles are selected from the group consisting of dioleoylphosphatidylglycerol, dimyristoylphosphatidylcholine, distearoylphosphatidylglycerol, dioleoylglycerophosphocholine, dipalmitoylglycerophosphoglycerol, distearoylglycerophosphoethanolamine, egg phosphatidylcholine and soy phosphatidylcholine,
and the pharmaceutically acceptable derivatives, salts and/or alcoholates thereof.

A Composition as described herein and especially as described in one or more of the paragraphs numbered [1] to [11] and preferably also as described in the paragraphs relating thereto, wherein amphiphilic compounds and/or the fatty acid di- or polyesters of polyphosphatidyl-polyoles are selected from the group consisting of dioleoylphosphatidylglycerol, dimyristoylphosphatidylglycerol, dimyristoylphosphatidylcholine, distearoylphosphatidylglycerol, dioleoylglycerophosphocholine, dipalmitoylglycerophosphoglycerol, distearoylglycerophosphoethanolamine, egg phosphatidylcholine and soy phosphatidylcholine, more preferably dioleoylphosphatidylglycerol and/or dimyristoylphosphatidylglycerol, and especially dimyristoylphosphatidylglycerol, and the pharmaceutically acceptable derivatives, salts and/or alcoholates thereof.

If the composition according to the invention comprises compounds and/or excipients other than a), b) and c), said compounds and/or excipients are preferably selected from further active ingredients, preferably further pharmaceutically active ingredients, and further excipients and/or auxiliaries, preferably pharmaceutically acceptable excipients and/or auxiliaries. Excipients and/or auxiliaries and especially pharmaceutically acceptable excipients and/or auxiliaries are known in the art, e.g. from Europäisches Arzneibuch, 6. Ausgabe, CD-ROM Official German Edition, US Pharmacopeia 29, European Pharmacopeia, and/or Deutsches Arzneimittelbuch, preferably in the respective current version or newer.

Preferably, the compositions according to the invention do not comprise active ingredients other than the oligopeptides as defined herein.

More preferably, the compositions according to the invention do not comprise further pharmaceutically active ingredients other than the oligopeptides as defined herein.

Preferred excipients include, but are not limited to tonicity agents and/or preservatives. Preservatives in this regard preferably are antimicrobial preservatives.

Examples of preservatives, preferably pharmaceutically acceptable preservatives are known in the art, e.g. from Swarbrick, Pharmaceutical Technology.

Examples of pharmaceutically acceptable preservatives are given in the table below:

TABLE 1

Commonly used preservatives and their preferred route of administration:

| Preservative | Preferred route of administration |
| --- | --- |
| Benzalkonium chloride | IM, inhalation, nasal, ophthalmic, otic, topical |
| Benzethonium chloride | IM, IV, ophthalmic, otic |
| Benzoic acid | IM, IV, irrigation, oral, rectal, topical, vaginal |
| Benzyl alcohol | Injections, oral, topical, vaginal |
| Bronopol | Topical |

TABLE 1-continued

Commonly used preservatives and their preferred route of administration:

| Preservative | Preferred route of administration |
| --- | --- |
| Butylparaben | Injections, oral, rectal, topical |
| Cetrimide | Topical, ophthalmic |
| Chlorhexidine | Topical, ophthalmic |
| Chlorobutanol | IM, IV, SC, inhalation, nasal, otic, ophthalmic, topical |
| Chlorocresol | Topical |
| Cresol | IM, intradermal, SC, topical |
| Ethylparaben | Oral, topical |
| Imidurea | Topical |
| Methylparaben | IM, IV, SC, ophthalmic, oral, otic, rectal, topical, vaginal |
| Phenol | Injections |
| Phenoxyethanol | Topical |
| Phenylethyl alcohol | Nasal, ophthalmic, otic |
| Phenylmercuric acetate/borate | Ophtalmic |
| Phenylmercuric nitrate | IM, ophthalmic, topical |
| Propylparaben | IM, IV, SC, inhalation, ophthalmic, oral, otic, rectal, topical, vaginal |
| Sodium benzoate | Dental, IM, IV, oral, rectal, topical |
| Sodium propionate | Oral |
| Sorbic acid | Oral, topical |
| Thimerosal | IM, IV, SC, ophthalmic, otic, topical |

Preferred preservatives, especially preferred preservatives for s.c. formulations, are selected from the group consisting of benzyl alcohol, phenol, cresol and cresol derivatives, e.g. chlorocresol, preferably selected from the group consisting of phenol, cresol and chlorocresol. Especially preferred is phenol.

Examples of tonicity agents, preferably pharmaceutically acceptable tonicity agents are known in the art, e.g. from Swarbrick, Pharmaceutical Technology.

Preferred tonicity agents are selected from the group consisting of alkali salts, preferably sodium chloride and/or potassium chloride, ammonium chloride, glycerol, sugars, preferably glucose and/or fructose, and urea.

However, suitable alternatives to the above given tonicity agents are known to the skilled artisan.

Especially preferred as tonicity agent is sodium chloride (NaCl).

Thus, in the context of the present invention, the water according to c) of the composition can optionally be substituted, partially or totally, by isotonic saline or physiologic saline, e.g. saline for infusion. In the context of the instant invention, the isotonic saline, physiologic saline or saline for infusion is preferably a solution of about 0.9 weight % of NaCl in water. More preferably, the composition is made using water (c)) and the tonicity is adjusted by addition of NaCl as a preferred excipient after the compounds according to a) and/or b) are added, if applicable.

Thus, tonicity agents and/or preservatives are preferred excipients according to d) and especially according to d2).

[13] Composition as described herein and especially as described in one or more of the paragraphs numbered [1] to [12] and preferably also as described in the paragraphs relating thereto, comprising
d) 0 to 50% of one or more compounds other than a), b) and c), selected from
d1) pharmaceutically active ingredients,
  d2) pharmaceutically acceptable excipients;
  preferably with the proviso that the sum of a), b), c) and d) makes up to 80% or more, preferably 90% or more, more preferably 95% or more, and especially 95 to 99.9% or 95 to 100% of the total composition.

[14] Composition as described herein and especially as described in one or more of the paragraphs numbered [1] to [13] and preferably also as described in the paragraphs relating thereto, comprising
d) 0 to 10% of one or more compounds other than a), b) and c), selected from pharmaceutically acceptable excipients (d2);
preferably with the proviso that the sum of a), b), c) and d2) and preferably a), b), c) and d) makes up to 80% or more, preferably 90% or more, more preferably 95% or more, and especially 95 to 99.9% or 95 to 100% of the total composition.

Thus, especially preferred is a composition as described herein, comprising
a) one or more oligopeptides as described herein in the amounts as described herein,
b) one or more amphiphilic compounds as described herein in the amounts as described herein,
c) water in the amounts as described herein, and
d) one or more compounds selected from
d1) 0 to 20%, preferably 0 to 10% and especially no or essentially no pharmaceutically active ingredients other than the oligopeptides according to a), and
d2) 0 to 20%, preferably 0.01 to 10%, more preferably 0.05 to 10%, even more preferably 0.1 to 10% and especially 0.1 to 5% of one or more, preferably two or more and especially 1, 2 or 3 pharmaceutically acceptable excipients,
preferably with the proviso that the sum of a), b), c) and d) makes up to 80 or more %, preferably 90 or more %, more preferably 95% or more, even more preferably 95 to 99.9%, even more preferably 98 to 99.9% and especially 99 to 100%, of the total composition.

Especially preferably, the above described compositions consists or essentially consists of a), b), c) and d).

Thus, also preferred is a composition, comprising, preferably essentially consisting of and especially consisting of:
a) 12 to 60% of at least one oligopeptide as described herein, more preferably of at least cyclic oligopeptide as described herein and especially at least one cyclic oligo peptidepeptide, selected from the group consisting of cyclo-(Arg-Gly-Asp-DPhe-NMeVal), cyclo-(Arg-Gly-Asp-DPhe-Val), and the pharmaceutically acceptable derivatives, solvates and/or salts thereof,
b) 0.01 to 30%, preferably 0.01 to 10% and especially 0.05 to 5% of one or more amphiphilic compounds, preferably amphiphilic compounds as described herein, more preferably selected from
b1) fatty acid di- or polyesters of phosphatidyl- or sulfatidyl-polyoles and
b2) fatty acid di- or polyethers of phosphatidyl- or sulfatidyl-polyoles, and derivatives, salts and/or alcoholates thereof,
c) 20 to 89.99% of water, and optionally
d) 0 to 50%, preferably 0 to 20%, more preferably 0.001 to 20%, even more preferably 0.01 to 10% and especially 0.1 to 5%, of one or more compounds other than a), b) and c), selected from
d1) pharmaceutically active ingredients,
d2) pharmaceutically acceptable excipients, more preferably selected from
d2) pharmaceutically acceptable excipients.

Preferably, the composition according the invention contains at least a part or a portion of the one or more oligopeptides as solid particles, preferably suspended or suspendable solid particles.

More preferably, the composition according the invention contains at least a part or a portion of the one or more oligopeptides as solid micro particles, preferably suspended or suspendable solid micro particles.

Even more preferably, the composition according the invention contains at least a part or a portion of the one or more oligopeptides as solid particles having a particle size less than 250 µm, preferably less than 150 µm, more preferably less than 100 µm, even more preferably less than 50 µm.

Even more preferably, the composition according the invention contains at least a part or a portion of the one or more oligopeptides as suspended or suspendable solid micro particles having a particle size less than 250 µm, preferably less than 150 µm, more preferably less than 100 µm, even more preferably less than 50 µm.

Typically, the suspended or suspendable solid micro particles of the one or more oligopeptides contained in said compositions have a particle size of more than 0.001 µm, preferably more than 0.01 µm and especially more than 0.1 µm. However, even smaller particle sizes are preferably not critical for the compositions according to the invention. Preferably, the compositions as described herein preferably contain only minor amounts of suspended or suspendable solid micro particles of the one or more oligopeptides having a particle size of 0.01 µm or less, preferably 0.1 µm or less, and especially 1 µm or less. Minor amounts in this regard are preferably 10% or less, 5% or less, 1% or less, 0.1% or less, or 0.01% or less, based on the total amount of the one or more oligopeptides as described herein contained in said composition. Percentages in this regard are preferably % w/w.

Preferably, the particle size distributions of the suspended or suspendable solid micro particles of the one or more oligopeptides contained in said compositions are characterised by d(10)=1-10 µm, d(50)=10-25 µm and/or d(90)=25-60 µm, more preferably by d(10)=1-10 µm, d(50)=10-25 µm and d(90)=25-60 µm.

Alternatively preferably, the particle size distributions of the suspended or suspendable solid micro particles of the one or more oligopeptides contained in said compositions are characterized by d(10)=1-5 µm, d(50)=5-10 µm and/or d(90)=20-30 µm, more preferably by d(10)=1-5 µm, d(50)=5-10 µm and d(90)=20-30 µm.

Thus, especially preferred are compositions as described herein, wherein the effective average particle size of the one or more oligopeptides contained in said compositions is in the range of 5 µm to 250 µm, preferably 5 µm to 150 µm, more preferably 10 µm to 250 µm, even more preferably 10 µm to 150 µm, even more preferably 10 µm to 100 µm and even more preferably 15 µm to 100 µm, and especially 20 µm to 100 µm.

Thus, especially preferred are compositions as described herein, preferably characterized or additionally characterized by a particle size of the one or more oligopeptides contained in said compositions having a d(90) value in the range of 5 µm to 150 µm, preferably 5 µm to 100 µm, more preferably 10 µm to 100 µm, even more preferably 15 µm to 100 µm, even more preferably 25 µm to 100 µm and even more preferably 20 µm to 50 µm, for example a d(90) of about 15 µm, a d(90) of about 20 µm, a d(90) of about 25 µm, a d(90) of about 30 µm, a d(90) of about 35 µm, a d(90) of about 40 µm or a d(90) of about 50 µm.

[15] Thus, preferred are compositions as described herein or as described in one or more of the paragraphs numbered [1] to [14] and/or the paragraphs relating thereto, wherein 10% or more, preferably 20 percent or more, more preferably 40%, even more preferably 60% or more, even more preferably 80% or more and especially 90% or more of the contained oligopeptide according to a) is present in the composition in a suspended or suspendable solid form at a temperature of 20° C. or at a temperature of 25° C., preferably at a temperature of 20° C. Preferably, the oligopeptide according to a) that is present in the composition in a suspended or suspendable solid form has a particle size as given above and preferably a particle size in the range between 0.1 to 150 µm and especially a particle size in the range between 1 and 100 µm.

Thus, preferred are compositions as described herein, wherein 20 to 99.9%, preferably 40 to 99.9%, more preferably 60 to 99.9%, even more preferably 80 to 99.9% and especially 85 to 99% of the contained oligopeptide according to a) is present in the composition in a suspended or suspendable solid form at a temperature of 20° C. or at a temperature of 25° C., preferably at a temperature of 20° C. Preferably, the oligopeptide according to a) that is present in the composition in a suspended or suspendable solid form has a particle size as given above and preferably a particle size in the range between 0.1 to 150 µm and especially a particle size in the range between 1 and 100 µm.

Thus, preferred are compositions as described herein, wherein 70 to 99%, preferably 80 to 98%, more preferably 85 to 97%, even more preferably 90 to 98% and especially 95 to 98% of the contained oligopeptide according to a) is present in the composition in a suspended or suspendable solid form at a temperature of 20° C. or at a temperature of 25° C., preferably at a temperature of 20° C. Preferably, the oligopeptide according to a) that is present in the composition in a suspended or suspendable solid form has a particle size as given above and preferably a particle size in the range between 0.1 to 150 µm and especially a particle size in the range between 1 and 100 µm.

Thus, a preferred aspect of the instant invention relates to compositions as described herein in the form of suspensions.

Suspensions in the context of the instant invention are preferably dispersed systems, comprising a disperse or dispersed phase, preferably as the discontinuous phase, which preferably consists of solid particles, and a liquid continuous phase, which acts as the dispersing agent. Typically, such suspensions comprise 0.5 to 90%, more preferably 0.5 to 60% and even more preferably 1 to 40% solid particles. Typically, the particle size of the solid particles in the said suspension is in the range between 0.1 and 200 µm, more preferably 0.1 and 150 µm and especially 1 to 100 µm. In the suspensions according to the invention, the continuous phase which acts as the dispersing agent is preferably liquid at about 20° C. or about 25° C., preferably at about 20° C. Even more preferably said continuous phase which acts as the dispersing agent is preferably liquid at a temperature of 10° C. and more preferably at a temperature of 0° C. Thus, the suspensions according to the invention are preferably liquid in a temperature range between 20° C. and 40° C., more preferably 10° C. and 40° C. and especially in the range of 0° C. and 40° C.

Preferably, the oligopeptide in suspended or suspendable solid form is present
a) partly or totally in the form of an amorphous solid, preferably partly or totally in the form of amorphous solid particles,
b) partly or totally in the form of a crystalline solid, preferably partly or totally in the form of crystalline particles,
c) partly or totally in the form of a mixture of amorphous and crystalline forms in one solid, preferably partly or totally in the form of a mixture of amorphous and crystalline solid in one particle,
and mixtures thereof.

Preferably, the (solid) particles of the oligopeptide is present:
a) partly or totally in the form amorphous solid particles,
b) party or totally in the form of crystalline particles,
c) partly or totally in the form of a mixture of amorphous and crystalline solid in one party,
and mixtures thereof.

Even more preferably, the oligopeptide in suspended or suspendable solid form and/or the (solid) particles of the oligopeptide, preferably the oligopeptide as described herein and especially cyclo-(Arg-Gly-Asp-DPhe-NMeVal), that are preferably present in the compositions according to the invention, are present
a) partly or totally in the form of a mixture of amorphous and crystalline solid in one particle,
b) party or totally in the form of crystalline particles,
and mixtures thereof,
and especially preferably are present
partly or totally in the form of crystalline particles.

Especially preferably, the cyclo-(Arg-Gly-Asp-DPhe-NMeVal) that is preferably present in the compositions according to the invention in suspended or suspendable solid form and/or the (solid) particles, preferably suspended or suspendable (solid) particles, is present partly or totally in the form of crystalline particles.

Thus, especially preferably, the cyclo-(Arg-Gly-Asp-DPhe-NMeVal) that is preferably present in the compositions according to the invention in suspended or suspendable solid form and/or (solid) particles, preferably in the form of suspended or suspendable (solid) particles, is present partly or totally in the form the solid materials as described herein, even more preferably the solid materials as described herein comprising or containing the solid form A1.

Thus, especially preferred are compositions that contain cyclo-(Arg-Gly-Asp-DPhe-NMeVal) in the form of suspended or suspendable (solid) particles comprising or essentially consisting of the solid materials described herein and even more preferably the solid materials as described herein comprising or essentially consisting of the solid form A1.

Thus, especially preferred are compositions that contain cyclo-(Arg-Gly-Asp-DPhe-NMeVal) in the form of suspended or suspendable (solid) particles comprising or essentially consisting of a solid material having a melting/decomposition temperature of higher than 250° C. and/or a solubility in water, preferably determined as described herein, in the range between 6 and 12 mg/ml.

Thus, especially preferred are compositions that contain the inner salt of cyclo-(Arg-Gly-Asp-DPhe-NMeVal) in the form of suspended or suspendable (solid) particles comprising or essentially consisting of a solid material having a melting/decomposition temperature of higher than 250° C. and/or a solubility in water, preferably determined as described herein, in the range between 6 and 12 mg/ml.

Thus, especially preferred are compositions that contain the inner salt of cyclo-(Arg-Gly-Asp-DPhe-NMeVal) in the form of suspended or suspendable (solid) particles comprising or essentially consisting of a solid material described herein as A1, form A1, solid form A1, crystalline form A1 and/or polymorphic form A1.

The compositions that comprise such suspended or suspendable (solid) particles preferably show an advantageous sustained release profile.

Physical principles and methods for producing or obtaining such solid materials or preferably such (solid) particles of the oligopeptides or cyclic oligopeptides are known in the art. As described herein, such particles preferably are formed spontaneously by contacting said oligopeptide or cyclic oligopeptide with the other components of the compositions according to the invention, preferably including the one or more lipophilic compounds or alternatively including the one or more amphiphilic compounds, the latter preferably in the presence of water. This spontaneous formation can preferably be improved and/or accelerated by exposure of the system to moderate mechanical energy, such as stirring or shaking. However, a plurality of alternative methods are known in the art. These alternative methods preferably include one or more methods, selected from the group consisting of milling, such as jet milling, pearl milling, ball milling, hammer milling, fluid energy milling, grinding, such as dry grinding or wet grinding, precipitation, such as micro-precipitation, emulsion precipitation, solvent/anti-solvent precipitation, phase inversion precipitation, pH shift precipitation, temperature shift precipitation, solvent evaporation precipitation, solvent evaporation precipitation, and the like. Suitable such processes are described in the art, e.g., in WO 2004/103348.

In the compositions according to the invention, the weight ratio between the oligopeptides according to a) as defined herein and the lipophilic compounds b) as defined herein is preferably in the range between 1:8 and 2:3, more preferably in the range between 1:8 and 1:2, even more preferably in the range between 1:7 and 1:2 and especially in the range between 1:6 and 1:3 Especially preferably, said weight ratio is about 1:5, about 1:4 or about 1:3.

In the compositions according to the invention, the weight ratio between the oligopeptides according to a) as defined herein and the amphiphilic compounds b) as defined herein is preferably in the range between 3000:1 and 3:1, more preferably in the range between 1500:1 and 5:1, even more preferably in the range between 1000:1 and 10:1, even more preferably in the range between 500:1 and 15:1 and especially in the range between 400:1 and 15:1 Especially preferably, said weight ratio is about 300:1, about 200:1, about 100:1, about 75:1, about 50:1, about 30:1, about 20:1 or about 15:1.

In the compositions according to the invention that comprise the amphiphilic compounds b) as defined herein and especially in the compositions according to the invention that comprise the amphiphilic compounds b) as defined herein in the amounts given in the paragraph above and also comprise water according to c), the weight ratio between the oligopeptides according to a) and the water according to c) contained in said composition is preferably in the range between 1:8 and 2:3, more preferably in the range between 1:7 and 1:2 and especially in the range between 1:6 and 1:3. Especially preferably, said weight ratio is about 1:1, about 1:7, about 1:6, about 1:5, about 1:4, about 1:3 or about 3:6.

The composition according to the invention, preferably the pharmaceutical composition according to the invention, comprises at least one oligopeptide, preferably as the main ingredient or one of the main ingredients of said composition. In said compositions and especially said pharmaceutical compositions, said at least one oligopeptide is the active ingredient or one of the active ingredients of said compositions. Preferably, said compositions comprise at least 12%, more preferably at least 20%, of the one or more oligopeptides, based on the total composition. Generally, the content of the one or more oligopeptides in said composition is 80% or less, more preferably 50% or less and especially preferably 40% or less, based on the total composition.

If not explicitly stated otherwise, the percentages (%) given with respect to the instant invention and especially the percentages (%) given with respect to the compositions according to the invention are preferably selected from
i) percent by weight (% by weight or % w/w),
ii) percent by volume (% by volume or % v/v), and
iii) percent weight by volume (% weight by volume or % w/v, e.g. % mg/mL or % g/mL).

For ease of use, percent by weight and percent weight by volume are preferred and percent weight by volume is especially preferred, especially with respect to the compositions according to the invention.

Oligopeptides according to the invention preferably comprise 3 to 20 amino acids, more preferably 4 to 15 and especially 3 to 10 amino acids. The amino acids are preferably selected from naturally occurring amino acids, synthetic amino acids and/or synthetically modified naturally occurring amino acids. Naturally occurring amino acids, synthetic amino acids and/or synthetically modified naturally occurring amino acids are known to the skilled artisan. Preferably, said naturally occurring amino acids, synthetic amino acids and/or synthetically modified naturally occurring amino acids are as defined herein.

Preferably, the oligopeptide according to the invention is a cyclic oligopeptide, more preferably a homodetic cyclic oligopeptide.

More preferably, the oligopeptide according to the invention is a cyclic oligopeptide, more preferably a cyclic homodetic oligopeptide, that comprises an Arg-Gly-Asp-motif, Arg-Gly-Asp-sequence or Arg-Gly-Asp-subsequence. The Arg-Gly-Asp-motif, Arg-Gly-Asp-sequence or Arg-Gly-Asp-subsequence is preferably also referred to as RGD-motif, RGD-sequence or RGD-subsequence. In the context of the present intervention, these terms are preferably regarded as equivalent or as synonyms.

More preferably, the oligopeptide, even more preferably the cyclic oligopeptide and especially preferably the homodetic cyclic oligopeptide consists of 2 to 6 naturally occurring amino acids and 0 to 4 amino acids, selected from synthetic amino acids or synthetically modified naturally occurring amino acids. More preferably, said oligopeptide consists of 3 to 6 naturally occurring amino acids and 1 to 4 amino acids, selected from synthetic amino acids or synthetically modified naturally occurring amino acids. Even more preferably, said oligopeptide consists of 3 to 5 naturally occurring amino acids and 2 to 3 amino acids, selected from synthetic amino acids or synthetically modified naturally occurring amino acids. Especially preferably, said oligopeptide consists of 2 to 4 naturally occurring amino acids, 1 or 2 synthetic amino acids and 1 or 2 synthetically modified naturally occurring amino acids.

Said oligopeptide, more preferably said cyclic oligopeptide and especially said homodetic cyclic oligopeptide is preferably also referred to as "one or more compounds a)", "compound a)" and or "a)", if not defined otherwise.

The meaning of the term "peptide" or "peptides" is known in the art. According to the invention, peptides are preferably defined as amides derived from two or more (the same or different) amino carboxylic acid molecules (i.e. amino acids) by formation of a covalent bond from the carbonyl carbon of one to the nitrogen atom of another with formal loss of water. The term is usually applied to structures formed from α-amino acids, but it preferably also includes those derived from any amino carboxylic acid or amino acid.

Cyclic peptides and more specifically cyclic oligopeptides and methods for obtaining them are known in the art. According to the invention, cyclic peptides are preferably peptides in which a bridge or a link is formed between two amino acids that are part of the peptide or constitute the peptide. The bridge can be formed between amino acids having a reactive group (other than the amino and the carboxyl group that are essential for the respective amino acid), preferably, such as a sulphide group. Generally, peptides comprising two or more, preferably two amino acids having such a reactive group can be cyclised. For example, a peptide comprising two amino acids that have a sulphide group can be cyclised under conditions wherein a disulphite bridge between the sulphide groups of the two amino acids containing a sulphide group is formed. Examples of amino acids having a sulphide group and thus being capable of forming a bridge, i.e. a disulphite bridge include, but are not limited to penicillamine and cysteine. Peptides in which the bonds forming the ring are not solely peptide linkages (or eupeptide linkages according to the IUPAC) are preferably referred to as heterodetic cyclic peptides. In this case, the bonds between the reactive groups (other than the amino and the carboxyl group that are essential for the respective amino acid) forming the ring are preferably referred to as "bridge". Alternatively, cyclic peptides in which the bonds forming the ring are solely peptide linkages (or eupeptide linkages according to the IUPAC) are preferably referred to as homodetic cyclic peptides. According to the invention, both heterodetic cyclic peptides and homodetic cyclic peptides can be used. Generally, peptides comprised of two or more, preferably three or more, even more preferably four or more amino acids can be cyclised. In principle, the number of amino acids in a cyclic peptide is not limited. According to the invention, the cyclic peptides and especially the cyclic oligopeptides generally do not comprise more than 20, more preferably not more than 15, even more preferably not more than 10 and especially not more than 6 or 8 amino acids.

The terms "naturally occurring amino acids", "non-naturally occurring amino acids" and "synthetically modified naturally occurring amino acids" are well understood in the art. However, a non-exhausting list of non-naturally amino acids, "synthetically modified naturally occurring amino acids" as well as naturally occurring amino acids can preferably be found in "The Peptides", Volume 5 (1983), Academic Press, Chapter VI, by D. C. Roberts and F. Vellacio.

Generally, the term "non-naturally occurring amino acids" is preferably intended to include any small molecule having at least one carboxyl group and at least one primary or secondary amino group capable of forming a peptide bond. The term "peptide" is preferably intended to include any molecule having at least one peptide bond. The term "peptide" preferably also embraces structures as defined above having one or more linkers, spacers, terminal groups or side chain groups which are not amino acids.

According to the invention, the naturally occurring amino acids are preferably selected from the group consisting of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val, and more preferably exclusively selected from the L forms thereof.

According to the invention, the non-naturally occurring amino acids or synthetically modified naturally occurring amino acids are preferably selected from the group consisting of:
i) the D forms of naturally occurring amino acids, i.e. the D forms of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val, ii) the N-alkyl derivatives of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val, preferably including both the D and L forms thereof, and iii) Lys(Ac), Lys(AcNH$_2$), Lys(AcSH), Tic, Asp(OR), Cha, NaI, 4-Hal-Phe, homo-Phe, Phg, Pya, Abu, Acha, Acpa, Aha, Ahds, Aib, Aos, N-Ac-Arg, Dab, Dap, Deg, hPro, Nhdg, homoPhe, 4-Hal-Phe, Phg, Sar, Tia, Tic and Tle, preferably including both the D and L forms thereof;

wherein

R is alkyl having 1-18 carbon atoms, preferably alkyl having 1-6 carbon atoms and especially alkyl having 1-4 carbon atoms, Hal is F, Cl, Br, I Ac is alkanoyl having 1-10 and more preferably 1-6 carbon atoms, aroyl having 7-11 carbon atoms or aralkanoyl having 8-12 carbon atoms.

With respect to the N-alkyl derivatives of said amino acids, alkyl is preferably selected from methyl, ethyl, isopropyl, n-butyl, sec-butyl and tert-butyl. However, alkyl is furthermore also preferably selected from n-pentyl, isopentyl, neopentyl, n-hexyl, n-heptyl, n-octyl, n-nonyl, n-decyl and n-hexadecyl.

According to the invention, the non-naturally occurring amino acids are preferably selected from the group consisting of the D forms of naturally occurring amino acids, i.e. the D forms of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val.

According to the invention, the synthetically modified naturally occurring amino acids are preferably selected from the group consisting of the N-alkyl derivatives of the L forms of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val, wherein the N-alkyl residues preferably consist of 1-18 carbon atoms, more preferably 1-6 carbon atoms and even more preferably 1-4 carbon atoms.

According to the invention, the synthetically modified naturally occurring amino acids are preferably selected from the group consisting of the N-methyl derivatives and/or N-ethyl derivatives of the L forms of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val. Especially preferably, the synthetically modified naturally occurring amino acids are selected from the group consisting of the L forms of N-Methyl-Gly, N-Methyl-Ala, N-Methyl-β-Ala, N-Methyl-Asn, N-Methyl-Asp, N-Methyl-Arg, N-Methyl-Cys, N-Methyl-Gln, N-Methyl-Glu, N-Methyl-His, N-Methyl-Ile, N-Methyl-Leu, N-Methyl-Lys, N-Methyl-Met, N-Methyl-Nle, N-Methyl-Orn, N-Methyl-Phe, N-Methyl-Pro, N-Methyl-Ser, N-Methyl-Thr, N-Methyl-Trp, N-Methyl-Tyr and N-Methyl-Val, which are preferably also referred to as NMeGly, NMeAla, NMeβ-Ala, NMeAsn, NMeAsp, NMeArg, NMeCys, NMeGln, NMeGlu, NMeHis, NMeIle, NMeLeu, NMeLys, NMeMet, NMeNle, NMeOrn, NMePhe, NMePro, NMeSer, NMeThr, NMeTrp, NMeTyr and NMeVal.

It is well within the skill in the art to prepare cyclic peptides, as well cyclic peptides being comprised of naturally occurring amino acids exclusively as cyclic peptides comprising non-natural amino acids. For example, conventional protection and activation chemistry can be used. Typically, the amino functionality of a first amino acid is protected with a removable amino protecting group and the carboxyl functionality of a second amino acid is protected with a removable carboxyl protecting group. Suitable amine protecting groups include, without limitation, benzoyloxycarbonyl (Cbz), tert-butoxycarbonyl (t-Boc), and 9-flourenylmethloxycarbonyl (FMOC). The carboxyl group may be protected protecting by forming an acid or base labile ester such as a methyl, ethyl, benzyl, or trimethylsilyl esters. After protection, the first and second amino acids are reacted in a suitable solvent such as water or DMF in the presence of an in situ activating agent such as N,N'-dicyclohexylcarbodiimide (DCCI), diisopropylcarbodiimide (DIPCDI), or 1-ethyl-3-(3'-dimethylaminopropyl)carbodiimide (EDCI) to effect peptide bond formation. Reactive moieties on the side chains of either amino acid are protected with protecting groups such as teff-butyl or benzyl for OH and SH; methyl, ethyl, tert-butyl or benzyl for carboxyl groups, 2,2,5,7,8-pentamethylchroman-6-sulphonyl for the —NHC(NH$_2$)=NH functionality of Arg, and trityl for the imidazole group of His. Following the coupling reaction, selective deprotection of the amino group of the first amino acid is accomplished by acid hydrolysis under conditions that do not remove the carboxyl protecting group of the second amino acid. The procedure is repeated with a additional amino protected amino acids. Solid phase synthesis, such as the well-known Merrifield method, is especially useful for synthesizing the peptides of the invention. Generally, the synthesis of the cyclic peptides is done by first synthesising a linear peptide of the desired sequence, for example as described above, followed by a cyclization step. Suitable methods and conditions for cyclizing a linear peptide into a cyclic peptide are known in the art.

The incorporation of non-natural amino acids into peptides is described in Hohsaka T, Sisido M "Incorporation of non-natural amino acids into proteins" Curr. Opin. Chem. Biol. 6: 809-815 (2002); Noren C J et al. "A general method for site-specific incorporation of unnatural amino acids into proteins" Science 244: 182-188 (1989); and Hodgson, David R. W., Sanderson, John M., "The Synthesis of Peptides and Proteins Containing Non-Natural Amino Acids", Chem. Soc. Rev., 2004, 33, 422-430, the disclosures of which are hereby incorporated by reference.

According to the invention, said cyclic peptide or cyclic oligopeptide is preferably a homodetic cyclic peptide or homodetic cyclic oligopeptide. The meaning of the terms "homodetic", "homodetic cyclic peptide" and homodetic cyclic oligopeptide is known in the art. According to the invention, a homodetic cyclic peptide or homodetic cyclic oligopeptide preferably is a cyclic peptide in which the ring (or backbone of the cyclic peptide) consists solely of aminoacid residues in peptide linkage (or in eupeptide linkage according to the nomenclature of the IUPAC).

Especially preferably, said cyclic oligopeptide comprises the Arg-Gly-Asp sequence (or RGD sequence in the one letter code for amino acids). According to the invention, the Arg-Gly-Asp sequence is preferably comprised exclusively of the respective L-amino acids, i.e comprised of L-Arg, L-Gly and L-Asp.

Preferred cyclic peptides according to the invention are the cyclic peptides according to formula I, $$\text{Cyclo-(Arg-Gly-Asp-}\Omega\text{)} \qquad \text{I,}$$

wherein

Ω is an amino acid subsequence comprised of 1 to 4 and especially 2 or 3 amino acids selected from the group consisting of the L- and D-forms of: hPro, Ahds, Aos, Nhdg, Acha, Aib, Acpa, Tle, Gly, Ala, β-Ala, Asn, Asp, Asp(OR), Arg, Cha, Cys, Gln, Glu, His, Ile, Leu, Lys, Lys(Ac), Lys(AcNH$_2$), Lys(AcSH), Met, NaI, Nle, Orn, Phe, 4-Hal-Phe, homo-Phe, Phg, Pro, Pya, Ser, Thr, Tia, Tic, Trp, Tyr or Val, and the N-alkyl derivatives thereof, wherein R is alkyl having 1-18 carbon atoms, preferably alkyl having 1-6 carbon atoms and especially alkyl having 1-4 carbon atoms, Hal is F, Cl, Br, I, Ac is alkanoyl having 1-10 and more preferably 1-6 carbon atoms, aroyl having 7-11 carbon atoms or aralkanoyl having 8-12 carbon atoms, and especially is alkanoyl having 1-6 and more preferably 1-3 carbon atoms, with the proviso that Ω comprises at least one non-naturally occurring amino acid or synthetically modified naturally occurring amino acid, preferably at least one non-naturally occurring amino acid and at least one synthetically modified naturally occurring amino acid, and especially preferably one non-naturally occurring amino acid and one synthetically modified naturally occurring amino acid, and the derivatives, salts and solvates thereof, more preferably the pharmaceutically acceptable derivatives, salts and/or solvates thereof.

In the cyclic peptide according to formula I,

Ω is especially preferably comprised of one non-naturally occurring amino acid and one synthetically modified naturally occurring amino acid, preferably as defined above/below.

Where the abovementioned amino acids can occur in a number of enantiomeric forms, then all of these forms and also their mixtures (e.g. the DL forms) are included above and below, for example as constituents of the compounds of the formula I. The amino acids, for example as a constituent of compounds to the formula I, can also be provided with appropriate protecting groups which are known per se.

Above and below, the radicals X and Y have the meanings given in the case of the formulae Ia and Ib unless expressly stated otherwise. The letters used for said radicals X and Y preferably have nothing to do with the corresponding single-letter codes for amino acids.

A preferred group of cyclic peptides according the invention are the cyclic peptides of formula subformula Ia, cyclo-(nArg-nGly-nAsp-nX-nY)   Ia, wherein X and Y in each case independently of one another are: Gly, Ala, β-Ala, Asn, Asp, Asp(OR), Arg, Cha, Cys, Gln, Glu, His, Ile, Leu, Lys, Lys(Ac), Lys(AcNH$_2$), Lys(AcSH), Met, NaI, Nle, Orn, Phe, 4-Hal-Phe, homo-Phe, Phg, Pro, Pya, Ser, Thr, Tia, Tic, Trp, Tyr or Val, which amino acid residues can also be derivatized, R is alkyl having 1-18 carbon atoms, preferably alkyl having 1-6 carbon atoms and especially alkyl having 1-4 carbon atoms, Hal is F, Cl, Br, I, Ac is alkanoyl having 1-10 carbon atoms and especially 2-4 carbon atoms, aroyl having 7-11 carbon atoms or aralkanoyl having 8-12 carbon atoms, n denotes no substituent or is a substituent on the α-amino function of the respective amino acid residue, selected from the group consisting of alkyl radicals R, benzyl and aralkyl radicals having 7-18 carbon atoms, and especially denotes no substituent or is a substituent on the α-amino function of the respective amino acid residue, selected from the group consisting of alkyl radicals having 1-4 carbon atoms, with the proviso that at least one amino acid residue has a substituent n and with the further proviso that, where residues of optically active amino acids and amino acid derivatives are involved, both the D and the L forms are included, and derivatives, salts and solvates thereof, more preferably the pharmaceutically acceptable derivatives, salts and/or solvates thereof.

A more preferred group of cyclic peptides according to formula I are the cyclic peptides of formula Ib, cyclo-(nArg-nGly-nAsp-nX-nY)   Ib, wherein nX is selected from D-Gly, D-Ala, D-β-Ala, D-Asn, D-Asp, D-Asp(OR), D-Arg, D-Cha, D-Cys, D-Gln, D-Glu, D-His, D-Ile, D-Leu, D-Lys, D-Lys(Ac), D-Lys(AcNH$_2$), D-Lys (AcSH), D-Met, D-NaI, D-Nle, D-Orn, D-Phe, D-4-Hal-Phe, D-homo-Phe, D-Phg, D-Pro, D-Pya, D-Ser, D-Thr, D-Tia, D-Tic, D-Trp, D-Tyr or D-Val, more preferably D-Gly, D-Ala, D-Asn, D-Asp, D-Arg, D-Cys, D-Gln, D-Glu, D-Lys, D-Lys(Ac), D-NaI, D-Nle, D-Phe, D-4-Hal-Phe, D-homo-Phe, D-Ser, D-Thr, D-Trp, D-Tyr or D-Val, nY is selected from NMeGly, NMeAla, NMeβ-Ala, NMeAsn, NMeAsp, NMeArg, NMeCha, NMeCys, NMeGln, NMeGlu, NMeHis, NMeIle, NMeLeu, NMeLys, NMe NMeMet, NMeNaI, NMeNle, NMeOrn, NMePhe, NMePhg, NMePro, NMePya, NMeSer, NMeThr, NMeTia, NMeTic, NMeTrp, NMeTyr or NMeVal, more preferably NMeGly, NMeAla, NMeAsn, NMeAsp, NMeArg, NMe-Cys, NMeGln, NMeGlu, NMeLys, NMeNaI, NMeNle, NMePhe, NMeSer, NMeThr, NMeTrp, NMeTyr or NMeVal, R is alkyl having 1-18 carbon atoms, preferably alkyl having 1-6 carbon atoms and especially alkyl having 1-4 carbon atoms, Hal is F, Cl, Br, I, Ac is alkanoyl having 1-10 and preferably 2-4 carbon atoms, aroyl having 7-11 carbon atoms or aralkanoyl having 8-12 carbon atoms, preferably alkanoyl having 1-6 and preferably 2-4 carbon atoms, and the derivatives, salts and solvates thereof, more preferably the pharmaceutically acceptable derivatives, salts and/or solvates thereof.

Preferably, the cyclic peptide of the formula I, Ia and Ib is not cyclo-(Arg-Gly-Asp-NMe-Phe-Gly).

According to the invention, the cyclic peptides that comprise the Arg-Gly-Asp sequence preferably comprise Arg, Gly and Asp in the natural L configuration.

A further preferred group of compounds can be expressed by the formulae Ia, in which only one of the amino acid residues X or Y is present in the D form, whereas all the others are in the L configuration.

Furthermore, particular preference is given to all physiologically acceptable salts of the compounds which come under one or more of formulae I, Ia and Ib.

A further preferred group of compounds can be expressed by the subformula Ib, in which only the amino acid residue X is present in the D form, whereas all the others are in the L configuration.

Especially preferred with respect to the invention is the cyclic peptide according to formula Ic, cyclo-(Arg-Gly-Asp-DPhe-Val)   Ic, and/or the derivatives, salts and solvates thereof, preferably the pharmaceutically acceptable derivatives, salts and/or solvates thereof, and especially the pharmaceutically acceptable salts and/or solvates thereof.

Even more preferred with respect to the invention is the cyclic peptide according to formula Id, cyclo-(Arg-Gly-Asp-DPhe-NMeVal)   Id, and/or the derivatives, salts and solvates thereof, preferably the pharmaceutically acceptable derivatives, salts and/or solvates thereof, and especially the pharmaceutically acceptable salts and/or solvates thereof.

The cyclic peptides according the invention and especially the cyclic peptides according to I, Ia, Ib, Ic and/or Id, and also the starting materials for their preparation are preferably prepared by known methods, preferably as described in the literature (for example in the standard works such as Houben-Weyl, Methoden der organischen Chemie [Methods of Organic Chemistry], Georg-Thieme-Verlag, Stuttgart), in particular under reaction conditions which are known and appropriate for the said reactions. In this context, use can also be made of known variants which are not mentioned in any greater detail here.

If desired, the starting substances can also be formed in situ, so that they are not isolated from the reaction mixture but are immediately reacted further to give the cyclic peptides according to the invention and especially the cyclic peptides according to formula I, Ia, Ib, Ic and/or Id. The cyclic peptides according to the invention and especially the cyclic peptides according to formula I, Ia, Ib, Ic and/or Id can be obtained by liberating them from their functional derivatives by solvolysis, in particular hydrolysis, or by hydrogenolysis.

Preferred starting materials for the solvolysis or hydrogenolysis are those which contain appropriate protected amino and/or hydroxyl groups instead of one or more free amino and/or hydroxyl groups, preferably those which carry an amino protecting group instead of a hydrogen atom which is attached to a nitrogen atom, examples being those which correspond to the formula I but which, instead of an $NH_2$ group, contain an NHR' group (where R' is an amino protecting group, e.g. BOC or CBZ).

Other preferred starting materials are those which carry a hydroxyl protecting group instead of the hydrogen atom of a hydroxyl group, for example those which correspond to the formula I but contain, instead of a hydroxyphenyl group, a R"O-phenyl group (where R" is a hydroxyl protecting group).

It is also possible for two or more—identical or different—protected amino and/or hydroxyl groups to be present in the molecule of the starting material. If the protecting groups present are different from one another, then in many cases they can be eliminated selectively.

The expression "amino protecting group" is generally known and relates to groups which are suitable for protecting (for blocking) an amino group from chemical reactions but which are readily removable after the desired chemical reaction has been carried out at other positions of the molecule. Typical of such groups are, in particular, unsubstituted or substituted acyl, aryl, aralkoxymethyl or arakyl groups. Since the amino protecting groups are removed after the desired reaction (or reaction sequence), their nature and size is otherwise not critical; however, preference is given to those having 1-20, in particular 1-8, carbon atoms. The term "acyl group" is to be interpreted in its widest sense in connection with the present process. It includes acyl groups derived from aliphatic, araliphatic, aromatic or heterocyclic carboxylic acids or sulfonic acids and, in particular, alkoxycarbonyl, aryloxycarbonyl and, above all, aralkoxycarbonyl groups. Examples of such acyl groups are alkanoyl such as acetyl, propionyl, butyryl; aralkanoyl such as phenylacetyl; aroyl such as benzoyl or toluoyl; aryloxyalkanoyl such as POA; alkoxycarbonyl such as methoxycarbonyl, ethoxycarbonyl, 2,2,2-trichlorethoxy-carbonyl, BOC, 2-iodoethoxy-carbonyl; aralkyloxycarbonyl such as CBZ ("carbobenzoxy"), 4-methoxybenzyloxy-carbonyl, FMOC; and arylsulfonyl such as Mtr. Preferred amino protecting groups are BOC and Mtr, and also CBZ, Fmoc, benzyl and acetyl.

The expression "hydroxyl protecting group" is also generally known and relates to groups which are suitable for protecting a hydroxyl group from chemical reactions but which are readily removable after the desired chemical reaction has been carried out at other positions of the molecule. Typical of such groups are the abovementioned unsubstituted or substituted aryl, aralkyl or acyl groups, and also alkyl groups. The nature and size of the hydroxyl protecting groups is not critical, since they are removed again after the desired chemical reaction or reaction sequence; preference is given to groups having 1-20, especially 1-10, carbon atoms. Examples of hydroxyl protecting groups include benzyl, p-nitrobenzoyl, p-toluenesulf-onyl, tert-butyl and acetyl, with particular preference being given to benzyl and tert-butyl. The COOH groups in aspartic acid and glutamic acid are preferably protected in the form of their tert-butyl esters (e.g. Asp(OBut)).

The functional derivatives of the cyclic peptides according to the invention and especially of the cyclic peptides according to formula I, Ia, Ib, Ic and/or Id which are to be used as starting materials can be prepared by customary methods of amino acid and peptide synthesis, as are described, for example, in the patent applications and standard works mentioned, including for example by the solid-phase method according to Merrifield (B. F. Gysin and R. B. Merrifield, J. Am. Chem. Soc. 94, 3102 ff. (1972)).

The liberation of the compounds of the cyclic peptides according to the invention and especially of the cyclic peptides according to formula I, Ia, Ib, Ic and/or Id from their functional derivatives is preferably carried out—depending on the protecting group used—with, for example, strong acids, expediently with TFA or perchloric acid, but also with other strong inorganic acids, such as hydrochloric acid or sulfuric acid, strong organic carboxylic acids, such as trichloroacetic acid, or sulfonic acids such as benzene- or p-toluenesulfonic acid. The presence of an additional inert solvent is possible but not always necessary. Suitable inert solvents are preferably organic, for example carboxylic, acids such as acetic acid, ether such as tetrahydrofuran or dioxane, amides such as DMF, halogenated hydrocarbons such as dichloromethane, and also alcohols such as methanol, ethanol or isopropanol, and water. Also suitable are mixtures of the abovementioned solvents. TFA is preferably used in excess without the addition of a further solvent, perchloric acid in the form of a mixture of acetic acid and 70% perchloric acid in a ratio of 9:1. The reaction temperatures for the cleavage are expediently between about 0 and about 50°; it is preferably carried out between 15 and 30° (room temperature).

The groups BOC, OBut and Mtr can be removed, for example, preferably using TFA in dichloromethane or with about 3 to 5 N HCl in dioxane at 15-30°, while the FMOC group can be eliminated with an approximately 5 to 50% solution of dimethylamine, diethylamine or piperidine in DMF at 15-30°.

Protecting groups which can be removed by hydrogenolysis (e.g. CBZ or benzyl) can be eliminated, for example, by treatment with hydrogen in the presence of a catalyst (e.g. a noble metal catalyst such as palladium, preferably on a support such as charcoal). Suitable solvents in this context are those mentioned above, especially, for example, alcohols such as methanol or ethanol or amides such as DMF. The hydrogenolysis is carried out, as a rule, at temperatures between about 0 and 100° and at pressures of between about 1 and 200 bar, preferably at 20-30° and 1-10 bar. Hydrogenolysis of the CBZ group, for example, takes place readily on 5 to 10% Pd—C in methanol or using ammonium formiate (instead of $H_2$) on Pd—C in methanol/DMF at 20-30°.

The cyclic peptides according to the invention and especially the cyclic peptides according to formula I, Ia, Ib, Ic and/or Id can also be obtained by cyclization of linear peptides having the same amino acid sequence as the desired cyclic peptide, preferably under the conditions of a peptide synthesis. In this case, the reaction is expediently carried out in accordance with customary methods of peptide synthesis as described, for example, in Houben-Weyl, l.c., Volume 15/II, Pages 1 to 806 (1974).

The reaction is preferably carried out in the presence of a dehydrating agent, for example a carbodiimide such as DCCI or EDCI, and additionally propanephosphonic anhydride (cf. Angew. Chem. 92, 129 (1980)), diphenyl phosphoryl azide or 2-ethoxy-N-ethoxycarbonyl-1,2-dihydroquinoline, in an inert solvent, for example a halogenated hydrocarbon such as dichloromethane, an ether such as tetrahydrofuran or dioxane, an amide such as DMF or dimethylacetamide, a nitrile such as acetonitrile, or in mixtures of these solvents, at temperatures between about −10 and 40°, preferably between 0 and 30°. In order to promote intramolecular cyclization over intermolecular peptide bonding, it is expedient to work in dilute solutions (dilution principle).

Instead of linear peptides having the same amino acid sequence as the desired cyclic peptide, suitable reactive derivatives of said linear peptides can also be employed in the reaction, for example those in which reactive groups are intermediately blocked by protecting groups. Said linear peptides can be used, for example, in the form of their activated esters which are expediently formed in situ, for example by addition of HOBt or N-hydroxysuccinimide.

The starting materials for the manufacture of the cyclic peptides are either novel, commercially available or they are readily available by methods known in the art. In any case, they can preferably be prepared by known methods, for example the abovementioned methods of peptide synthesis and of elimination of protecting groups.

The derivatization of a cyclopeptide which corresponds per se to a compound of the formula I, Ia, Ib, Ic and/or Id is preferably likewise effected by methods known per se, as are known for the alkylation of amines, the esterification of carboxylic acids or nucleophilic substitution at aliphatic carbon atoms and are described in any textbook of organic chemistry, for example J. March, Adv. Org. Chem., John Wiley & Sons N.Y. (1985).

A base of a cyclic peptide according to the invention and especially the days of a cyclic peptide according to formula I, Ia, Ib, Ic and/or Id can be converted into the associated acid addition salt using an acid. Suitable acids for this reaction are, in particular, those which yield physiologically acceptable salts. Thus inorganic acids can be used, examples being sulfuric acid, nitric acid, hydrohalic acids such as hydrochloric acid or hydrobromic acid, phosphoric acid such as orthophosphoric acid, sulfamic acid, and also organic acids, especially aliphatic, alicyclic, araliphatic, aromatic or heterocyclic mono- or polybasic carboxylic, sulfonic or sulfuric acids, for example formic acid, acetic acid, propionic acid, pivalic acid, diethyl-acetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids, laurylsulfuric acid. Salts with physiologically unacceptable acids, for example picrates, can be used for isolating and/or purifying the compounds of the formula I.

Alternatively, an acid of a cyclic peptide according to the invention and especially an acid of a cyclic peptide according to formula I, Ia, Ib, Ic and/or Id can be converted into one of its physiologically acceptable metal or ammonium salts by reaction with a base. Particularly suitable salts in this context are the sodium, potassium, magnesium, calcium and ammonium salts, and also substituted ammonium salts, for example the dimethyl-, diethyl- or diisopropylammonium salts, monoethanol-, diethanol- or triethanolammonium salts, cyclohexylammonium salts, dicyclohexylammonium salts, dibenzylethylenediammonium salts, and also, for example, salts with N-methyl-D-glucamine or with arginine or lysine.

Preferred cyclic peptides for all aspects of the instant invention are preferably selected from the group consisting of the cyclic peptides according to formula I, Ia, Ib, Ic and/or Id, more preferably selected from consisting of the cyclic peptides according to formula Ia, Ib, Ic and/or Id, even more preferably selected from the group consisting of the cyclic peptides according to formula Ib, Ic and/or Id, and especially preferred selected from the group consisting of the cyclic peptides according to formula Ic and/or Id.

According to the invention, the at least one cyclopeptide preferably comprises cyclo-(Arg-Gly-Asp-DPhe-NMeVal) and/or cyclo-(Arg-Gly-Asp-DPhe-Val),
and/or a salt or solvate thereof.

According to the invention, the at least one cyclopeptide is especially preferably selected from cyclo-(Arg-Gly-Asp-DPhe-NMeVal) and cyclo-(Arg-Gly-Asp-DPhe-Val), and/or a salt or solvate thereof.

Especially preferably, the at least one cyclopeptide preferably is cyclo-(Arg-Gly-Asp-DPhe-NMeVal) and/or a salt or solvate thereof.

The peptide of the formula Cyclo-(Arg-Gly-Asp-DPhe-NMeVal) is preferably employed as a pharmaceutically acceptable salt, more preferably the pharmacologically acceptable hydrochloride salt, and especially preferably applied as the inner (or internal) salt, which is the compound cyclo-(Arg-Gly-Asp-DPhe-NMeVal) as such.

With regard to the peptide of the formula cyclo-(Arg-Gly-Asp-DPhe-NMeVal), the following kinds of writing the name are preferably to be regarded as equivalent:
Cyclo-(Arg-Gly-Asp-DPhe-NMeVal)=cyclo-(Arg-Gly-Asp-DPhe-NMeVal)=cyclo-(Arg-Gly-Asp-DPhe-[NMe]Val)=cyclo-(Arg-Gly-Asp-DPhe-[NMe]-Val)=cyclo-(Arg-Gly-Asp-DPhe-NMeVal)=cyclo-(Arg-Gly-Asp-DPhe-NMe-Val)=cyclo(Arg-Gly-Asp-DPhe-NMeVal)=cyclo(Arg-Gly-Asp-DPhe-NMe-Val)=cRGDfNMeV=c(RGDfNMeV).

The peptide of the formula cyclo-(Arg-Gly-Asp-DPhe-NMeVal) is preferably also referred to as Cilengitide, which is the INN (International Non-propriety Name) of said compound.

The peptide of the formula cyclo-(Arg-Gly-Asp-DPhe-NMeVal) is also described in EP 0 770 622 A, U.S. Pat. No. 6,001,961, WO 00/15244 and PCT/US07/01446 of the same applicant, the disclosure of which is explicitly incorporated into the instant application by reference.

The oligopeptides, preferably the cyclic oligopeptides for use according to the invention and especially the cyclic oligopeptides according to formula I, Ia, Ib, Ic and/or Id possess very valuable properties. In particular, they act as integrin inhibitors, in which context they preferably modulate and especially preferably inhibit the interactions of $\beta_3$- or $\beta_5$-integrin receptors with ligands. The compounds are preferably particularly active in the case of the integrins $a_V\beta_3$, $a_V\beta_5$ and/or $a_{II}\beta_5$, and more preferably particularly active in the case of the integrins $a_V\beta_3$ and/or $a_V\beta_5$, but preferably also relative to $a_V\beta_1$-, $a_V\beta_6$- and/or $a_V\beta_8$ receptors. These actions can be demonstrated, for example, according to the method described by J. W. Smith et al. in J. Biol. Chem. 265, 12267-12271 (1990).

[16] Thus, preferred are compositions as described herein or as described in one or more of the paragraphs numbered [1] to [15] and/or the paragraphs relating thereto, wherein the oligopeptide comprises the Arg-Gly-Asp-subsequence.

[17] Preferred are compositions as described herein or as described in one or more of the paragraphs numbered [1] to [16] and/or the paragraphs relating thereto, wherein the oligopeptide is a cyclic oligopeptide.

[18] Preferred are compositions as described herein or as described in one or more of the paragraphs numbered [1] to [17] and/or the paragraphs relating thereto, wherein the oligopeptide or cyclic oligopeptide is selected from the group consisting of cyclo-(Arg-Gly-Asp-DPhe-NMeVal), cyclo-(Arg-Gly-Asp-DPhe-Val),
and the pharmaceutically acceptable derivatives, solvates and/or salts thereof.

[19] Preferred are compositions as described herein or as described in one or more of the paragraphs numbered [1] to [18] and/or the paragraphs relating thereto, wherein the oligopeptide or cyclic oligopeptide is selected from the group consisting of cyclo-(Arg-Gly-Asp-DPhe-NMeVal) and the pharmaceutically acceptable derivatives, solvates and/or salts thereof having a solubility in water at 20° C. or at 25° C., preferably at at 20° C., between 1 mg/mL and 15 mg/mL, more preferably between 2 mg/mL and 12 mg/mL, even more preferably between 3 mg/mL and 10 mg/mL and especially between 4 mg/mL and 9 mg/mL.

According to the invention, the at least one cyclopeptide is especially preferably selected from cyclo-(Arg-Gly-Asp-DPhe-NMeVal), and/or a salt or solvate thereof.

Especially preferred are solid materials comprising solid forms, more preferably solid amorphous and/or crystalline forms, of cyclo-(Arg-Gly-Asp-DPhe-NMeVal) and/or a salt or solvate thereof. Especially preferred are solid materials comprising solid forms, more preferably amorphous and/or crystalline solid forms, of cyclo-(Arg-Gly-Asp-DPhe-NMe-Val) and/or a salt or solvate thereof, which have a solubility in water at 20° C. between 1 mg/ml and 25 mg/ml. Preferably, the solubility in water at 20° C. is 20 mg/ml or lower, more preferably 18 mg/ml or lower, even more preferably 15 mg/ml or lower, even more preferably 12 mg/ml and especially 10 mg/ml or lower. Preferably, the solubility in water at 20° C. is 1 mg/ml or higher, more preferably 2 mg/ml or higher, even more preferably 3 mg/ml or higher, even more preferably 4 mg/ml or higher and especially 6 mg/ml or higher, but preferably not higher than the above given upper limits given for the solubility. Accordingly, the solubility in water at 20° C. is preferably in the range between 2 mg/ml and 15 mg/ml, even more preferably between 3 mg/ml and 12 mg/ml and especially between 4 mg/ml and 10 mg/ml, e.g. about 4 mg/ml, about 6 mg/ml, about 8 mg/ml, about 10 mg/ml or about 13 mg/ml.

Methods for determining the solubility of said cyclic oligopeptide(s) in water are known in the art. Preferably, the solubility in water at 20° C. or at 25° C., preferably at 20° C., is determined at an about neutral pH of the solution of said cyclic oligopeptide(s) in water. Even more preferably, the solubility in water at 20° C. or at 25° C., preferably at 20° C., is determined at a pH=7+/−0.5 of the solution of said cyclic oligopeptide(s) in water. Accordingly, the solubility is preferably determined in water at 20° C. or at 25° C., preferably at 20° C., at a pH in the range of 6.5 to 7.5, more preferably in the range of 6.5 to 7.0, such as at a pH value of about 6.8, about 7.0 or about 7.4.

The solubility of the inner (or internal) salt of the peptide of the formula cyclo-(Arg-Gly-Asp-DPhe-NMeVal) in water at 20° C. or at 25° C., preferably at 20° C., is preferably determined at the isoelectric point, which preferably corresponds to a pH value of about 6.8 and especially preferably corresponds to a pH value in the range of 6.7 to 6.9.

Preferred in this regard are amorphous solid forms and crystalline solid forms, more preferably crystalline solid forms, of cyclo-(Arg-Gly-Asp-DPhe-NMeVal) and/or the salts thereof, and preferably the solid materials containing them. Especially preferred in this regard amorphous solid forms and crystalline solid forms, more preferably crystalline solid forms of the inner salt of cyclo-(Arg-Gly-Asp-DPhe-NMeVal), and preferably the solid materials containing them or consisting of them.

Preferred in this regard are crystalline solid forms, more preferably crystalline solid forms of cyclo-(Arg-Gly-Asp-DPhe-NMeVal) and/or the salts thereof which are solvates or anhydrates, and preferably the solid materials containing them or consisting of them.

The salts and especially the inner salt of cyclo-(Arg-Gly-Asp-DPhe-NMeVal) can be present as a solvate or anhydrate. The solvates and anhydrates, more preferably the anhydrates, of the inner salt of cyclo-(Arg-Gly-Asp-DPhe-NMeVal) are especially preferred, especially the crystalline form of the anhydrate, and preferably the solid materials containing them or consisting of them.

Preferred solid materials comprising crystalline forms of cyclo-(Arg-Gly-Asp-DPhe-NMeVal) and especially comprising crystalline forms of the inner salt of cyclo-(Arg-Gly-Asp-DPhe-NMeVal) are described in detail below:

Cyclo-(Arg-Gly-Asp-DPhe-NMe-Val) or {[(2S,5R,8S,11S)-5-Benzyl-11-(3-guanidino-propyl)-8-isopropyl-7-methyl-3,6,9,12,15-pentaoxo-1,4,7,10,13-pentaaza-cyclopentadec-2-yl]-acetic acid} was first described in the patents/patent applications U.S. Pat. No. 6,001,961 and EP 0 770 622, which were first published in 1997. In said patents, various salt forms of said compound were described, e.g. the hydrochloride, the acetate and the methansulfonate. Later, an improved method of manufacture that led to the inner salt of cyclo-(Arg-Gly-Asp-DPhe-NMe-Val) was described in WO 00/53627. However, the solids obtained according to the described procedures appeared to be amorphous material.

Described hereinafter are novel solid materials that comprise cyclo-(Arg-Gly-Asp-DPhe-NMe-Val) in one or more crystalline form.

Preferred solid materials are described below:

A solid material of a compound according to formula Id, $$\text{cyclo-(Arg-Gly-Asp-DPhe-NMeVal)} \quad (Id)$$

wherein said solid material comprises one or more crystalline forms of the compound of formula Id, characterised by a unit cell with the lattice parameters
a=9.5±0.5 Å,
b=23.0±5.0 Å, and
c=14.7±1.0 Å.

Said unit cell is preferably a crystallographic unit cell or a crystallographically determined unit cell.

In said unit cell, the angle α preferably is 90°±2°, the angle β preferably is 90°±2° and/or the angle γ preferably is 90°±2°.

Preferably, said solid material comprises at least 10% by weight, more preferably at least 30% by weight, even more preferably 60% by weight and especially at least 90% by weight or at least 95% by weight, of one or more crystalline forms of the compound of formula Id as defined above and/or below. For example, said solid material comprises about 25, about 50, about 75, about 95 or about 99% by weight of one or more crystalline forms of the compound of formula Id as defined above and/or below.

Especially preferably, the solid material comprises at least 10% by weight, more preferably at least 30 mole %, even more preferably 60 mole % and especially at least 90 mole % or at least 95 mole %, of one or more crystalline forms of the compound of formula Id as defined above and/or below. For example, the solid material comprises about 25, about 50, about 75, about 95 or about 99 mole % of one or more crystalline forms of the compound of formula Id as defined above and/or below.

The percentages by weight given for the solid material as described herein preferably relate to the ratio between the weight of the one or more crystalline forms as defined above/below contained in said solid material and the total amount by weight of the compound of formula Id contained in said solid material. In other words, the percentages by weight given preferably are the weight percentages of the sum of the one or more crystalline forms as defined above and/or below based on the total amount by weight of the compound of formula Id. Thus, the weight percentages given for the content of the one or more crystalline forms with in the solid material as described herein are preferably independent of the amount or content of compounds or impurities other than the compound according to formula Id contained in said solid material.

One or more crystalline forms in regard to said solid material preferably means that the solid material comprises at least one or more crystalline form or modification of the compound of formula Id having a unit cell within the lattice parameters as defined above and/or below, or that the solid material comprises mixtures of two or more, for example two or three, crystalline forms or modifications of the compound of formula Id, each having a unit cell within the lattice parameters as defined above and/or below.

Preferably, the solid material comprises one, two, three or four crystalline forms of the compound of formula Id as defined above and/or below.

More preferably, the solid material comprises one or more, preferably one, two, three or four, even more preferably one or two, crystalline forms of the compound of formula Id, each having a unit cell with lattice parameters (ULP) selected from a group consisting of
ULP1: a1=9.5±0.5 Å,
  b1=26.0±1.5 Å, and
  c1=14.3±0.7 Å,
and
ULP2: a2=9.8±0.5 Å,
  b2=20.0±1.5 Å, and
  c2=15.4±0.7 Å.

More preferably, the solid material comprises one or more, preferably one, two, three or four, even more preferably one or two, crystalline forms of the compound of formula Id, each having a unit cell with lattice parameters (ULP) selected from a group consisting of
ULP1: a1=9.5±0.3 Å,
  b1=26.0±1.0 Å, and
  c1=14.3±0.5 Å,
and
ULP2: a2=9.8±0.3 Å,
  b2=20.0±1.0 Å, and
  c2=15.4±0.5 Å.

In the unit cell with lattice parameters ULP1 and/or ULP2, the angle $\alpha$ preferably is 90°±2°, the angle $\beta$ preferably is 90°±2° and/or the angle $\gamma$ preferably is 90°±2°.

Preferably, the unit cell with lattice parameters ULP1 can be characterised, alternatively or additionally, preferably additionally, by a content of about 4 molecules of the compound of formula Id within said unit cell.

In the unit cell with lattice parameters ULP2, the angle $\alpha$ preferably is 90°±0.5°, the angle $\beta$ preferably is 90°±0.5° and/or the angle $\gamma$ preferably is 90°±0.5°. In the unit cell with lattice parameters ULP2, the angles $\alpha$, $\beta$ and $\gamma$ more preferably are 90°±0.1°.

Preferably, the unit cell with lattice parameters ULP2 can be characterised, alternatively or additionally, preferably additionally, by a content of about 4 molecules of the compound of formula Id within said unit cell.

More preferably, the solid material comprises one or more, preferably one, two, three or four, even more preferably one or two, crystalline forms of the compound of formula Id, selected from
crystalline form A1, characterised by a unit cell with the lattice parameters a=9.8±0.1 Å, b=19.5±0.5 Å, and c=15.4±0.1 Å,
crystalline form S1, characterised by a unit cell with the lattice parameters a=9.4±0.1 Å, b=25.9±0.5 Å, and c=14.1±0.1 Å,
crystalline form S2, characterised by a unit cell with the lattice parameters a=9.3±0.1 Å, b=26.6±0.5 Å, and c=14.7±0.1 Å, and
crystalline form S3, characterised by a unit cell with the lattice parameters a=9.6±0.1 Å, b=25.9±0.5 Å, and c=13.9±0.1 Å.

More preferably, the solid material comprises one or more, preferably one, two, three or four, even more preferably one or two, crystalline forms of the compound of formula Id, selected from
crystalline form A1, characterised by a unit cell with the lattice parameters a=9.8±0.1 Å, b=19.5±0.5 Å, and c=15.4±0.1 Å, preferably with $\alpha=\beta=\gamma=90°\pm1°$ and especially with $\alpha=\beta=\gamma=90°$;
crystalline form S1, characterised by a unit cell with the lattice parameters a=9.4±0.1 Å, b=25.9±0.5 Å, and c=14.1±0.1 Å, preferably with $\alpha=\beta=\gamma=90°\pm2°$, and especially with $\alpha=90°\pm1°$, $\beta=91°\pm1$, $\gamma=90°\pm1°$ and especially with $\alpha=90°$, $\beta=91.2°$, $\gamma=90°$;
crystalline form S2, characterised by a unit cell with the lattice parameters a=9.3±0.1 Å, b=26.6±0.5 Å, and c=14.7±0.1 Å, preferably with $\alpha=\beta=\gamma=90°\pm1°$ and especially with $\alpha=\beta=\gamma=90°$; and
crystalline form S3, characterised by a unit cell with the lattice parameters a=9.6±0.1 Å, b=25.9±0.5 Å, and c=13.9±0.1 Å, preferably with $\alpha=\beta=\gamma=90°\pm1°$ and especially with $\alpha=\beta=\gamma=90°$.

The crystalline forms S1, S2 and S3 are preferably further characterised as solvates.

Preferably, the crystalline forms S1, S2 and S3 can be characterised, alternatively or additionally, preferably additionally, by a content of about 4 molecules of the compound of formula Id within said unit cells.

The crystalline forms A1, S2 and/or S3 are preferably further characterised by orthorhombic unit cell.

The crystalline form S1 is preferably further characterised by a monoclinic in unit cell.

The unit cell and the lattice parameters, preferably including, but not limited to a, b, c, $\alpha$, $\beta$ and/or $\gamma$, are crystallographic parameters known to the ones skilled in the art. Hence, they can be determined according to methods known in the art. The same preferably holds true for the orthorhombic and/or monoclinic form of the unit cell.

The above given unit cells and the lattice parameters relating thereto are preferably determined by X-Ray Diffraction, more preferably Single Crystal X-Ray Diffraction and/or Powder X-Ray Diffraction, according to standard methods, for example methods or techniques as described in the European Pharmacopeia 6$^{th}$ Edition chapter 2.9.33, and/or as described in Rolf Hilfiker, 'Polymorphism in the Pharmaceutical Industry', Wiley-VCH. Weinheim 2006 (Chapter 6: X-Ray Diffraction), and/or H. G. Brittain, 'Polymorphism in Pharmaceutical Solids, Vol. 95, Marcel Dekker Inc., New York 1999 (Chapter 6 and references therein).

Alternatively preferably, the above given unit cells and the lattice parameters relating thereto can be obtained by single crystal X-Ray, optionally together with additional structure data, preferably conducted on a XCalibur diffractometer from Oxford Diffraction equiped with graphite monochromator and CCD Detector using Mo $K_\alpha$ radiation, preferably at a temperature of 298 K±5 K, and/or on a CAD4 four circle diffractometer from Nonius equiped with graphite monochromator and scintillation counter using Mo $K_\alpha$ radiation, preferably at a temperature of 298 K±5 K.

The above given unit cells and the lattice parameters relating thereto are preferably determined by X-Ray Diffraction, more preferably Powder X-Ray Diffraction, according to standard methods, for example methods or techniques as described in the European Pharmacopeia 6$^{th}$ Edition chapter 2.9.33, and/or as described in Rolf Hilfiker, 'Polymorphism in the Pharmaceutical Industry', Wiley-VCH. Weinheim 2006 (Chapter 6: X-Ray Diffraction), and/or H. G. Brittain, 'Polymorphism in Pharmaceutical Solids, Vol. 95, Marcel Dekker Inc., New York 1999 (Chapter 6 and references therein).

Higher contents of the one or more crystalline forms as defined above and/or below in the solid material as described above and/or below are generally preferred.

Preferred solid materials for use in the compositions according to the invention are described in PCT/EP2010/003100, titled "Novel solid materials of {[(2S,5R,8S,11S)-5-Benzyl-11-(3-guanidino-propyl)-8-isopropyl-7-methyl-3,6,9,12,15-pentaoxo-1,4,7,10,13-pentaaza-cyclopentadec-2-yl]-acetic acid} and methods for obtaining them", of the same applicant, the disclosure of which is incorporated into this application by reference in its entirety.

A solid material as described above and/or below, essentially consisting of one or more crystalline forms of the compound of formula Id, characterised by a unit cell with the lattice parameters
a=9.5±0.5 Å,
b=23.0±5.0 Å, and
c=14.7±1.0 Å,
and especially characterised as described above and/or below.

Essentially consisting of one or more crystalline forms of the compound of formula Id preferably means that the compound of formula Id contained in said solid material is essentially selected from said one or more crystalline forms of the compound of formula Id, or in other words, that the one or more crystalline forms in said solid form provide for the essential amount of compound of formula Id in said solid form. More specifically, essentially in this regard preferably means that the one or more crystalline forms in said solid form provide for 90% or more, preferably 95% or more, even more preferably 99% or more and especially 99.9% or more, of the amount of compound of formula Id in said solid form. In this regard, the given percentages (%) are preferably selected from mole % and % by weight and especially preferably are mole %.

Said amounts can be provided by one single crystalline form as described herein, or by mixtures of two or more crystalline form as described herein. Preferably, said amounts are provided by one single crystalline form as described herein. More preferably, said amounts are provided by one single crystalline form, selected from crystalline form A1, crystalline form S1, crystalline form S2 and crystalline form S3 as described herein.

The crystalline form A1, crystalline form S1, crystalline form S2 and crystalline form S3 is further described in PCT/EP2010/003100 of the same applicant, the disclosure of which is incorporated into this application by reference in its entirety.

If the solid material comprises two or more of the crystalline forms as described herein, one of these crystalline forms is preferably the major crystalline form and the one or more further crystalline forms present are present in minor amounts. The major crystalline form preferably provides for 60% by weight or more, more preferably 75% or more, even more preferably 90% or more and especially 95 or 99% or more, of the total amount of the crystalline forms present. In this regard, the given percentages (%) are preferably selected from mole % and % by weight and especially preferably are mole %.

If not specified otherwise, percentages (or %) given herein for compounds and/or solvents are preferably either percentages by weight or mole percent, preferably mole percent. Since the content of the one or more crystalline forms in the solid material as described herein, and, if applicable, the ratio of two or more crystalline forms in the solid material as described herein, can advantageously be determined via methods including, but not limited to, Powder X-Ray-Diffraction, Raman-spectroscopy and infrared spectroscopy, and more preferably are determined by Powder X-Ray-Diffraction, Raman-spectroscopy and/or infrared spectroscopy, percent values related thereto are especially preferably mole percent values, if not explicitly stated otherwise.

Preferably, if not specified otherwise, percentages (or %) given herein
i) for spectral data, such as transmission, especially IR transmission, Raman intensity;
ii) Powder X-Ray diffraction intensities (PXRD intensitiel); and/or
iii) or analytical parameters, such as relative humidity (rh or r.h.), and the like,
are preferably relative percentages (i.e. percent of the respective maximum value).

A preferred subject of the invention are the one or more crystalline forms of the compound of formula Id as described herein and especially as described above and/or below.

Preferably, the one or more crystalline forms of the compound of formula Id are selected from the crystalline forms as described above and/or below having a monoclinic unit cell or a orthorhombic unit cell.

Preferably, the one or more crystalline forms of the compound of formula Id are selected from anhydrates and solvates.

Preferably, the anhydrates as described herein and especially the crystalline form A1 can be characterised, alternatively or additionally, by a melting/decomposition temperature of >282° C., more preferably 288±5° C. or higher, and especially 288±5° C.

The melting/decomposition temperatures and/or thermal behaviors described herein are preferably determined by DSC (Differential Scanning Calorimetry) and TGA ((ThermoGravimetric Analysis). DSC and/or TGA methods or generally thermoanalytic methods and suitable devices for determining them are known in the art, for examples from European Pharmacopeia 6$^{th}$ Edition chapter 2.02.34, wherein suitable standard techniques are described. More preferably, for the melting/decomposition temperatures or behaviors and/or the thermoanalysis in generally, a Mettler Toledo DSC 821 and/or Mettler Toledo TGA 851 are used, preferably as described in the European Pharmacopeia 6$^{th}$ Edition chapter 2.02.34.

Figure 2:
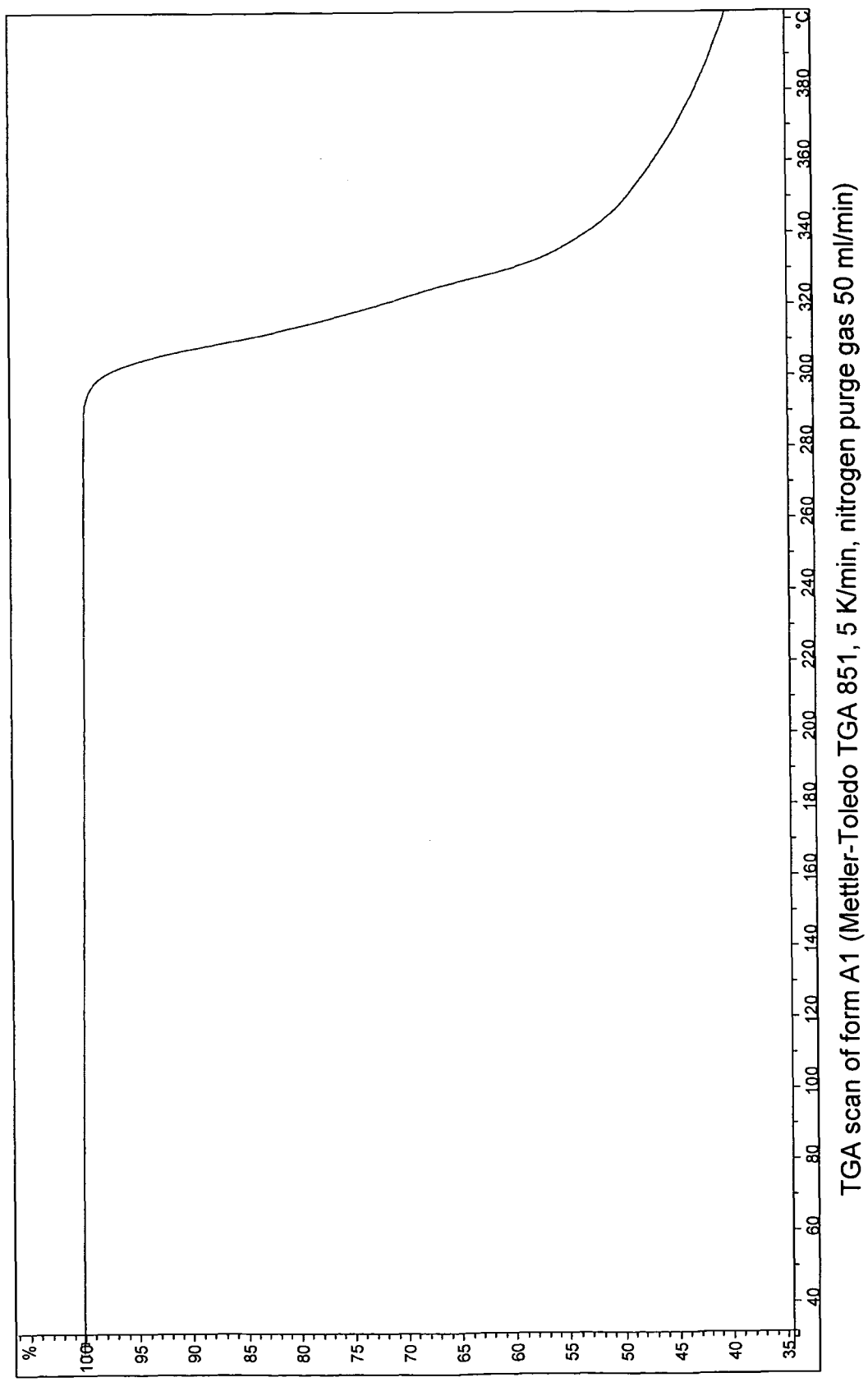
FIG. 2 shows a TGA scan of form A1 (Mettler-Toledo TGA 851, 5 K/min, nitrogen purge gas 50 ml/min).

The DSC and TGA measurements showing the thermal analysis (Mettler-Toledo DSC 821, 5 K/min, nitrogen purge gas 50 ml/min; Mettler-Toledo TGA 851, 5 K/min, nitrogen purge gas 50 ml/min) and the melting/decomposition temperature given above is shown in FIG. 1 and FIG. 2.

Preferably, the anhydrates as described herein and especially the crystalline form A1 can be characterised, alternatively or additionally, by Powder X-Ray Diffraction and more preferably by the Powder X-Ray Diffraction pattern comprising one or more of the Powder X-ray peaks given below, more preferably comprising 6 or more of the Powder X-ray peaks given below, even more preferably 8 or more of the Powder X-ray peaks given below, and especially comprising all of the of the Powder X-ray peaks given below:

a)

| No. | D ± 0.1 [Å] | °2 θ (Cu—Kα$_1$ radiation) ± 0.1° | Miller indizes h | k | l |
|---|---|---|---|---|---|
| 1 | 12.08 | 7.3 | 0 | 1 | 1 |
| 2 | 9.75 | 9.1 | 0 | 0 | 2 |
| 4 | 8.24 | 10.7 | 1 | 1 | 0 |
| 7 | 6.91 | 12.8 | 1 | 0 | 2 |
| 8 | 6.05 | 14.6 | 1 | 2 | 0 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.2 | 2 | 0 | 2 |
| 13 | 4.21 | 21.1 | 2 | 1 | 2 |
| 14 | 4.12 | 21.2 | 2 | 2 | 0 |
| 15 | 3.79 | 23.4 | 2 | 1 | 3 | or more preferably b)

| No. | D ± 0.1 [Å] | °2 θ (Cu—Kα$_1$ radiation) ± 0.1° | Miller indizes h | k | l |
|---|---|---|---|---|---|
| 1 | 12.08 | 7.3 | 0 | 1 | 1 |
| 2 | 9.75 | 9.1 | 0 | 0 | 2 |
| 4 | 8.24 | 10.7 | 1 | 1 | 0 |
| 7 | 6.91 | 12.8 | 1 | 0 | 2 |
| 8 | 6.05 | 14.7 | 0 | 2 | 2 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.3 | 2 | 0 | 2 |
| 13 | 4.21 | 21.1 | 2 | 1 | 2 |
| 14 | 4.12 | 21.5 | 2 | 2 | 0 |
| 15 | 3.79 | 23.4 | 2 | 1 | 3 |

Preferably, the anhydrates as described herein and especially the crystalline form A1 can be characterised, alternatively or additionally, by Powder X-Ray Diffraction and more preferably by the Powder X-Ray Diffraction pattern comprising the Powder X-ray peaks given below:

a)

| No. | D [Å] | °2 θ (Cu—Kα$_1$ radiation) ± 0.1° | Miller indizes h | k | l |
|---|---|---|---|---|---|
| 1 | 12.08 | 7.3 | 0 | 1 | 1 |
| 2 | 9.75 | 9.1 | 0 | 0 | 2 |
| 4 | 8.24 | 10.7 | 1 | 1 | 0 |
| 7 | 6.91 | 12.8 | 1 | 0 | 2 |
| 8 | 6.05 | 14.6 | 1 | 2 | 0 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.2 | 2 | 0 | 2 |
| 13 | 4.21 | 21.1 | 2 | 1 | 2 |
| 14 | 4.12 | 21.2 | 2 | 2 | 0 |
| 15 | 3.79 | 23.4 | 2 | 1 | 3 | or more preferably b)

| No. | D [Å] | °2 θ (Cu—Kα$_1$ radiation) ± 0.1° | Miller indizes h | k | l |
|---|---|---|---|---|---|
| 1 | 12.08 | 7.3 | 0 | 1 | 1 |
| 2 | 9.75 | 9.1 | 0 | 0 | 2 |
| 4 | 8.24 | 10.7 | 1 | 1 | 0 |
| 7 | 6.91 | 12.8 | 1 | 0 | 2 |
| 8 | 6.05 | 14.7 | 0 | 2 | 2 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.3 | 2 | 0 | 2 |
| 13 | 4.21 | 21.1 | 2 | 1 | 2 |
| 14 | 4.12 | 21.5 | 2 | 2 | 0 |
| 15 | 3.79 | 23.4 | 2 | 1 | 3 |

Preferably, the anhydrates as described herein and especially the crystalline form A1 can be characterised, alternatively or additionally, by Powder X-Ray Diffraction and more preferably by the Powder X-Ray Diffraction pattern comprising one or more of the Powder X-ray peaks given below, more preferably comprising 10 or more of the Powder X-ray peaks given below, even more preferably 12 or more of the Powder X-ray peaks given below, and especially comprising all of the of the Powder X-ray peaks given below:

a)

| No. | D ± 0.1 [Å] | °2 θ (Cu—Kα$_1$ radiation) ± 0.1° | Miller indizes h | k | l |
|---|---|---|---|---|---|
| 1 | 12.08 | 7.3 | 0 | 1 | 1 |
| 2 | 9.75 | 9.1 | 0 | 0 | 2 |
| 3 | 8.75 | 10.1 | 1 | 0 | 1 |
| 4 | 8.24 | 10.7 | 1 | 1 | 0 |
| 5 | 7.69 | 11.5 | 0 | 2 | 0 |
| 6 | 7.16 | 12.4 | 0 | 2 | 1 |
| 7 | 6.91 | 12.8 | 1 | 0 | 2 |
| 8 | 6.05 | 14.6 | 1 | 2 | 0 |
| 9 | 4.88 | 18.2 | 0 | 0 | 4 |

-continued a)

| No. | D ± 0.1 [Å] | °2 θ (Cu—Kα₁ radiation) ± 0.1° | Miller indizes h | k | l |
|---|---|---|---|---|---|
| 10 | 4.54 | 19.5 | 2 | 1 | 1 |
| 11 | 4.43 | 20.0 | 1 | 3 | 1 |
| 12 | 4.37 | 20.2 | 2 | 0 | 2 |
| 13 | 4.21 | 21.1 | 2 | 1 | 2 |
| 14 | 4.12 | 21.2 | 2 | 2 | 0 |
| 15 | 3.79 | 23.4 | 2 | 1 | 3 | or more preferably b)

| No. | D ± 0.1 [Å] | °2 θ (Cu—Kα₁ radiation) ± 0.1° | Miller indizes h | k | l |
|---|---|---|---|---|---|
| 1 | 12.08 | 7.3 | 0 | 1 | 1 |
| 2 | 9.75 | 9.1 | 0 | 0 | 2 |
| 3 | 8.75 | 10.1 | 1 | 0 | 1 |
| 4 | 8.24 | 10.7 | 1 | 1 | 0 |
| 5 | 7.69 | 11.5 | 0 | 2 | 0 |
| 6 | 7.16 | 12.4 | 0 | 2 | 1 |
| 7 | 6.91 | 12.8 | 1 | 0 | 2 |
| 8 | 6.05 | 14.7 | 0 | 2 | 2 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.3 | 2 | 0 | 2 |
| 13 | 4.21 | 21.1 | 2 | 1 | 2 |
| 14 | 4.12 | 21.5 | 2 | 2 | 0 |
| 15 | 3.79 | 23.4 | 2 | 1 | 3 |

The Powder X-Ray Diffraction and more preferably the Powder X-Ray Diffraction pattern is preferably performed or determined as described herein and especially performed or determined by standard techniques as described in the European Pharmacopeia 6$^{th}$ Edition chapter 2.9.33, and is even more preferably obtained with the parameters Cu—Kα₁ radiation and/or λ=1.5406 Å, preferably on a Stoe StadiP 611 KL diffractometer.

Figure 3:
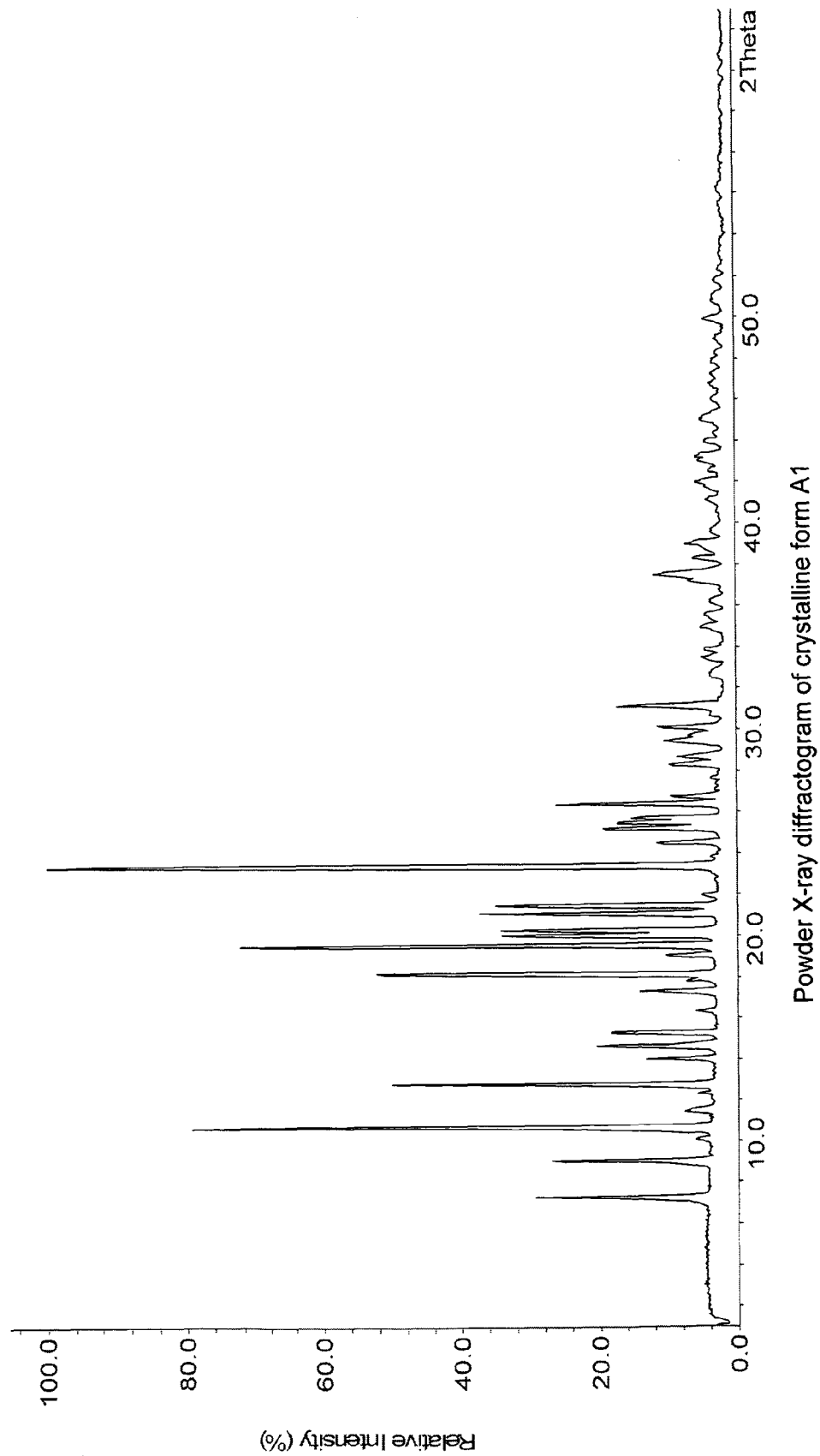
FIG. 3 shows a powder X-ray diffractogram of crystalline form A1.

FIG. 3 shows the Powder X-ray diffractogram of crystalline form A1

Preferably, the anhydrates as described herein and especially the crystalline form A1 can be characterised, alternatively or additionally, by Single Crystal X-Ray Structure Data, for example Single Crystal X-Ray Structure Data obtained on a diffractometer preferably equipped with a graphite monochromator and CCD Detector, preferably using Mo K$_\alpha$ radiation, preferably at a temperature of 298 K±5 K, and even more preferably on a XCalibur diffractometer from Oxford Diffraction equiped with graphite monochromator and CCD Detector using Mo K$_\alpha$ radiation at about 298 K.

According to the Single Crystal X-Ray Structure Data obtained, the anhydrate of the compound of formula Id and especially crystalline form A1 crystallises in the orthorhombic space group P 2₁ 2₁ 2₁ with the lattice parameters a=9.8 Å, b=15.4 Å, c=19.5 Å (±0.1 Å) and the unit cell volume is preferably 2940 (±10) Å³

From the single crystal structure it is obvious that form A1 represents an anhydrate or ansolvate.

Figure 4:
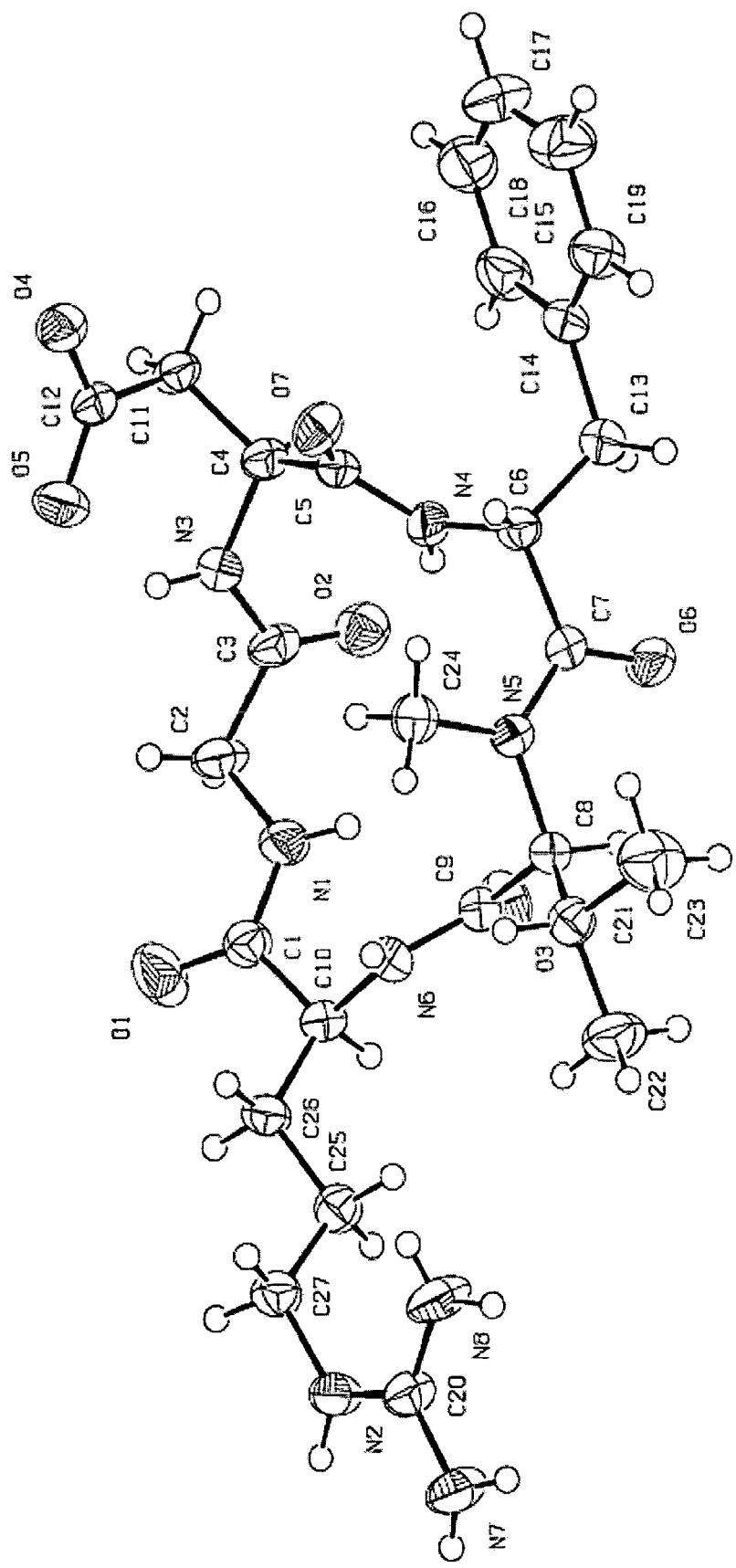
FIG. 4 shows a single crystal structure of form A1.

The Single Crystal X-Ray Structure is depicted in FIG. 4.

Preferably, the anhydrates as described herein and especially the crystalline form A1 can be characterised, alternatively or additionally, by the infrared-spectroscopy data comprising one or more of the band positions (±2 cm$^{-1}$) given below, more preferably comprising 6 or more of the band positions (±2 cm$^{-1}$) given below, even more preferably comprising 9 or more of the band positions (±2 cm$^{-1}$) given below, and especially comprising all the band positions (±2 cm$^{-1}$) given below, preferably together with the relative intensities given in brackets:

3431 cm$^{-1}$ (s), 3339 cm$^{-1}$ (s), 3189 cm$^{-1}$ (s), 2962 cm$^{-1}$ (m), 2872 cm$^{-1}$ (m), 1676 cm$^{-1}$ (s), 1660 cm$^{-1}$ (s), 1617 cm$^{-1}$ (s), 1407 cm$^{-1}$ (s), 1316 cm$^{-1}$ (m), 1224 cm$^{-1}$ (m), 1186 cm$^{-1}$ (m), 711 cm$^{-1}$ (m).

More preferably, the anhydrates as described herein and especially the crystalline form A1 can be characterised, alternatively or additionally, by the infrared-spectroscopy data comprising one or more of the band positions (±2 cm$^{-1}$) given below, more preferably comprising 9 or more of the band positions (±2 cm$^{-1}$) given below, even more preferably comprising 12 or more of the band positions (±2 cm$^{-1}$) given below, and especially comprising all the band positions (±2 cm$^{-1}$) given below, preferably together with the relative intensities given in brackets:

3431 cm$^{-1}$ (s), 3339 cm$^{-1}$ (s), 3189 cm$^{-1}$ (s), 3031 cm$^{-1}$ (m), 2962 cm$^{-1}$ (m), 2872 cm$^{-1}$ (m), 1676 cm$^{-1}$ (s), 1660 cm$^{-1}$ (s), 1617 cm$^{-1}$ (s), 1539 cm$^{-1}$ (s), 1493 cm$^{-1}$ (s), 1407 cm$^{-1}$ (s), 1358 cm$^{-1}$ (m), 1316 cm$^{-1}$ (m), 1247 cm$^{-1}$ (m), 1224 cm$^{-1}$ (m), 1186 cm$^{-1}$ (m), 994 cm$^{-1}$ (w), 921 cm$^{-1}$ (w), 711 cm$^{-1}$ (m), 599 cm$^{-1}$ (m).

The relative intensities given in brackets are preferably defined as follows:* "s"=strong (transmittance preferably ≤50%), "m"=medium (preferably 50%<transmittance≤70%), "w"=weak (transmittance preferably >70%)

The IR or FT-IR spectrum is preferably obtained using a KBr pellet as sample preparation technique.

The IR-spectroscopy data is preferably obtained by FT-IR-spectroscopy, The IR-spectroscopy data or FT-IR-spectroscopy data is preferably obtained by standard techniques as described in the European Pharmacopeia 6$^{th}$ Edition chapter 2.02.24. For the measurement of the FT-IR-spectra, preferably a Bruker Vector 22 spectrometer is used. FT-IR spectra are preferably base-line corrected, preferably using Bruker OPUS software.

Figure 5:
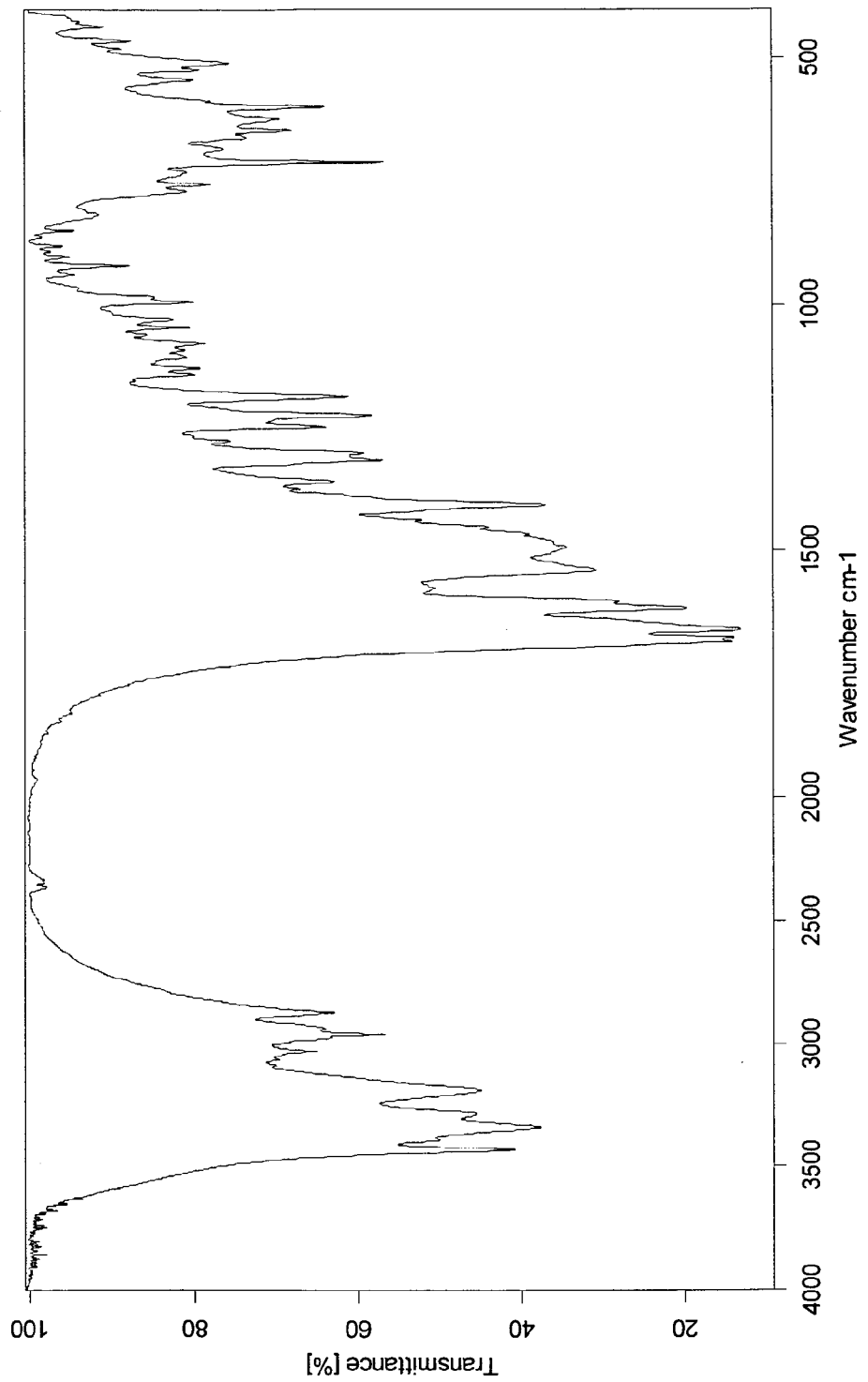
FIG. 5 shows an FTIR spectrum of form A1.

The FT-IR spectra of the anhydrates as described herein and especially the crystalline form A1 is given in FIG. 5.

Preferably, the anhydrates as described herein and especially the crystalline form A1 can be characterised, alternatively or additionally, by the Raman-spectroscopy data comprising one or more of the band positions (±2 cm$^{-1}$) given below, more preferably comprising 9 or more of the band positions (±2 cm$^{-1}$) given below, even more preferably comprising 9 or more of the band positions (±2 cm$^{-1}$) given below, and especially comprising all the band positions (±2 cm$^{-1}$) given below, preferably together with the relative intensities given in brackets:

3064 cm$^{-1}$ (w), 2976 cm$^{-1}$ (m), 2934 cm$^{-1}$ (m), 2912 cm$^{-1}$ (m), 2881 cm$^{-1}$ (m), 1603 cm$^{-1}$ (w), 1209 cm$^{-1}$ (w), 1029 cm$^{-1}$ (w), 1003 cm$^{-1}$ (m), 852 cm$^{-1}$ (w).

More preferably, the anhydrates as described herein and especially the crystalline form A1 can be characterised, alternatively or additionally, by the Raman-spectroscopy data comprising one or more of the band positions (±2 cm$^{-1}$)

given below, more preferably comprising 12 or more of the band positions (±2 cm$^{-1}$) given below, even more preferably comprising 18 or more of the band positions (±2 cm$^{-1}$) given below, and especially comprising all the band positions (±2 cm$^{-1}$) given below, preferably together with the relative intensities given in brackets:
3064 cm$^{-1}$ (w), 2976 cm$^{-1}$ (m), 2934 cm$^{-1}$ (m), 2912 cm$^{-1}$ (m), 2881 cm$^{-1}$ (m), 1677 cm$^{-1}$ (w), 1648 cm$^{-1}$ (w), 1603 cm$^{-1}$ (w), 1584 cm$^{-1}$ (w), 1465 cm$^{-1}$ (w), 1407 cm$^{-1}$ (w), 1314 cm$^{-1}$ (w), 1242 cm$^{-1}$ (w), 1209 cm$^{-1}$ (w), 1129 cm$^{-1}$ (w), 1029 cm$^{-1}$ (w), 1003 cm$^{-1}$ (m), 943 cm$^{-1}$ (w), 901 cm$^{-1}$ (w), 852 cm$^{-1}$ (w), 623 cm$^{-1}$ (w), 589 cm$^{-1}$ (w).

The relative intensities given in brackets are preferably defined as follows: "s"=strong (relative Raman intensity preferably ≥0.04), "m"=medium (preferably 0.04>relative Raman intensity≥0.02), "w"=weak (relative Raman intensity preferably <0.02)

The Raman or FT-Raman spectrum is preferably obtained using Aluminium-cups as sample holders for the respective solid material.

The Raman-spectroscopy data is preferably obtained by FT-Raman-spectroscopy, The Raman-spectroscopy data or FT-Raman-spectroscopy data is preferably obtained by standard techniques as described in the European Pharmacopeia 6$^{th}$ Edition chapter 2.02.48. For the measurement of the FT-Raman-spectra, preferably a Bruker RFS100 spectrometer is used. FT-Raman spectra are preferably base-line corrected, preferably using Bruker OPUS software.

Figure 6:
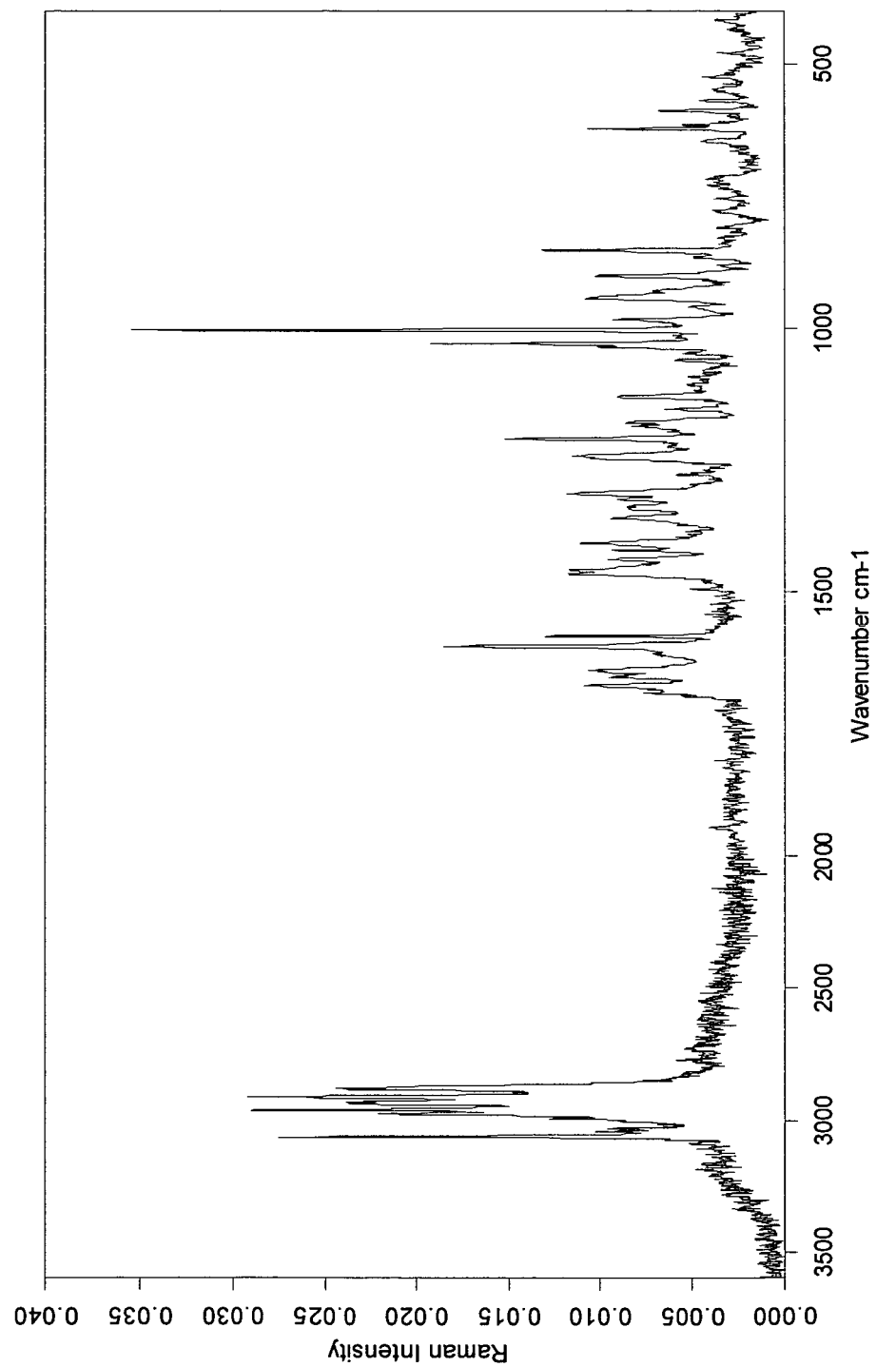
FIG. 6 shows an FT Raman spectrum of form A1.

The FT-Raman spectra of the anhydrates as described herein and especially the crystalline form A1 is given in FIG. 6.

Preferably, the anhydrates as described herein and especially the crystalline form A1 can be characterised, alternatively or additionally, by a solubility in water at 20° C. or 25° C., preferably at 20° C., in the range between 5 and 9 mg/mL, preferably in the range between 6 and 8 mg/mL and especially by a solubility in water at 20° C. or 25° C., preferably at 20° C., of about 7 mg/mL.

Figure 7:
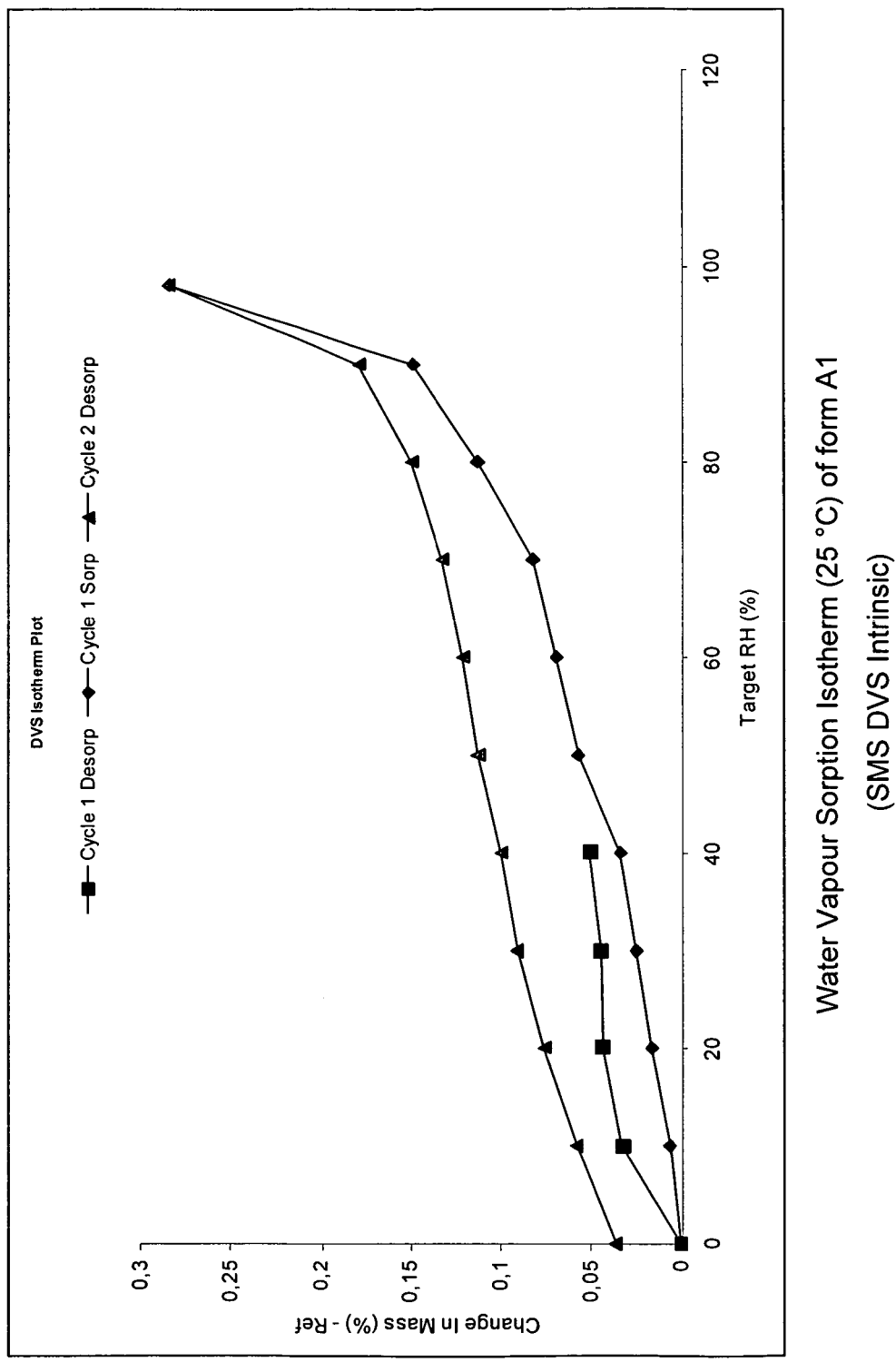
FIG. 7 shows a water vapor sorption isotherm (25° C.) of form A1 (SMS DVS Instinsic).

Preferably, the anhydrates as described herein and especially the crystalline form A1 can be characterised, alternatively or additionally, by dynamic vapour experiments. The results can be obtained by standard techniques as described in Rolf Hilfiker, 'Polymorphism in the Pharmaceutical Industry', Wiley-VCH. Weinheim 2006 (Chapter 9: Water Vapour Sorption, and references therein). The Water Vapour Sorption behaviour shows small water uptake levels up to 98% relative humidity (rh or r.h.), and the anhydrates as described herein and especially the crystalline form A1 can be classified as non-hygroscopic acc. to Ph. Eur. criteria. No formation or conversion to a hydrate is observed. Water Vapor Sorption isotherm (25° C.) of crystalline form A1 (SMS DVS Intrinsic) is given in FIG. 7.

The crystalline form A1 preferably can be characterised as an anhydrate or ansolvate.

In this regard, anhydrate or ansolvate preferably means that the unit cell is free or essentially free of about stoichiometric amounts of solvent molecules of one or more solvents. In this regard, anhydrate or ansolvate more preferably means that the unit cell is essentially free of water and solvent molecules. Essentially free of solvent molecules in this regard preferably means that the amount of solvent molecules in the unit cell is lower than 0.5, more preferably lower than 0.1, even more preferably lower than 0.01 and especially lower than 0.001.

Since both ansolvates and an anhydrates are characterised by the absence of the respective solvents and thus characterised by the absence of any solvent, the terms anhydrate and ansolvate are preferably to be regarded as synonyms in the context of the present invention.

The amount of molecules in the unit cell is preferably determined by crystallographic methods, more preferably by single crystal X-ray diffraction and/or powder X-ray diffraction.

Alternatively, the amount of solvent in said crystalline forms, said solvates and/or in the respective unit cell can be determined or estimated by elemental analysis, gas chromatography or Karl-Fischer titration. In this context, essentially free of solvent molecules preferably means a solvent content of less than 5%, even more preferably less than 2%, even more preferably less than 1% and especially less than 0.1%, for example 5% to 0.1% or 2% to 0.01%. In this regard, the given percentages (%) are preferably selected from mole % and % by weight and especially preferably are % by weight.

The anhydrates as described herein and especially the crystalline form A1 shows one or more properties selected from the advantageous properties discussed above. More specifically, the anhydrates as described herein and especially the crystalline form A1 can shown to be the thermodynamically stable ansolvated form and/or thermodynamic stable form and surprisingly the thermodynamically stable form in the presence of aqueous based solvents, preferably including, but not limited to, suspensions and wetted material, and especially in essentially aqueous systems, such as water saline anthe like, such as, but not limited to, suspensions and wetted material, and especially in such aqueous systems in the absence of methanol and/or ethanol. Wetted material in this regard is preferably a mixture of the respective anhydrate with at least 5% by weight, more preferably at least 10% by weight and especially 20% by weight, of the respective aqueous system. Furthermore, the anhydrates as described herein and especially the crystalline form A1 shows superior properties in terms of hygroscopicity behaviour, with physical stability of the crystal form throughout the entire relative humidity range (0-98%) and/or the crystallinity and thermal behaviour are excellent.

This results in excellent properties for processing (e.g. phase separation by filtration, drying, milling, micronisation) and storage, thus being i.a. superior for the formulation of suspensions. The anhydrates as described herein and especially the crystalline form A1 exhibit superior properties for the purification of the compound of formula Id, since a reduction of structurally related impurities, ionic compounds and residual solvent can be easily achieved. Thus, purification can be achieved in one step, where the solid forms, e.g. amorphous forms according to the conventional, prior known processes, and/or other, non-anhydrate polymorphic crystalline forms require significantly higher effort for a purity in line with GMP standards, e.g. three or more subsequent purification procedures.

The compound of formula Id also forms a class of pseudopolymorphs which incorporate different solvents in variable amounts and/or ratios, preferably ratios, and thus are solvates. These solvates are structurally closely related as shown, e.g. by Powder X-Ray Diffraction data, including Indexing of these forms, which leads to similar unit cells. Also, selected examples for the structures will be discussed based on single-crystal structure and structure solutions based on powder data. Finally a discussion on the specific beneficial properties of this pseudopolymorphic class will be given.

Following, three preferred examples for the pseudopolymorphic forms of Cilengitide are described: S1 (Methanol solvate), S2 (Ethanol solvate) and form S3 (hydrate). These preferred examples can be further characterised as tetrasolvates.

Thus, the solid crystalline forms having a unit cell with lattice parameters ULP1 as defined before are preferably further characterised herein as solvates and more preferably as tetrasolvates. The solvates and/or tetrasolvates preferably include one or more crystalline forms selected from S1, S2 and S3 as defined herein, and preferably also mixtures thereof.

The crystalline forms S1, S2 and/or S3 are preferably further characterised as solvates and especially as tetrasolvates, i.e. they preferably show an about stoichiometric amount of solvent molecules in the respective unit cell, which is about 4 solvent molecules per unit cell and per molecule of the compound according to formula Id.

In these tetrasolvates, the solvent molecules are preferably selected from molecules of water and alcohols and more preferably selected from water, methanol and ethanol, and mixtures thereof.

Accordingly, the solvates can preferably be further characterised as hydrates or alcohol solvates (or alcoholates), and more preferably as hydrates, methanol solvates (or methanolates) and/or ethanol solvates (or ethanolates). However, if said solvates are produced from or contacted with mixtures of solvents, mixed solvates can also be obtained. Additionally, the solvent molecules within one solvate are partially or completely interchangeable for a the solvent molecules of another solvent. Thus, it is clear that the solvates, more preferably the tetrasolvates and especially the crystalline forms S1, S2 and S3 all belong to a specific class of solid crystalline forms.

Preferably, the tetrasolvates as described herein, more preferably the tetrasolvates as described herein, more preferably the tetrahydrates as described herein and especially the crystalline form S3 can be characterised, alternatively or additionally, by a melting/decomposition temperature of >210° C., more preferably 217±5° C. melting/decomposition ° C. or higher, and especially 217±5° C. melting/decomposition. Preferably, the melting/decomposition temperature obtained for the tetrasolvates as described herein, more preferably the tetrahydrates as described herein and especially obtained for the crystalline form S3 is <250° C.

The melting/decomposition temperatures and/or thermal behaviors described herein are preferably determined by DSC (Differential Scanning calorimetry) and TGA ((ThermoGravimetric Analysis). DSC and/or TGA methods or generally thermoanalysis methods and suitable devices for determining them are known in the art, for examples from European Pharmacopeia 6$^{th}$ Edition chapter 2.02.34, wherein suitable standard techniques are described. More preferably, for the melting/decomposition temperatures or behaviors and/or the thermoanalysis in general, a Mettler Toledo DSC 821 and/or Mettler Toledo TGA 851 are used, preferably as described in the European Pharmacopeia 6$^{th}$ Edition chapter 2.02.34.

Figure 8:
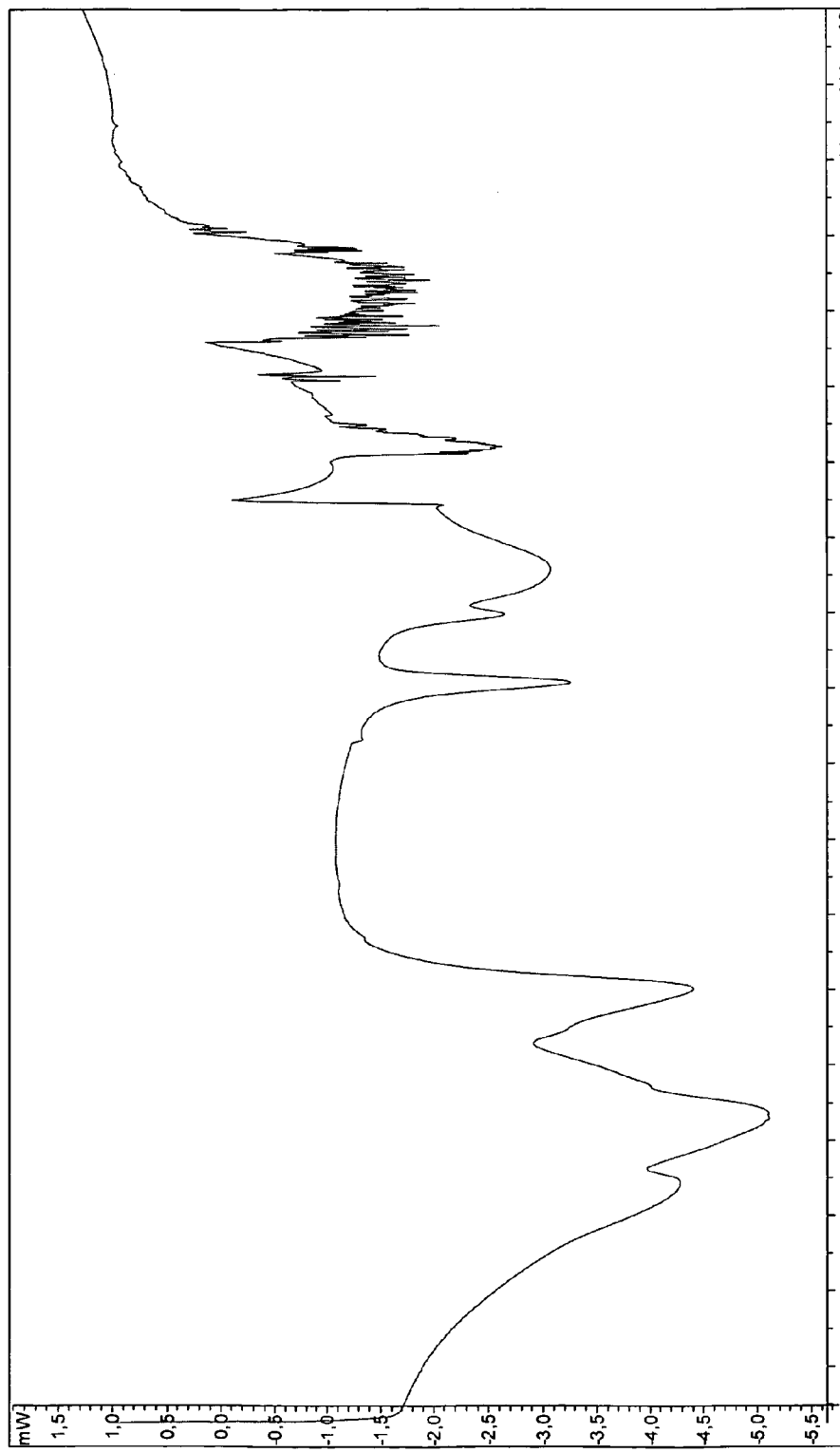
FIG. 8 shows a DSC scan of form S3 (Mettler-Toledo DSC 821, 5 K/min, nitrogen purge gas 50 ml/min).
Figure 9:
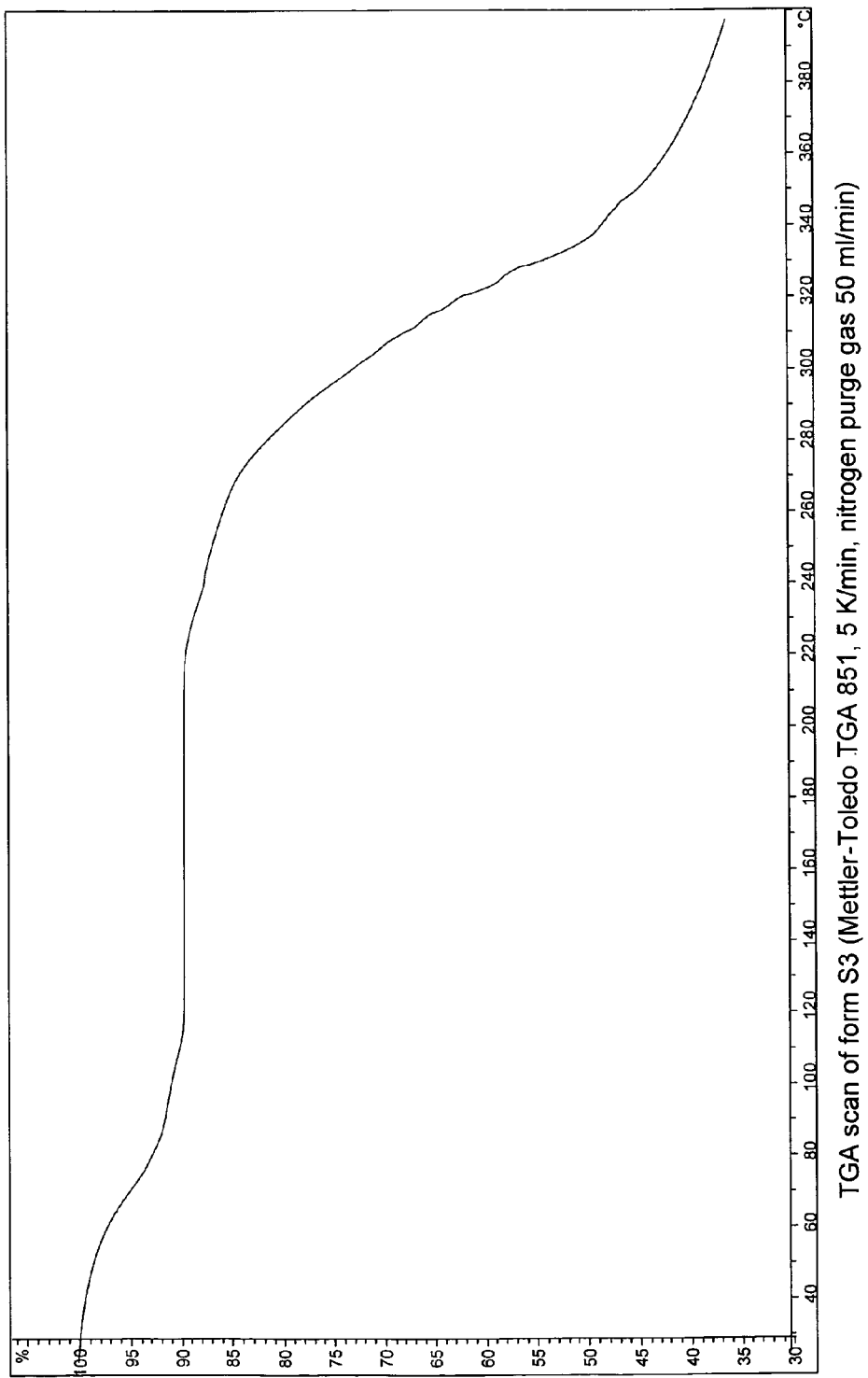
FIG. 9 shows a TGA scan of form S3 (Mettler-Toledo TGA 851, 5 K/min, nitrogen purge gas 50 ml/min).

The DSC and TGA spectra showing the thermal analysis (Mettler-Toledo DSC 821, 5 K/min, nitrogen purge gas 50 ml/min; Mettler-Toledo TGA 851, 5 K/min, nitrogen purge gas 50 ml/min) and the melting/decomposition temperature given above is shown in FIG. 8 and FIG. 9.

Preferably, the tetrasolvates as described herein, more preferably the tetrahydrates as described herein and especially the crystalline form S3 can be characterised, alternatively or additionally, by Powder X-Ray Diffraction and more preferably by the Powder X-Ray Diffraction pattern comprising one or more of the Powder X-ray peaks given below, more preferably comprising 3 or more of the Powder X-ray peaks given below, even more preferably 6 or more of the Powder X-ray peaks given below, and especially comprising all of the of the Powder X-ray peaks given below:

| No. | D ± 0.1 [Å] | °2 θ (Cu—Kα$_1$ radiation) ± 0.1° | Miller indizes | | |
|---|---|---|---|---|---|
| | | | h | k | l |
| 1 | 12.98 | 6.8 | 0 | 2 | 0 |
| 2 | 12.25 | 7.2 | 0 | 1 | 1 |
| 5 | 7.50 | 11.8 | 1 | 1 | 1 |
| 11 | 4.88 | 18.2 | 0 | 5 | 1 |
| 12 | 4.67 | 19.0 | 2 | 0 | 1 |
| 13 | 4.49 | 19.8 | 2 | 1 | 0 |
| 14 | 4.11 | 21.6 | 1 | 3 | 1 |
| 15 | 3.99 | 22.3 | 2 | 1 | 3 |

Preferably, the tetrasolvates as described herein, more preferably the tetrahydrates as described herein and especially the crystalline form S3 can be characterised, alternatively or additionally, by Powder X-Ray Diffraction more preferably by the Powder X-Ray Diffraction pattern comprising one or more of the Powder X-ray peaks given below, more preferably comprising 9 or more of the Powder X-ray peaks given below, even more preferably 12 or more of the Powder X-ray peaks given below, and especially comprising all of the of the Powder X-ray peaks given below:

| No. | D [Å] | °2 θ (Cu—Kα$_1$ radiation) ± 0.1° | Miller indizes | | |
|---|---|---|---|---|---|
| | | | h | k | l |
| 1 | 12.98 | 6.8 | 0 | 2 | 0 |
| 2 | 12.25 | 7.2 | 0 | 1 | 1 |
| 3 | 8.91 | 9.9 | 1 | 0 | 1 |
| 4 | 7.83 | 11.3 | 1 | 1 | 0 |
| 5 | 7.50 | 11.8 | 1 | 1 | 1 |
| 6 | 7.34 | 12.1 | 0 | 3 | 1 |
| 7 | 6.94 | 12.7 | 0 | 0 | 2 |
| 9 | 6.13 | 14.5 | 0 | 2 | 2 |
| 10 | 5.15 | 17.2 | 1 | 2 | 2 |
| 11 | 4.88 | 18.2 | 0 | 5 | 1 |
| 12 | 4.67 | 19.0 | 2 | 0 | 1 |
| 13 | 4.49 | 19.8 | 2 | 1 | 0 |
| 14 | 4.11 | 21.6 | 1 | 3 | 1 |
| 15 | 3.99 | 22.3 | 2 | 1 | 3 |

Preferably, the tetrasolvates as described herein, more preferably the tetrahydrates as described herein and especially the crystalline form S3 can be characterised, alternatively or additionally, by Powder X-Ray Diffraction and more preferably by the Powder X-Ray Diffraction pattern comprising one or more of the Powder X-ray peaks given below, more preferably comprising 10 or more of the Powder X-ray peaks given below, even more preferably 13 or more of the Powder X-ray peaks given below, and especially comprising all of the of the Powder X-ray peaks given below:

| No. | D ± 0.1 [Å] | °2 θ (Cu—Kα$_1$ radiation) ± 0.1° | Miller indizes | | |
|---|---|---|---|---|---|
| | | | h | k | l |
| 1 | 12.98 | 6.8 | 0 | 2 | 0 |
| 2 | 12.25 | 7.2 | 0 | 1 | 1 |
| 3 | 8.91 | 9.9 | 1 | 0 | 1 |

-continued

| No. | D ± 0.1 [Å] | °2 θ (Cu—Kα₁ radiation) ± 0.1° | Miller indizes | | |
|---|---|---|---|---|---|
| | | | h | k | l |
| 4 | 7.83 | 11.3 | 1 | 1 | 0 |
| 5 | 7.50 | 11.8 | 1 | 1 | 1 |
| 6 | 7.34 | 12.1 | 0 | 3 | 1 |
| 7 | 6.94 | 12.7 | 0 | 0 | 2 |
| 8 | 6.50 | 13.6 | 0 | 4 | 0 |
| 9 | 6.13 | 14.5 | 0 | 2 | 2 |
| 10 | 5.15 | 17.2 | 1 | 2 | 2 |
| 11 | 4.88 | 18.2 | 0 | 5 | 1 |
| 12 | 4.67 | 19.0 | 2 | 0 | 1 |
| 13 | 4.49 | 19.8 | 2 | 1 | 0 |
| 14 | 4.11 | 21.6 | 1 | 3 | 1 |
| 15 | 3.99 | 22.3 | 2 | 1 | 3 |

Figure 10:
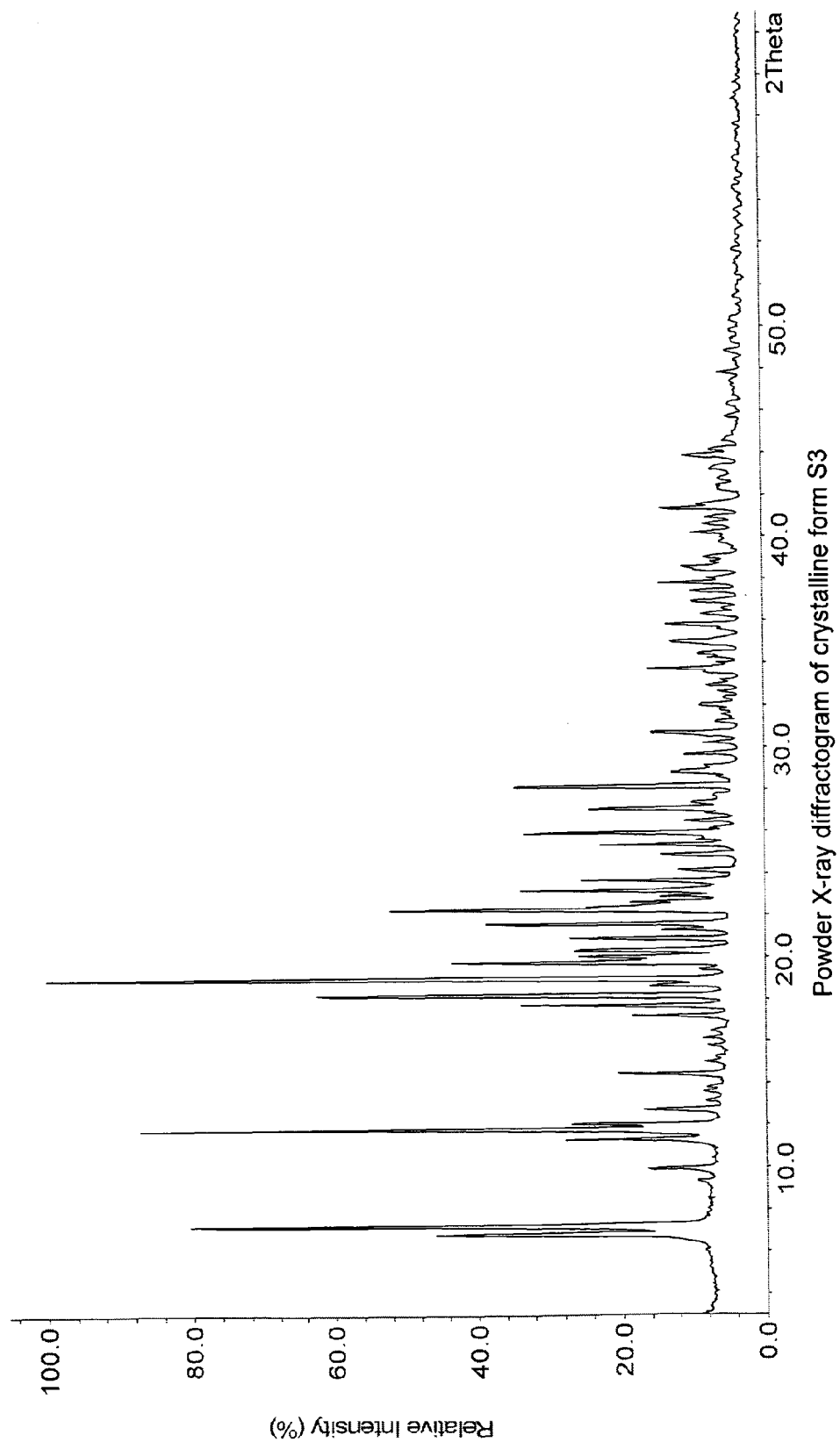
FIG. 10 shows a powder X-ray diffractogram of crystalline form S3.

FIG. 10 shows the Powder X-ray diffractogram of crystalline form S3

The Powder X-Ray Diffraction and more preferably the Powder X-Ray Diffraction pattern is preferably performed or determined as described herein and especially performed or determined by standard techniques as described in the European Pharmacopeia 6$^{th}$ Edition chapter 2.9.33, and is even more preferably obtained with the parameters Cu—Kα₁ radiation and/or λ=1.5406 Å, preferably on a Stoe StadiP 611 KL diffractometer.

Preferably, the tetrasolvates as described herein, more preferably the tetrahydrates as described herein and especially the crystalline form S3 can be characterised, alternatively or additionally, by Single Crystal X-Ray Structure Data, for example Single Crystal X-Ray Structure Data obtained on a diffractometer preferably equipped with a graphite monochromator and CCD Detector, preferably using Mo K$_α$ radiation, preferably at a temperature of 298 K±5 K, and even more preferably on a XCalibur diffractometer from Oxford Diffraction equiped with graphite monochromator and CCD Detector using Mo K$_α$ radiation at about 298 K.

According to the Single Crystal X-Ray Structure Data obtained, the tetrahydrates of the compound of formula Id as described herein and especially the crystalline form S3 crystallises in the orthorhombic space group P 2₁ 2₁ 2₁ with the lattice parameters a=9.6 Å, b=25.9 Å, c=13.9 Å (±0.1 Å) and the unit cell volume is preferably is 3396 (±10) Å³ From the single crystal structure it is obvious that form S3 represents a tetrasolvate and more specifically a tetrahydrate.

Figure 11:
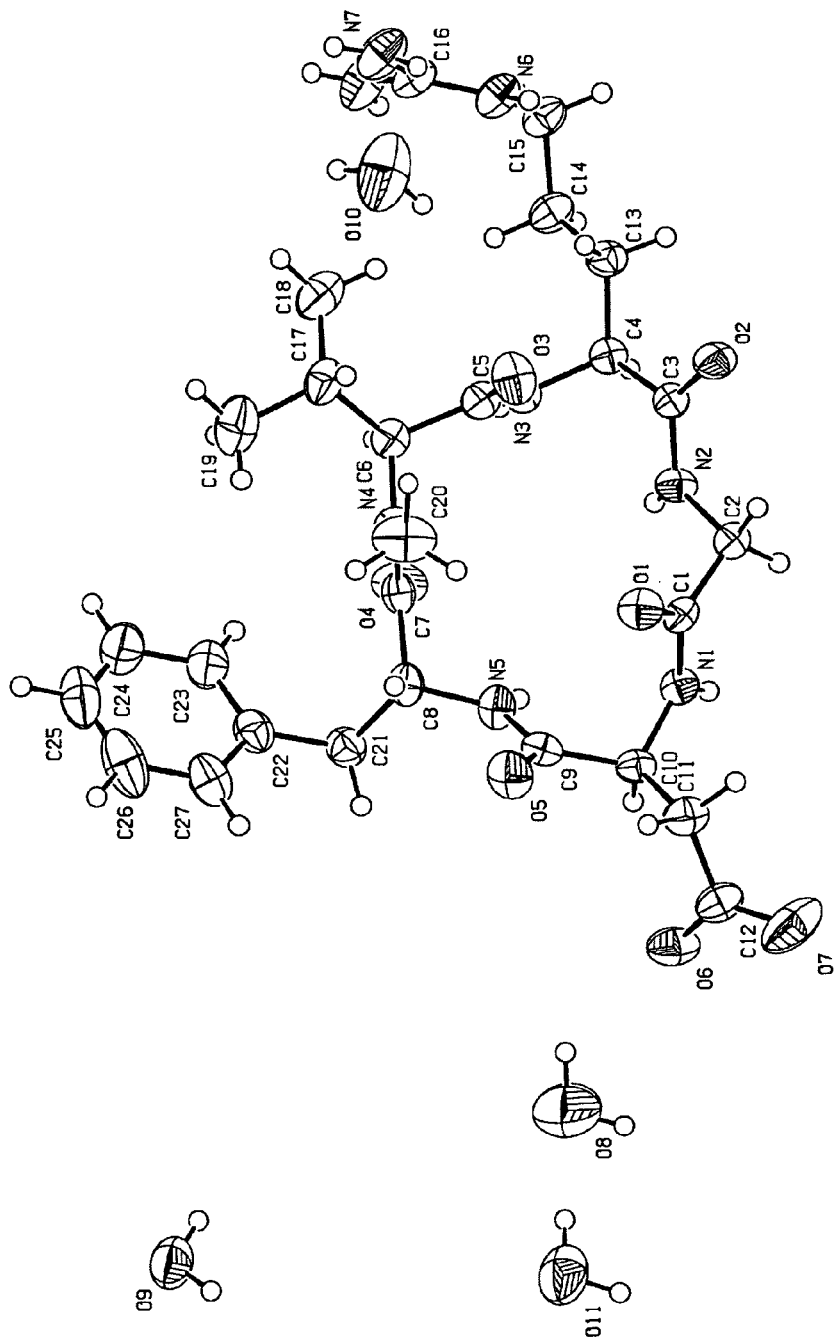
FIG. 11 shows a single crystal structure of form S3.

The Single Crystal X-Ray Structure is depicted in FIG. 11.

Preferably, the tetrasolvates as described herein, more preferably the tetrahydrates as described herein and especially the crystalline form S3 can be characterised, alternatively or additionally, by the infrared-spectroscopy data comprising one or more of the band positions (±2 cm$^{-1}$) given below, more preferably comprising 3 or more of the band positions (±2 cm$^{-1}$) given below, even more preferably comprising 6 or more of the band positions (±2 cm$^{-1}$) given below, and especially comprising all the band positions (±2 cm$^{-1}$) given below, preferably together with the relative intensities given in brackets:

3319 cm$^{-1}$ (s), 3067 cm$^{-1}$ (s), 2966 cm$^{-1}$ (s), 1668 cm$^{-1}$ (s), 1541 cm$^{-1}$ (s), 1395 cm$^{-1}$ (s), 704 cm$^{-1}$ (m)

More preferably, the tetrasolvates as described herein, more preferably the tetrahydrates as described herein and especially the crystalline form S3 can be characterised, alternatively or additionally, by the infrared-spectroscopy data comprising one or more of the band positions (±2 cm$^{-1}$) given below, more preferably comprising 6 or more of the band positions (±2 cm$^{-1}$) given below, even more preferably comprising 9 or more of the band positions (±2 cm$^{-1}$) given below, and especially comprising all the band positions (±2 cm$^{-1}$) given below, preferably together with the relative intensities given in brackets:

3428 cm$^{-1}$ (s), 3319 cm$^{-1}$ (s), 3067 cm$^{-1}$ (s), 2966 cm$^{-1}$ (s), 2874 cm$^{-1}$ (m), 1668 cm$^{-1}$ (s), 1541 cm$^{-1}$ (s), 1455 cm$^{-1}$ (s), 1395 cm$^{-1}$ (s), 1232 cm$^{-1}$ (m), 704 cm$^{-1}$ (m)

The relative intensities given in brackets are preferably defined as follows:* "s"=strong (transmittance preferably ≤50%), "m"=medium (preferably 50%<transmittance≤70%), "w"=weak (transmittance preferably >70%)

The IR or FT-IR spectrum is preferably obtained using a KBr pellet as sample preparation technique.

The IR-spectroscopy data is preferably obtained by FT-IR-spectroscopy, The IR-spectroscopy data or FT-IR-spectroscopy data is preferably obtained by standard techniques as described in the European Pharmacopeia 6$^{th}$ Edition chapter 2.02.24. For the measurement of the FT-IR-spectra, preferably a Bruker Vector 22 spectrometer is used. FT-IR spectra are preferably base-line corrected, preferably using Bruker OPUS software.

Figure 12:
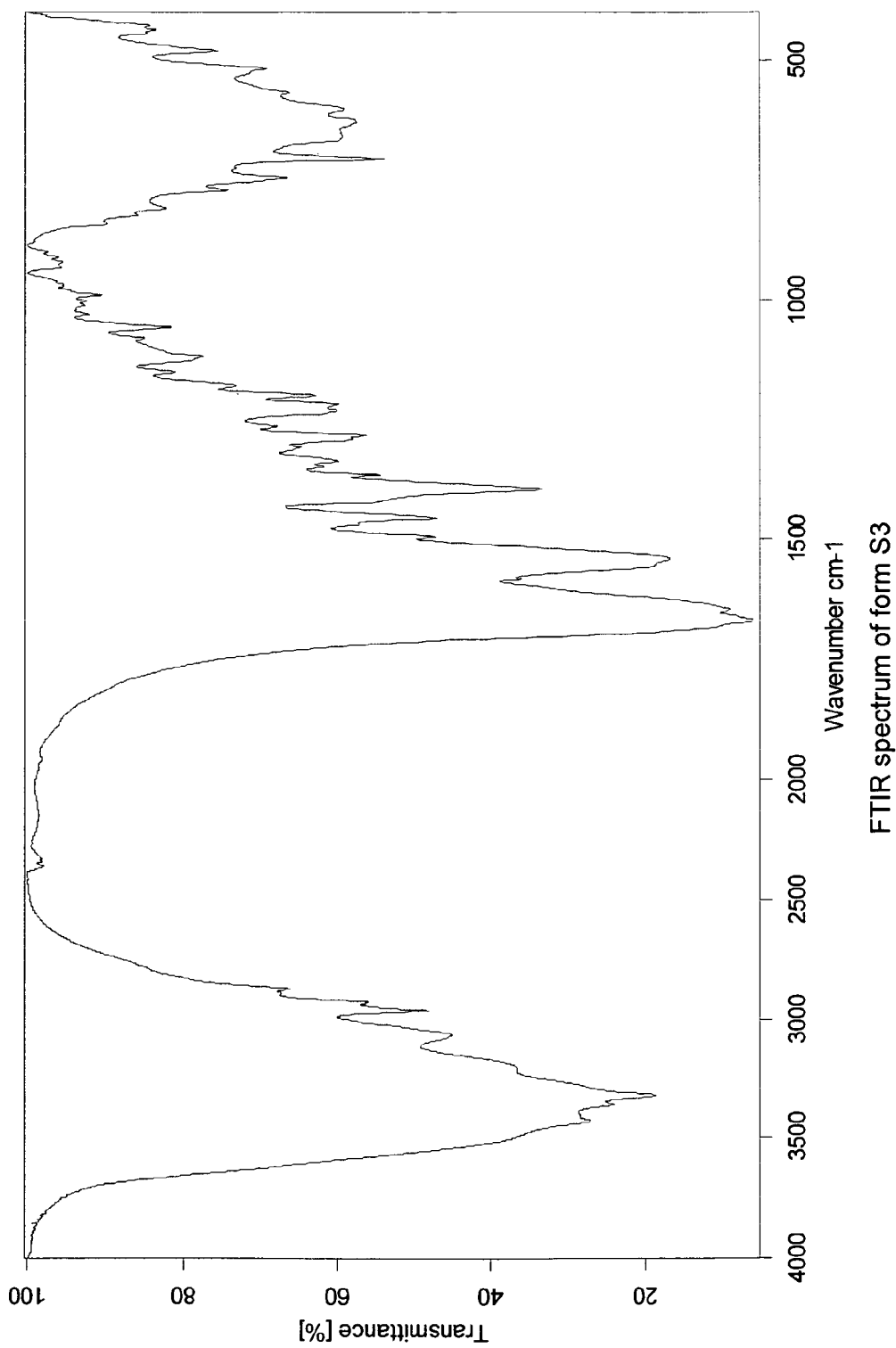
FIG. 12 shows an FTIR spectrum of form S3.

The FT-IR spectra of the tetrasolvates as described herein, more preferably the tetrahydrates as described herein and especially the crystalline form S3 is given in FIG. 12.

Preferably, the tetrasolvates as described herein, more preferably the tetrahydrates as described herein and especially the crystalline form S3 can be characterised, alternatively or additionally, by the Raman-spectroscopy data comprising one or more of the band positions (±2 cm$^{-1}$) given below, more preferably comprising 4 or more of the band positions (±2 cm$^{-1}$) given below, even more preferably comprising 7 or more of the band positions (±2 cm$^{-1}$) given below, and especially comprising all the band positions (±2 cm$^{-1}$) given below, preferably together with the relative intensities given in brackets:

3069 cm$^{-1}$ (m), 2931 cm$^{-1}$ (s), 1666 cm$^{-1}$ (m), 1607 cm$^{-1}$ (w), 1443 cm$^{-1}$ (w), 1339 cm$^{-1}$ (w), 1205 cm$^{-1}$ (w), 1004 cm$^{-1}$ (s), 911 cm$^{-1}$ (m).

More preferably, the tetrasolvates as described herein, more preferably the tetrahydrates as described herein and especially the crystalline form S3 can be characterised, alternatively or additionally, by the Raman-spectroscopy data comprising one or more of the and positions (±2 cm$^{-1}$) given below, more preferably comprising 9 or more of the band positions (±2 cm$^{-1}$) given below, even more preferably comprising 12 or more of the band positions (±2 cm$^{-1}$) given below, and especially comprising all the band positions (±2 cm$^{-1}$) given below, preferably together with the relative intensities given in brackets:

3069 cm$^{-1}$ (m), 2931 cm$^{-1}$ (s), 1666 cm$^{-1}$ (m), 1607 cm$^{-1}$ (w), 1585 cm$^{-1}$ (w), 1443 cm$^{-1}$ (w), 1339 cm$^{-1}$ (w), 1205 cm$^{-1}$ (w), 1122 cm$^{-1}$ (w), 1033 cm$^{-1}$ (w), 1004 cm$^{-1}$ (s), 936 cm$^{-1}$ (w), 911 cm$^{-1}$ (m), 825 cm$^{-1}$ (w), 624 cm$^{-1}$ (w), 519 cm$^{-1}$ (w),

The relative intensities given in brackets are preferably defined as follows: "s"=strong (relative Raman intensity preferably ≥0.04), "m"=medium (preferably 0.04>relative Raman intensity≥0.02), "w"=weak (relative Raman intensity preferably <0.02)

The Raman or FT-Raman spectrum is preferably obtained using Aluminium-cups as sample holders for the respective solid material.

The Raman-spectroscopy data is preferably obtained by FT-Raman-spectroscopy, The Raman-spectroscopy data or FT-Raman-spectroscopy data is preferably obtained by standard techniques as described in the European Pharmacopeia 6$^{th}$ Edition chapter 2.02.24 and/or 2.02.48. For the measurement of the FT-Raman-spectra, preferably a Bruker RFS 100 spectrometer is used. FT-Raman spectra are preferably baseline corrected, preferably using Bruker OPUS software.

Figure 13:
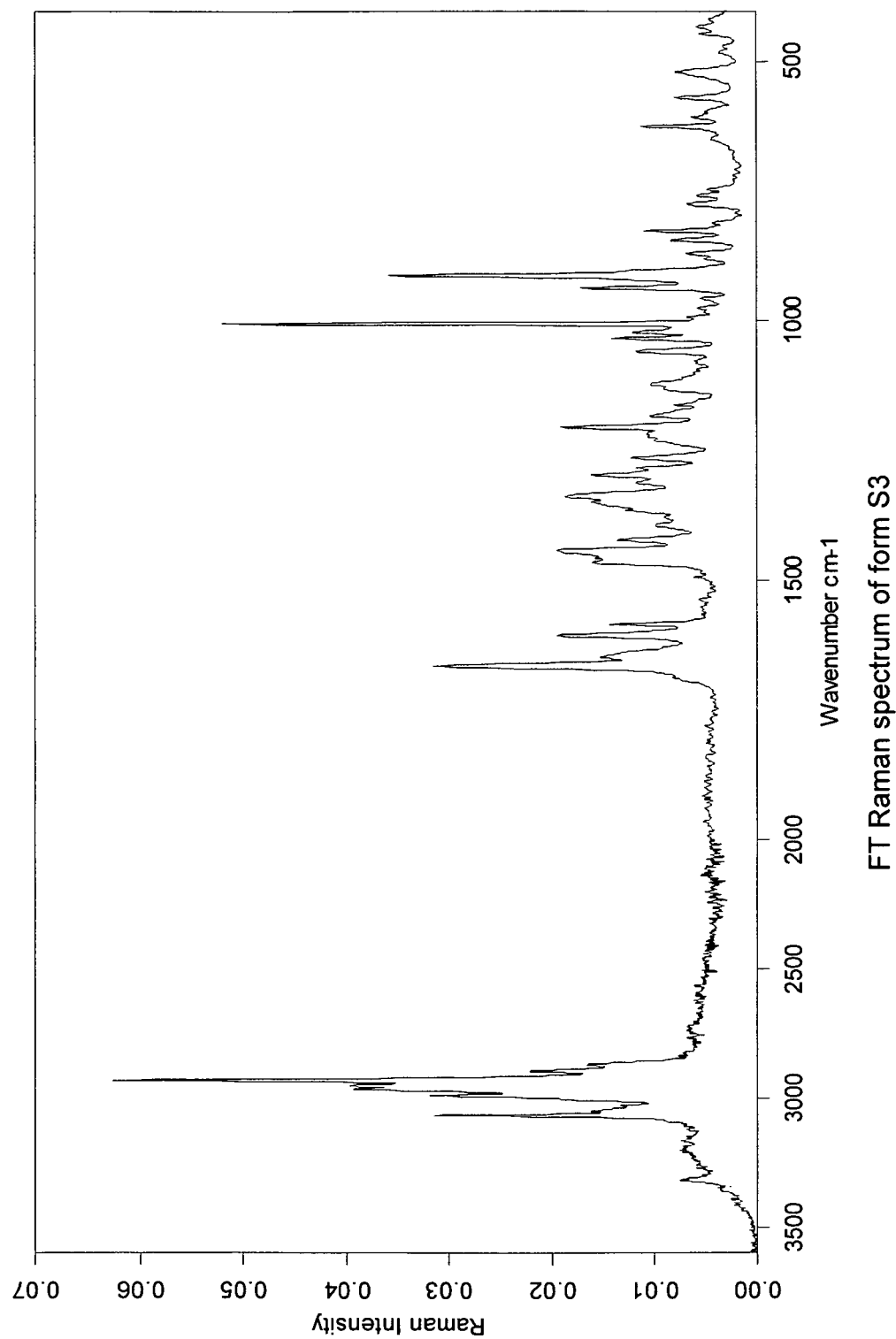
FIG. 13 shows an FT Raman spectrum of form S3.

The FT-Raman spectra of the tetrasolvates as described herein and especially the crystalline form S3 is given in FIG. 13.

Figure 14:
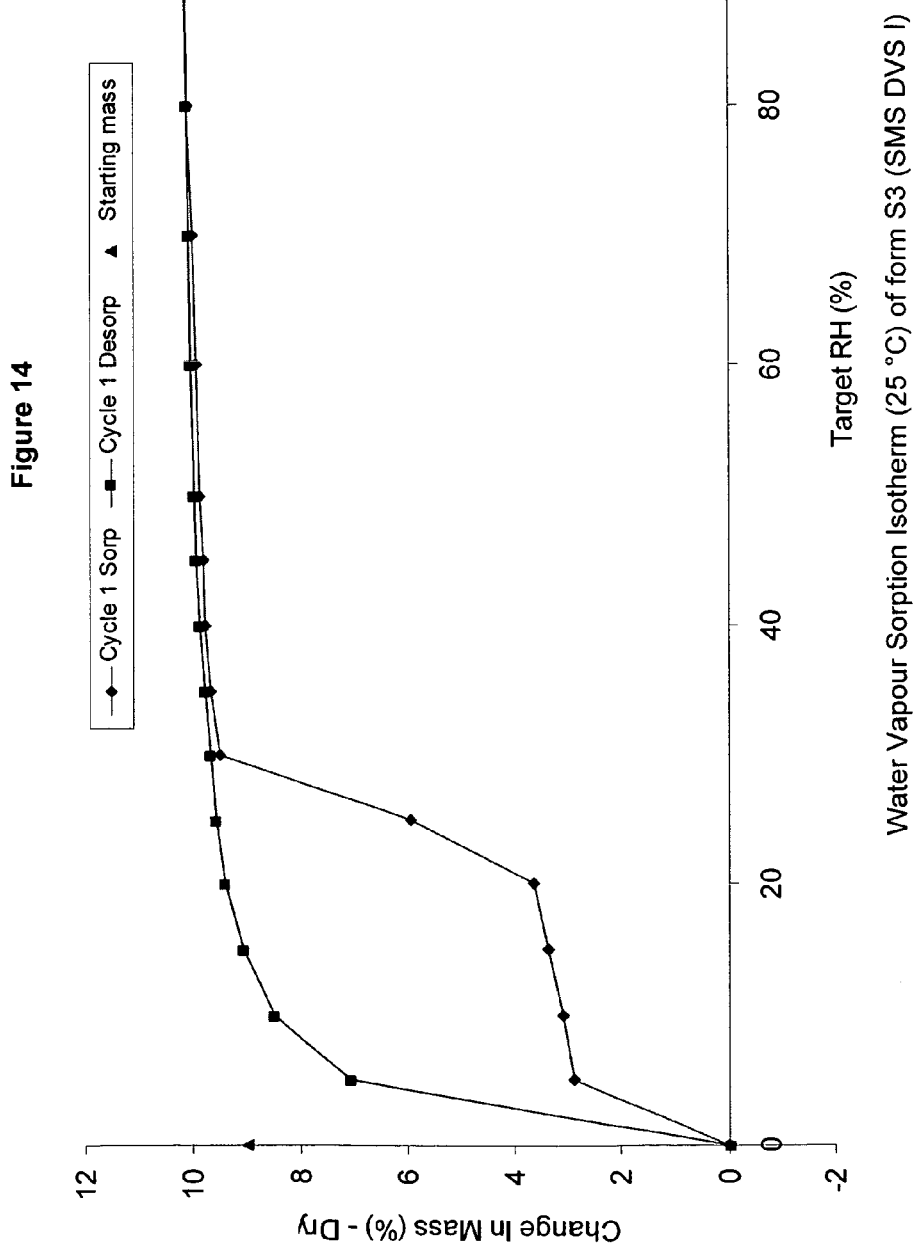
FIG. 14 shows a water vapor sorption isotherm (25° C.) of form S3 (SMS DVS Instinsic).

Preferably, the tetrasolvates as described herein, more preferably the tetrahydrates as described herein and especially the crystalline form S3 can be characterised, alternatively or additionally, by dynamic vapour experiments. The results can be obtained by standard techniques as described in Rolf Hilfiker, 'Polymorphism in the Pharmaceutical Industry', Wiley-VCH. Weinheim 2006 (Chapter 9: Water Vapour Sorption, and references therein). The Water Vapour Sorption behaviour shows small water uptake levels up to 98% rh, and the anhydrates as described herein and especially the crystalline form S3 can be classified as non-hygroscopic acc. to Ph. Eur. criteria. No formation or conversion to a hydrate is observed. Water Vapor Sorption isotherm (25° C.) of crystalline form S3 (SMS DVS Intrinsic) is given in FIG. 14.

Overall, the thermal analysis data given herein confirms the tetrahydrate structure, with complete dehydration observed at elevated temperature (for the tetrahydrate the calculated water content is 10.9 wt %) in the TGA.

Water vapour sorption data show that even under dry conditions (0% rh) at 25° C., only ~9 wt % water are split-off, showing that preferably no complete dehydration of the structure occurs.

Surprisingly, it has been found that the water molecules within the hydrates as described herein and especially the water molecules within the tetrahydrates as described herein can be substituted, partially or totally, by alcohol molecules, preferably by alcohol molecules selected from the group consisting of monools, diols or triols having 1 to 6 carbon atoms, more preferably monools having 1 to 4 carbon atoms and especially monools selected from the group consisting of methanol and ethanol, and mixtures thereof.

Experimental methods, such as dynamic vapour sorption/desorption experiments, single crystal X-Ray experiments and/or powder x-ray experiments show that starting e.g. from the tetrahydrate characterized as crystalline form S3, the water molecules of said tetrahydrate can be partly and/or about totally removed from said tetrahydrate and/or be substituted by methanol and/or ethanol.

For example, dynamic vapour sorption/desorption experiments, preferably using vapours of organic solvents and/or water, preferably vapours of organic solvents selected from one or more alcohols preferably alcohols as defined herein, and/or water and especially vapours of methanol, ethanol and/water, show that the water molecules from said tetrahydrate can continuously be substituted by alcohol molecules and especially methanol and/or ethanol molecules, until a tetra alcohol solvate is formed.

Thus, crystalline forms that can be characterised as tetrasolvates are obtainable, which have a solvent content between up to approximately 100% of water (referring to 4 molecules of water per molecule of the compound according to formula Id, i.e. referring a tetrahydrate) and a solvent content of up to approximately 100% of alcohol (referring to 4 molecules of alcohol per molecule of the compound according to formula Id, i.e. referring a tetraalcoholate) and preferably the intermediates in between.

The results are further discussed above and/or below and especially discussed in the Tables 1 and 2 given below. For example, metastable crystalline solvates being mixed Dihydrate-dialcoholates (referring to 2 molecules of water and 2 molecules of alcohol per molecule of the compound according to formula Id), later in detail characterized as Dihydrate-dimethanolate and crystalline form S1 and as Dihydrate-diethanolate and crystalline form S2, respectively, can be obtained and are discussed in detail above and/or below.

Special reference in this regard is given to the Tables 1 and 2 given below and the paragraphs relating thereto.

The following tables show the respective calculated gravimetric water and/or methanol contents for tetrasolvates ranging from tetrahydrate to tetraacoholate; in this calculation, integer steps in the solvate stoichiometry have been used based on one molecule of the compound according to formula Id, and in total four molecules of the respective solvent or solvent mixture in said tetrasolvates. This can preferably be expressed by the following formula: [cyclo-(Arg-Gly-Asp-DPhe-NMe-Val)].[Alcohol]$_x$.[H$_2$O]$_{(4-x)}$ with $0 \leq x \leq 4$).

TABLE 1

(water/methanol exchange)

| Methanol equivalents [x] | Water equivalents [4-x] | molar mass [g/mol] | gravimetric methanol content [%] | gravimetric water content [%] | molar mass of solvate relative to tetrahydrate [%] |
|---|---|---|---|---|---|
| 0 | 4 | 660.75 | 0.0 | 10.9 | 100.0% |
| 1 | 3 | 674.77 | 4.7 | 8.0 | 102.1% |
| 2 | 2 | 688.79 | 9.3 | 5.2 | 104.2% |
| 3 | 1 | 702.81 | 13.7 | 2.6 | 106.4% |
| 4 | 0 | 716.83 | 17.9 | 0.0 | 108.5% |

TABLE 2

(water/ethanol exchange)

| Ethanol equivalents [x] | Water equivalents [4-x] | molar mass [g/mol] | gravimetric ethanol content [%] | gravimetric water content [%] | molar mass of solvate relative to tetrahydrate [%] |
|---|---|---|---|---|---|
| 0 | 4 | 660.75 | 0.0 | 10.9 | 100.0 |
| 1 | 3 | 688.80 | 6.7 | 7.8 | 104.3 |
| 2 | 2 | 716.85 | 12.9 | 5.0 | 108.5 |
| 3 | 1 | 744.90 | 18.6 | 2.4 | 112.7 |
| 4 | 0 | 772.95 | 23.8 | 0.0 | 117.0 |

In the respective dynamic vapor sorption experiments discussed in more detail herein using methanol vapor at 98% relative saturation for the Dihydrate-dimethanolate/crystalline form S1 at 25° C. starting with the tetrahydrate a mass gain of 9% has been obtained. This is in good agreement with the above shown results for the tetramethanolate (calculated 108.5%, i.e. 8.5% of mass gain).

In the respective dynamic vapor sorption experiments discussed in more detail herein using ethanol vapor at 98% relative saturation for the Dihydrate-diethanolate/crystalline form S2 at 25° C. starting with the tetrahydrate a mass gain of 17% has been obtained. This is in good agreement with the above shown results for the tetraethanolate (calculated 117.0%, i.e. 17.0% of mass gain).

As is shown above and/or below, the tetrasolvates as described herein are preferably convertible, more preferably convertible between essentially pure tetrahydrates and essentially pure tetraalcoholates, and potentially all intermediates in between, preferably exemplified by the mixed Dihydrate-dialcoholates which are discussed in detail below. Since those tetrasolvates have very similar structural features, e.g. the crystallographic parameters, the analytical data and/or physical properties and additionally are convertible, it is clear that the tetrasolvates form a class or subclass of the crystalline forms as described herein and/or of the solid materials as described herein.

For reasons of clarity, tetrasolvates that contain three or more equivalents of water (i.e. have a water content of >75 mole %, based on the total amount of solvent contained in the respective crystalline form) and contain less than one equivalent of one or more solvents other than water, preferably less than one equivalent of one or more alcohols, preferably selected from methanol and ethanol, are preferably referred to as hydrates, hydrates as described herein or hydrate-tetrasolvates.

For reasons of clarity, tetrasolvates that contain close to four equivalents of water (i.e. have a water content of >90 mole % and preferably of >95 mole %, based on the total amount of solvent contained in the respective crystalline form) are preferably referred to as tetrahydrates or tetrahydrates as described herein.

For reasons of clarity, tetrasolvates that contain one or more equivalents of alcohol (i.e. have an alcohol content of 25 mole % or higher, based on the total amount of solvent contained in the respective crystalline form) are preferably referred to as alcoholates, alcoholates as described herein or alcoholate-tetrasolvates. Examples of such alcoholates or alcoholate-tetrasolvates are the methanolate and/or ethanolate (or methanolate-tetrasolvate and/or ethanolate-tetrasolvate) as described herein.

For reasons of clarity, tetrasolvates that contain close to four equivalents of one or more alcohols (i.e. have an total alcohol content of >90 mole % and preferably of >95 mole %, based on the total amount of solvent contained in the respective crystalline form) are preferably referred to as tetraalcoholates or tetraalcoholates as described herein. Examples of such tetraalcoholates are the tetramethanolate and/or tetraethanolate or the tetramethanolate and/or tetraethanolate as described herein.

Two more tetrasolvates that are alcohol solvates or alcoholate-tetrasolvates in this regard and that can be further characterised as Dihydrate-dialcoholates are described below:

Preferably, the tetrasolvates as described herein, more preferably the Dihydrate-dimethanolate and especially the crystalline form S1 can be characterised, alternatively or additionally, by a melting/decomposition temperature of >205° C., more preferably 210±5° C. melting/decomposition ° C. or higher, and especially 210±5° C. melting/decomposition. Preferably, said melting/decomposition temperature obtained for the tetrasolvates as described herein, more preferably obtained for the Dihydrate-dimethanolate and especially obtained for the crystalline form S1 is <250° C.

The melting/decomposition temperatures and/or thermal behaviors described herein are preferably determined by DSC (Differential Scanning calorimetry) and TGA ((ThermoGravimetric Analysis). DSC and/or TGA methods or generally thermoanalytic methods and suitable devices for determining them are known in the art, for examples from European Pharmacopeia 6$^{th}$ Edition chapter 2.02.34, wherein suitable standard techniques are described. More preferably, for the melting/decomposition temperatures or behaviors and/or the thermoanalysis in general, a Mettler Toledo DSC 821 and/or Mettler Toledo TGA 851 are used, preferably as described in the European Pharmacopeia 6$^{th}$ Edition chapter 2.02.34.

The DSC and TGA measurements of the thermal analysis were performed as given belowe: Mettler-Toledo DSC 821, 5 K/min, nitrogen purge gas 50 ml/min; Mettler-Toledo TGA 851, 5 K/min, nitrogen purge gas 50 ml/min. Preferably, the tetrasolvates as described herein, more preferably the Dihydrate-dimethanolate and especially the crystalline form S1 can be characterised, alternatively or additionally, by Powder X-Ray Diffraction and more preferably by the Powder X-Ray Diffraction pattern comprising one or more of the Powder X-ray peaks given below, more preferably comprising 10 or more of the Powder X-ray peaks given below, even more preferably 12 or more of the Powder X-ray peaks given below, and especially comprising all of the of the Powder X-ray peaks given below:

| No. | D ± 0.1 [Å] | °2 θ (Co—Kα$_1$ radiation) ± 0.1° | Miller indizes | | |
|---|---|---|---|---|---|
| | | | h | k | l |
| 0 | 14.20 | 7.3 | 0 | 0 | 1 |
| 1 | 13.05 | 7.9 | 0 | 2 | 0 |
| 2 | 12.47 | 8.3 | 0 | 1 | 1 |
| 3 | 9.62 | 10.7 | 0 | 2 | 1 |
| 4 | 8.81 | 11.7 | 1 | 1 | 0 |
| 5 | 7.88 | 13.1 | 1 | 0 | −1 |
| 6 | 7.74 | 13.3 | 1 | 0 | 1 |
| 7 | 7.60 | 13.6 | 1 | 1 | −1 |
| 8 | 7.41 | 13.9 | 0 | 3 | 1 |
| 9 | 7.09 | 14.5 | 0 | 0 | 2 |
| 10 | 6.51 | 15.8 | 0 | 4 | 0 |
| 11 | 6.23 | 16.5 | 0 | 2 | 2 |
| 12 | 5.92 | 17.4 | 0 | 4 | 1 |
| 13 | 4.89 | 21.1 | 0 | 5 | 1 |
| 14 | 4.80 | 21.5 | 0 | 4 | 2 |

The PXRD pattern can be successfully indexed with the following monoclinic unit cell (space group P21):
a=9.4 Å, b=25.9 Å, c=14.1 Å(±0.1 Å), β=91.2° (±0.1), V~3430 (±10) Å$^3$ The Powder X-Ray Diffraction and more preferably the Powder X-Ray Diffraction pattern is preferably performed or determined as described herein and especially performed or determined by standard techniques as described in the European Pharmacopeia 6$^{th}$ Edition chapter 2.9.33, and is even more preferably obtained with the parameters Cu—Kα$_1$ radiation and/or λ=1.5406 Å, preferably on a Stoe StadiP 611 KL diffractometer.

Preferably, the tetrasolvates as described herein, more preferably the Dihydrate-dimethanolate and especially the crystalline form S1 can be characterised, alternatively or additionally, by Single Crystal X-Ray Structure Data, for example Single Crystal X-Ray Structure Data obtained on a diffractometer preferably equipped with a graphite monochromator and CCD Detector, preferably using Mo K$_α$ radiation, preferably at a temperature of 298 K±5 K, and even more preferably on a XCalibur diffractometer from Oxford Diffraction equiped with graphite monochromator and CCD Detector using Mo K$_α$ radiation at about 298 K.

More preferably, the tetrasolvates as described herein, more preferably the Dihydrate-dimethanolate and especially the crystalline form S1 can be characterised, alternatively or additionally, by the infrared-spectroscopy data comprising one or more of the band positions (±2 cm$^{-1}$) given below, more preferably comprising 6 or more of the band positions (±2 cm$^{-1}$) given below, even more preferably comprising 9 or more of the band positions (±2 cm$^{-1}$) given below, and especially comprising all the band positions (±2 cm$^{-1}$) given below, preferably together with the relative intensities given in brackets:

3311 cm$^{-1}$ (s), 3067 cm$^{-1}$ (m), 2965 cm$^{-1}$ (m), 2937 cm$^{-1}$ (m), 2875 cm$^{-1}$ (w), 1668 cm$^{-1}$ (s), 1542 cm$^{-1}$ (s), 1456 cm$^{-1}$ (m), 1396 cm$^{-1}$ (m), 1028 cm$^{-1}$ (w), 707 cm$^{-1}$ (m)

The relative intensities given in brackets are preferably defined as follows:* "s"=strong (transmittance preferably ≤50%), "m"=medium (preferably 50%<transmittance≤70%), "w"=weak (transmittance preferably >70%)

The IR or FT-IR spectrum is preferably obtained using a KBr pellet as sample preparation technique.

The IR-spectroscopy data is preferably obtained by FT-IR-spectroscopy, The IR-spectroscopy data or FT-IR-spectroscopy data is preferably obtained by standard techniques as described in the European Pharmacopeia 6$^{th}$ Edition chapter 2.02.24. For the measurement of the FT-IR-spectra, preferably a Bruker Vector 22 spectrometer is used. FT-IR spectra are preferably base-line corrected, preferably using Bruker OPUS software.

More preferably, the tetrasolvates as described herein, more preferably the Dihydrate-dimethanolate and especially the crystalline form S1 can be characterised, alternatively or additionally, by the Raman-spectroscopy data comprising one or more of the and positions (±2 cm$^{-1}$) given below, more preferably comprising 9 or more of the band positions (±2 cm$^{-1}$) given below, even more preferably comprising 12 or more of the band positions (±2 cm$^{-1}$) given below, and especially comprising all the band positions (±2 cm$^{-1}$) given below, preferably together with the relative intensities given in brackets:

3067 cm$^{-1}$ (w), 2936 cm$^{-1}$ (s), 1668 cm$^{-1}$ (m), 1606 cm$^{-1}$ (w), 1585 cm$^{-1}$ (w), 1446 cm$^{-1}$ (w), 1338 cm$^{-1}$ (w), 1203 cm$^{-1}$ (w), 1123 cm$^{-1}$ (w), 1033 cm$^{-1}$ (w), 1004 cm$^{-1}$ (s), 904 cm$^{-1}$ (m), 824 cm$^{-1}$ (w), 624 cm$^{-1}$ (w), 523 cm$^{-1}$ (w).

The relative intensities given in brackets are preferably defined as follows:
"s"=strong (relative Raman intensity preferably ≥0.04), "m"=medium (preferably 0.04>relative Raman intensity≥0.02), "w"=weak (relative Raman intensity preferably <0.02)

The Raman or FT-Raman spectrum is preferably obtained using Aluminium-cups as sample holders for the respective solid material.

The Raman-spectroscopy data is preferably obtained by FT-Raman-spectroscopy, The Raman-spectroscopy data or FT-Raman-spectroscopy data is preferably obtained by standard techniques as described in the European Pharmacopeia 6$^{th}$ Edition chapter 2.02.48. For the measurement of the FT-Raman-spectra, preferably a Bruker RFS 100 spectrometer is used. FT-Raman spectra are preferably base-line corrected, preferably using Bruker OPUS software.

Preferably, the tetrasolvates as described herein, more preferably the Dihydrate-diethanolate and especially the crystalline form S2 can be characterised, alternatively or additionally, by a melting/decomposition temperature of >205° C., more preferably 210±5° C. melting/decomposition ° C. or higher, and especially 210±5° C. melting/decomposition. Preferably, said melting/decomposition temperature obtained for the tetrasolvates as described herein, more preferably the Dihydrate-diethanolate and especially obtained for the crystalline form S2 is <250° C.

The melting/decomposition temperatures and/or thermal behaviors described herein are preferably determined by DSC (Differential Scanning calorimetry) and TGA ((ThermoGravimetric Analysis). DSC and/or TGA methods or generally thermoanalysis methods and suitable devices for determining them are known in the art, for examples from European Pharmacopeia 6$^{th}$ Edition chapter 2.02.34, wherein suitable standard techniques are described. More preferably, for the melting/decomposition temperatures or behaviors and/or the thermoanalysis in general, a Mettler Toledo DSC 821 and/or Mettler Toledo TGA 851 are used, preferably as described in the European Pharmacopeia 6$^{th}$ Edition chapter 2.02.34.

Figure 16:
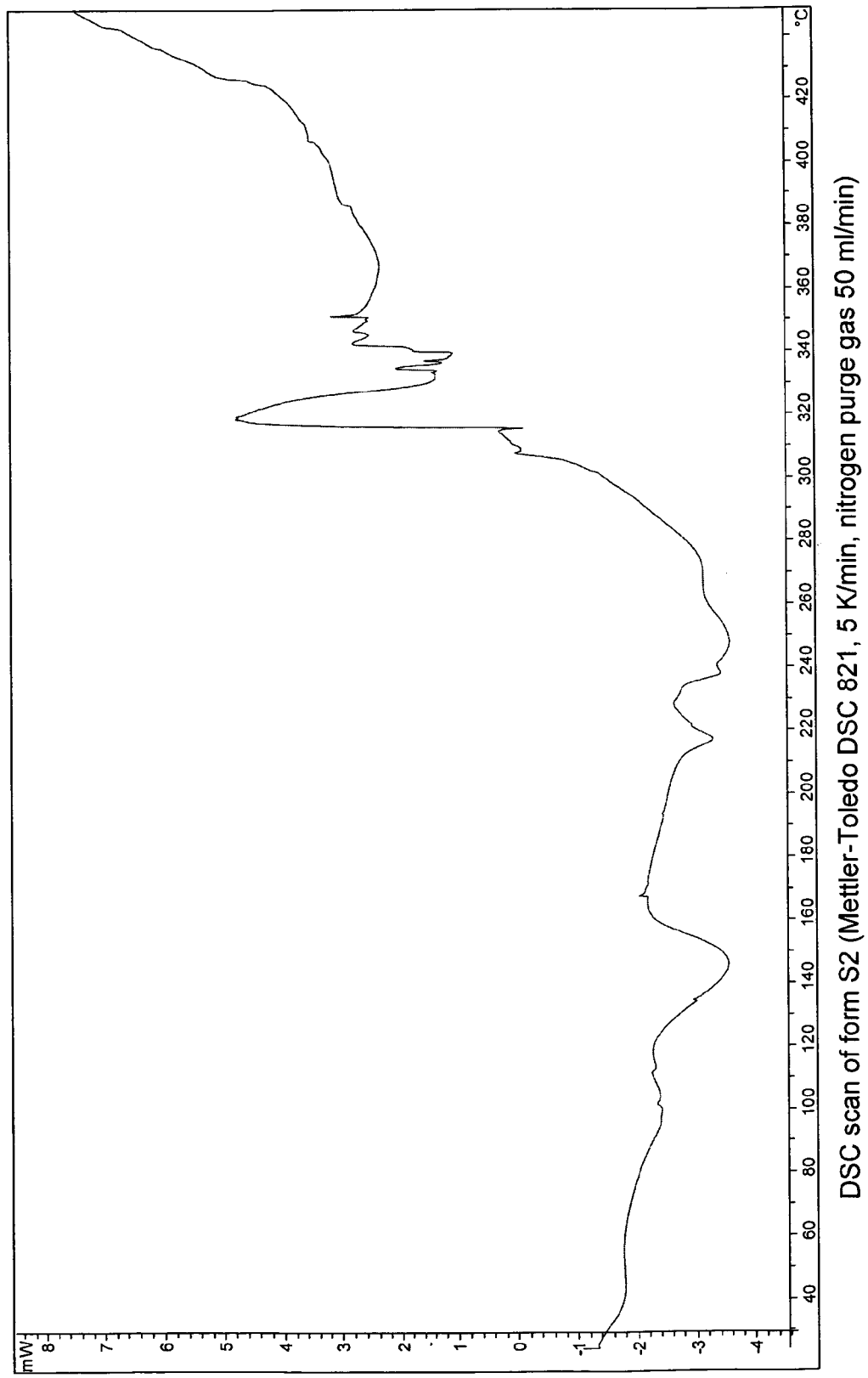
FIG. 16 shows a TGA scan of form S2 (Mettler-Toledo TGA 851, 5 K/min, nitrogen purge gas 50 ml/min).
Figure 17:
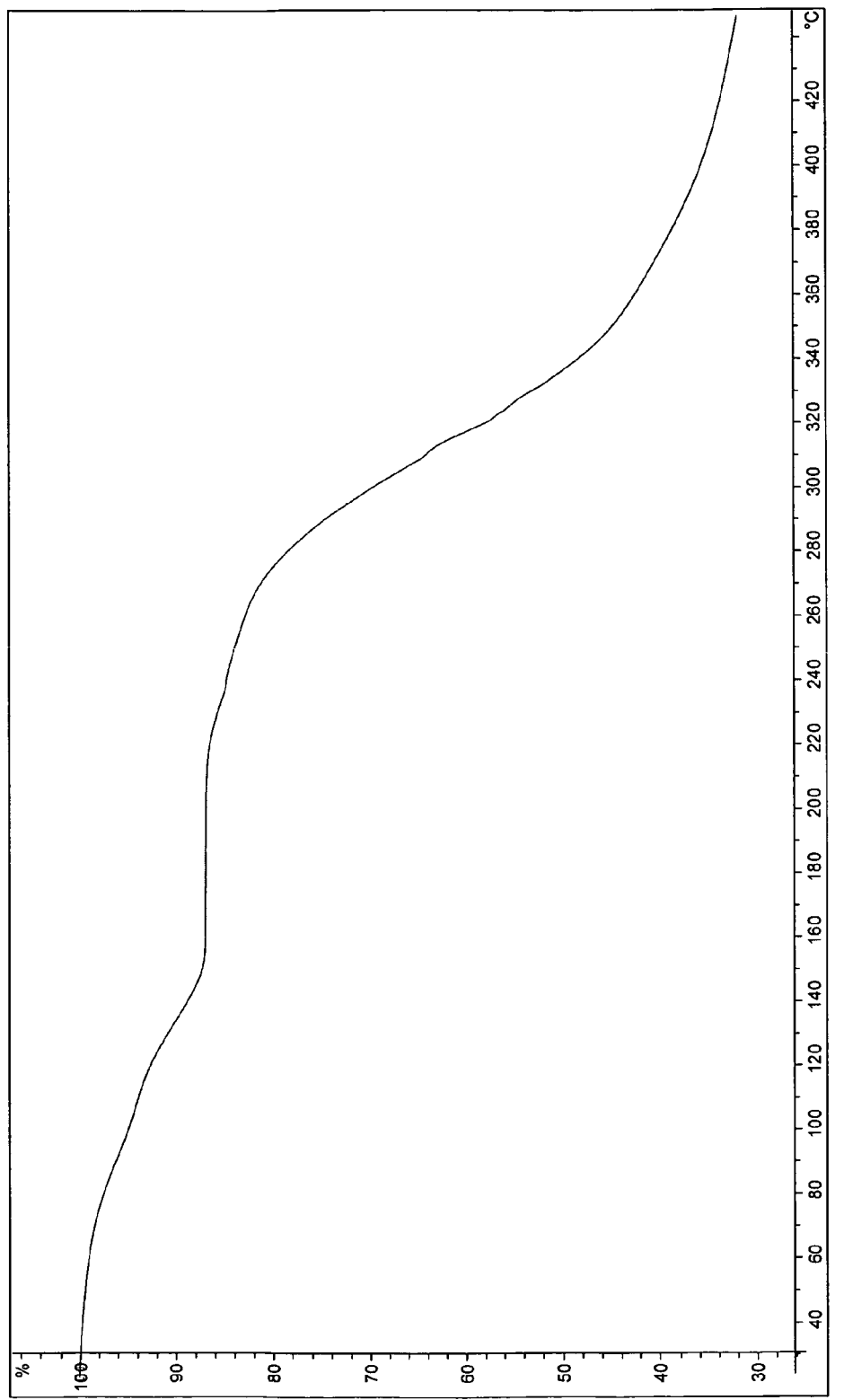
FIG. 17 shows a TGA scan of form S2 (Mettler-Toledo TGA 851, 5 K/min, nitrogen purge gas 50 ml/min).

The DSC and TGA measurements showing the thermal analysis (Mettler-Toledo DSC 821, 5 K/min, nitrogen purge gas 50 ml/min; Mettler-Toledo TGA 851, 5 K/min, nitrogen purge gas 50 ml/min) and the melting/decomposition temperature given above is shown in FIG. 16 and FIG. 17.

Preferably, the tetrasolvates as described herein, more preferably the Dihydrate-diethanolate and especially the crystalline form S2 can be characterised, alternatively or additionally, by Powder X-Ray Diffraction and more preferably by the Powder X-Ray Diffraction pattern comprising one or more of the Powder X-ray peaks given below, more preferably comprising 3 or more of the Powder X-ray peaks given below, even more preferably 5 or more of the Powder X-ray peaks given below, and especially comprising all of the of the Powder X-ray peaks given below:

| No. | D ± 0.1 [Å] | °2 θ (Co—Kα$_1$ radiation) ± 0.1° | Miller indizes h | k | l |
|---|---|---|---|---|---|
| 1 | 13.32 | 7.7 | 2 | 0 | 0 |
| 2 | 12.89 | 8.0 | 1 | 1 | 0 |
| 4 | 7.87 | 13.1 | 0 | 1 | 1 |
| 5 | 7.54 | 13.6 | 1 | 1 | 1 |
| 6 | 7.36 | 14.0 | 0 | 2 | 0 |
| 9 | 4.82 | 21.3 | 1 | 3 | 0 |
| 10 | 4.58 | 22.5 | 1 | 0 | 2 |

Preferably, the tetrasolvates as described herein, more preferably the Dihydrate-diethanolate and especially the crystalline form S2 can be characterised, alternatively or additionally, by Powder X-Ray Diffraction more preferably by the Powder X-Ray Diffraction pattern comprising one or more of the Powder X-ray peaks given below, more preferably comprising 4 or more of the Powder X-ray peaks given below, even more preferably 6 or more of the Powder X-ray peaks given below, and especially comprising all of the of the Powder X-ray peaks given below:

| No. | D [Å] | °2 θ (Co—Kα$_1$ radiation) ± 0.1° | Miller indizes h | k | l |
|---|---|---|---|---|---|
| 1 | 13.32 | 7.7 | 2 | 0 | 0 |
| 2 | 12.89 | 8.0 | 1 | 1 | 0 |
| 4 | 7.87 | 13.1 | 0 | 1 | 1 |
| 5 | 7.54 | 13.6 | 1 | 1 | 1 |
| 6 | 7.36 | 14.0 | 0 | 2 | 0 |
| 7 | 5.01 | 20.6 | 5 | 1 | 0 |
| 9 | 4.82 | 21.3 | 1 | 3 | 0 |
| 10 | 4.58 | 22.5 | 1 | 0 | 2 |

Preferably, the tetrasolvates as described herein, more preferably the Dihydrate-diethanolate and especially the crystalline form S2 can be characterised, alternatively or additionally, by Powder X-Ray Diffraction and more preferably by the Powder X-Ray Diffraction pattern comprising one or more of the Powder X-ray peaks given below, more preferably comprising 10 or more of the Powder X-ray peaks given below, even more preferably 12 or more of the Powder X-ray peaks given below, and especially comprising all of the of the Powder X-ray peaks given below:

| No. | D ± 0.1 [Å] | °2 θ (Co—Kα$_1$ radiation) ± 0.1° | Miller indizes h | k | l |
|---|---|---|---|---|---|
| 0 | 14.73 | 6.9 | 0 | 1 | 0 |
| 1 | 13.32 | 7.7 | 2 | 0 | 0 |
| 2 | 12.89 | 8.0 | 1 | 1 | 0 |
| 3 | 8.78 | 11.7 | 1 | 0 | 1 |
| 4 | 7.87 | 13.1 | 0 | 1 | 1 |
| 5 | 7.54 | 13.6 | 1 | 1 | 1 |
| 6 | 7.36 | 14.0 | 0 | 2 | 0 |
| 7 | 7.10 | 14.5 | 1 | 2 | 0 |
| 8 | 5.01 | 20.6 | 5 | 1 | 0 |
| 9 | 4.82 | 21.3 | 1 | 3 | 0 |
| 10 | 4.58 | 22.5 | 1 | 0 | 2 |
| 11 | 4.38 | 23.6 | 1 | 1 | 2 |
| 12 | 4.28 | 24.1 | 1 | 3 | 1 |
| 13 | 3.81 | 27.1 | 4 | 0 | 2 |
| 14 | 3.69 | 28.0 | 4 | 1 | 2 |

Figure 18:
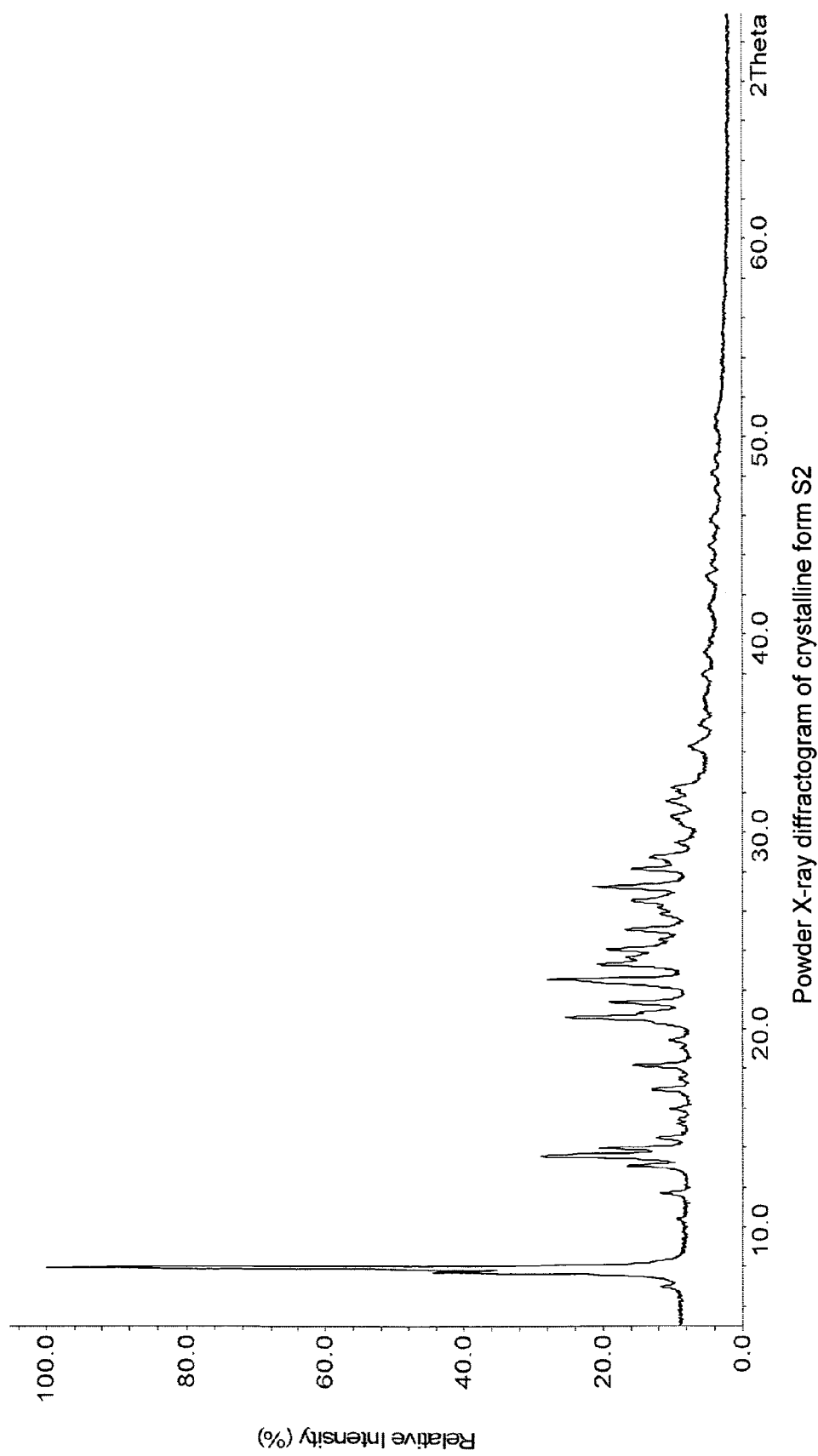
FIG. 18 shows a powder X-ray diffractogram of crystalline form S2.

The Powder X-ray diffractogram of crystalline form S2 is shown in FIG. 18

The PXRD pattern can be successfully indexed with the following orthorhombic unit cell (space group P2$_1$2$_1$2$_1$): a=9.3 Å, b=26.6 Å, c=14.7 Å (±0.1 Å), V~3600 (±10) Å$^3$ The Powder X-Ray Diffraction and more preferably the Powder X-Ray Diffraction pattern is preferably performed or determined as described herein and especially performed or determined by standard techniques as described in the European Pharmacopeia 6$^{th}$ Edition chapter 2.9.33, and is even more preferably obtained with the parameters Cu—Kα$_1$ radiation and/or =1.5406 Å, preferably on a Stoe StadiP 611 KL diffractometer.

Preferably, the tetrasolvates as described herein, more preferably the Dihydrate-diethanolate and especially the crystalline form S2 can be characterised, alternatively or additionally, by Single Crystal X-Ray Structure Data, for example Single Crystal X-Ray Structure Data obtained on a diffractometer preferably equipped with a graphite monochromator and CCD Detector, preferably using Mo K$_\alpha$ radiation, preferably at a temperature of 298 K±5 K, and even more preferably on a XCalibur diffractometer from Oxford Diffraction equipped with graphite monochromator and CCD Detector using Mo K$_\alpha$ radiation at about 298 K.

Preferably, the tetrasolvates as described herein, more preferably the Dihydrate-diethanolate and especially the crystalline form S2 can be characterised, alternatively or additionally, by the infrared-spectroscopy data comprising one or more of the band positions (±2 cm$^{-1}$) given below, more preferably comprising 3 or more of the band positions (±2 cm$^{-1}$) given below, even more preferably comprising 6 or more of the band positions (±2 cm$^{-1}$) given below, and especially comprising all the band positions (±2 cm$^{-1}$) given below, preferably together with the relative intensities given in brackets:
3306 cm$^{-1}$ (s), 2968 cm$^{-1}$ (m), 1668 cm$^{-1}$ (s), 1546 cm$^{-1}$ (s), 1395 cm$^{-1}$ (m), 1223 cm$^{-1}$ (w), 1049 cm$^{-1}$ (w), 705 cm$^{-1}$ (w).

More preferably, the tetrasolvates as described herein, more preferably the Dihydrate-diethanolate and especially the crystalline form S2 can be characterised, alternatively or additionally, by the infrared-spectroscopy data comprising one or more of the band positions (±2 cm$^{-1}$) given below, more preferably comprising 6 or more of the band positions (±2 cm$^{-1}$) given below, even more preferably comprising 9 or more of the band positions (±2 cm$^{-1}$) given below, and especially comprising all the band positions (±2 cm$^{-1}$) given below, preferably together with the relative intensities given in brackets: 3306 cm$^{-1}$ (s), 2968 cm$^{-1}$ (m), 2872 cm$^{-1}$ (m), 1668 cm$^{-1}$ (s), 1546 cm$^{-1}$ (s), 1452 cm$^{-1}$ (w), 1395 cm$^{-1}$ (m), 1223 cm$^{-1}$ (w), 1086 cm$^{-1}$ (w), 1049 cm$^{-1}$ (w), 746 cm$^{-1}$ (w), 705 cm$^{-1}$ (w).

The relative intensities given in brackets are preferably defined as follows:* "s"=strong (transmittance preferably ≤50%), "m"=medium (preferably 50%<transmittance≤70%), "w"=weak (transmittance preferably >70%)

The IR or FT-IR spectrum is preferably obtained using a KBr pellet as sample preparation technique.

The IR-spectroscopy data is preferably obtained by FT-IR-spectroscopy, The IR-spectroscopy data or FT-IR-spectroscopy data is preferably obtained by standard techniques as described in the European Pharmacopeia 6$^{th}$ Edition chapter 2.02.24. For the measurement of the FT-IR-spectra, preferably a Bruker Vector 22 spectrometer is used. FT-IR spectra are preferably base-line corrected, preferably using Bruker OPUS software.

Figure 19:
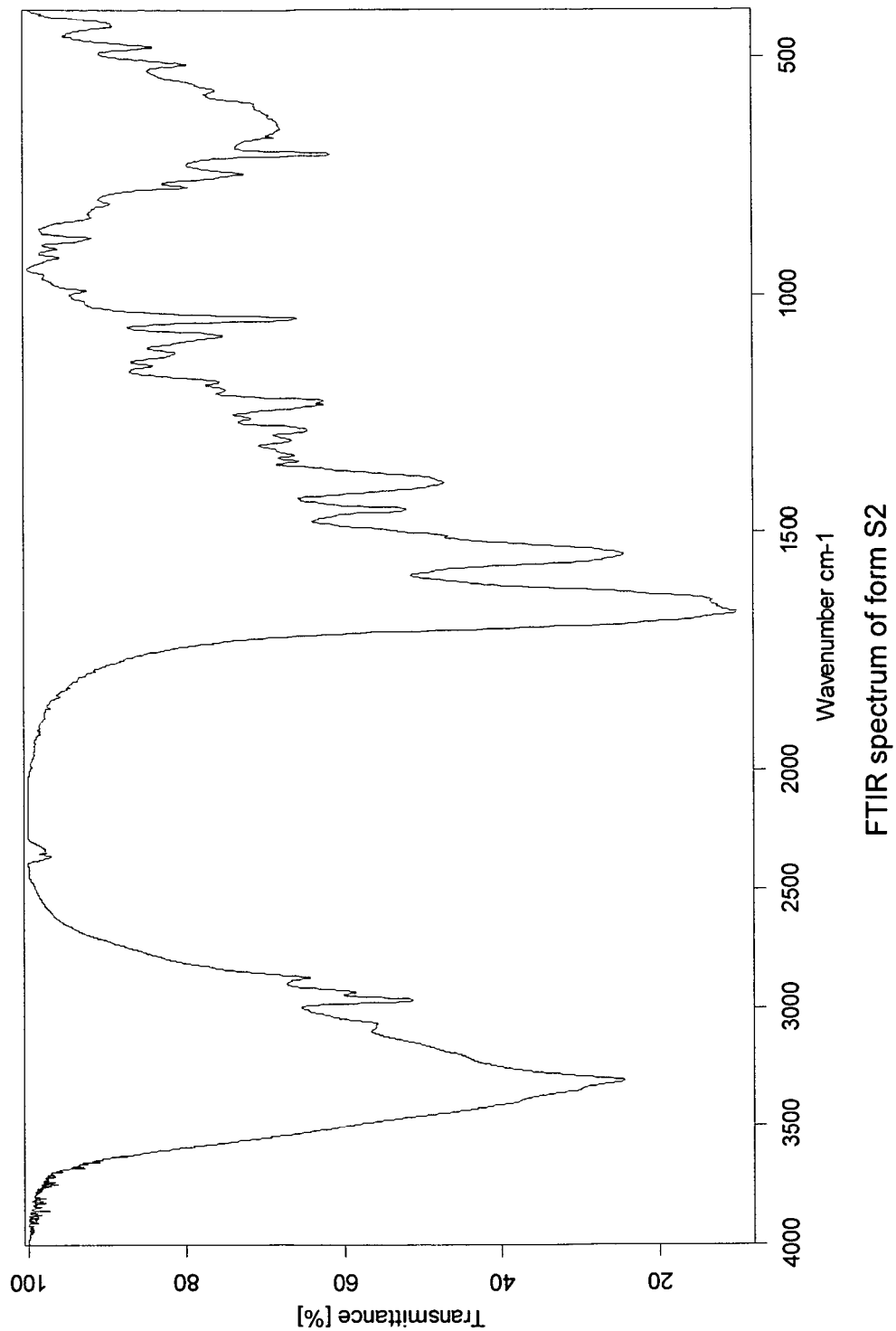
FIG. 19 shows an FTIR spectrum of form S2.

The FT-IR spectra of the tetrasolvates as described herein and especially the crystalline form S2 is given in FIG. 19.

Preferably, the tetrasolvates as described herein and, more preferably the Dihydrate-diethanolate especially the crystalline form S2 can be characterised, alternatively or additionally, by the Raman-spectroscopy data comprising one or more of the band positions (±2 cm$^{-1}$) given below, more preferably comprising 5 or more of the band positions (±2 cm$^{-1}$) given below, even more preferably comprising 8 or more of the band positions (±2 cm$^{-1}$) given below, and especially comprising all the band positions (±2 cm$^{-1}$) given below, preferably together with the relative intensities given in brackets:
3068 cm$^{-1}$ (w), 2934 cm$^{-1}$ (s), 1668 cm$^{-1}$ (w), 1606 cm$^{-1}$ (w), 1449 cm$^{-1}$ (w), 1337 cm$^{-1}$ (w), 1204 cm$^{-1}$ (w), 1120 cm$^{-1}$ (w), 1004 cm$^{-1}$ (m), 904 cm$^{-1}$ (w), 825 cm$^{-1}$ (w), 624 cm$^{-1}$ (w), 521 cm$^{-1}$ (w).

More preferably, the tetrasolvates as described herein, more preferably the Dihydrate-diethanolate and especially the crystalline form S2 can be characterised, alternatively or additionally, by the Raman-spectroscopy data comprising one or more of the and positions (±2 cm$^{-1}$) given below, more preferably comprising 9 or more of the band positions (±2 cm$^{-1}$) given below, even more preferably comprising 12 or more of the band positions (±2 cm$^{-1}$) given below, and especially comprising all the band positions (±2 cm$^{-1}$) given below, preferably together with the relative intensities given in brackets:
3068 cm$^{-1}$ (w), 2934 cm$^{-1}$ (s), 1668 cm$^{-1}$ (w), 1606 cm$^{-1}$ (w), 1586 cm$^{-1}$ (w), 1449 cm$^{-1}$ (w), 1337 cm$^{-1}$ (w), 1204 cm$^{-1}$ (w), 1120 cm$^{-1}$ (w), 1033 cm$^{-1}$ (w), 1004 cm$^{-1}$ (m), 904 cm$^{-1}$ (w), 825 cm$^{-1}$ (w), 624 cm$^{-1}$ (w), 521 cm$^{-1}$ (w).

The relative intensities given in brackets are preferably defined as follows: "s"=strong (relative Raman intensity preferably ≥0.04), "m"=medium (preferably 0.04>relative Raman intensity≥0.02), "w"=weak (relative Raman intensity preferably <0.02)

The Raman or FT-Raman spectrum is preferably obtained using Aluminium-cups as sample holders for the respective solid material.

The Raman-spectroscopy data is preferably obtained by FT-Raman-spectroscopy, The Raman-spectroscopy data or FT-Raman-spectroscopy data is preferably obtained by standard techniques as described in the European Pharmacopeia 6$^{th}$ Edition chapter 2.02.48. For the measurement of the FT-Raman-spectra, preferably a Bruker RFS 100 spectrometer is used. FT-Raman spectra are preferably base-line corrected, preferably using Bruker OPUS software.

Figure 20:
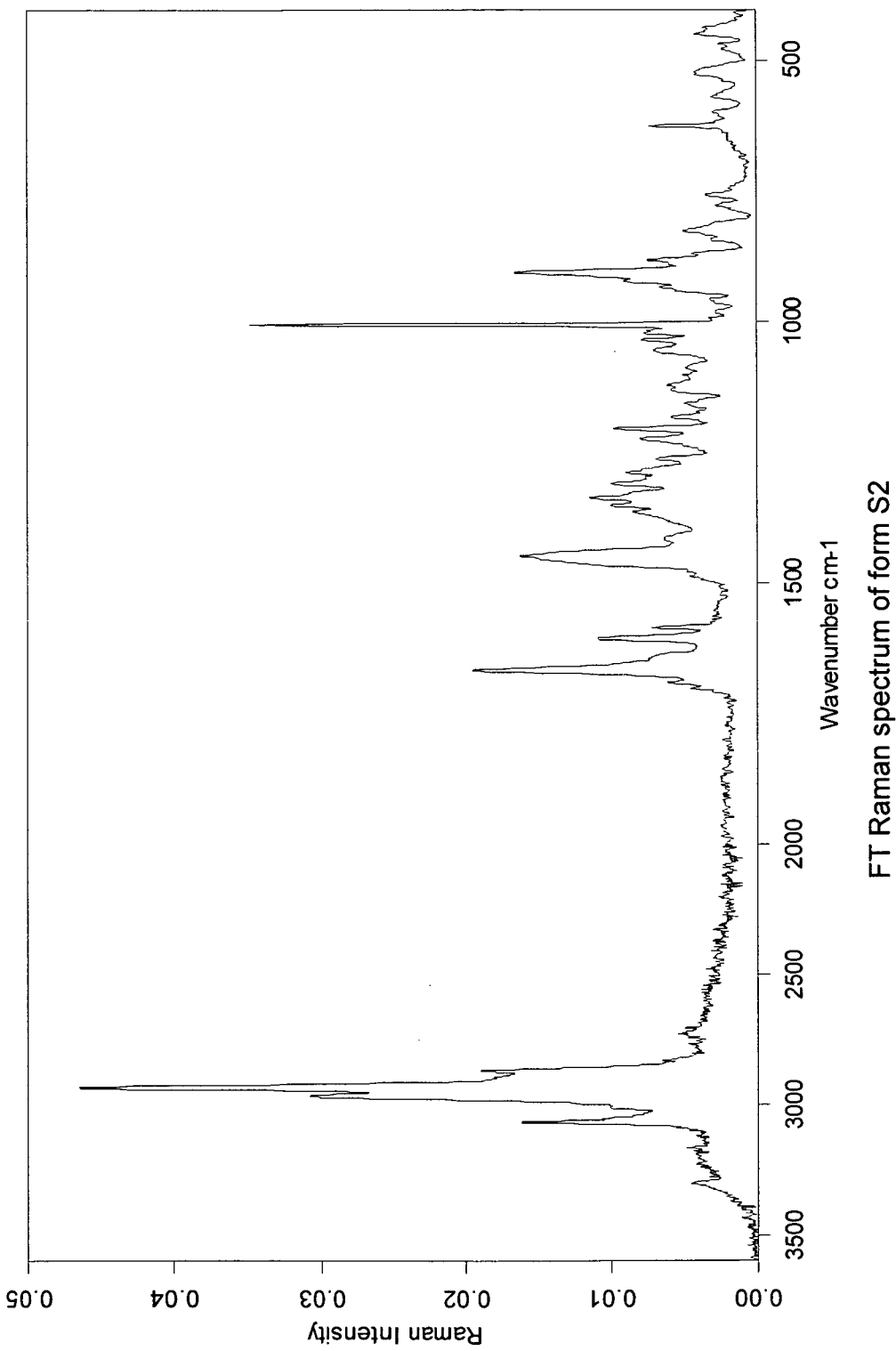
FIG. 20 shows an FT Raman spectrum of form S2.

The FT-Raman spectra of the tetrahydrates as described herein, more preferably the Dihydrate-diethanolate and especially the crystalline form S2 is given in FIG. 20.

Preferably, the tetrasolvates as described herein, more preferably the Dihydrate-diethanolate and especially the crystalline form S2 can be characterised, alternatively or additionally, by dynamic vapour experiments using water vapour and/or methanol vapour. The results can be obtained by standard techniques as described in Rolf Hilfiker, 'Polymorphism in the Pharmaceutical Industry', Wiley-VCH. Weinheim 2006 (Chapter 9: Water Vapour Sorption, and references therein).

Figure 21:
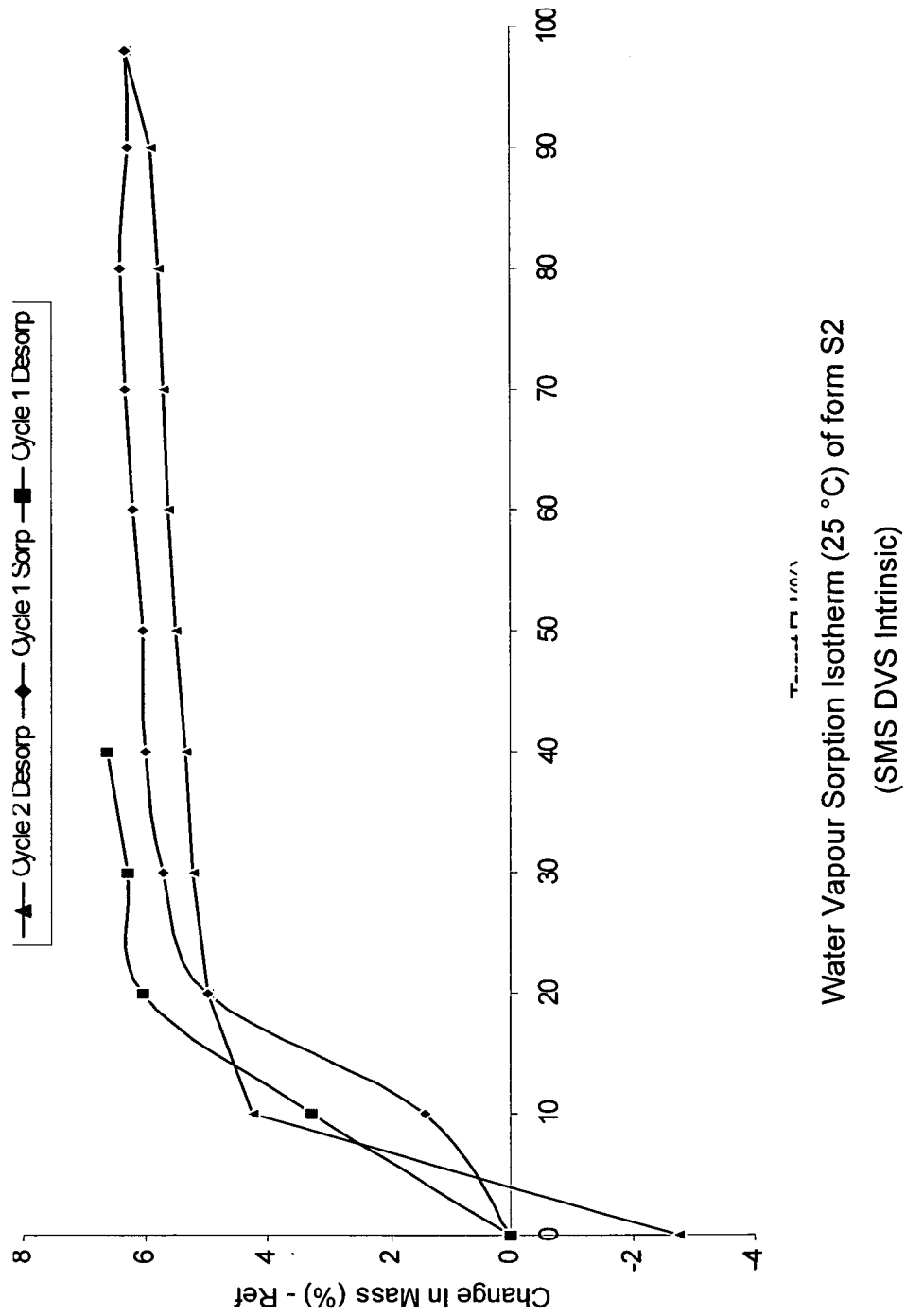
FIG. 21 shows a water vapor sorption isotherm (25° C.) of form S2 (SMS DVS Instinsic).
Figure 22:
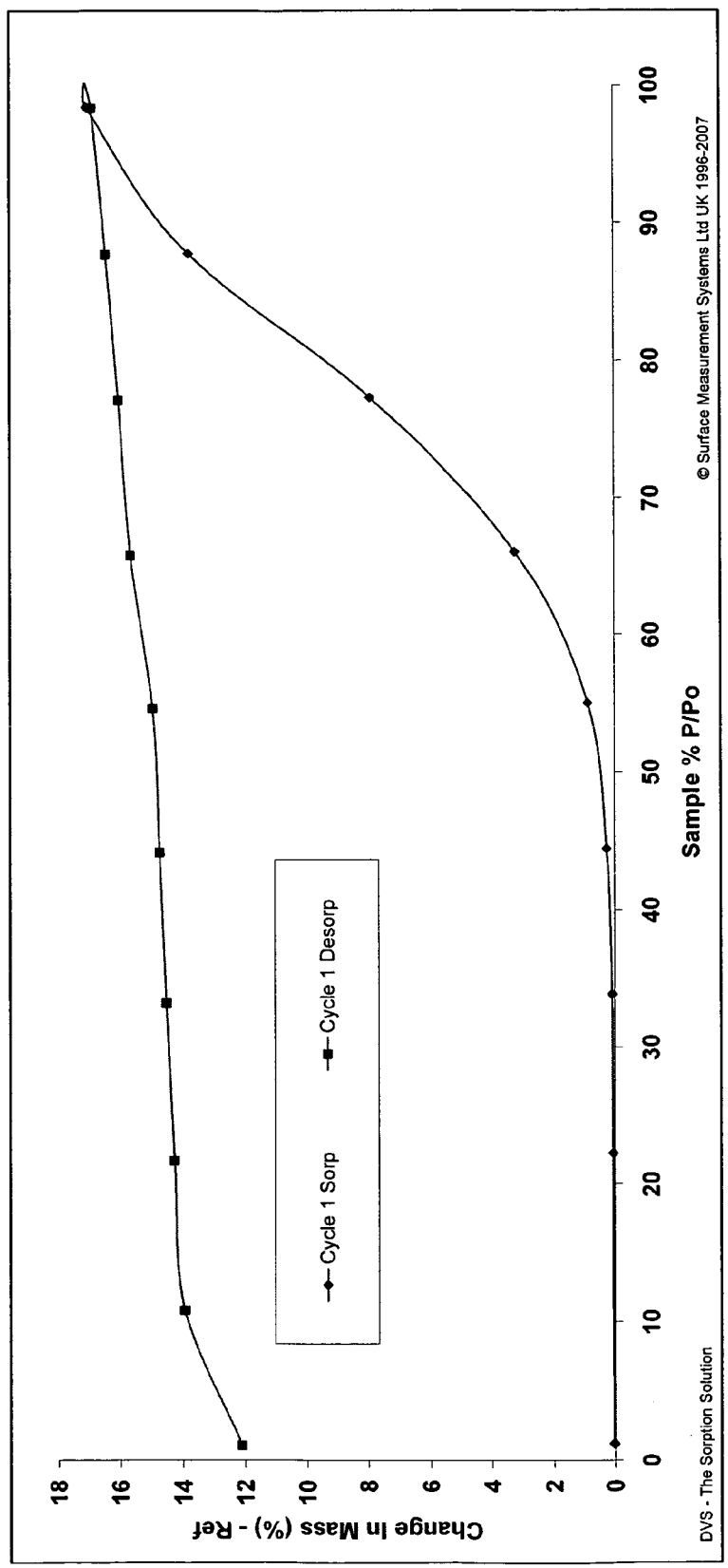
FIG. 22 shows an Ethanol Vapour Sorption Isotherm (25° C.) of a hydrate form to form S2.

The Water Vapour Sorption behaviour of the tetrasolvates as described herein, more preferably the Dihydrate-diethanolate and especially the crystalline form S2 shows a mass loss of approx. 6.5 wt % in the first desorption cycle (which is lower than the observed Ethanol mass gain in the Ethanol Vapour Sorption experiment). Upon water vapour adsorption, an assembly of water molecules in the lattice is observed, with a maximum weight gain of approx. 6.4 wt % at elevated rh. In the second desorption cycle a total mass loss of approx. 9.2 wt % is observed. For a Dihydrate Di-Ethanolate of the compound of formula Id, the calculated Ethanol content equals 12.5 wt %. Form S2 can be shown to be the thermodynamically stable form in an atmosphere of 100% Ethanol vapour. The Water Vapor Sorption isotherm (25° C.) of crystalline form S2 (SMS DVS Intrinsic) is given in FIG. 21. The Methanol Vapour Sorption Isotherm (25° C.) of a hydrate form to form S2 (SMS DVS Advantage) is given in FIG. 22.

Thus, crystalline form S2 is a crystalline Ethanol solvate form, which can be obtained e.g. via Methanol Vapour Sorption, preferably via Ethanol Vapour Sorption starting with a hydrate structure, such as the hydrates as described herein and especially the tetrahydrate as described herein, i.e. crystalline form S3. From the Ethanol Vapour Sorption curve as shown in FIG. 13 and as discussed above, it can be seen that at elevated Ethanol partial pressure, approx. 17 wt % Ethanol are taken up by the sample.

As can be seen from the data given and discussed herein, the solvates and especially the tetrasolvates of the compound of formula Id form a class of novel crystalline forms (further also to be named pseudopolymorphic forms or abbreviated PP) based on the same structural type, having highly similar physical properties and being easily convertible, preferably with potentially all transition forms being derivable and especially all transition forms between the pseudopolymorphic forms described herein being potentially derivable.

Figure 15:
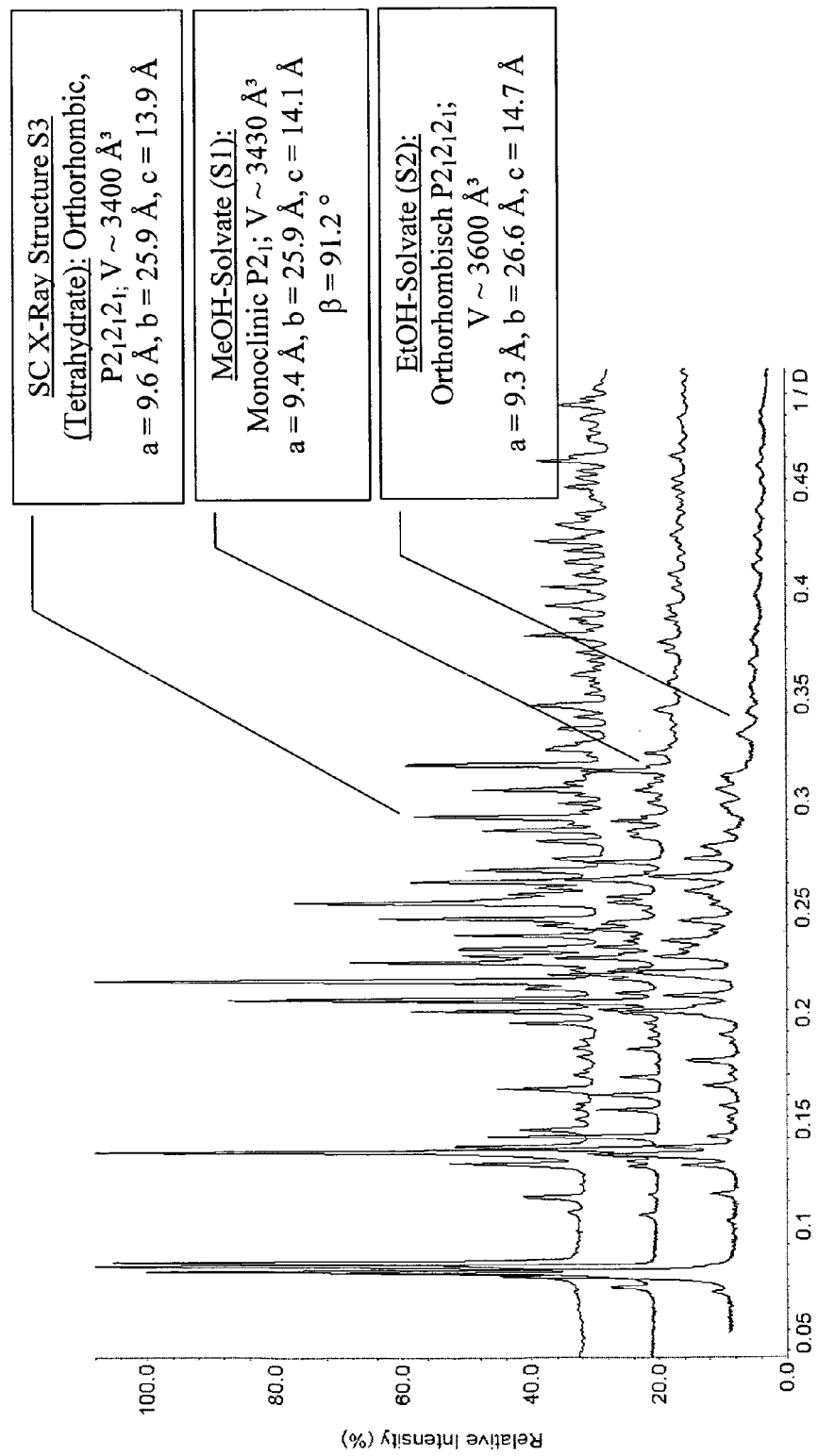
FIG. 15 shows a DSC scan of form S2 (Mettler-Toledo DSC 821, 5 K/min, nitrogen purge gas 50 ml/min).

The similarity of the structural type is additionally shown by a superimposed plot of PXRD patterns of the three selected pseudopolymophs S1, S2 and S3 given in FIG. 15. It can be seen that all three selected pseudopolymorphs exhibit very similar PXRD patterns, and, moreover, lead to basically same unit cells, as a replacement of water by Methanol or Ethanol only leads to a slight expansion of the unit cells and thus to a slight increase in unit cell volume. As expected from the molar volumes of the solvents, this is more pronounced for the Ethanol solvate than for the Methanol solvate.

In the presence of alcohols, preferably Methanol and/or Ethanol, interconversion within the pseudopolymorphic class, comprising the solvates and especially the tetrasolvates according the invention, occurs easily. As alcohols, preferably Methanol and/or Ethanol, are useful solvents in the manufacturing process, usage of the pseudopolymorphs is preferably beneficial to obtain the compound of formula Id in a crystalline solid-state modification exhibiting an advantageously high solubility combined with good crystallinity.

The solvates and especially the tetrasolvates within the pseudopolymorphic class or system are crystalline and preferably exhibit advantageous solid-state stability without loss of the Cilengitide host structure, in comparison to the previously described amorphous solid material. Said class of pseudopolymorphic forms described herein exhibit a surprisingly high solubility, especially in aqueous media, which makes them especially useful for preparation of liquid formulations. Additionally, said class of polymorphic forms show a advantageously reduced hygroscopicity in comparison to the previously known amorphous material.

Solubility of tetrahydrate Form S3 in different solvents:

| Solvent | Solubility |
| --- | --- |
| $H_2O$ | 21.6 mg/ml |
| physiological NaCl solution | 21.1 mg/ml |
| buffer pH 7.4 | 24.4 mg/ml |
| $H_2O$/MeOH (1:1) | 12.8 mg/ml |
| $H_2O$/EtOH (1:1) | 13.0 mg/ml |
| $H_2O$/iPrOH (1:1) | 22.9 mg/ml |
| $H_2O$/Acetone (1:1) | 22.7 mg/ml |
| $H_2O$/Acetonitrile (1:1) | 24.3 mg/ml |

The combination of reduced hygroscopicity, good solubility and good crystallinity leads to superior properties compared to the amorphous phase. In comparison, the purification, the handling and the processing of the amorphous material is very difficult, due to, e.g. the very high hygroscopicity and the low stability of the amorphous solid material.

Further, the pseudopolymorphic forms and/or the anhydrates according the invention show improved physical and/or chemical stability compared to the amorphous phase, preferably leading to a reduced formation of degradation products during storage, for example by hydrolysis. This improved hydrolytic stability of the solid material as described herein and especially of the crystalline forms as described herein is believed to be caused by the reduction of trace amounts of ionic impurities that are normally present in the amorphous material of prior art.

As a result, all those factors discussed herein are believed to account for the advantageously improved solid state stability of the solid material as described herein, the crystalline forms as described herein and especially of the solvates and/or anhydrates as described herein.

The solid material as described herein and especially the one or more crystalline forms as described herein can be prepared by contacting the compound according to formula Id with a solvent or solvent mixture, preferably a polar and/or protic solvent or solvent mixture.

Thus, preferred is a process for the preparation or manufacture of the solid material as described herein and especially for the preparation or manufacture of one or more of the crystalline forms as described herein, comprising contacting a compound according to formula Id with a solvent or solvent mixture, preferably a polar and/or protic solvent or solvent mixture, and isolating the solid material as described herein obtained by said contacting from said solvent or solvent mixture.

Said isolation from said solvent or solvent is preferably achieved by
i) crystallisation and/or precipitation of the solid material as described herein from said solvent or solvent mixture, and/or
ii) separating the solid material as described herein from said solvent, preferably by physical means, such as filtration or centrifugation, or alternatively by sedimentation and/or decanting.

However, a plurality of separation techniques for achieving a solid/fluid separation are known in the art. Preferably, either one of them can be successfully applied for said separation.

Preferably, the solid material as described herein and especially the one or more crystalline forms as described herein can be prepared starting with a solid material of the compound according to formula Id that is essentially free or preferably free of one or more of the crystalline forms as described herein, and then by contacting it with a solvent or solvent mixture, preferably a polar and/or protic solvent or solvent mixture.

Alternatively preferably, the solid material as described herein and especially the one or more crystalline forms as described herein can be prepared starting with a solution of the compound according to formula Id that is essentially free or preferably free of one or more of the crystalline forms as described herein, and then by contacting it with a solvent or solvent mixture, preferably a polar and/or protic solvent or solvent mixture, or transferring said solution of the compound according to formula Id that is essentially free or preferably free of one or more of the crystalline forms as described herein into said solvent or solvent mixture, preferably said polar and/or protic solvent or solvent mixture.

Generally, to obtain the solid form as described herein and/or one or more of the crystalline forms as described herein, the contacting with said solvent or solvent mixture, preferably said polar and/or protic solvent or solvent mixture or the contact with said solvent or solvent mixture, preferably said polar and/or protic solvent or solvent mixture is followed by an isolating step, wherein the solid material as described herein and/or one or more of the crystalline forms as described herein can be obtained in a solid state.

Contacting or contact in this regard preferably means contacting in the broadest sense, such as "being in the presence of". Accordingly, examples of contacting or contact with said solvent or solvent mixture include, but are not limited to, dissolving or partly dissolving in said solvent or solvent mixture, suspending in said solvent or solvent mixture, stirring in the presence of said solvent or solvent mixture, triturating with or in the presence of said solvent or solvent mixture, allowing to stand in the presence of said solvent or solvent mixture, heating in the presence of said solvent or solvent mixture, cooling in the presence of said solvent or solvent mixture, crystallizing or re-crystallising from said solvent or solvent mixture and/or precipitating from said solvent or solvent mixture.

Preferred ways of contacting or contact in this regard are preferably selected from a group consisting of: dissolving or partly dissolving in said solvent or solvent mixture, stirring in the presence of said solvent or solvent mixture, triturating with or in the presence of said solvent or solvent mixture, heating or cooling, preferably heating in the presence of said solvent or solvent mixture, crystallising or re-crystallising from said solvent or solvent mixture and/or precipitating from said solvent or solvent mixture.

An especially preferred way of contacting in this regard comprises dissolving, essentially dissolving or suspending the starting material of the compound of formula Id and/or salts thereof in a (first) polar and/or protic solvent or solvent mixture, preferably followed by re-crystallising, crystallising and/or precipitating of the product formed from said solventor solvent mixture, which is preferably a solid material as described herein. Preferably, re-crystallisation, crystallisation and/or precipitation of the product formed is induced or facilitated by cooling and/or the addition of further (or second) solvent or solvent mixture, preferably a further solvent or solvent mixture having a different polarity and more preferably having a lower polarity than the (first) solvent or solvent mixture in which the contacting was started.

Another especially preferred way of contacting in this regard comprises the formation of a slurry of the starting material of the compound of formula Id as described above and/or below and a polar and/or protic solvent or solvent mixture, and stirring and/or agitating said slurry, preferably for a reaction time as described herein and a reaction temperature or processed temperature as described herein. This is preferably also referred to as "slurry conversion"

Suitable solvents and solvent mixtures for use in the methods and/or processes as described herein are known in the art. Preferred solvents and solvent mixtures are preferably selected from the group consisting of organic solvents, water, saline, buffer solutions, and mixtures thereof.

The terms "polar and/or protic solvent or solvent mixture" are known and clear to the ones skilled in the art.

Examples polar and/or protic solvents include, but are not limited to, water, saline or physiological NaCl solution, phosphate buffer solution, lower alcohols, such as monools, diols or triols having 1 to 6 carbon atoms, lower ketones, such as acetone or methyl ethly ketone, acetonitrile, propionitrile, DMF, DMSO, and the like. Preferred polar and/or protic solvents are selected from the group consisting of water, saline, methanol, ethanol, propanol, isopropanol, acetone, acetonitrile, propionitrile, DMF and DMSO.

Examples of polar and/or protic solvent mixtures include, but are not limited to, mixtures of the above given polar and/or protic solvents, more preferably mixtures of water with one or more of the above given polar and/or protic solvents other than water, mixtures of saline or physiological NaCl solution or phosphate buffer solution with one or more of the above given polar and/or protic solvents.

Preferred polar and/or protic solvent mixtures are selected from the group consisting of mixtures of water with methanol, ethanol and/or isopropanol, mixtures of methanol, ethanol and/or isopropanol, mixtures of acetone with water and/or acetonitrile, mixtures of methanol with acetone, acetonitrile and/or water, and mixtures of ethanol with acetone, acetonitrile, and preferably also selected from the above given mixtures, wherein the water is substituted for saline, physiological NaCl solution, or phosphate buffer solution. Preferred within said mixtures are mixtures comprising all preferably essentially consisting of 2, 3 or 4 of the given solvents. Especially preferred within said mixtures are mixtures that comprise at least 5% and especially at least 10% of each of the solvents contained in the mixture.

Examples of preferred solvents and/or solvent mixture in this regard are selected from the group consisting of water, methanol, ethanol, isopropanol, and mixtures thereof, more preferably selected from the group consisting of water, methanol, ethanol, and mixtures thereof.

In said method of manufacture of a solid material as described herein, the starting material of compound of formula Id is preferably selected from the group consisting of a) amorphous or essentially amorphous material of the compound of formula Id, b) an acid-addition or a base-addition salt of the compound of formula Id, c) an amorphous or essentially amorphous solid material of an acid-addition or a base-addition salt of the compound of formula Id, and b) a solution of crude compound of formula Id and/or an acid-addition or a base-addition salt thereof, preferably as obtained from the synthesis of said compound and/or salt thereof, and mixtures thereof.

Additionally, it was surprisingly found that one first crystalline form as described herein can be transformed into one or more other crystalline forms as described herein, preferably reversibly. Furthermore, it was found that one first mixture of one or more crystalline forms as described herein can be either transformed into a second mixture of crystalline forms as described herein being different from said first mixture, or into a pure or essentially pure single crystalline form as described herein.

Accordingly, the invention also provides a process for transforming one first solid material as described herein, comprising one or more first crystalline forms, into a second solid material as described herein, comprising one or more second crystalline forms. This method can be preferably done in the same way and preferably using the same solvent and/or solvent mixtures as the method of manufacture described above and/or below, but is using a (first) solid material as described herein as the starting material of the method.

Thus, preferred is a process for the manufacture or the transformation, preferably manufacture, of a solid material as described herein, comprising a) contacting cyclo-(Arg-Gly-Asp-DPhe-NMeVal) and/or an acid-addition or a base-addition salt thereof with a solvent or solvent mixture, preferably a polar and/or protic solvent or solvent mixture, b) precipitating and/or crystallising the internal salt of cyclo-(Arg-Gly-Asp-DPhe-NMeVal) from a polar and/or protic solvent or solvent mixture, and c) optionally isolating a solid material according the invention.

In said process for the transformation, the starting material employed in step a) is preferably a (first) solid form as described herein, containing cyclo-(Arg-Gly-Asp-DPhe-NMeVal) as the inner salt, and the solid material as described herein obtained under step b) and optionally isolated according to step c) is a (second) different solid material as described herein. Preferably, the difference between the first solid material as described herein and the second different solid material as described herein is the amount of crystalline forms contained in said second solid form, the selection of the crystalline forms contained in said solid form or the ratio of the crystalline forms contained in said solid form.

In said process for the manufacture, the starting material employed in step a) is preferably selected from i) a solid form of the compound of formula Id different from the solid form as described herein, ii) a solution of cyclo-(Arg-Gly-Asp-DPhe-NMeVal) and/or an acid-addition or a base-addition salt thereof, wherein the solution is preferably either a crude solution or obtained, more preferably directly obtained, from the synthesis of the cyclo-(Arg-Gly-Asp-DPhe-NMeVal), and/or iii) obtained from dissolving a solid form of the compound of formula Id different from the solid form as described herein.

Thus, preferred is a process for the manufacture of a solid material as described herein, comprising a) contacting an acid-addition or a base-addition salt of cyclo-(Arg-Gly-Asp-DPhe-NMeVal) with a polar and/or protic solvent or solvent mixture, b) precipitating and/or crystallising the internal salt of cyclo-(Arg-Gly-Asp-DPhe-NMeVal) from a polar and/or protic solvent or solvent mixture, and c) optionally isolating a solid material according the invention.

In said process for the manufacture and/or the transformation, step a), b) and/or c) is preferably performed at a pH value in the range of 5.5 to 8, more preferably at a pH value in the range of 6 to 7.5, more preferably at a pH value in the range of 6.5 to 7.2 and especially at a pH value in the range of 6.7 to 6.9, for example at a pH value of about 6.8. More preferably, two or more of the steps selected from a), b) and c) are performed at the pH values given above, and especially all the steps a), b) and c) are performed at the pH values given above. Performing one or more of the steps selected from a), b) and c) at the pH values given above is advantageous to convert an acid-addition or a base-addition salt of cyclo-(Arg-Gly-Asp-DPhe-NMeVal) into the inner salt of cyclo-(Arg-Gly-Asp-DPhe-NMeVal), or to maintain or stabilize the inner salt of cyclo-(Arg-Gly-Asp-DPhe-NMeVal) within said process.

In said process for the manufacture and/or the transformation, step a), b) and/or c) is preferably performed under about isoelectric conditions. More preferably, two or more of the steps selected from a), b) and c) are performed under about isoelectric conditions, and especially all the steps a), b) and c) are performed under about isoelectric conditions. Performing one or more of the steps selected from a), b) and c) under about isoelectric conditions is also advantageous to convert an acid-addition or a base-addition salt of cyclo-(Arg-Gly-Asp-DPhe-NMeVal) into the inner salt of cyclo-(Arg-Gly-Asp-DPhe-NMeVal), or to maintain or stabilize the inner salt of cyclo-(Arg-Gly-Asp-DPhe-NMeVal) within said process.

In said process for the manufacture and/or the transformation, step a), b) and/or c) is preferably performed at a temperature in the range between −20° C. and +200° C., more preferably in the range between −5° C. and +150° C., even more preferably in the range between +5° C. and +110° C. and especially in the range between +10° C. and +100° C., for example at about room temperature (about 25° C.), at about 50° C. or at about 75° C. or at about 100° C.

Generally, higher temperatures tend to accelerate the processes for the manufacture and/or the processes for the transformation as described herein.

Generally, temperatures at the higher end of the given temperature ranges tend to promote the formation the anhydrates as described herein.

Generally, temperatures at the lower end of the given temperature ranges tend to promote the formation of the solvates as described herein.

In the processes for the manufacture of the solid materials as described herein and/or in the processes for the conversion or transformation of the solid materials as described herein and/or to crystallise form as described herein, the processing time or "reaction time", i.e. the time during which the contacting, the precipitation, the crystallization and/or the isolation preferably takes place is generally between five minutes to four weeks. Said processing time is preferably not a very crucial factor for the processes as described herein since during the above given times, very little or no decomposition of the compound according to formula Id takes place, especially within the preferred process parameters or process conditions described herein.

Additionally, the product of the process, i.e. the solid material as described herein, is generally stable under the conditions it is formed.

Accordingly, processing times preferably are the range of 10 minutes to three weeks, more preferably 15 minutes to one week, more preferably 30 minutes to 72 hours and especially one hour to 48 hours.

Processing times for the formation or conversion, preferably formation, of the anhydrates as described herein, and especially for the formation of the crystalline form A1 are preferably in the range of one hour to three weeks, more preferably in the range of one hour to two weeks and especially in the range of one hour to 72 hours.

Processing times for the formation or conversion, preferably formation, of the solvates as described herein, more preferably the tetrasolvates as described herein, even more preferably the one or more crystalline forms S1, S2 and/or S3 and especially for the formation of the crystalline form S1 are preferably in the range of five minutes to three weeks, more preferably in the range of five minutes to one week, even more preferably in the range of five minutes to 48 hours and especially in the range of 10 minutes to 24 hours.

Generally, lower temperatures during said processes lead to longer processing times, as it is known in the art.

Generally, water, methanol and/or ethanol, and mixtures thereof are preferred polar and/or protic solvents or solvent mixtures for use in step a), b) and/or c) and especially for use in step a), b) and c).

In said process for the manufacture and/or the transformation, the solvent of step a), b) and/or c), preferably a), b) and c), essentially consists of water, methanol or ethanol.

Preferably, the same or essentially the same solvent or solvent mixture, preferably a polar and/or protic solvent or solvent mixture is used in process steps a), b) and c).

Generally, the use of solvent or solvent mixtures in step a), b) and/or c) that contain at least 5% by weight, more preferably at least 10% by weight and especially at least 20% by weight of one or more alcohols, preferably selected from methanol, ethanol and isopropanol, more preferably selected from methanol and ethanol, promote the formation of the solvates as described herein.

More specifically, the use of solvent mixtures in step a), b) and/or c) that comprise
i) 5 to 90% by weight of at least one alcohol, selected from the group consisting of methanol and ethanol, and
ii) 10 to 95% by weight of water,
preferably promote the formation of the solvates as described herein.

Even more specifically, the use of solvent mixtures in step a), b) and/or c) that comprise
i) 5 to 50% by weight and especially 10 to 60% by weight of at least one alcohol, preferably selected from the group consisting of methanol and ethanol, and
ii) 50 to 95% by weight and especially 40 to 90% by weight of water, preferably promote the formation of the solvates as described herein.

Thus, preferred is a process as described above and/or below for the manufacture of a solid material as described herein, preferably solvates according to the invention, and especially of one or more tetrasovates as described herein, wherein the solvent or solvent mixture of step a), b) and/or c) comprises
i) 5 to 90% by weight, preferably 5 to 50% by weight, of at least one alcohol, selected from the group consisting of methanol and ethanol, and
ii) 10 to 95% by, weight preferably 50 to 95% by weight, of water.

Thus, preferred is a process as described above and/or below for the manufacture of a solid material as described herein, preferably anhydrates as described herein, and especially of crystalline form A1, wherein solvent of step a), b) and/or c) essentially consists of water, methanol and ethanol and more preferably essentially consists of water.

Thus, preferred is a process as described above and/or below for the manufacture of a solid material as described herein, preferably anhydrates as described herein, and especially of crystalline form A1, wherein steps a), b) and/or c) are performed at a temperature above +40° C., more preferably at a temperature of +50° or higher and especially at a temperature of +60° or higher.

Within the process parameters that are preferred for the formation of solvates and especially tetrasolvates as described herein, an alcohol content at the lower end of the given ranges and/or a water content at the higher end of the given ranges promote the formation of the hydrates as described herein. Alternatively, an alcohol content at the higher end of the given ranges and/or a water content at the lower end of the given ranges promote the formation of alcohol solvates.

Especially preferred solvates in this regard are the tetrasolvates, preferably selected from the tetrahydrate, the methanol solvates and the ethanol solvates, and mixed forms thereof, even more preferably selected from the tetrahydrate, the methanol solvate S1 and the ethanol solvate S2, and especially the tetrahydrate S3.

Thus, one preferred process for the manufacture of a solid material as described herein comprises or preferably essentially consists of
i) crystallising or re-crystallising an amorphous material or an essentially amorphous material of the compound of formula Id from a solvent or solvent mixture, preferably a polar and/or protic solvent or solvent mixture, preferably a solvent or solvent mixture, preferably a polar and/or protic solvent or solvent mixture as described herein, and optionally
ii) isolating the thus obtained solid material as described herein from said solvent or solvent mixture by a solid/fluid separation technique, preferably a solid/fluid separation technique as described herein and especially by filtration.

Thus, one preferred process for the transformation of a first solid material as described herein into a second solid material as described herein comprises or preferably essentially consists of
a) precipitating, crystallising or re-crystallising a first solid material as described herein from a solvent or solvent mixture, preferably a polar and/or protic solvent or solvent mixture, preferably a solvent or solvent mixture, preferably a polar and/or protic solvent or solvent mixture as described herein, and optionally
b) isolating the thus obtained second solid material as described herein from said solvent or solvent mixture by a solid/fluid separation technique, preferably a solid/fluid separation technique as described herein and especially by filtration.

In the synthesis of the compound cyclo-(Arg-Gly-Asp-DPhe-NMe-Val), the final product or crude product of said synthesis is in many cases an acid-addition or a base-addition salt of the compound cyclo-(Arg-Gly-Asp-DPhe-NMe-Val), preferably an acid-addition salt of the compound cyclo-(Arg-Gly-Asp-DPhe-NMe-Val), e.g. the hydrochloride salt of cyclo-(Arg-Gly-Asp-DPhe-NMe-Val) (=cyclo-(Arg-Gly-Asp-DPhe-NMe-Val) x HCl), the trifluoroacetic acid salt of cyclo-(Arg-Gly-Asp-DPhe-NMe-Val) (=cyclo-(Arg-Gly-Asp-DPhe-NMe-Val)×TFA), the sulphate salt of cyclo-(Arg-Gly-Asp-DPhe-NMe-Val) (=cyclo-(Arg-Gly-Asp-DPhe-NMe-Val)×$SO_4$ or, more specifically cyclo-(Arg-Gly-Asp-DPhe-NMe-Val)×0.5 $SO_4$), or mixtures thereof.

Thus, preferred examples of processes for the manufacture of the solid material as described herein start from said crude product in the form of acid-addition or a base-addition salts, preferably acid-addition salts.

Thus, preferred is a process for the manufacture of a solid material as described herein, comprising:
a) contacting an acid-addition or a base-addition salt, preferably an acid-addition salt, of the compound cyclo-(Arg-Gly-Asp-DPhe-NMe-Val) with a polar and/or protic solvent or solid mixture, preferably as defined herein, preferably by dissolving and/or suspending said salt in said solvent,
b) converting said salt into the free base or preferably the internal salt of the compound cyclo-(Arg-Gly-Asp-DPhe-NMe-Val), preferably by adjusting the pH value, and
c) crystallising and/or precipitating, and optionally isolating, the thus obtained solid material as described herein from said solvent or solvent mixture.

Thus, more preferred is a process for the manufacture of a solid material as described herein, comprising:
a) contacting an acid-addition or a base-addition salt, preferably an acid-addition salt, of the compound cyclo-(Arg-Gly-Asp-DPhe-NMe-Val) with a solvent or solvent mixture, preferably a polar and/or protic solvent or solvent mixture, essentially consisting of or consisting of water, preferably by dissolving and/or suspending said salt in said solvent,
b) converting said salt into the free base or preferably the internal salt of the compound cyclo-(Arg-Gly-Asp-DPhe-NMe-Val), preferably by adjusting the pH value, and
c) preferably crystallising and/or precipitating, and optionally isolating, the thus obtained solid material as described herein from said solvent or solvent mixture.

This process is advantageous for the manufacture of solid materials as described herein that essentially consist of or preferably consist of the anhydrates as described herein and especially essentially consist of or preferably consist of the crystalline form A1.

Thus, preferred is a process for the manufacture of a solid material as described herein, comprising:
a) contacting an acid-addition or a base-addition salt, preferably an acid-addition salt, of the compound cyclo-(Arg-Gly-Asp-DPhe-NMe-Val) with a polar and/or protic solvent or solvent mixture,
wherein said solvent or solvent mixture is selected from water and mixtures of 60 to 99.9% per weight water and 0.1 to 40% per weight of at least one alcohol, preferably selected from methanol and ethanol,
and more preferably wherein said solvent or solvent mixture is water, preferably by dissolving and/or suspending said salt in said solvent or solvent mixture, b) converting said salt into the free base or preferably the internal salt of the compound cyclo-(Arg-Gly-Asp-DPhe-NMe-Val), preferably by adjusting the pH value, and
c) crystallising and/or precipitating the thus obtained solid material as described herein, preferably by adding alcohol, preferably methanol and/or ethanol, to said solvent or solvent mixture until the weight ratio between water and alcohol in the resulting solvent mixture is between about 1:1 and about 1:9, and optionally isolating said solid material from said resulting solvent mixture.

This process is advantageous for the manufacture of solid materials as described herein that essentially consist of or preferably consist of the solvates as described herein and especially essentially consist of or preferably consist of one or more of the crystalline forms S1, S2 and S3.

Preferred solvents or solvent mixtures, preferably polar and/or protic solvents or solid mixtures, pH values to be adjusted as well as temperatures for the above described processes are given and discussed herein.

Preferred parameters for a process for the manufacture of a solid material as described herein or a process for the transformation conversion of one or more crystalline forms as described herein are presented by the below graphically depicted results of the following slurry conversion experiments.

Preferred solvents or solvent mixtures, preferably polar and/or protic solvents or solid mixtures, pH values to be adjusted as well as temperatures for the above described processes are given and discussed herein.

Preferred parameters for a process for the manufacture of a solid according to the invention or a process for the transformation conversion of one or more crystalline forms according to the invention are presented by the below graphically depicted results of the following slurry conversion experiments.

Figure 24A:
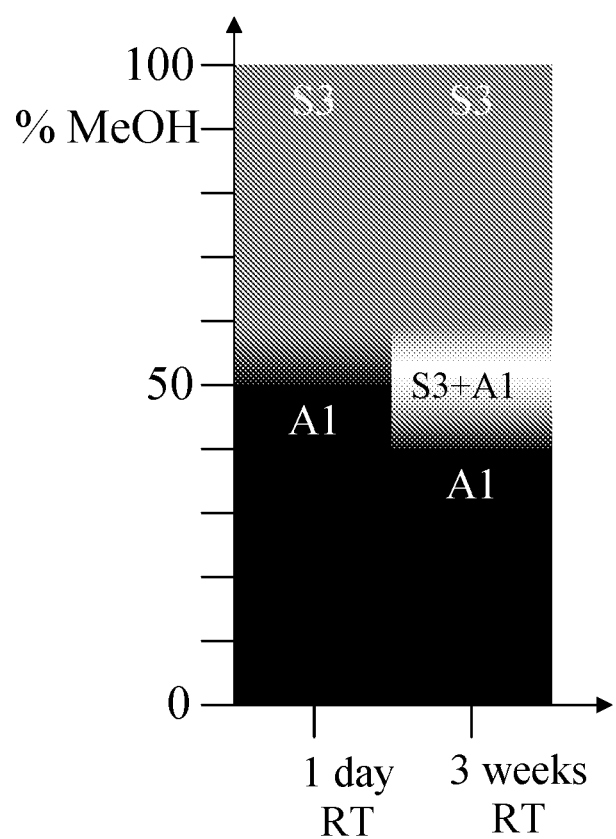
FIGS. 24A and 24B show the parameters and results of competitive slurries of polymorphic forms S3/A1 and S1/A1, respectively, in MeOH/water-mixtures at RT (25° C.) as a function of the methanol content in the respective mixture and the respective processing time.
Figure 24B:
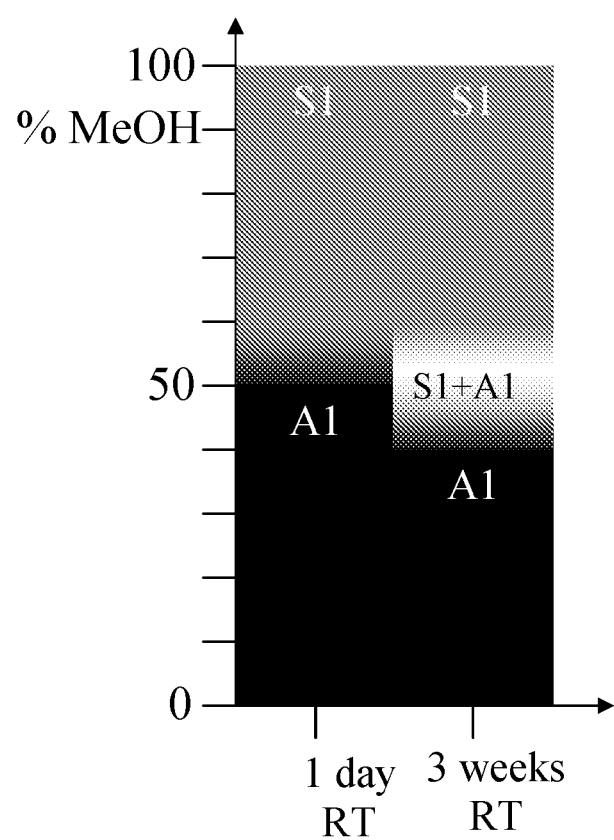

FIGS. 24A and 24B show the parameters and results of competitive slurries in MeOH/water-mixtures at RT (25° C.) as a function of the methanol content in the respective mixture and the respective processing time, i.e. after one day and after three weeks:

Based on additional PXRD investigations it has been shown that the residues obtained from the competitive slurries represented solvates including water and methanol. Accordingly, the residues have later been denominated S1 instead of S3.

Figure 25A:
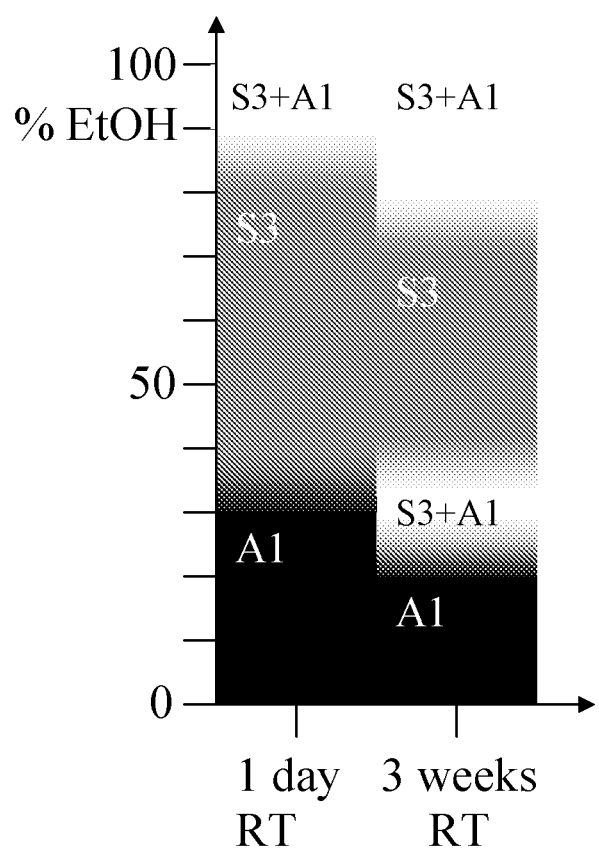
FIGS. 25A and 25B show the parameters and results of competitive slurries of polymorphic forms S3/A1 and S2/A1, respectively, in EtOH/water-mixtures at RT (25° C.) as a function of the ethanol content in the respective mixture and the respective processing time.
Figure 25B:
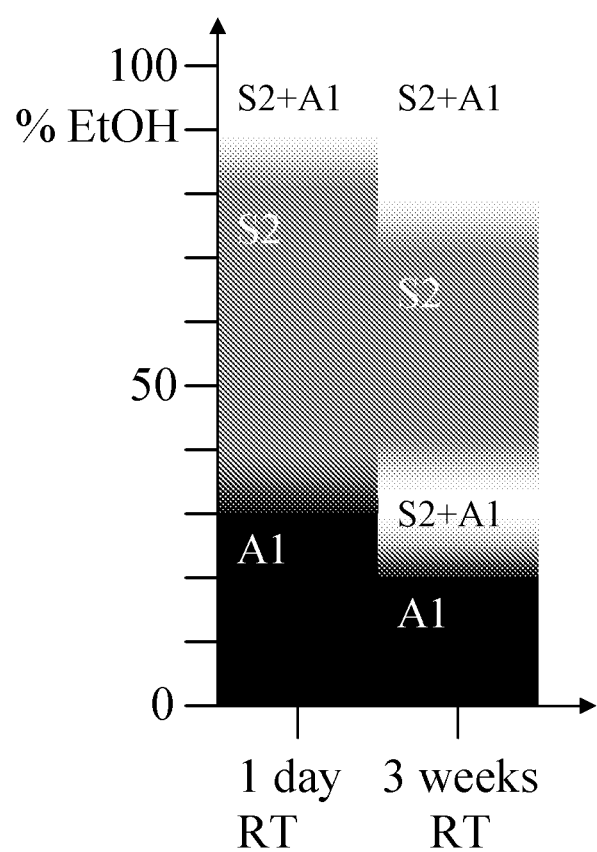

FIGS. 25A and 25B show the parameters and results of competitive slurries in EtOH/water-mixtures at RT (25° C.) as a function of the ethanol content in the respective mixture and the respective processing time, i.e. after one day and after three weeks:

Based on additional PXRD investigations it has been shown that the residues obtained from the competitive slurries represented solvates including water and ethanol. Accordingly, the residues have later been denominated S1 instead of S2.

Especially preferred processes for the manufacture, processes for the transformation or conversion and additionally preferred temperatures, solvents, solvent mixtures, reaction times, starting materials and/or additional process parameters are given in the examples. Thus, the examples provide sufficient guidance, together with the description of the instant invention and/or the claims, to carry out the invention in its full breadth. However, processes and especially process parameters can be taken out of the examples, as well individually as in combinations of one or more of those processes and/or parameters, and used together with the disclosure in the description and/or claims.

Thus, preferred is a composition as described herein, wherein the oligopeptide or cyclic oligopeptide comprises or is solid cyclo-(Arg-Gly-Asp-DPhe-NMeVal) in a polymorphic form having crystallographic unit cell with the lattice parameters
a=9.8±0.5 Å, b=19.5±1.0 Å, and c=15.4±0.5 Å.

[20] Thus, preferred is a composition as described herein or as described in one or more of the paragraphs numbered [1] to [19] and/or the paragraphs relating thereto, wherein the oligopeptide or cyclic oligopeptide comprises or is solid cyclo-(Arg-Gly-Asp-DPhe-NMeVal) in a polymorphic form having crystallographic unit cell with the lattice parameters
a=9.8±0.1 Å, b=19.5±0.5 Å, and c=15.4±0.1 Å.

Preferably, said composition comprises 5% or more, preferably 10% or more, more preferably 20% or more, even more preferably 40%, even more preferably 60% or more, even more preferably 80% or more and especially 90% or more of the contained solid cyclo-(Arg-Gly-Asp-DPhe-NMeVal) in a polymorphic form having crystallographic unit cell with the lattice parameters
a=9.8±0.5 Å, b=19.5±1.0 Å, and c=15.4±0.5 Å.

Preferably, said composition comprises 5% or more, preferably 10% or more, more preferably 20% or more, even more preferably 40%, even more preferably 60% or more, even more preferably 80% or more and especially 90% or more of the contained solid cyclo-(Arg-Gly-Asp-DPhe-NMeVal) in a polymorphic form having crystallographic unit cell with the lattice parameters
a=9.8±0.1 Å, b=19.5±0.5 Å, and c=15.4±0.1 Å.

Said solid cyclo-(Arg-Gly-Asp-DPhe-NMeVal) in a polymorphic form having a crystallographic unit cell with the lattice parameters as described in one or more of the four paragraphs above is preferably also referred to as A1, form A1, solid form A1, crystalline form A1 and/or polymorphic form A1.

[21] Preferred are compositions as described herein or as described in one or more of the paragraphs numbered [1] to [20] and/or the paragraphs relating thereto, comprising
a) 20 to 40% of cyclo-(Arg-Gly-Asp-DPhe-Val) or cyclo-(Arg-Gly-Asp-DPhe-NMeVal), the pharmaceutically acceptable derivatives, solvates and/or salts thereof,
b) 0.01 to 10% of one or more amphiphilic compounds as described herein and especially as described in one or more of the paragraphs numbered [1] to [13] and preferably also as described in the paragraphs relating thereto,
c) water, and optionally
d1) 0 to 20% of one or more pharmaceutically active ingredients other than the compound according to a), and/or.
d2) 0 to 20 of one or more pharmaceutically acceptable excipients other than the compounds according to b) and c), with the proviso that the sum of a), b), c), d1) and d2) makes up to 99%, 99.9% or 100% of the composition.

More preferred are compositions as described herein, comprising
a) 20 to 40% of cyclo-(Arg-Gly-Asp-DPhe-Val) or cyclo-(Arg-Gly-Asp-DPhe-NMeVal), the pharmaceutically acceptable derivatives, solvates and/or salts thereof,
b) 0.01 to 10% of one or more amphiphilic compounds, selected from dioleoylphosphatidylglycerol, distearoylphosphatidylglycerol, dipalmitoylglycerophosphoglycerol and mixtures thereof, and the alkali salts thereof,
c) water, and optionally
d1) 0 to 20%, preferably 0 to 10% and especially 0.01 to 5%, of one or more pharmaceutically active ingredients other than the compound according to a), and/or.
d2) 0 to 20%, preferably 0.01 to 20%, more preferably 0.1 to 10%, even more preferably 0.1 to 5%, of one or more pharmaceutically acceptable excipients other than the compounds according to b) and c),
with the proviso that the sum of a), b), c), d1) and d2) makes up to 99%, 99.9% or 100% of the composition.

Preferably, said compositions are free or essentially free of pharmaceutically active ingredients other than the compounds according to a).

Preferably in said compositions, the pharmaceutically acceptable excipients other than the compounds according to b) and c) selected from tonicity agents and preservatives, preferably tonicity agents and preservatives as described herein.

[22] Preferred are compositions as described herein or as described in one or more of the paragraphs numbered [1] to [21] and/or the paragraphs relating thereto, comprising,
a) 12 to 60% of solid cyclo-(Arg-Gly-Asp-DPhe-Val) or cyclo-(Arg-Gly-Asp-DPhe-NMeVal),
the pharmaceutically acceptable derivatives, solvates and/or salts thereof in suspended or suspendable form,
b) 0.01 to 60% of one or more lipophilic and/or amphiphilic compounds as described herein and especially as described in one or more of the paragraphs numbered [1] to [13] and preferably also as described in the paragraphs relating thereto, and
c) 0 to 89.99% of water,
with the proviso that the sum of a), b) and c) makes up to 80 or more %, preferably 90% or more and especially 90 to 100% of the total composition.

[23] Preferred are compositions as described herein or as described in one or more of the paragraphs numbered [1] to [22] and/or the paragraphs relating thereto, wherein the molar ratio between the one or more amphiphilic compounds and the one or more oligopeptides is in the range between 0.0001 and 1, more preferably in a range between 0.001 and 0.5 and especially in the range between 0.002 and 0.1, for example about 0.001, about 0.002, about 0.0025, about 0.005, about 0.01, about 0.05, about 0.1 or about 0.5.

Thus, especially preferred are compositions as described herein, wherein the molar ratio between the one or more amphiphilic compounds and the one or more oligopeptides is in the range between 0.0001 and 0.05, preferably in the range between 0.0005 and 0.05 and especially in the range between 0.001 and 0.05.

Especially preferred is a composition containing cyclo-(Arg-Gly-Asp-DPhe-NMeVal), preferably in the form of a suspension, said composition comprising or essentially consisting of:
a) 15 to 40%, preferably 25 to 35%, of cyclo-(Arg-Gly-Asp-DPhe-NMeVal) having a solubility in water at 20° C. between 6 and 10 mg/ml, more preferably cyclo-(Arg-Gly-Asp-DPhe-NMeVal) in the polymorphic form A1 as described herein,
b) 0.01 to 3%, preferably 0.05 to 1% and especially 0.1 to 1% of dimyristoylphosphatidylglycerol (DMPG), more preferably dimyristoylphosphatidylglycerol (DMPG) sodium salt,
c) 0.1 to 3%, preferably 0.5 to 2% and especially 0.5 to 1.5% of one or more tonicity agents as described herein, preferably NaCl,
d) 0 to 5%, preferably 0 to 2%, more preferably 0 to 1% and especially 0.001 to 1% of one or more pharmaceutically acceptable preservatives as described herein and more preferably one pharmaceutically acceptable preservative as described herein,
e) 0 to 5%, preferably 0 to 2%, more preferably 0 to 1% and especially 0.001 to 1% of one or more further pharmaceutically acceptable excipients, and f) 44 to 84.89% of water, more preferably water add 100%, preferably with the proviso that the sum of a), b), c), d), e) and f) sum up to 99% and even more preferably sum up to 100%. The percentages in this regard are preferably selected from % w/v and % w/w and more preferably are % w/w. In this regard, the one or more further pharmaceutically acceptable excipients are preferably other than lipophilic and/or amphiphilic compounds as described herein. In this regard, the one or more pharmaceutically acceptable preservative is preferably selected from Benzyl alcohol, Benzalkonium chloride, Benzethonium chloride, Benzoic acid, Chlorobutanol, Cresol, Methylparaben, Phenol, Propylparaben, Butylparaben, Thimerosal, Sodium benzoate and Phenylmercuric nitrate, more preferably from Benzyl alcohol, Chlorobutanol, Cresol, Methylparaben, Phenol, Propylparaben, Butylparaben and Thimerosal and even more preferably from Phenol, Chlorobutanol, Cresol, Methylparaben, Propylparaben and Thimerosal.

Alternatively preferred is a composition, preferably a pharmaceutical composition, comprising
a) 5 to 15% of at least one oligopeptide, preferably at least one cyclic oligopeptide, said oligopeptide or cyclic oligopeptide having a solubility in water at 20° C. between 1 mg/ml and 15 mg/ml, preferably between 3 mg/ml and 15 mg/ml, more preferably between 5 mg/ml and 15 mg/ml, more preferably between 2 mg/ml and 10 mg/ml, more preferably between 5 mg/ml and 10 mg/ml, even more preferably between 6 mg/ml and 10 mg/ml, and especially between 5 mg/ml and 9 mg/ml, in the form of solid particles,
b) 0.001 to 50%, preferably 0.005 to 40% more preferably, 0.01 to 30% and especially 0.01 to 10%, of one or more lipophilic and/or amphiphilic compounds having a molar weight in the range of 200 g/mol to 2000 g/mol, preferably 300 g/mol to 1500 g/mol, more preferably 500 g/mol to 1000 g/mol, and especially 700 g/mol to 900 g/mol,
and optionally
c) 0 to 94.999% of water,
with the proviso that the sum of a), b) and c) makes up to 40 or more %, preferably 50 or more percent, more preferably 70 or more percent, even more preferably 90 percent or more and especially 95 percent or more, of the total composition.

More preferred is a composition as described herein and especially as described in the paragraph above, comprising
a) 5 to 15%, preferably 6 to 12%, preferably 8 to 12%, and especially 10 to 12% of at least one oligopeptide, preferably at least one cyclic oligopeptide, more preferably at least one oligopeptide or cyclic oligopeptide as described herein, said oligopeptide or cyclic oligopeptide having a solubility in water at 20° C. between 1 mg/ml and 15 mg/ml, preferably between 3 mg/ml and 15 mg/ml, more preferably between 5 mg/ml and 15 mg/ml, more preferably between 2 mg/ml and 10 mg/ml, more preferably between 5 mg/ml and 10 mg/ml, even more preferably between 6 mg/ml and 10 mg/ml, and especially between 5 mg/ml and 9 mg/ml, in the form of solid particles,
b) 0.001 to 25%, preferably 0.005 to 15% more preferably, 0.01 to 10% and especially 0.01 to 5%, of one or more amphiphilic compounds,
c) 40 to 94.999%, preferably 50 to 94.999%, more preferably 60 to 94.99%,
even more preferably 84.999 to 94.999%, of water,
with the proviso that the sum of a), b) and c) makes up to 70 or more %, preferably 80 or more %, more preferably 90 or more %, even more preferably 95 or more % and especially 95 to 99.9% of the total composition.

Even more preferred is a composition as described in one or more of the two paragraphs above, wherein the one or more amphiphilic compounds are selected from
b1) fatty acid mono-, di- or polyesters of phosphatidyl- or sulfatidyl-polyoles, and derivatives, salts and/or alcoholates thereof, and
b2) fatty alcohol mono-, di- or polyethers of phosphatidyl- or sulfatidyl-polyoles, and derivatives, salts and/or alcoholates thereof.

Even more preferred is a composition as described in one or more of the three paragraphs above, wherein amphiphilic compounds and/or the fatty acid di- or polyesters of polyphosphatidyl-polyoles are selected from the group consisting of dioleoylphosphatidylglycerol, dimyristoylphosphatidylglycerol, dimyristoylphosphatidylcholine, distearoylphosphatidylglycerol, dioleoylglycerophosphocholine, dipalmitoylglycerophosphoglycerol, distearoylglycerophosphoethanolamine, egg phosphatidylcholine and soy phosphatidylcholine, more preferably dioleoylphosphatidylglycerol and/or dimyristoylphosphatidylglycerol, and especially dimyristoylphosphatidylglycerol,
and the pharmaceutically acceptable derivatives, salts and/or alcoholates thereof.

Even more preferred is a composition as described in one or more of the four paragraphs above, wherein said oligopeptide or cyclic oligopeptide is selected from cyclo-(Arg-Gly-Asp-DPhe-NMeVal), an anhydrate of the inner salt of cyclo-(Arg-Gly-Asp-DPhe-NMeVal) and the crystalline form A1 of the inner salt of cyclo-(Arg-Gly-Asp-DPhe-NMeVal), said oligopeptide or cyclic oligopeptide preferably having a solubility in water at 20° C. between 1 mg/ml and 15 mg/ml, preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml.

Thus, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml, is preferably selected from cyclo-(Arg-Gly-Asp-DPhe-NMeVal), an anhydrate of the inner salt of cyclo-(Arg-Gly-Asp-DPhe-NMeVal), a crystalline anhydrate of the inner salt of cyclo-(Arg-Gly-Asp-DPhe-NMeVal), and the crystalline form A1 of the inner salt of cyclo-(Arg-Gly-Asp-DPhe-NMeVal) an. Thus, said oligopeptide or cyclic oligopeptide preferably comprises, essentially consists or consists of crystalline form A1.

Thus, also preferred is a composition containing cyclo-(Arg-Gly-Asp-DPhe-NMeVal) in the form of a suspension, said composition comprising or essentially consisting of:
a) 5 to 15%, preferably 6 to 12%, preferably 8 to 12%, and especially 10 to 12%, of cyclo-(Arg-Gly-Asp-DPhe-NMeVal) having a solubility in water at 20° C. between 6 and 10 mg/ml, more preferably cyclo-(Arg-Gly-Asp-DPhe-NMeVal) in the polymorphic form A1 as described herein,
b) 0.005 to 2%, preferably 0.001 to 1% and especially 0.05 to 1% of dimyristoylphosphatidylglycerol (DMPG), more preferably dimyristoylphosphatidylglycerol (DMPG) sodium salt,
c) 0.1 to 3%, preferably 0.5 to 2% and especially 0.5 to 1.5% of one or more tonicity agents s described herein, preferably NaCl, d) 0 to 5%, preferably 0 to 2%, more preferably 0 to 1% and especially 0.001 to 1% of one or more pharmaceutically acceptable preservatives as described herein and more preferably one pharmaceutically acceptable preservative as described herein, e) 0 to 5%, preferably 0 to 2%, more preferably 0 to 1% and especially 0.001 to 1% of one or more further pharmaceutically acceptable excipients, and f) 70 to 94.895% of water, more preferably water add 100%, preferably with the proviso that the sum of a), b), c), d), e) and f) sum up to 99% and even more preferably sum up to 100%. The percentages in this regard are preferably selected from % w/v and % w/w and more preferably are % w/w. In this regard, the one or more further pharmaceutically acceptable excipients are preferably other than lipophilic and/or amphiphilic compounds as described herein. In this regard, the one or more pharmaceutically acceptable preservative is preferably selected from Benzyl alcohol, Benzalkonium chloride, Benzethonium chloride, Benzoic acid, Chlorobutanol, Cresol, Methylparaben, Phenol, Propylparaben, Butylparaben, Thimerosal, Sodium benzoate and Phenylmercuric nitrate, more preferably from Benzyl alcohol, Chlorobutanol, Cresol, Methylparaben, Phenol, Propylparaben, Butylparaben and Thimerosal and even more preferably from Phenol, Chlorobutanol, Cresol, Methylparaben, Propylparaben and Thimerosal.

If the compositions contain more than one amphiphilic compound and/or one or more oligopeptides, the molar ratio is preferably the one between the molar amount of all contained oligopeptides and/or the amount of all contained amphiphilic compounds, respectively.

If the compositions contain more than one compound of a respective class of compound, e.g. more than one amphiphilic compound and/or one or more oligopeptide, the percentages given herein preferably relate to the total amount of the respective class of compound, i.e. the total amount of all contained oligopeptides and the total amount of all contained amphiphilic compounds, respectively. The same holds preferably true for the other classes of compounds contained in the compositions according to the invention.

Preferably, the compositions according to the invention and especially the pharmaceutical compositions according to the invention are compositions for subcutaneous (s.c.) administration and/or intramuscular (i.m.) administration. Administration in this regard preferably relates to the administration of said compositions to a mammal, preferably a human mammal, even more preferably to a patient and especially to a human patient. In this regard, subcutaneous administration or subcutaneous is preferably also abbreviated as s.c. administration or s.c., respectively; also in this regard, intramuscular administration or intramuscular is preferably abbreviated as i.m. administration or i.m.

Compositions according to the invention which comprise lipophilic compounds according to b) as defined herein and especially compositions which comprise predominantly or exclusively lipophilic compounds according to b) as defined herein, but which preferably contain no or only minor amounts of amphiphilic compounds according to b) as defined herein, are preferred as pharmaceutical compositions for intramuscular administration.

Compositions according to the invention which comprise amphiphilic compounds according to b) as defined herein and especially compositions which comprise predominantly or exclusively amphiphilic compounds according to b) as defined herein, but which preferably contain no or only minor amounts of lipophilic compounds according to b) as defined herein, are preferred as pharmaceutical compositions for subcutaneous administration.

A further preferred subject of the instant invention is a process for the manufacture of a composition as described herein.

[24] Preferably, the process for the manufacture of a composition as described herein, or as described in one or more of the paragraphs numbered [1] to [23] and/or the paragraphs relating thereto, comprises one or more of the following steps, preferably two or more and more preferably comprises all the given steps:

i) solubilising the one or more amphiphilic compounds in water, ii) adding or preferably suspending the one or more oligopeptides in the mixture or solution, preferably solution, obtained according to i), and optionally iii) adding the of one or more pharmaceutically active ingredients other than the compound according to a), and/or the one or more pharmaceutically acceptable excipients other than the water and the one or more amphiphilic compounds.

Even more preferably, the process for the manufacture of a composition as described herein comprises one or more of the following steps, preferably two or more and more preferably comprises all the given steps:

i) solubilising the one or more amphiphilic compounds in water, ii) adding or preferably suspending the one or more oligopeptides in the mixture or solution, preferably solution, obtained according to i), and optionally iii) adding the one or more pharmaceutically acceptable excipients, selected from the group consisting of tonicity agents and preservatives, optionally followed by iv) adding the of one or more pharmaceutically active ingredients other than the compound according to a).

Preferably, the mixture obtained according to steps ii), iii) and/or iv) is mixed, stirred and/or agitated until a stable particle size and/or particle size distribution is obtained.

Preferably, the two or more of the steps of the above given processes are performed in the above given order.

Preferably, an alternative process for the manufacture of a composition as described herein comprises one or more of the following steps, preferably two or more and more preferably comprises all the given steps:

i) contacting the one or more oligopeptides with the one or more lipophilic compounds; and optionally ii) mixing, stirring and/or agitating the mixture according to step i), preferably until a stable particle size and/or particle size distribution is obtained, and/or iii) adding the of one or more pharmaceutically active ingredients other than the compound according to a), and/or the one or more pharmaceutically acceptable excipients other than the water and the one or more amphiphilic compounds.

Even more preferably, the process for the manufacture of a composition as described herein comprises one or more of the following steps, preferably two or more and more preferably comprises all the given steps:

i) contacting the one or more oligopeptides with the one or more lipophilic compounds; and optionally ii) mixing, stirring and/or agitating the mixture according to step i), preferably until a stable particle size and/or particle size distribution is obtained, and optionally iii) adding the one or more pharmaceutically acceptable excipients, selected from the group consisting of tonicity agents and preservatives, optionally followed by iv) adding the of one or more pharmaceutically active ingredients other than the compound according to a).

Preferably, the two or more of the steps of the above given processes are performed in the above given order.

Advantageously, the oligopeptide, preferably the solid oligopeptide and especially the particulate solid oligopeptide preferably undergoes degradation (preferably spontaneous degradation or self-degradation) or even preferably micronization (preferably spontaneous micronization or self-micronization) to yield suspended or suspendable particles on contacting it with the lipophilic compound or the amphiphilic compound, the latter preferably in the presence of water. Generally, mixing, stirring and/or agitating accelerates this process.

Means for solubilising the one or more amphiphilic compounds in water in step i), the adding or preferably suspending of the one or more oligopeptides in step ii) and/or the addition of the further compounds in step iii) can advantageously be performed by mixing, stirring and/or agitating the respective compounds in the respective step.

Preferably, the mixing, stirring and/or agitating is continued after the completion of the one or more reaction steps, preferably after the completion of all reaction steps. Generally, the mixing, stirring and/or agitating is continued until a stable suspension and/or stable particle size distribution in the suspension is obtained. The mixing, stirring and/or agitating time is mainly dependent from the respective particle size of the solid oligopeptide. Thus, starting with coarse particles of the oligopeptide generally leads to longer processing times and/or mixing, stirring and/or agitating times, whereas starting with fine particles of the oligopeptides or micronized oligopeptide will lead to shorter processing times and/or shorter mixing, stirring and/or agitating times or generally a reduced need for mixing, stirring and/or agitating.

Thus, the mixing, stirring and/or agitating is then continued 1 to 96 hours, preferably 1 to 72 hours, more preferably 1 to 48 hours, even more preferably 2 to 72 hours and especially 2 to 48 hours. Even more preferably, the mixing, stirring and/or agitating is then continued 2 to 96 hours, preferably 2 to 72 hours, more preferably 2 to 48 hours, even more preferably 3 to 72 hours and especially 3 to 48 hours.

Generally, the process for the manufacture of the compositions according to the invention, preferably including the mixing, stirring and/or agitating time after the completion of the one or more reaction steps, takes a processing time of 1 to 100 hours, preferably 1 to 80 hours, more preferably 1 to 56 hours, even more preferably 2 to 78 hours and especially 2 to 56 hours.

Thus, on starting with already micronized oligopeptide, processing times and especially mixing, stirring and/or agitating times will be in the range of 1 to 24 hours, more preferably 1 to 12 hours, more preferably 2 to 12 hours, even more preferably 2 to 8 hours and especially 3 to 6 hours, for example about 3 hours, about 4 hours, about 5 hours or about 6 hours.

Thus, on starting with coarse particles of the oligopeptide, processing times and especially mixing, stirring and/or agitating times will be in the range of 3 to 96 hours, more preferably 4 to 72 hours, more preferably 6 to 48 hours, even more preferably 8 to 48 hours and especially 10 to 48 hours, for example about 3 hours, about 4 hours, about 5 hours or about 6 hours.

Thus, preferred is a process as described herein and especially as described in the paragraph numbered [24] and preferably also the paragraphs relating thereto, wherein one or more, preferably two or more and especially three or four of these steps comprise mixing, stirring and/or agitating the respective compounds in the respective step.

Preferably, the oligopeptide is employed in the process in a solid form, preferably a solid particulate form an even more preferably in a solid crystalline particulate form. Even more preferably the oligopeptide is employed in the process in a milled or even more preferably micronized form.

Generally, the process according to the invention is performed at normal temperatures, such as room temperature (20° C. or 25° C., preferably 20° C.), or at elevated temperatures, preferably normal temperatures or moderately elevated temperatures. Moderately elevated temperatures according to the invention preferably are the range between 25° C. and 80° C., more preferably 30° C. and 60° C. and especially between 30° C. and 50° C., for example at about 30° C., about 40° C. or about 50° C.

Preferably, only one, or only one or two, of the process steps are performed at elevated temperatures and even more preferably moderately elevated temperatures.

Depending on the physical properties of the amphiphilic compound used in the instant process, it can be advantageous to perform the solubilising the one or more amphiphilic compounds in water at elevated temperatures and more preferably at moderately elevated temperatures as described herein. Even more preferably, only this step is performed at moderately elevated temperatures.

[26] A preferred subject of the instant invention is a composition, obtainable by the process according as described herein and especially as described in the paragraph numbered [25] and preferably also the paragraphs relating thereto and especially as described in one or more of the examples 1 to 9 or 1 to 15.

Thus, a preferred subject of the instant invention is a composition obtainable by the process according to one or more of the examples 1 to 9 or 1 to 15.

Means for adding, mixing, stirring and/or agitating the compounds in the respective steps are known in the art.

The process for the manufacture according to the invention is described in more detail in the examples.

Another preferred subject of the invention are powders, preferably free-flowing and/or reconstitutable powders, which correspond to the compositions as described herein but are free of or essentially free of water or other solvents. Preferably, such powders are obtainable from the compositions as described herein that contain water and/or are obtainable by the process for the manufacture of the compositions as described herein, by suitable steps that are known in the art for reducing the amount of water and/or other solvents from said compositions, or that are known in the art for removing the water and/or the other solvents. Preferred suitable steps are selected from drying, vacuum drying, fluid-drying, spray-drying, evaporation and lyophilisation, and combinations thereof. These steps can be optionally performed in the presence of suitable pharmaceutically acceptable excipients that facilitate the drying step and/or the reconstitution or resuspension of said powders into injectable formulations or compositions. Suitable pharmaceutically acceptable excipients for that purpose are known in the art. Preferably, pharmaceutically acceptable excipients for that purpose preferably include carbohydrates or sugars, e.g. mannitol, dispersing aids, binders, and the like.

Thus, a preferred subject of the invention is a composition, preferably in the form a powder, more preferably a free-flowing and/or reconstitutable powder, comprising
a) 80 to 99.99% of at least one oligopeptide, said oligopeptide having a solubility in water at 20° C. between 5 mg/ml and 20 mg/ml, b) 0.01 to 20% of one or more lipophilic and/or amphiphilic compounds having a molar weight in the range of 200 g/mol to 2000 g/mol, and
c) 0 to 20% of water,
with the proviso that the sum of a), b) and c) sums up to 80 or more % of the total composition.

Thus, a more preferred subject of the invention is a composition, preferably in the form a powder, more preferably a free-flowing and/or reconstitutable powder, comprising
a) 80 to 99.99% of cyclo-(Arg-Gly-Asp-DPhe-NMeVal), the pharmaceutically acceptable derivatives, solvates and/or salts thereof, preferably having a solubility in water at 20° C. between 5 mg/ml and 20 mg/ml,
b) 0.01 to 20% of one or more lipophilic and/or amphiphilic compounds as described herein and more preferably selected from dioleoylphosphatidylglycerol and dimyristoylphosphatidylglycerol, and
c) 0 to 20% of water,
with the proviso that the sum of a), b) and c) sums up to 80 or more %, more preferably to 90 or more % and especially to 95-100%, of the total composition.

Thus, and even more preferred subject of the invention is a composition, preferably in the form a powder, more preferably a free-flowing and/or reconstitutable powder, comprising
a) 80 to 99.99% of cyclo-(Arg-Gly-Asp-DPhe-NMeVal), the pharmaceutically acceptable derivatives, solvates and/or salts thereof, preferably having a solubility in water at 20° C. between 5 mg/ml and 20 mg/ml,
b) 0.01 to 20% of one or more lipophilic and/or amphiphilic compounds as described herein and more preferably selected from dioleoylphosphatidylglycerol and dimyristoylphosphatidylglycerol, and optionally
c) 0 to 20% of one or more pharmaceutically acceptable excipients,
with the proviso that the sum of a), b) and c) sums up to 90% or more, preferably 95% or more and especially 99 to 100% of the total composition, and with the further proviso that the water content of said composition is in the range between 0.001 and 10%, more preferably 0.01 and 5% and especially 0.01 to 1%.

Thus, preferred is a composition in the form of a free-flowing or reconstitutable powder, which corresponds to a composition as described herein and more preferably water-based compositions as described herein, wherein the water-content is reduced to residual water content in the range of 0 to 20% or 0.001 to 10%, preferably based on the total (dried) composition or (dried) powder and more preferably based on the total weight of the (dried) composition or (dried) powder. Water-based compositions in this regard are preferably compositions that that contain 20% more, preferably 30% or more, more preferably 40% more and especially 60% or more of water, preferably based on the total composition. Preferably, such water based compositions contain 30 to 90%, more preferably 40 to 80% and especially 50 to 75% of water, preferably based on the total composition.

Thus, preferred is a composition form of a free-flowing or reconstitutable powder, obtainable from a composition as described herein and more preferably a water-based composition as described herein by reducing the water content until a residual water content of 0 to 20% or 0.001 to 10 percent is achieved, preferably based on the total (dried) composition or (dried) powder and more preferably based on the total weight of the (dried) composition or (dried) powder.

Thus, the compositions according to the invention are preferably either
a) in the form of suspensions, preferably a suspension of the contained oligopeptide in an aqueous medium, such as water, water for injection, buffered water, phosphate-buffered saline or other pharmaceutically acceptable aqueous media, or
b) in the form of dried powders, preferably powders which are substantially free or free of water, which are obtainable from the (aqueous) compositions as described herein, and which can preferably be resuspended in such an equation medium as described before.

Preferably, both the compositions in the form of (aqueous) suspensions as well as the compositions in the form of (dried) powders are suitable for injection into a patient or subject, preferably suitable for a subcutaneous injection into a patient or subject, the suspensions preferably directly and the powders obviously after resuspension or re-constitution in an aqueous medium as described before.

Preferably, the compositions according to the invention comprise 10% or more, preferably 30% or more, more preferably 50% or more, even more preferably 70% or more and especially 70 to 99%, 70 to 99.9% or 80 to 99.99, of the contained one or more oligopeptides, cyclic oligopeptides or cyclo-(Arg-Gly-Asp-DPhe-NMeVal) in the form of solid particles and/or solid crystalline particles.

Preferably, the solid compositions according to the invention comprise 50% or more, preferably 70% or more, more preferably 90% or more, even more preferably 95% or more and especially 80 to 99%, 80 to 99.9% or 90 to 99.99, of the contained one or more oligopeptides, cyclic oligopeptides or cyclo-(Arg-Gly-Asp-DPhe-NMeVal) in the form of solid particles and/or solid crystalline particles.

Thus, preferred are compositions as described herein, wherein the one or more oligopeptides, cyclic oligopeptides or cyclo-(Arg-Gly-Asp-DPhe-NMeVal) are at least partly present in the form of solid particles and/or solid crystalline particles, said particles having an average particle size or an effective average particle size in the range of 5 µm to 250 µm, 8 µm to 150 µm, 10 µm to 100 µm, 10 µm to 80 µm, and especially 15 µm to 60 µm. In this regard, the average particle size or effective average particle size is volume-weighted or number-weighted, preferably volume-weighted. Preferably, it is determined as described herein. At least partly present in this regard preferably means 10% or more, preferably 30% or more, more preferably 50% or more, even more preferably 70% or more and especially 70 to 99%, 70 to 99.9% or 80 to 99.99. Percentages in this regard are preferably given as described herein and more preferably are % w/w.

Preferably, said cyclo-(Arg-Gly-Asp-DPhe-NMeVal) in the form of solid particles and/or solid crystalline particles is preferably selected from an anhydrate of the inner salt of cyclo-(Arg-Gly-Asp-DPhe-NMeVal), a crystalline anhydrate of the inner salt of cyclo-(Arg-Gly-Asp-DPhe-NMeVal), and the crystalline form A1 of the inner salt of cyclo-(Arg-Gly-Asp-DPhe-NMeVal) an. Thus, said solid particles and/or solid crystalline particles preferably comprise crystalline form A1 and more preferably essentially consist of crystalline form A1 or consist of crystalline form A1.

A preferred subject of the instant invention is the use of cyclo-(Arg-Gly-Asp-DPhe-NMeVal), the pharmaceutically acceptable derivatives, solvates and/or salts thereof and especially the use of the inner salt of cyclo-(Arg-Gly-Asp-DPhe-NMeVal), a crystalline anhydrate of the inner salt of cyclo-(Arg-Gly-Asp-DPhe-NMeVal), and/or the crystalline form A1 of the inner salt of cyclo-(Arg-Gly-Asp-DPhe-NMeVal), for the manufacture of a composition as described herein and especially for a pharmaceutical composition as described herein. Thus, a preferred subject of the instant invention is the use of crystalline form A1 for the manufacture of a composition as described herein and especially for a pharmaceutical composition as described herein.

Thus, a preferred subject of the instant invention are compositions, preferably pharmaceutical compositions and especially compositions or pharmaceutical compositions as described herein that comprise crystalline form A1. Preferably, said compositions comprise 5 to 100%, more preferably 5 to 99%, even more preferably 10 to 70%, even more preferably 12 to 60%, even more preferably 15 to 50% and especially 20 to 40%, of crystalline form A1, e.g. about 10%, about 15%, about 20%, about 25%, about 30% or about 35% of crystalline form A1. Said percentages are preferably based on the total composition. Percentages in this regard are preferably given as described herein and more preferably are % w/w or % w/v, and especially are % w/w.

A preferred subject of the instant invention is the use of the compositions as described herein and/or the use of the solid compositions as described herein as a pharmaceutical. A preferred subject of the instant invention is the use of the compositions as described in this specification, as described in the claims and/or as described or essentially described in the Examples as a pharmaceutical. Preferred Examples in this regard are one or more of Examples 1 to 17.

If not explicitly stated otherwise, the terms "solid material(s) as described herein", "solid form(s) as described herein", "crystalline form(s) as described herein", "solvate(s) as described herein", "hydrate(s) as described herein", "tetrasolvate(s) as described herein", "tetrahydrate(s) as described herein", "anhydrate(s) as described herein", "alcoholate(s) as described herein", "methanolate(s) as described herein", "ethanolate(s) as described herein", "tetraalcoholate(s) as described herein", "tetramethanolate(s) as described herein" and/or "tetraethanolate(s) as described herein" preferably refer to the "solid material(s)", "solid form(s)", "crystalline form(s)", "solvate(s)", "hydrate(s)", "tetrasolvate(s)", "tetrahydrate(s)", "anhydrate(s)", "alcoholate(s)", "methanolate(s)", "ethanolate(s)", "tetraalcoholate(s)", "tetramethanolate(s)" and/or "tetraethanolate(s)" of the compound of formula Id.

Methods and means for determining the solubilities of the compounds described herein are known in the art. Preferably, the solubilities of the compounds described herein are determined by methods and means accepted by the FDA and/or EMEA.

Solubility in this regard is preferably refers to the saturation solubility, which is preferably the maximum mass of the respective compound, which can be solubilised or dissolved in a solvent at a respective temperature and at a specific pressure, preferably atmospheric pressure.

With regard to the present invention, the solubilities in water given herein for the respective compound preferably refer to the saturation solubility of the respective compound in water, which is preferably the maximum mass of the respective compound which can be solubilised or dissolved in water at the respective given temperature and at the respective pressure, preferably atmospheric pressure, and even more preferably the maximum mass of the respective compound which can be solubilised or dissolved in water at the respective temperatures given herein, i.e. 20° C. and/or 25° C., preferably 20° C., a and at the respective pressure, preferably atmospheric pressure, which is here preferably normal atmospheric pressure and especially the standardised "normal" atmospheric pressure, i.e. 1 atm=1.01325 bar.

Even more preferably, they can be determined by the method described below:
10 mL of solvent is placed in an amber glass ampul and sufficient substance is added to yield a distinct sediment that remains on the bottom after mixing thoroughly. After standing for 15 minutes and mixing again the ampuls are sealed and shaken in a thermostatically controlled water bath (20° C./16 hours or 25° C./16 hours, preferably 20° C./16 hours). Afterwards the ampuls are opened and the supernatant solution is filtered until the filtrate is clear. The content of the substance is determined photometrically in an aliquot by means of the specific adsorption coefficient. The respective dilution of the solvent without substance serves as blank. The solubility is expressed in the dimension of g substance in 100 mL or mg substance in 1 mL, preferably in mg substance in 1 mL. Preferably, this method is performed at normal atmospheric pressure and especially at the standardised "normal" atmospheric pressure, i.e. 1 atm=1.01325 bar.

The term "particle size" as used herein is known and understood in the art. Preferably, the particle size is determined on the basis of the weight average particle size, preferably as measured by conventional particle size measuring techniques well known to those skilled in the art. Such techniques preferably include, for example, sedimentation field flow fractionation, photon correlation spectroscopy, light scattering, and disk centrifugation.

The term "average particle size" as used herein is known and understood in the art. Preferably, the average particle size is selected from the weight-average particle size, the volume-weighted average particle size and the number-weighted average particle size.

Preferably, the particle size and/or the average particle size is measured by light-scattering methods, microscopy or other appropriate methods known in the art. Appropriate methods in this regard preferably include, but are not limited to sedimentation field flow fractionation, photon correlation spectroscopy, light scattering, laser dynamic light scattering, and disk centrifugation. Furthermore, dynamic light scattering methods (e.g., photocorrelation spectroscopy, laser diffraction, low angle laser light scattering (LALLS), medium-angle laser light scattering (MALLS), light obscuration methods (Courter method, for example), rheology, or microscopy (light or electron) can be used.

The determination of the particle size distribution is especially preferably performed by laser diffraction, preferably on a Malvern Mastersizer 2000, preferably using the wet modul Hydro 2000 SM. The evaluation model is preferably Universal (normal sensitivity), the dispersion medium is preferably saturated placebo solution, the stirrer speed is preferably about 2000 rpm, the obscuration is preferably 10-15%, the background measuring time is preferably about 7500 ms (milliseconds), and/or the measuring time is preferably about 7500 ms.

The term "at least one" preferably comprises the terms "at least two" and/or "at least three", and preferably the like. The term "at least one" thus preferably includes "one", "two", "three" and preferably also higher numbers.

The term "one or more" preferably has the same meaning as "at least one", and thus preferably also includes the meanings "two or more" and/or "three or more", and preferably the like. The term "one or more" thus preferably also includes "one", "two", "three" and preferably also higher numbers.

If not explicitly stated otherwise, the term "solid composition" or "solid compositions" preferably exclusively refers to such compositions that are free of water or essentially free of water. Essentially free of water with regard to said solid compositions means a residual water content of less than 10%, more preferably less than 5%, even more preferably less than 2% and especially preferably less than 1%, e.g. 0.001 to 5% or 0.01 to 2%, preferably based on the total weight of the (dried) composition If not explicitly stated otherwise, the term "composition" or "compositions" in the absence of the term "solid" preferably refers to both a) "non-solid compositions", i.e. compositions that preferably have a water content of more than 1%, more preferably a water content of more than 2%, even more preferably a water content of more than 5% and especially a water content of more than 10%, preferably based on the total weight of the respective composition, and b) "solid compositions", preferably as defined above.

However, if not explicitly stated otherwise, the amounts given herein for the respective ingredients in the compositions in the absence of the term "solid" preferably refer to the amounts in "non-solid compositions", preferably water-based compositions as described herein, and even more preferably refer to suspensions and especially preferably aquaous suspensions as described herein.

Preferably, the compositions of the present invention are surprisingly stable to storage, preferably including both the chemical stability of the components and especially the chemical stability of the cyclic oligopeptide and/or the physical stability, preferably including the physical stability of the solid particles thereof. In particular, the solutions of the invention are generally stable to storage at ambient temperature (e.g. 25° C./60% rel. hum.) for a period of no less than 4 weeks (e.g. 4 weeks to 3 years), preferably no less than three months, more preferably no less than 6 months.

Chemical stability in this regard preferably refers to the absence of significant degradation of one or more of the contained components and especially refers to the absence of significant degradation of the contained cyclic oligopeptide(s).

Physical stability in this regard preferably refers to a) the absence of significant precipitation, segregation and/or exsolution of originally dissolved components, and/or b) the absence of significant changes in particle sizes, average particle size and/or particle size distribution of originally contained solid (particulate) components.

Physical stability in this regard more preferably refers to the absence of significant changes in particle sizes, average particle size and/or particle size distribution of originally contained solid particles of the cyclic oligopeptide(s).

Physical stability in this regard even more preferably refers to the absence of significant "Ostwald ripening" of the contained solid particles of the cyclic oligopeptide(s).

Said chemical and/or physical stability of the compositions described herein is preferably found even on prolonged storage at typical storage conditions for pharmaceutical products.

Typical storage conditions for pharmaceutical products are preferably selected from storage at 2-8° C. and storage at 25° C./60% relative humidity. For liquid pharmaceutical products, storage at 2-8° C. is especially preferred.

Preferably, the compositions according to the invention show an at least suitable or preferably good syringeability. Preferably, the particle size in the composition and/or the viscosity of the composition enables convenient administration to a patient using syringes or other devices for injection equipped with up to 23 gauge needless, up to 24 gauge needles, up to 25 gauge needles, up to 26 gauge needles, up to 27 gauge needles or up to 28 gauge needles.

Preferably, the compositions according to the invention show both a fast onset and a sustained release characteristic for the contained cyclic oligopeptide(s). The term "fast onset" is known and understood in the art. Fast onset in this regard more preferably means that generally 3 to 15% and preferably 5 to 15% of the cyclic oligopeptide(s) contained in said compositions is released within the first 1 to 5 hours and more preferably the first 1 to 3 hours after injection, preferably subcutaneous injection, into the patient or subject. The term "sustained-release" is known and understood in the art. Sustained release in this regard more preferably means that generally 85 to 95% of the cyclic oligopeptide(s) contained in said compositions is released over a period of 8 hours or more, preferably 16 hours or more, even more preferably 24 hours or more, even more preferably 36 hours or more, even more preferably 48 hours or more and especially preferably 72 hours or more after injection, preferably subcutaneous injection, into the patient or subject.

Preferably, the compositions according to the invention show, after administration to a patient or subject, preferably after subcutaneous administration to a patient or subject, an about linear release characteristics over one or more prolonged time periods. A prolonged time period in this regard preferably means 8 or more hours, preferably 16 or more hours, more preferably 32 hours or more and especially 48 hours or more. Thus, if administered to a patient or subject, the compositions according to the invention preferably show at least one prolonged time period, preferably at least one prolonged time period in the range between 8 to 48 hours and especially in the range of 16 to 32 hours, wherein the contained cyclic oligopeptide(s) is released from said composition in an about linear release characteristic and/or concentration. Thus, if administered to a patient or subject, the compositions according to the invention preferably show an about linear pharmacokinetic profile for the contained cyclic oligopeptide(s) over at least one prolonged time period as described above, preferably based on the plasma level of said cyclic oligopeptide(s) in said patient or subject.

Preferably, the compositions according to the invention are free or essentially free of water insoluble compounds. Preferably, the compositions according to the invention are free or essentially free of water insoluble pharmaceutically active ingredients. Preferably, the compositions according to the invention are free or essentially free of water insoluble oligopeptides or cyclic oligopeptides. Water insoluble in this regard preferably means that the compounds and/or pharmaceutically active ingredients have a solubility in water that is 0.1 mg/ml or less, more preferably 1 mg/ml or less and especially 5 mg/ml or less. Preferably, the water solubility in this regard can be determined as it is known in the art or as is described herein. More preferably, the water solubility in this regard is determined at physiological pH (6.5-7.4), preferably according to methods known in the art or according to methods as described herein.

Preferably, the compositions according to the invention do not contain one or more antigens. More preferably, the compositions according to the invention are free or essentially free of antigens or compounds that act as antigens.

Preferably, the composition according to the invention provides a dosageform, especially a dosageform for injection and more preferably subcutaneous injection that enables a high drug load or high concentration of API based on the total composition. For example the concentration of the contained oligopeptide drug or API can preferably be 20% or more, more preferably 30% or more and especially 40% or more, based on the total composition. Percentages in this regard are preferably % v/v, % w/v or % w/w. Preferably, the compositions according to the invention with high concentrations nevertheless show an at least suitable or preferably good syringeability.

Preferably, the oligopeptide(s) contained in the compositions according to the invention do not act as an antigen.

Preferably, the compositions according to the invention do not contain one or more anticonvulsant agent. More preferably, the compositions according to the invention are free or essentially free of antigens or compounds that act as an anticonvulsant agent.

Preferably, the oligopeptide(s) contained in the compositions according to the invention do not act as an anticonvulsant agent.

Preferably, the compositions according to the invention do not contain one or more anti-retroviral agents. More preferably, the compositions according to the invention are free or essentially free of anti-retroviral agents or compounds that act as an anti-retroviral agent.

Preferably, the compositions according to the invention contain one or more lipophilic and/or amphiphilic compounds as described herein.

More preferably, the compositions according to the invention contain either
a) one or more lipophilic compounds as described herein, or
b) one or more amphiphilic compounds as described herein.

Even more preferably, the compositions according to the invention contain one or more amphiphilic compounds as described herein, but contain only minor amounts of lipophilic compounds as described herein, or are free or essentially free of lipophilic compounds as described herein. Minor amounts in this regard are 10% or less, 5% or less, 1% or less, 0.1% or less, or 0.01% or less, based on the amount of the one or more amphiphilic compounds as described herein contained in said composition. Percentages in this regard are preferably mole-% or % w/w, more preferably % w/w.

Preferably, the one or more amphiphilic compounds as described herein are selected from
a) anionic amphiphilic compounds as described herein,
b) non-ionic amphiphilic compounds as described herein,
c) cationic amphiphilic compounds as described herein, and/or
d) amphoteric or zwitterionic amphiphilic compounds as described herein.

Preferably, the one or more amphiphilic compounds as described herein are selected from
a) anionic amphiphilic compounds as described herein, and/or
b) non-ionic amphiphilic compounds as described herein.

Thus, the compositions according to the invention that contain one or more anionic amphiphilic compounds as described herein preferably contain only minor amounts of or are free or essentially free of non-ionic amphiphilic compounds, cationic amphiphilic compounds and amphoteric (or zwitterionic) amphiphilic compounds. Minor amounts in this regard are 10% or less, 5% or less, 1% or less, 0.1% or less, or 0.01% or less, based on the amount of the one or more anionic amphiphilic compounds as described herein contained in said composition. Percentages in this regard are preferably mole-% or % w/w, more preferably % w/w.

Preferably, the one or more amphiphilic compounds as described herein are exclusively selected from anionic amphiphilic compounds as described herein.

Generally, it is preferred to have a small number of different components in the compositions that are suitable for use as pharmaceutical compositions, e.g. to avoid unwanted chemical or physical interactions between the different compounds in that compositions, but also to avoid unwanted physiological or toxicological into action in the patient or subject that the composition is applied or administered to. Furthermore, pharmaceutical compositions containing an as little as number of components as possible have a lower risk of unwanted adverse effects and thus are also preferred from regulatory point of view with regard to the approval by the health authorities.

Thus, the compositions according to the invention preferably contain only one amphiphilic compound as described herein, preferably one anionic amphiphilic compounds as described herein. Preferably they contain only minor amounts of or are especially preferably free or essentially free of further amphiphilic compounds, preferably amphiphilic compounds as described herein. Thus, they preferably contain no second or third amphiphilic compound, especially no second or third amphiphilic compounds selected from non-ionic amphiphilic compounds, cationic amphiphilic compounds and amphoteric (or zwitterionic) amphiphilic compounds. Minor amounts in this regard are 10% or less, 5% or less, 1% or less, 0.1% or less, or 0.01% or less, based on the amount of the one anionic amphiphilic compound as described herein contained in said composition. Percentages in this regard are preferably mole-% or % w/w, more preferably % w/w.

Preferably, the amphiphilic compounds for use in the compositions according to the invention are selected from natural amphiphilic compounds and naturally derived amphiphilic compounds, preferably purified naturally derived amphiphilic compounds, and synthetic amphiphilic compounds, more preferably synthetically derived amphiphilic compounds. Especially preferred for use in the compositions according to the invention are synthetic amphiphilic compounds and/or synthetically derived amphiphilic compounds.

Thus, the compositions according to the invention preferably contain only minor amounts of or are especially preferably free or essentially free of natural amphiphilic compounds and/or naturally derived amphiphilic compounds. Such natural amphiphilic compounds or naturally derived amphiphilic compounds include, but are preferably not limited to natural cholines, such as as egg phophatidylcholine, soy phosphatidylcholine, lecthine and the like. Minor amounts in this regard are preferably 0.5% or less, 0.1% or less, 0.01% or less, 0.001% or less, or 0.0001% or less, based on the amount of the one or more oligopeptides or cyclic oligopeptides as described herein contained in said composition. Percentages in this regard are preferably mole-% or % w/w, more preferably % w/w.

The term "ad. 100%", "add 100%" and/or "add. 100%" with respect to a component of a composition is known in the art. Preferably, it means that this component is added to the other given components until 100% of the composition or total composition is achieved. Accordingly, the term "ad. 100 v %" preferably means that this component is added to the other given components until 100 v % of the composition or total composition is achieved, and the like.

Especially preferred according to the invention are subjects as described herein, wherein the characteristics of two or more preferred, more preferred and/or especially preferred embodiments, aspects and/or subjects are combined into one embodiment, aspect and/or subject. Preferably, according to this invention, preferred subjects or embodiments can be combined with other preferred subjects or embodiments; more preferred subjects or embodiments can be combined with other less preferred or even more preferred subjects or embodiments; especially preferred subjects or embodiments can be combined with other just preferred or just even more preferred subjects or embodiments, and the like.

The term "about" as used herein with respect to numbers, figures, ranges and/or amounts is preferably meant to mean "circa" and/or "approximately". The meaning of those terms is well known in the art and preferably includes a variance, deviation and/or variability of the respective number, figure, range and/or amount of plus/minus 15% and especially of plus/minus 10%.

The invention is explained in greater detail below by means of examples. The invention preferably can be carried out throughout the range claimed and is not restricted to the examples given here.

Moreover, the following examples are given in order to assist the skilled artisan to better understand the present invention by way of exemplification. The examples are not intended to limit the scope of protection conferred by the claims. The features, properties and advantages exemplified for the processes, compounds, compositions and/or uses defined in the examples may be assigned to other processes, compounds, compositions and/or uses not specifically described and/or defined in the examples, but falling under the scope of what is defined in the claims.

EXPERIMENTAL SECTION

Example 1

This Example of a typical composition in the form of a suspension comprising a lipophilic compound and preferably no water may contain per mL:
150 to 300 mg/mL of solid Cilengitide, preferably in amorphous or crystalline form, more preferably the crystalline form A1-Cilengitide
optionally 9 mg/mL sodium chloride
optionally 5 mg/mL phenol
Seasame oil (add 100%)

The composition of Example 1 is preferably prepared by suspending the solid Cilengitide and especially the solid A1-Cilengitide in the oil by adding it to the oil under stirring. Preferably, the stirring is continued for 4 to 20 h. If desired, the sodium chloride can then be added for adjusting the tonicity of decomposition and/or the phenol can be added for the preservation of the composition. If necessary, further amounts of the oil can be added (add 100%) to achieve the total volume of the composition i.e. 1 mL.

Example 2

This Example of a typical composition in the form of a suspension comprising a lipophilic compound and preferably no water may contain per mL:
200 mg/mL of Cilengitide in the crystalline form A1
optionally 9 mg/mL sodium chloride
optionally 5 mg/mL phenol
Miglyol 812 (add 100%)

The composition of Example 2 is preferably prepared by suspending the solid Cilengitide in the crystalline form A1 in the oil (Miglyol 812) by adding it to the oil under stirring. Preferably, the stirring is continued for 4 to 48 h. If desired, the sodium chloride can then be added for adjusting the tonicity of decomposition and/or the phenol can be added for the preservation of the composition. If necessary, further amounts of the oil can be added (add 100%) to achieve the total volume of the composition i.e. 1 mL.

Example 3

This Example of a typical composition (5 mL) in the form of a suspension comprising a lipophilic compound and preferably no water may contain per mL:
200 mg/mL of micronized A1-Cilengitide, e.g. micronized A1-Cilengitide with a typical particle size distribution of d(10)=1-5 µm, d(50)=5-10 µm, and d(90)=20-30 µm,
optionally 9 mg/mL sodium chloride
optionally 5 mg/mL phenol
seasame oil (add 100%)

The composition of Example 3 is preferably prepared by suspending the solid micronized A1-Cilengitide (1000 mg) in an aliquot of the seasame oil (3 mL) by adding it to the oil under stirring. Preferably, the stirring is continued for 4 to 48 h. If desired, the sodium chloride can then be added for adjusting the tonicity of decomposition and/or the phenol can be added for the preservation of the composition. If necessary, further amounts of the oil can be added (add 100%) to achieve the total volume of the composition i.e. 5 mL.

Example 4

This Example of a typical composition (5 mL) in the form of a suspension comprising an amphiphilic compound and water may contain per mL:
200 mg/mL of micronized A1-Cilengitide, e.g. micronized A1-Cilengitide with a typical particle size distribution of d(10)=1-5 µm, d(50)=5-10 µm, and d(90)=20-30 µm,
1 to 20 mg/mL DOPG
optionally 9 mg/mL sodium chloride
optionally 5 mg/mL phenol
water for injection (add 100%)

The composition of Example 4 is preferably prepared by solubilization of the DOPG in water, preferably water for injection, at about room temperature or preferably at slightly elevated temperature, e.g. at about at about 30° C. or at about 40° C. After the solubilization, the micronized A1-Cilengitide (1000 mg) is added subsequently under stirring. Preferably, the stirring is continued for 4 to 20 h. If desired, the sodium chloride can then be added for adjusting the tonicity of decomposition and/or the phenol can be added for the preservation of the composition. If necessary, further amounts of water can be added (add 100%) to achieve the total volume of the composition, i.e. 5 mL.

Example 5

This Example of a typical suspension may contain per mL:
200 to 300 mg/mL of micronized A1-Cilengitide, e.g. micronized A1-Cilengitide with a typical particle size distribution of d(10)=1-5 µm, d(50)=5-10 µm, and d(90)=20-30 µm, or micronized A1-Cilengitide with an even more narrow particle size distribution optionally
1 to 20 mg/mL DOPG
optionally 9 mg/mL sodium chloride
optionally 5 mg/mL phenol
water for injection (add 100%)

The composition of Example 2 is preferably prepared by solubilization of DOPG in water, preferably water for injection, at about room temperature or preferably at slightly elevated temperature, e.g. at about 30° C. or at about 40° C. After the solubilization, the solid A1-Cilengitide is added subsequently under stirring. Preferably, the stirring is continued for 2 to 6 h. If desired, the sodium chloride can then be added for adjusting the tonicity of the composition and/or the phenol can be added for the preservation of the composition. Then water is added (add 100%) i.e. until the total volume of 1 mL of the composition is obtained Example 6

A preferred method of manufacture comprises the following steps, preferably in the given order:
1. Dissolution or solubilisation of solid DOPG in water under stirring at a temperature between 20° C. and 40° C.
2. Addition of solid Cilengitide, preferably crystalline Cilengitide, more preferably crystalline Cilengitide anhydrate and especially crystalline Cilengitide of the form A1
3. Stirring of the obtained suspension until a stable particle distribution is obtained, generally 24 h or more and especially 24 to 48 h
4. Addition of NaCl, generally about 9 mg/mL, to the suspension under continued stirring, and optionally
5. Continuation of the stirring process (in order to prevent sedimentation of the Cilengitide) until the suspension is filled in the respective container, vial or the like.

Example 7

A preferred alternate method of manufacture comprises the following steps, preferably in the given order:
1. Dissolution of solid DOPG in water under stirring at a temperature between 20° C. and 40° C.
2. Addition of NaCl, generally about 9 mg/mL, to the suspension under continued stirring
3. Addition of solid Cilengitide, preferably crystalline Cilengitide, more preferably crystalline Cilengitide anhydrate and especially crystalline Cilengitide of the form A1
4. Stirring of the obtained suspension until a stable particle distribution is obtained, generally 24 h or more and especially 24 to 48 h, and optionally
5. Continuation of the stirring process (in order to prevent sedimentation of the Cilengitide) until the suspension is filled in the respective container, vial or the like Example 8

An especially preferred method of manufacture comprises the following steps, preferably in the given order:
1. Dissolution of solid DOPG in water under stirring at a temperature between 20° C. and 40° C.
2. Addition of micronised Cilengitide, preferably micronised Cilengitide anhydrate and especially micronised Cilengitide of the form A1
3. Stirring of the obtained suspension until a stable particle distribution is obtained, generally 4 h or more and especially 6 to 12 h
4. Addition of NaCl, generally about 9 mg/mL, to the suspension under continued stirring, and optionally
5. Continuation of the stirring process (in order to prevent sedimentation of the Cilengitide) until the suspension is filled in the respective container, vial or the like.

Example 9

An especially preferred alternate method of manufacture comprises the following steps, preferably in the given order:
1. Dissolution of solid DOPG in water under stirring at a temperature between 20° C. and 40° C.
2. Addition of NaCl, generally about 9 mg/mL, to the suspension under continued stirring
3. Addition of micronised Cilengitide, preferably micronised Cilengitide anhydrate and especially micronised Cilengitide of the form A1
4. Stirring of the obtained suspension until a stable particle distribution is obtained, generally 4 h or more and especially 6 to 12 h, and optionally
5. Continuation of the stirring process (in order to prevent sedimentation of the Cilengitide) until the suspension is filled in the respective container, vial or the like Example 10

This Example of a typical composition (5 mL) in the form of a suspension comprising an amphiphilic compound and water may contain per mL:
200 mg/mL of micronized A1-Cilengitide, e.g. micronized A1-Cilengitide with a typical particle size distribution of d(10)=1-5 µm, d(50)=5-10 µm, and d(90)=20-30 µm,
1 to 20 mg/mL DMPG
optionally 9 mg/mL sodium chloride
optionally 5 mg/mL phenol
water for injection (add 100%)
The composition of Example 4 is preferably prepared by solubilization of the DMPG in water, preferably water for injection, at about room temperature or preferably at slightly elevated temperature, e.g. at about at about 30° C. or at about 40° C. After the solubilization, the micronized A1-Cilengitide (1000 mg) is added subsequently under stirring. Preferably, the stirring is continued for 4 to 20 h. If desired, the sodium chloride can then be added for adjusting the tonicity of decomposition and/or the phenol can be added for the preservation of the composition. If necessary, further amounts of water can be added (add 100%) to achieve the total volume of the composition, i.e. 5 mL.

Example 11

This Example of a typical suspension may contain per mL:
200 to 300 mg/mL of micronized A1-Cilengitide, e.g. micronized A1-Cilengitide with a typical particle size distribution of d(10)=1-5 µm, d(50)=5-10 µm, and d(90)=20-30 µm, or micronized A1-Cilengitide with an even more narrow particle size distribution optionally
1 to 20 mg/mL DMPG
optionally 9 mg/mL sodium chloride
optionally 5 mg/mL phenol
water for injection (add 100%)
The composition of Example 2 is preferably prepared by solubilization of DMPG in water, preferably water for injection, at about room temperature or preferably at slightly elevated temperature, e.g. at about 30° C. or at about 40° C. After the solubilization, the solid A1-Cilengitide is added subsequently under stirring. Preferably, the stirring is continued for 2 to 6 h. If desired, the sodium chloride can then be added for adjusting the tonicity of the composition and/or the phenol can be added for the preservation of the composition. Then water is added (add 100%) i.e. until the total volume of 1 mL of the composition is obtained Example 12

A preferred method of manufacture comprises the following steps, preferably in the given order:
1. Dissolution or solubilisation of solid DMPG in water under stirring at a temperature between 20° C. and 40° C.
2. Addition of solid Cilengitide, preferably crystalline Cilengitide, more preferably crystalline Cilengitide anhydrate and especially crystalline Cilengitide of the form A1
3. Stirring of the obtained suspension until a stable particle distribution is obtained, generally 24 h or more and especially 24 to 48 h
4. Addition of NaCl, generally about 9 mg/mL, to the suspension under continued stirring, and optionally
5. Continuation of the stirring process (in order to prevent sedimentation of the Cilengitide) until the suspension is filled in the respective container, vial or the like.

Example 13

A preferred alternate method of manufacture comprises the following steps, preferably in the given order:
1. Dissolution of solid DMPG in water under stirring at a temperature between 20° C. and 40° C.
2. Addition of NaCl, generally about 9 mg/mL, to the suspension under continued stirring
3. Addition of solid Cilengitide, preferably crystalline Cilengitide, more preferably crystalline Cilengitide anhydrate and especially crystalline Cilengitide of the form A1
4. Stirring of the obtained suspension until a stable particle distribution is obtained, generally 24 h or more and especially 24 to 48 h, and optionally
5. Continuation of the stirring process (in order to prevent sedimentation of the Cilengitide) until the suspension is filled in the respective container, vial or the like Example 14

An especially preferred method of manufacture comprises the following steps, preferably in the given order:
1. Dissolution of solid DMPG in water under stirring at a temperature between 20° C. and 40° C.
2. Addition of micronised Cilengitide, preferably micronised Cilengitide anhydrate and especially micronised Cilengitide of the form A1
3. Stirring of the obtained suspension until a stable particle distribution is obtained, generally 4 h or more and especially 6 to 12 h
4. Addition of NaCl, generally about 9 mg/mL, to the suspension under continued stirring, and optionally
5. Continuation of the stirring process (in order to prevent sedimentation of the Cilengitide) until the suspension is filled in the respective container, vial or the like.

Example 15

An especially preferred alternate method of manufacture comprises the following steps, preferably in the given order:
1. Dissolution of solid DMPG in water under stirring at a temperature between 20° C. and 40° C.
2. Addition of NaCl, generally about 9 mg/mL, to the suspension under continued stirring
3. Addition of micronised Cilengitide, preferably micronised Cilengitide anhydrate and especially micronised Cilengitide of the form A1
4. Stirring of the obtained suspension until a stable particle distribution is obtained, generally 4 h or more and especially 6 to 12 h, and optionally
5. Continuation of the stirring process (in order to prevent sedimentation of the Cilengitide) until the suspension is filled in the respective container, vial or the like Example 16

Pharmacokinetic Study in Mice

A composition/formulation composed of
200 micronized A1-Cilengitide with a typical particle size distribution of d(10)=1-5 µm, d(50)=5-10 µm, and d(90)=20-30 µm
1 mg/mL DOPG
9 mg/mL sodium chloride
water for injection,
was administered subcutaneously in a pharmacokinetic study in mice (Group A) versus two control groups (Groups B and C):
Group A (squares/sc-DOPG-50 mg/kg): A1-DOPG-Cilengitide suspension (200 mg/mL A1-Cilengitide, 1 mg/mL DOPG, 9 mg/mL DOPG in water for injection) by SC administration at a dose of 50 mg/KG.
Group B (tilted squares/iv-NaCl-5 mg/kg): Cilengitide infusion solution (8 mg/mL S3-Cilengitide in isotonic sodium chloride solution) by IV administration at a dose 5 mg/KG
Group C (triangles/sc-NaCl-10 mg/kg): Cilengitide infusion solution (8 mg/mL S3-Cilengitide in isotonic sodium chloride solution) by SC administration at a dose 10 mg/KG

| Route | Dose (mg/kg) | Data | 0.1 h | 0.25 h | 0.5 h | 1 h | 2 h | 3 h | 4 h | 6 h | 8 h |
|---|---|---|---|---|---|---|---|---|---|---|---|
| iv | 5 | Cilengitide IV solution (8 mg/mL in 0.9% NaCl) | | | | | | | | | |
| | | Average of EMD 121974 (ng/mL) | 2613.3 | 1370.0 | 1155.3 | 861.3 | 131.7 | — | 10.2 | — | — |
| | | StdDev of EMD 121974 (ng/mL) | 1610.7 | 295.1 | 785.5 | 672.2 | 103.6 | — | 6.1 | — | — |
| | | Sample size n | 3 | 3 | 3 | 3 | 3 | — | 3 | — | — |
| sc | 10 | Cilengitide IV solution (8 mg/mL in 0.9% NaCl) | | | | | | | | | |
| | | Average of EMD 121974 (ng/mL) | 7540.0 | 8200.0 | 3720.0 | 496.0 | 56.1 | 5.6 | — | — | — |
| | | StdDev of EMD 121974 (ng/mL) | 1131.4 | 933.4 | 594.0 | 22.6 | 2.8 | 0.3 | — | — | — |
| | | Sample size n | 2 | 2 | 2 | 2 | 2 | 2 | — | — | — |

| Route | Dose (mg/kg) | Data | 0.1 h | 0.25 h | 0.5 h | 1 h | 2 h | 3 h | 4 h | 6 h | 8 h |
|---|---|---|---|---|---|---|---|---|---|---|---|
| sc | 50 | Cilengitide A1-DOPG suspension (200 mg/mL) | | | | | | | | | |
| | | Average of EMD 121974 (ng/mL) | 2673.3 | 3790.0 | 4853.3 | 3966.7 | 2600.0 | — | 1640.0 | 1079.3 | 928.0 |
| | | StdDev of EMD 121974 (ng/mL) | 207.4 | 466.7 | 1397.9 | 556.4 | 254.6 | — | 481.2 | 351.1 | 158.4 |
| | | Sample size n | 3 | 2 | 3 | 3 | 2 | — | 3 | 3 | 2 |

Group A on A1-DOPG-Cilengitide suspension shows close to complete (>98%) bioavailability with a sustained-release profile compared to I.V. infusion of an isotonic Cilengitide solution (8 mg/mL). The observed t(max) of A1-DOPG suspension is comparable to the isotonic Cilengitide solution (8 mg/mL), as both formulations contain readily dissolved drug which is instantly available for absorption, also resulting into comparable c(max) values. A1-DOPG-Cilengitide suspension truly provides a controlled-/sustained drug release resulting in in-vivo drug concentrations above 1000 ng/mL up over 8 hours as a pronounced advantage over any isotonic Cilengitide solution (8 mg/mL) intended for I.V. infusion.

Furthermore, A1-DOPG suspensions were tested in in-vitro $\alpha_v\beta_{3/5}$ receptor assays showing that the specific activity of the Cilengitide in these suspensions is maintained.

Example 17

Pharmacokinetic Study in Monkeys

Composition (Suspension) administered
  Cilengitide: 300 mg/mL
  DMPG: 2 mg/mL
  Phenol: 0.5%
  NaCl: 0.9%
Species/strain and number of animals
  Monkey, Cynomolgus
Dose: 12 mg/kg (40 μL suspension/kg)
Sampling time points: 0.25, 0.5, 2, 4, 8 hours post dose:

| | | Time (h) | | | |
|---|---|---|---|---|---|
| | | 0.250 | 0.500 | 2.00 | 4.00 | 8.00 |
| Animal_No | Dose (mg/kg) | MSC1097999 (ng/mL) | | | | |
| 583 | 11.8 | 586 | 967 | 892 | 605 | 537 |

Example 18

Crystallization of the Inner Salt from the Hydrochloride 1.25 g of cyclo-(Arg-Gly-Asp-DPhe-NMeVal) x HCl are dissolved in 10 ml water. By use of conc. aqueous ammonia pH is adjusted to ~6.8. After standing over night at 4 C, crystals appear, which are separated by filtration, washed with ice-cold water, and dried on air. Mother liquor is concentrated to yield additional crystalline product.

Example 19

Crystallization of the Inner Salt from the Trifluoroacetate 1.41 g cyclo-(Arg-Gly-Asp-DPhe-NMeVal)×TFA are dissolved in 10 ml water. By use of conc. aqueous ammonia pH is adjusted to ~6.8. After standing over night at ambient temperature, crystals appear, which are separated by filtration, washed with ice-cold water, and dried on air. Mother liquor is concentrated to yield addition crystalline product.

Example 20

Chromatographic Production of the Inner Salt 5.04 g cyclo-(Arg-Gly-Asp-DPhe-NMeVal) x TFA are dissolved in 100 ml water and pH adjusted to ~7.0 with 25% NH3 aq. The solution is infused with aid of pump A onto a 2-pump gradient system RP-HPLC column (Lichrosorb RP8 (10 um) 50×250 mm). First, column is eluted with water, second, chromatographic purification of compound is by elution with a gradient of 15-25% 2-propanol in water at 20 ml/min in 2 hrs. Detection is at 215/254 nm. Fractions are collected and pooled. During evaporation of 2-propanol from pool crystalline inner salt cyclo-(Arg-Gly-Asp-DPhe-NMeVal) precipitates and is collected by filtration. Mother liquor is concentrated to yield additional crystalline product.

Example 21

Production of Crystals of the Inner Salt from a Co-Solvent Mixture 1 g cyclo-(Arg-Gly-Asp-DPhe-NMeVal) is dissolved in 20 ml water/2-propanol 8:2 vol at 40° C. After 2 days at RT (25° C.) crystalline compound has precipitated.

Example 22

X-Ray Structure Determination of Inner Salt

A crystal from crystalline form S3 is selected for x-ray analysis. Correct covalent structure of the peptide and conformation of the product in crystalline solid state showed a tetrahydrate has formed with 4 peptides per crystal unit.

| | |
|---|---|
| mol formula | $C_{27}H_{40}N_8O_7 \times 4\,H_2O$ |
| mol weight | 661.25 |
| crystal size | (0.65 × 0.45 × 008)mm$^3$ |
| temp | 298 K |
| diffractometer | Nonius - CAD4 |
| rays | Mo Kα |
| length | 0.71093 Å |
| monochrome | graphit |
| crystal | orthorhombic |
| group | P 2$_1$ 2$_1$ 2$_1$ |
| lattice | a 9.640(2) Å |
| | b 13.853(3) Å |
| | c 25.910(6) Å |
| | $\alpha = \beta = \gamma = 90°$ | mols of the compound of formula Id per unit cell 4

Example 23

Procedure to Obtain Pseudopolymorphic Forms by Stirring in Methanol/Water and Ethanol/Water Mixtures a) Form S3 of Cilengitide can be obtained by slurry conversion from form A1 in a Methanol/Water mixture (70 v %:30 v %) at 25° C. for 2 days stirring time and Ethanol/Water mixture (60 v %:40 v %) at 25° C. for 18 days stirring time. Approx. 500 mg of form A1 of Cilengitide are dispersed in 5 ml solvent at room temperature. The dispersion is stirred for the mentioned time by a magnetic stirrer and finally filtered.

b) Additionally form S3 can be manufactured by competitive slurry conversion experiments with a mixture of a pseudopolymorphic form (for example S1, S2, S3 or mixtures of these) with form A1 (1:1) in Water/Methanol and Water/Ethanol mixtures with different alcohol contents at different temperatures.

Approx. 20 mg of a pseudopolymorphic form (for example S1, S2, S3 or mixtures of these) and 20 mg of form A1 of Cilengitide are dispersed in 300 µl Water/alcohol mixture at 0° C. or room temperature (25° C.). The dispersion is stirred for 24 h and additionally for 3 weeks at RT (25° C.) (long-term experiment) by a magnetic stirrer and finally filtered In the following table the conditions for the experiments leading to form S3 are listed.

| solvent in the mixture with Water | 0° C. for 1 day | RT for 1 day | RT for 3 weeks |
|---|---|---|---|
| Methanol | 40-100 v % | 60-100 v % | 60-100 v % |
| Water | ad. 100 v % | ad. 100 v % | ad. 100 v % |
| Ethanol | 20-80 v % | 40-80 v % | 40-70 v % |
| Water | ad. 100 v % | ad. 100 v % | ad. 100 v % | c) In contrast thereto, under the following conditions, none of the pseudopolymorphic forms could be obtained, but essentially pure anhydrate A1 is formed instead.

Approx. 20 mg of a pseudopolymorphic form (for example S1, S2, S3 or mixtures of these) and 20 mg of form A1 of Cilengitide are dispersed in 300 µl Water/alcohol mixture at 50° C. The dispersion is stirred for 24 h by a magnetic stirrer and finally filtered.

In the following table the conditions for the experiments leading to form A1 are listed.

| solvent in the mixture with Water | 50° C. for 1 day |
|---|---|
| Methanol | 90-100 v % |
| Water | ad. 100 v % |
| Ethanol | 90-100 v % |
| Water | ad. 100 v % |

Water "ad. 100 v %" preferably means that water is added to the before specified amount of solvent other than water (in volume percent (v %)) in an amount to make up for 100 v % of the respective solvent/water mixture.

Example 24

Procedure to Obtain form S1 by Conditioning Experiments Under Methanol Atmosphere in an Desiccator Approx. 1 g of a pseudopolymorphic form (for example S2, S3 or mixtures of these) are dried in an dessicator above silica gel. Then the material is stored in an desiccator with 100% Methanol vapour atmosphere for 5 days.

Example 25

Procedure to Obtain form S2 by Conditioning Experiments Under Ethanol Atmosphere in an Desiccator Approx. 1 g of a pseudopolymorphic form (for example S3, S1, or mixtures of these) are dried in an dessicator above silica gel. Then the material is stored in an desiccator with 100% Ethanol vapour atmosphere for 5 days.

Example 26

Procedure to Convert A1/S3 Polymorphic Mixtures to S3 by Stirring in Ethanol/Water Mixtures Cilengitide (mixture of polymorph A1 and S3, 275.5 g) is suspended in a mixture of deionized water (700 ml) and ethanol (700 ml). The suspension is stirred at room temperature for 24 h and then cooled to 5° C. The product is isolated by suction filtration and washed with cold ethanol. Drying under vacuum for 72 h at 60° C. yields 270 g of Cilengitide (crystal form S3, 3.6% EtOH, HPLC purity: 99.9%).

Example 27

Manufacture of Crystalline form A1 by Slurry Conversion

Form A1 of Cilengitide can be obtained by slurry conversion from pseudopolymorphic forms (for example S1, S2, S3 or mixtures of these) in Water at 25° C. An increased temperature (50° C.) accelerates the conversion to form A1.

Approx. 10 g of a pseudopolymorphic form (for example S1, S2, S3 or mixtures of these) of Cilengitide are dispersed in 50 ml deionised water at room temperature. The dispersion is stirred for 24 h by a magnetic stirrer and finally filtered.

Example 28

Manufacture of Crystalline form A1 by Competitive Slurry Conversion

Also the pure form A1 can be manufactured by competitive slurry conversion experiments with a mixture of a pseudopolymorphic form (for example S1, S2, S3 or mixtures of these) and A1 (1:1) in Acetone, Acetonitrile, Isopropanol, physiological NaCl solution, Phosphate buffer (pH 7.4) and 1:1 (v:v) mixtures of Acetone, Acetonitrile, Isopropanol with Water at RT (25° C.).

Approx. 20 mg of a pseudopolymorphic form (for example S1, S2, S3 or mixtures of these) and 20 mg of form A1 of Cilengitide are dispersed in 200-700 µl solvent at room temperature. The dispersion is stirred for 5 days and additionally 26 days (long-term experiment) at RT (25° C.) by a magnetic stirrer and finally filtered.

Example 29

Competitive Slurry Conversion

Additionally form A1 can be manufactured by competitive slurry conversion experiments with a mixture of a pseudopolymorphic form (for example S1, S2, S3 or mixtures of these) and form A1 (1:1) in Water/Methanol and Water/Ethanol mixtures with different alcohol contents at different temperatures. In the following table the conditions for the experiments leading to the pure form A1 are listed.

| solvent in the mixture with Water | 0° C. for 1 day | RT for 1 day | RT for 3 weeks | 50° C. for 1 day |
|---|---|---|---|---|
| Methanol | 0 v % | 0-50 v % | 0-40 v % | 0-70 v % |
| water | 100 v % | ad. 100 v % | ad. 100 v % | ad. 100 v % |
| Ethanol | 0-10 v % | 0-30 v % | 0-20 v % | 0-80 v % |
| water | ad. 100 v % | ad. 100 v % | ad. 100 v % | 100 v % |

Approx. 20 mg of a pseudopolymorphic form (for example S1, S2, S3 or mixtures of these) and 20 mg of form A1 of Cilengitide are dispersed in 300 µl Water/alcohol mixture at 0° C., room temperature and 50° C. The dispersion is stirred for 24 h and additionally for 3 weeks at RT (25° C.) (long-term experiment) by a magnetic stirrer and finally filtered.

Example 30

Procedure to obtain Crystalline form S3 Including Crystallization from Ethanol/Water Mixtures Cyclo-(Arg-Gly-Asp-DPhe-NMeVal) x TFA x $H_2SO_4$ (400 g) is dissolved in water (1600 ml) at 59° C. The pH is adjusted to pH=6.8 by addition of aqueous ammonia (30%). Methanol (9600 ml) is added to the solution over a period of 3 h. The obtained mixture is cooled to 23° C. within 3 h and stirred at this temperature over night. Then, the mixture is cooled to 5° C. and stirred another 2 h. The precipitated raw product is isolated by suction filtration and washed with cold methanol. Drying under vacuum for 48 h at 50° C. yields 335 g of Cilengitide (crystalline form S3, HPLC: 99.8%).

The raw material (335 g) is dissolved in water (1507 g) at 58° C. Methanol (8040 ml) is added to the solution over a period of 3 h. The thus formed suspension is then cooled to 23° C. within 3 h and stirred at this temperature over night. The suspension is then cooled to 5° C. and stirred for another 3 h. The product is isolated by suction filtration and washed with methanol. Drying under vacuum for 48 h at 60° C. yields 309 g of Cilengitide (crystalline form S3, HPLC: 99.9%, 3.8% MeOH, IC: <0.1% $Cl^{-1}$, 0.0007% TFA and 10.3% $SO_4$).

The 150 g of the above obtained material are dissolved in water (600 ml) and ethanol (600 ml) at 56° C. The mixture is cooled to 23° C. within 3 h and stirred over night. The mixture (suspension) is cooled to 5° C. and stirred for 2 h at this temperature. The product is isolated by suction filtration and washed with cold water. Drying under vacuum for 48 h at 60° C. yields 115.4 g of Cilengitide (crystalline form S3, ≤0.05% Methanol, 5.3% EtOH IC: <0.01% $Cl^-$, <0.0011% TFA, 0.34% $SO_4$).

Example 31

Manufacture of Crystalline Form A1 by Crystallization from Water

A preferred and very efficient method to obtain A1 is by crystallization from water starting from the raw material of Cilengitide as it evolves from the manufacturing processes:

Raw Cilengitide (300 g, either amorphous material, form S3 or mixtures thereof) are dissolved in deionized water (1200 ml) at 58° C. The solution is cooled to 23° C. within 3 h and stirred at this temperature over night. The suspension is then cooled to 5° C. and stirred for 2 h at this temperature. The product is isolated by suction filtration and washed with cold deionized water. Drying under vacuum for 48 h at 50° C. yields about 230 g of Cilengitide (crystal form A1, <0.001% TFA, 0.22% $SO_4$, 0.06% Ammonium, 99% HPLC purity, 0.027% water).

Example 32

Dynamic Vapour Experiments of Crystalline Form S3

A SMS DVS I system is used for the dynamic vapour experiments regarding crystalline form S3. The results have been obtained by standard techniques as described in Rolf Hilfiker, 'Polymorphism in the Pharmaceutical Industry', Wiley-VCH. Weinheim 2006 (Chapter 9: Water Vapour Sorption, and references therein). Water Vapour Sorption behaviour shows a loss of water molecules (ca. 9 wt %) within the initial drying step (0% rh). During the water adsorption cycle there is shown an assembly of water molecules (ca. 10 wt %) in the lattice at elevated rh. In the second desorption cycle there is a loss of this amount of water. Water Vapor Sorption isotherm (25° C.) of form S3 is displayed in FIG. 25.

Example 33

Dynamic Vapour Experiments of Crystalline Form S1

A SMS DVS Intrinsic is used for the dynamic vapour experiments. The results are obtained by standard techniques as described in Rolf Hilfiker, 'Polymorphism in the Pharmaceutical Industry', Wiley-VCH. Weinheim 2006 (Chapter 9: Water Vapour Sorption, and references therein). Water Vapour Sorption behaviour shows a mass loss of approx. 8 wt % in the first desorption cycle, which is slightly lower than the observed Methanol mass gain in the Methanol Vapour Sorption experiment. Upon water vapour sorption, an assembly of water molecules in the lattice is observed, with a maximum weight gain of approx. 8 wt % at elevated rh. In the second desorption cycle a total mass loss of approx. 9.9 wt % is observed. For a Cilengitide Dihydrate Di-Methanolate, the calculated Methanol content equals 9.3 wt %. Water Vapor Sorption isotherm (25° C.) of form S1 is displayed below.

Example 34

Dynamic Vapour Experiments of Crystalline Form S2

A SMS DVS Intrinsic is used for the dynamic vapour experiments. The results are obtained by standard techniques as described in Rolf Hilfiker, 'Polymorphism in the Pharmaceutical Industry', Wiley-VCH. Weinheim 2006 (Chapter 9: Water Vapour Sorption, and references therein). Water Vapour Sorption behaviour shows a mass loss of approx. 6.5 wt % in the first desorption cycle, which is lower than the observed Ethanol mass gain in the Ethanol Vapour Sorption experiment. Upon water vapour adsorption, an assembly of water molecules in the lattice is observed, with a maximum weight gain of approx. 6.4 wt % at elevated rh. In the second desorption cycle a total mass loss of approx. 9.2 wt % is observed. For a Cilengitide Dihydrate Di-Ethanolate, the calculated Ethanol content equals 12.5 wt %. Water Vapor Sorption isotherm (25° C.) of form S2 is displayed below.

Example 35

X-Ray Structure Determination of the Anhydrate

A crystal from crystalline form A1 is selected for X-ray analysis. Correct covalent structure of the peptide and conformation of the product in crystalline solid state showed a anhydrate has formed with 4 cyclopeptides per crystal unit.

| | |
|---|---|
| mol formula | $C_{27}H_{40}N_8O_7$ |
| mol weight | 588.67 |
| crystal size | $(0.30 \times 0.24 \times 0.24) mm^3$ |
| temp | 298 K |
| diffractometer | XCalibur - Oxford Diffration |
| rays | Mo Ka |
| length | 0.71093 Å |
| monochrome | graphit |
| crystal | orthorhombic |
| group | P $2_1 2_1 2_1$ |
| lattice | a 9.7944(5) Å |
| | b 15.3877(7) Å |
| | c 19.5090(2) Å |
| | $\alpha = \beta = \gamma = 90°$ | mols of the compound of formula Id per unit cell 4

The invention claimed is:

1. A composition comprising
a) 20 to 80% of polymorphic form A1 of the inner salt of cyclo-(Arg-Gly-Asp-DPhe-NMeVal), said polymorphic form having a solubility in water at 20° C. between 3 mg/ml and 10 mg/ml,
b) 0.01 to 10% of one or more amphiphilic compounds having a molar weight in the range of 200 g/mol to 2000 g/mol, and
c) 10 to 79.9% of water,
with the proviso that the sum of a), b) and c) sums up to 70 or more % of the total composition and wherein at least 10% of the polymorphic form A1 present in the composition is in a suspended or suspendable solid form at a temperature of 20° C.

2. The composition according to claim 1, wherein at least one of the amphiphilic compounds according to b) comprises
α) a glycerol moiety,
β) one or more fatty acid moieties, and/or
γ) one or more fatty alcohol moieties.

3. The composition according to claim 2, wherein
i) the fatty acid moieties are of acids independently selected from the group consisting of oleic acid, myristic acid, palmitic acid, stearic acid, margaric acid, arachic acid, behenic acid, erucic acid, linolic acid and linolenic acid, and
ii) the fatty alcohol moieties are of alcohols independently selected from the group consisting of oleic alcohol, myristic alcohol, palmitic alcohol, stearic alcohol, margaric alcohol, arachic alcohol, behenic alcohol, erucic alcohol, linolic alcohol and linolenic alcohol.

4. The composition according to claim 1, wherein the sum of a), b) and c) sums up to 90 or more % of the total composition.

5. The composition according to claim 4, wherein the one or more amphiphilic compounds comprise an ethanolamine moiety, a choline moiety, a phosphatidyl moiety and/or a sulfatidyl moiety, and/or a salt thereof.

6. The composition according to claim 4, wherein the one or more amphiphilic compounds comprise a phosphoethanolamine moiety, a phosphatidylcholine moiety, a phosphatidylglycerol moiety and/or a sulfatidylglycerol moiety, and/or a salt thereof.

7. The composition according to claim 4, comprising
d) 0 to 10% of one or more compounds other than a), b) and c), selected from pharmaceutically acceptable excipients.

8. The composition according to claim 1, comprising
a) 20 to 59.99% of said polymorphic form A1 of the inner salt of cyclo-(Arg-Gly-Asp-DPhe-NMeVal),
b) 0.01 to 5% of one or more amphiphilic compounds,
c) 20 to 79.9% of water,
with the proviso that the sum of a), b) and c) sums up to 90 or more % of the total composition.

9. The composition according to claim 1, additionally comprising
d) 0 to 30% of one or more compounds other than a), b) and c), selected from the group consisting of:
d1) pharmaceutically active ingredients, and
d2) pharmaceutically acceptable excipients.

10. The composition according to claim 1, wherein at least 50% of the polymorphic form A1 according to a) is present in the composition in a suspended or suspendable solid form at a temperature of 20° C.

11. The composition according to claim 1, wherein the polymorphic form A1 of the inner salt of cyclo-(Arg-Gly-Asp-DPhe-NMeVal) is in a polymorphic form having a crystallographic unit cell with the lattice parameters a=9.8±0.1 Å, b=19.5±0.5 Å, and c=15.4±0.1 Å.

12. The composition according to claim 1, wherein the polymorphic form A1 of the inner salt of cyclo-(Arg-Gly-Asp-DPhe-NMeVal) is at least partly present in the form of solid crystalline particles, said solid crystalline particles having an average particle size in the range of 5 μm to 250 μm.

13. A composition comprising
a) 12 to 90% of polymorphic form A1 of the inner salt of cyclo-(Arg-Gly-Asp-DPhe-NMeVal), said polymorphic form having a solubility in water at 20° C. between 3 mg/ml and 10 mg/ml, b) 10 to 90% of at least one lipophilic compound selected from natural oils and synthetic oils, and mixtures thereof, and optionally c) 0 to 10% of water, with the proviso that the sum of a), b) and c) sums up to 70 or more % of the total composition and wherein at least 20% of the polymorphic form A1 present in the composition is in a suspended or suspendable solid form at a temperature of 20° C.

14. The composition according to claim 13, wherein the at least one lipophilic compounds according to b) are selected from one or more compounds selected from natural oils and synthetic oils, and mixtures thereof, and said composition optionally comprises pharmaceutically active ingredients or pharmaceutically acceptable excipients other than a), b) and c).

15. A composition comprising
   a) 20 to 79.99% of polymorphic form A1 of the inner salt of cyclo-(Arg-Gly-Asp-DPhe-NMeVal), said polymorphic form having a solubility in water at 20° C. between 3 mg/ml and 10 mg/ml,
   b) 0.01 to 10% of one or more amphiphilic compounds, selected from the group consisting of:
      b1) fatty acid mono-, di- or polyesters of phosphatidyl- or sulfatidyl-polyols, and derivatives, salts and/or alcoholates thereof, and
      b2) fatty alcohol mono-, di- or polyethers of phosphatidyl- or sulfatidyl-polyols, and derivatives, salts and/or alcoholates thereof,
   c) 20 to 79.9% of water,
   with the proviso that the sum of a), b) and c) sums up to 70 or more % of the total weight of the composition.

16. The composition according to claim 15, wherein the phosphatidyl- or sulfatidyl-polyols are selected from the group consisting of:
   a) polyphosphatidylglycerol, triphosphatidylglycerol, diphosphatidylglycerol, monophosphatidylglycerol, and
   b) polysulfatidylglycerol, trisulfatidylglycerol, disulfatidylglycerol, and monosulfatidylglycerol.

17. The composition according to claim 16, wherein the one or more amphiphilic compounds are selected from the group consisting of dioleoylphosphatidylglycerol, dimyristoylphosphatidylglycerol, distearoylphosphatidylglycerol, dipalmitoylglycerophosphoglycerol, and pharmaceutically acceptable derivatives, salts and/or alcoholates thereof.

18. The composition according to claim 16, wherein the one or more amphiphilic compounds are selected from the group consisting of dioleoylphosphatidylglycerol and dimyristoylphosphatidylglycerol, and pharmaceutically acceptable derivatives, salts and/or alcoholates thereof.

19. A composition comprising
   a) 20 to 40% of polymorphic form A1 of the inner salt of cyclo-(Arg-Gly-Asp-DPhe-NMeVal), said polymorphic form having a solubility in water at 20° C. between 3 mg/ml and 10 mg/ml,
   b) 0.01 to 10% of one or more amphiphilic compounds selected from the group consisting of: dioleoylphosphatidylglycerol, distearoylphosphatidylglycerol, dipalmitoylglycerophosphoglycerol and mixtures thereof, and the alkali salts thereof,
   c) water, and optionally
   d1) 0 to 20% of one or more pharmaceutically active ingredients other than the compound according to a), and/or
   d2) 0 to 20% of one or more pharmaceutically acceptable excipients other than the compounds according to b) and c),
   with the proviso that the sum of a), b), c), d1) and d2) sums up to 100% of the composition and wherein at least 10% of the polymorphic form A1 present in the composition is in a suspended or suspendable solid form at a temperature of 20° C.

20. The composition according to claim 19, wherein at least 50% of the polymorphic form A1 of the inner salt of cyclo-(Arg-Gly-Asp-DPhe-NMeVal) present in the composition is in a suspended or suspendable solid form at a temperature of 20° C.

21. The composition according to claim 19, wherein the molar ratio between the one or more amphiphilic compounds and a) is in the range between 0.01 and 0.5.

22. The composition according to claim 19, wherein the molar ratio between the one or more amphiphilic compounds and a) is in the range between 0.001 and 0.05.

23. The composition according to claim 19, comprising 10% or more of a) in the form of solid particles and/or solid crystalline particles.

24. The composition according to claim 19, wherein the polymorphic form A1 of the inner salt of cyclo-(Arg-Gly-Asp-DPhe-NMeVal) is at least partly present in the form of solid particles and/or solid crystalline particles, said particles having an average particle size in the range of 5 µm to 250 µm.

25. A composition comprising
   a) 20 to 40% of polymorphic form A1 of the inner salt of cyclo-(Arg-Gly-Asp-DPhe-NMeVal) said polymorphic form having a solubility in water at 20 degrees Celsius between 3 mg/ml and 10 mg/ml,
   b) 0.01 to 1% of one or more amphiphilic compounds selected from the group consisting of: dioleoylphosphatidylglycerol and dimyristoylphosphatidylglycerol, and mixtures thereof, and the alkali salts thereof,
   c) water, and optionally
   d1) 0 to 20% of one or more pharmaceutically active ingredients other than the compound according to a), and/or
   d2) 0 to 20% of one or more pharmaceutically acceptable excipients other than the compounds according to b) and c),
   with the proviso that the sum of a), b), c), d1) and d2) sums up to 100% of the composition.

26. A composition comprising
   a) 20 to 40% of the polymorphic form A1 of the inner salt of cyclo-(Arg-Gly-Asp-DPhe-NMeVal) said polymorphic form having a solubility in water at 20 degrees Celsius between 3 mg/ml and 10 mg/ml,
   b) 0.01 to 5% of one or more amphiphilic compounds having a molar weight in the range of 200 g/mol to 2000 g/mol, and
   c) 0 to 79.99% of water,
   with the proviso that the sum of a), b) and c) sums up to 90 or more % of the total composition.

27. A process for the manufacture of a composition according to claim 22, comprising one or more of the following steps:
   i) solubilising the one or more amphiphilic compounds in water,
   ii) adding or suspending the polymorphic form A1 of the inner salt of cyclo-(Arg-Gly-Asp-DPhe-NMeVal) in the mixture or solution obtained according to i), and optionally iii) adding the one or more pharmaceutically active ingredients other than the compound according to a), and/or the one or more pharmaceutically acceptable excipients other than the water and the one or more amphiphilic compounds.

28. The composition according to claim 20, wherein said suspended or suspendable solid form consists of solid crystalline particles, said solid crystalline particles having an average particle size in the range of 5 μm to 250 μm.

29. A solid composition in the form of a free-flowing or reconstitutable powder, obtained from a composition according to claim 19 by reducing the water content until a residual water content in the range of 0 to 20%, 0.001 to 10% or 0.001 to 2% is achieved.

* * * * *